US011685773B2

(12) United States Patent
Glanville et al.

(10) Patent No.: US 11,685,773 B2
(45) Date of Patent: Jun. 27, 2023

(54) METHOD FOR MASS HUMANIZATION OF RABBIT ANTIBODIES

(71) Applicants: AbCheck s.r.o., Plzen (CZ); CHARLES RIVER LABORATORIES, INC., Wilmington, MA (US)

(72) Inventors: Jacob E. Gunn Glanville, San Francisco, CA (US); Vera Molkenthin, Tännesberg (DE); Remko Albert Griep, Plzen (CZ); Ahmad Trad, Plzen (CZ); Peter Milovnik, Plzen (CZ); Volker Lang, Wolnzach (DE)

(73) Assignees: ABCHECK s.r.o., Plzen (CZ); CHARLES RIVER LABORATORIES, INC., Wilmington, MA (US)

( * ) Notice: Subject to any disclaimer, the term of this patent is extended or adjusted under 35 U.S.C. 154(b) by 193 days.

(21) Appl. No.: 15/577,153

(22) PCT Filed: Apr. 29, 2016

(86) PCT No.: PCT/EP2016/000701
§ 371 (c)(1),
(2) Date: Nov. 27, 2017

(87) PCT Pub. No.: WO2016/173719
PCT Pub. Date: Nov. 3, 2016

(65) Prior Publication Data
US 2018/0319869 A1    Nov. 8, 2018

(30) Foreign Application Priority Data

Apr. 30, 2015    (EP) .................................... 15001304

(51) Int. Cl.
| C07K 16/06 | (2006.01) |
| C07K 16/46 | (2006.01) |
| C07K 16/00 | (2006.01) |
| C07K 16/40 | (2006.01) |

(52) U.S. Cl.
CPC ............ *C07K 16/005* (2013.01); *C07K 16/40* (2013.01); *C07K 2317/24* (2013.01); *C07K 2317/56* (2013.01); *C07K 2317/565* (2013.01); *C07K 2317/567* (2013.01); *C07K 2317/622* (2013.01); *C07K 2317/92* (2013.01)

(58) Field of Classification Search
CPC .... C07K 16/464; C12N 15/1037; C40B 30/04
See application file for complete search history.

(56) References Cited

U.S. PATENT DOCUMENTS

| 4,683,195 A | 7/1987 | Mullis et al. | |
| 5,530,101 A * | 6/1996 | Queen ..................... | C07K 16/00 424/133.1 |
| 10,125,198 B2 | 11/2018 | Glanville | |
| 2009/0104187 A1 * | 4/2009 | Kovacevich ......... | C07K 16/241 424/133.1 |
| 2011/0065610 A1 * | 3/2011 | Fischer ................ | C07K 16/005 506/26 |
| 2014/0045703 A1 * | 2/2014 | Kotsbak ............... | C12Q 1/6874 506/2 |
| 2019/0263936 A1 | 8/2019 | Glanville | |

FOREIGN PATENT DOCUMENTS

| WO | 1991/018989 A1 | 12/1991 |
| WO | 1991/019818 A1 | 12/1991 |
| WO | 1992/001047 A1 | 1/1992 |
| WO | 1992/006204 A1 | 4/1992 |
| WO | 1992/018619 A1 | 10/1992 |
| WO | 1999/036569 A1 | 7/1999 |
| WO | 2008/136694 A1 | 11/2008 |
| WO | 2008/144757 A1 | 11/2008 |
| WO | 2009/155726 A2 | 12/2009 |
| WO | 2014/127811 A1 | 8/2014 |

OTHER PUBLICATIONS

Panka et al. (Proceedings of the National Academy of Sciences USA, vol. 85, p. 3080-3084, 1988) (Year: 1988).*
Rudikoff et al. (Proceedings of the National Academy of Sciences USA, vol. 79, p. 1979-1983, 1982) (Year: 1982).*
Bendig M. M. (Methods: A Companion to Methods in Enzymology, 1995; 8:83-93) (Year: 1995).*
Paul, Fundamental Immunology, 3rd Edition, 1993, pp. 292-295 (Year: 1993).*
Rader (The Journal of Biological Chemistry, vol. 275, No. 18, p. 13668-13676, 2000) (Year: 2000).*
Al-Lazikani et al. (1997) "Standard conformations for the canonical structures of immunoglobulins," Journal of Molecular Biology. 273:927-948.
Auf Der Maur et al. (2004) "Antigen-independent selection of intracellular stable antibody frameworks," Methods 34(2):215-224.
Bernett et al. (2010) "Engineering Fully Human Monoclonal Antibodies from Murine Variable Regions," J. Mol. Biol. 396(5):1474-1490.
Bowers et al. (Mar. 15, 2013) "Humanization of Antibodies Using Heavy Chain Complementarity-determining Region 3 Grafting Coupled with in Vitro Somatic Hypermutation," J. Biol. Chem. 288(11):7688-7696.
Brown et al. (1996) "Tolerance of single, but not multiple, amino acid replacements in antibody VH CDR 2: a means of minimizing B cell wastage from somatic hypermutation?" J. Immunol. 156(9):3285-3291.

(Continued)

*Primary Examiner* — Michael Allen
(74) *Attorney, Agent, or Firm* — Dechert LLP

(57) ABSTRACT

The present invention relates to a method for producing a population of 20 or more nucleic acids, each encoding at least one protein comprising at least one immunoglobulin variable domain having a rabbit-derived CDR3 amino acid sequence embedded in essentially human framework sequences, as well as to a population of nucleic acids and a population of proteins relates thereto and uses thereof.

17 Claims, 46 Drawing Sheets

Specification includes a Sequence Listing.

(56) References Cited

OTHER PUBLICATIONS

Carter et al. (1992) "Humanization of an anti-p185HER2 antibody for human cancer therapy," Proc. Natl. Acad. Sci. USA 89:4285-9.
Chothia et al. (1985) "Domain Association in Immunoglobulin Molecules," J. Mol. Biol. 186:651-663.
Clackson et al. (1991) "Making antibody fragments using phage display libraries," Nature. 352(6336):624-8.
Donovan et al. (1987) "Genes encoding spore coat polypeptides from Bacillus subtilis," J. Mol. Biol. 196:1-10.
Dunbar et al. (May 24, 2013) "ABangle: characterizing the VH-VL orientation in antibodies," Protein Engineering, Design, and Selection. 26:611-620.
Han et al. (1995) "Ligand-directed retroviral targeting of human breast cancer cells," Proc. Natl. Acad. Sci. USA. 92:9747-9751.
Hanes et al. (1997) "In vitro selection and evolution of functional proteins by using ribosome display," Proc. Natl. Acad. Sci. USA. 94(10):4937-42.
He et al. (2007) "Eukaryotic ribosome display with in situ DNA recovery," Nature Methods. 4(3):281-288.
Huse et al. (1989) "Generation of a large combinatorial library of the immunoglobulin repertoire in phage lambda," Science. 246(4935):1275-81.
Jones et al. (1986) "Replacing the complementarity-determining regions in a human antibody with those from a mouse," Nature. 321:522-5.
MacCallum et al. (1996) "Antibody-antigen interactions: Contact analysis and binding site topography," J. Mol. Biol. 262:732-745.
Marks et al. (1992) "Molecular evolution of proteins on filamentous phage. Mimicking the strategy of the immune system," J. Biol. Chem. 267(23):16007-10.
Mullis et al. (1987) "Specific enzymatic amplification of DNA in vitro: the polymerase chain reaction," Cold Spring Harbor Symp. Quant. Biol. 51:263-73.
Novotny et al. (1985) "Structural invariants of antigen binding: comparison of immunoglobulin VL-VH and VL-VL domain dimers," Proc Natl Acad. Sci. USA. 82:4592-4596.
Osbourn et al. (2005) "From rodent reagents to human therapeutics using antibody guided selection," Methods. 36(1):61-68.
Pingoud et al. (2001) "Structure and function of type II restriction endonucleases," Nucleic Acids Research. 29(18):3705-3727.
Riechmann et al. (1988) "Reshaping human antibodies for therapy," Nature. 332:323-327.
Winkler et al. (2000) "Changing the Antigen Binding Specificity by Single Point Mutations of an Anti-p24 (HIV-1) Antibody," J. Immunol. 165(8):4505-4514.
International Search Report with Written Opinion crorresponding to International Patent Application No. PCT/EP2016/000701, dated Jun. 14, 2016.

* cited by examiner

Figure 1
A)
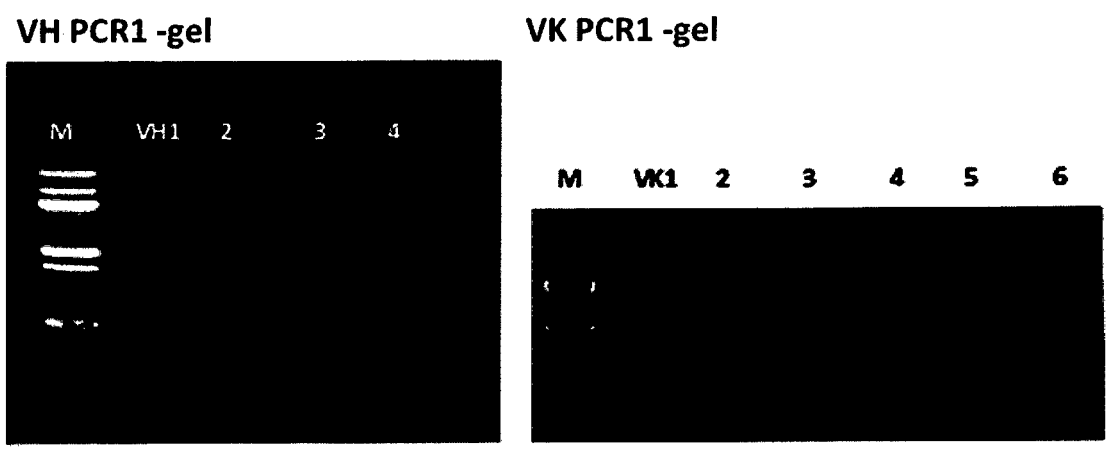
B)
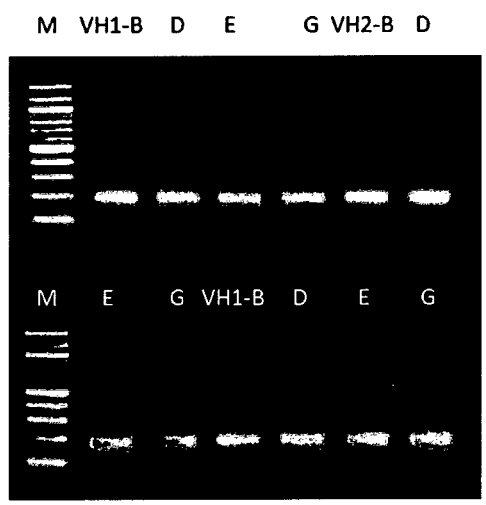

VK PCR2

Figure 2
A)
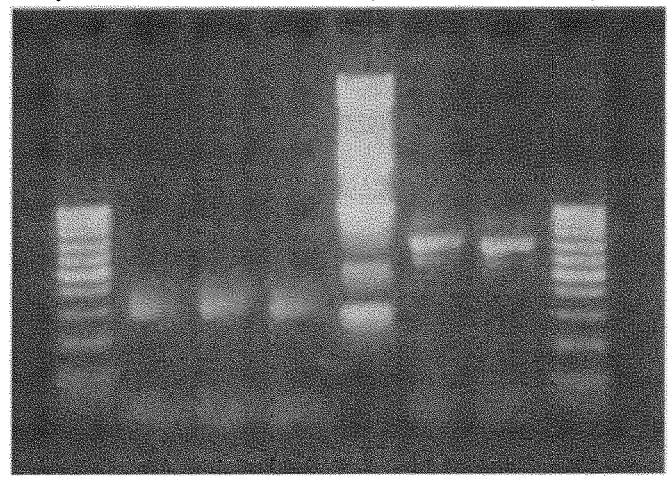
B)
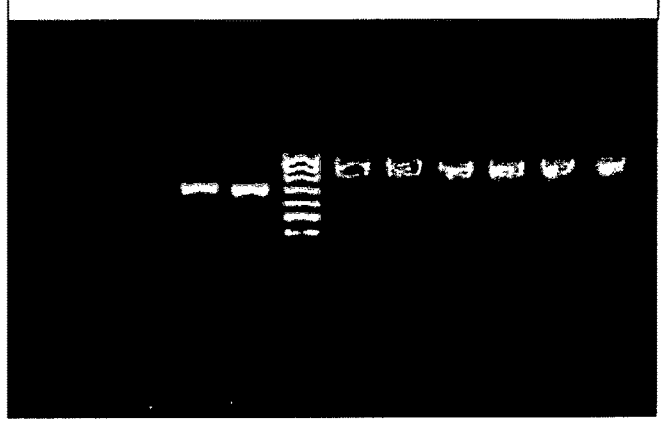
C)
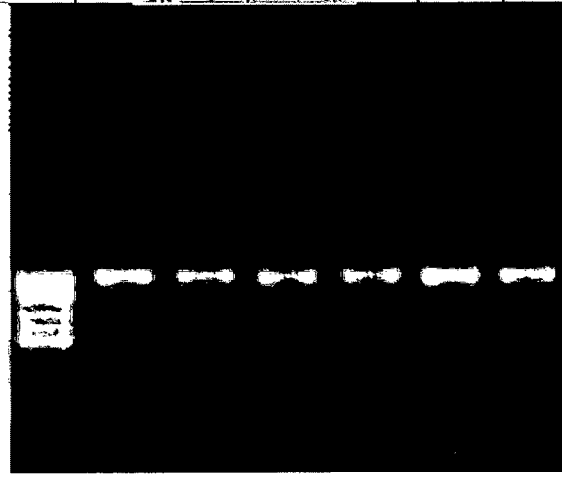

Figure 3
A)
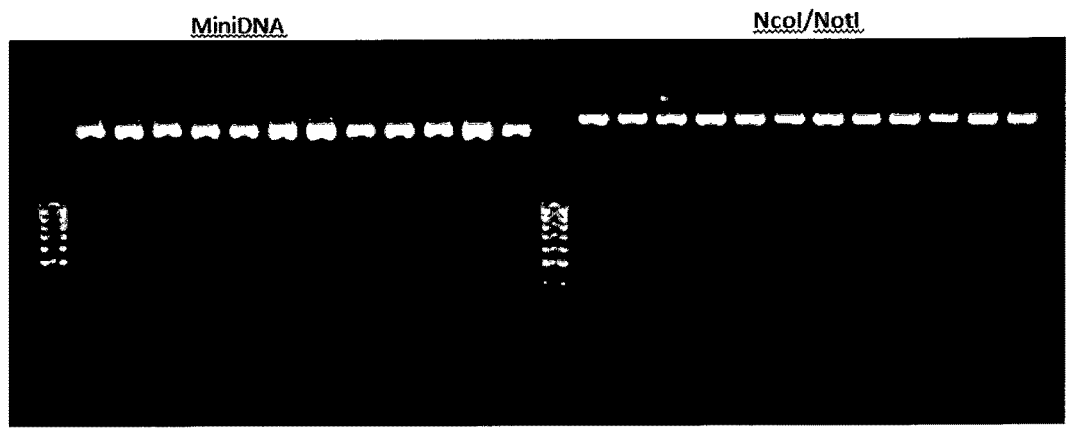
B)
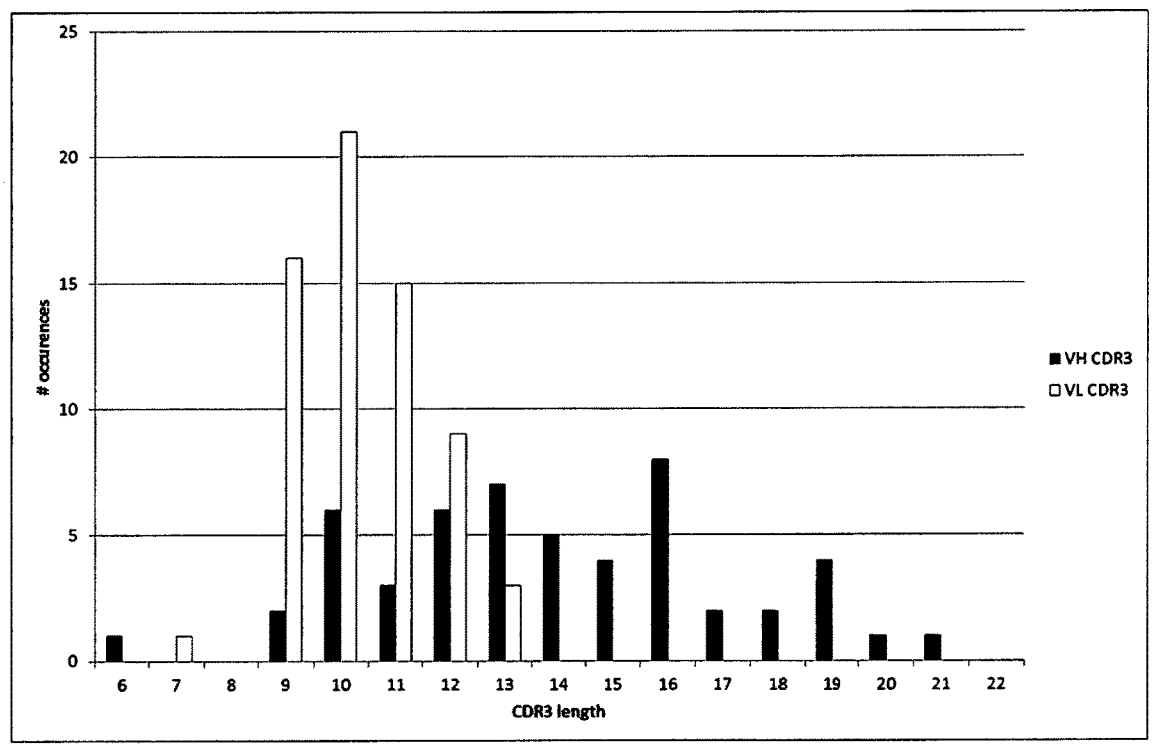

Figure 4
A)
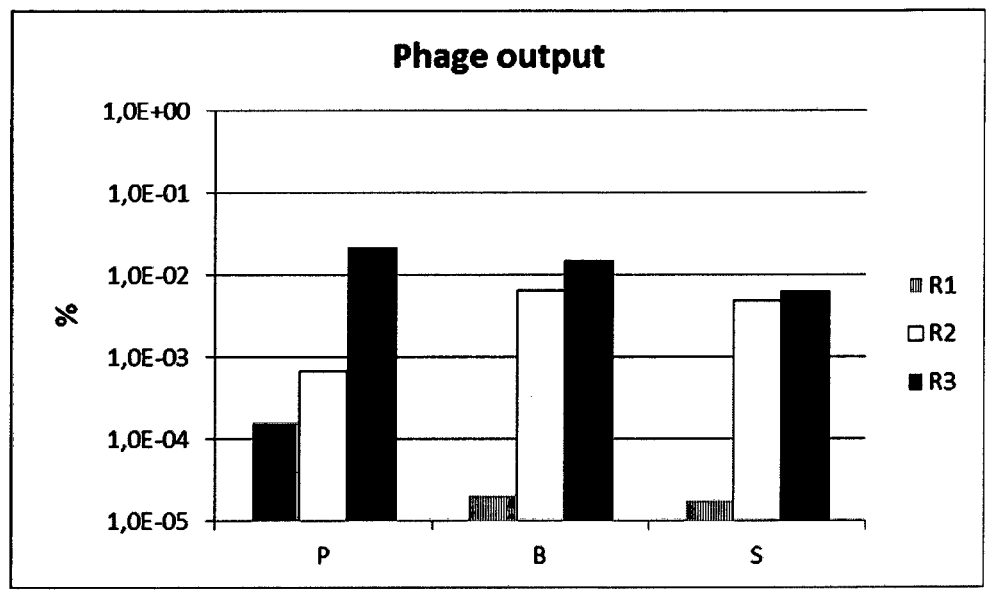
B)
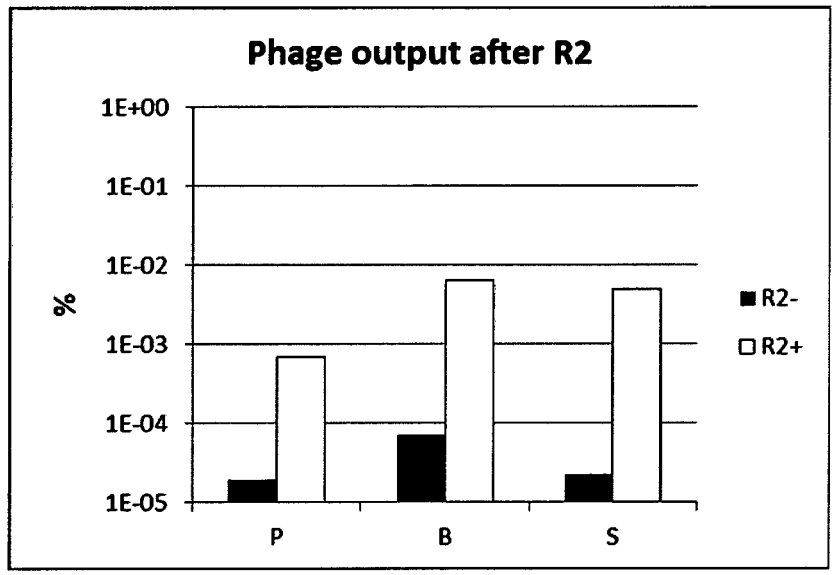

Figure 6
A)
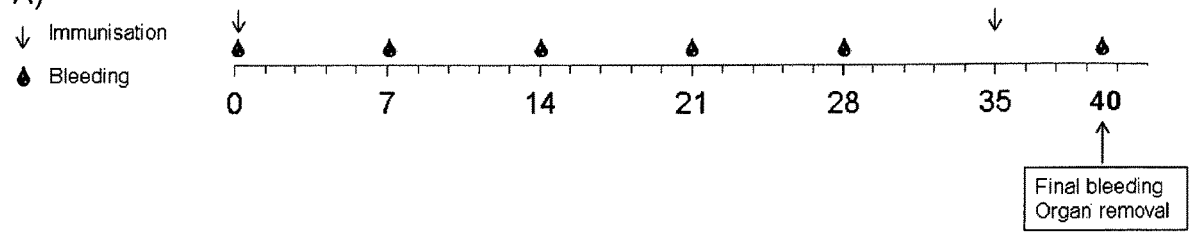
B)
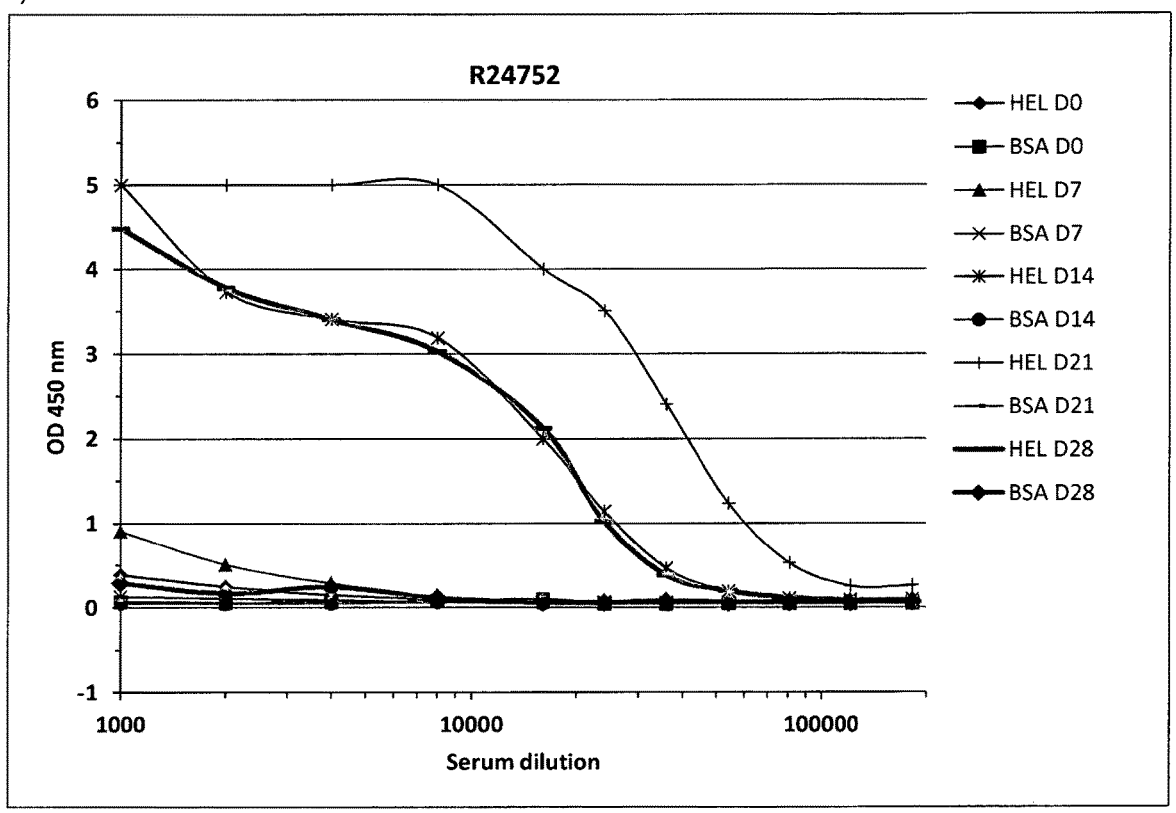

Figure 7
A)
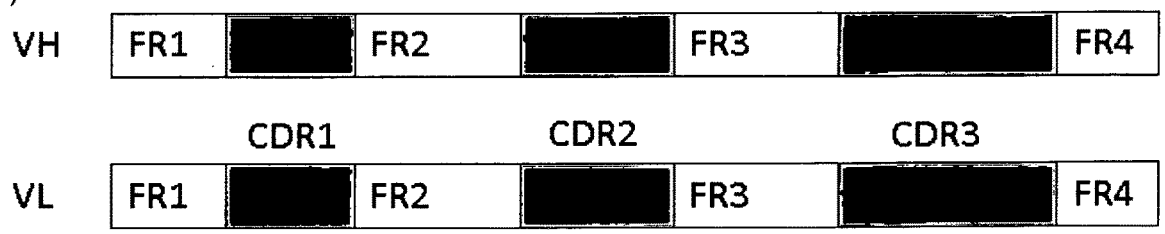
B)
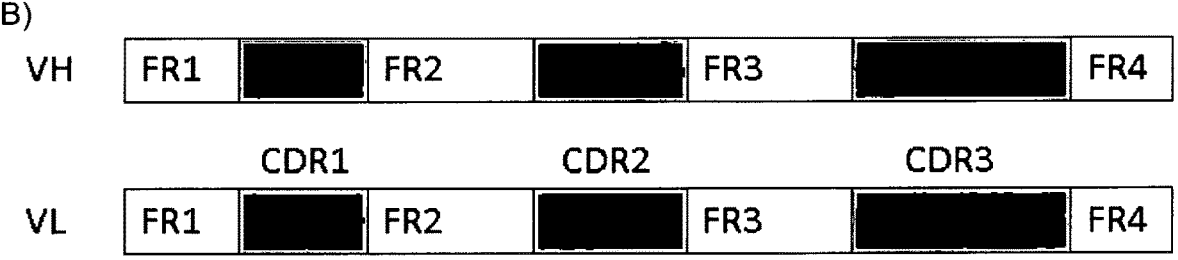

Figure 8A (nucleic acid: SEQ ID No: 41; protein SEQ ID No. 44)

```
+1    Q   S   V   K   E   S   E   G   G   L   F   K   P   M   D   T   L   T   C   T   V   S   G   F   S   L   S   S
      |------------------------------Rab VH1 FP 95.7%-------------------------------------------------------------
1     CAGTCAGTGA AGGAGTCCGA GGGAGGTCTC TTCAAGCCAA TGGATACCCT GACACTCACC TGCACAGTCT CCTCAGTTCT
      GTCAGTCACT TCCTCAGGCT CCCTCCAGAG AAGTTCGGTT ACCTATGGGA CTGTGAGTGG ACGTGTCAGA GGAGTCAAGA

+1    Y   G   V   N   W   V   R   Q   A   P   G   K   G   L   E   W   I   G   Y   I   G   T   G   T   Y   L   A   N   W   A
91    TATGGCGTGA ACTGGGTCCG CCAGGCTCCA GGGAAGGGGC TGGAGTGGAT CGGATATATT GGTACTGGTA CATATCTTGC GAACTGGGCG
      ATACCGCACT TGACCCAGGC GGTCCGAGGT CCCTTCCCCG ACCTCACCTA GCCTATATAA CCATGACCAT GTATAGAACG CTTGACCCGC

+1    K   S   R   S   T   I   T   S   N   T   N   E   N   T   V   T   L   K   M   T   S   L   T   G   A   D   T   A   T   Y
181   AAAAGCCGAT CCACCATCAC CAGCAACACC AACGAGAACA CGGTGACTCT GAAAATGACC AGTCTGACAG GCGCGGACAC GGCCACCTAT
      TTTTCGGCTA GGTGGTAGTG GTCGTTGTGG TTGCTCTTGT GCCACTGAGA CTTTTACTGG TCAGACTGTC CGCGCCTGTG CCGGTGGATA

+1    F   C   G   S   G   A   N   I   E   N   E   F   F   N   A   I   W   G   P   G   T   L   V   T   V   S   S   G   Q   P
271   TTCTGTGGGA GTGGCGCCAA TATTGAAAAT GAGTTTTTCA ATGCCATCTG GGGCCCAGGC ACCCTGGTCA CCGTCTCCTC AGGGCAACCT
      AAGACACCCT CACCGCGGTT ATAACTTTTA CTCAAAAAGT TACGGTAGAC CCCGGGTCCG TGGGACCAGT GGCAGAGGAG TCCCGTTGGA

+1    K   A   P   S   V   F   P   L   A   P   C   C   G   D
361   AAGGCTCCGT CAGTCTTCCC ACTGGCCCCC TGCTGCGGGG
      TTCCGAGGCA GTCAGAAGGG TGACCGGGGG ACGACGCCCC
      |-Rab IgG RP 100.0%-|
```

Figure 8B (nucleic acid: SEQ ID No: 42; protein SEQ ID No. 45)

```
+1    D   P   V   L   T   Q   T   P   S   S   A   C   E   P   V   G   G   T   V   T   I   K   C   Q   A   S   E   S   I   S
      ─────────────────────────────────────────────────────── Rab Vk5 FP 84.1% ───────────────────────────────────────────────────────
  1   GACCCTGTGC TGACCCAGAC TCCATCTTCC GCGTGTGAAC CTGTGGGAGG CACAGTCACC ATCAAGTGCC AGGCCAGTGA GAGCATTAGT
      CTGGGACACG ACTGGGTCTG AGGTAGAAGG CGCACACTTG GACACCCTCC GTGTCAGTGG TAGTTCACGG TCCGGTCACT CTCGTAATCA

+1    S   R   L   A   W   Y   Q   Q   K   P   G   Q   Q   P   K   L   L   I   Y   S   A   S   T   L   A   S   G   V   P   S
 91   AGTAGATTAG CCTGGTATCA GCAGAAAACCA GGGCAGTCTC CCAAGCTCCT GATCTATTCT GCATCCACTC TGGCATCTGG GGTCCCATCG
      TCATCTAATC GGACCATAGT CGTCTTTGGT CCCGTCAGAG GGTTCGAGGA CTAGATAAGA CGTAGGTGAG ACCGTAGACC CCAGGGTAGC

+1    R   F   K   G   S   G   S   G   T   E   Y   T   L   T   I   S   D   L   E   C   A   D   A   A   T   Y   Y   C   Q   N
181   CGGTTCAAAG GCAGTGGATC TGGGACAGAG TACACACTCTCA CCATCAGCGA CCTGGAGTGT GCCGATGCTG CCACTTACTA CTGTCAAAAC
      GCCAAGTTTC CGTCACCTAG ACCCTGTCTC ATGTGAGAGT GGTAGTCGCT GGACCTCACA CGGCTACGAC GGTGAATGAT GACAGTTTTG

+1    N   N   G   V   Y   S   G   V   S   S   A   V   A   F   P   G   E   E   T   K   L   E   I   K   R   D   P   V   A   P
271   AATAATGGTG TAGTAGCGGA TAGTAGCGCT GTCGCTTTCA CCTTTGGCGA GGAGACCAAG CTGGAGATCA AACGTGATCC AGTTGCACCT
      TTATTACCAC ATCATCGCCT ATCATCGCGA CAGCGAAAGT GGAAACCGCT CCTCTGGTTC GACCTCTAGT TTGCACTAGG TCAACGTGGA

+1    T   V   L   I   F   P   P   A   A   D   Q   V   A   T   G   T   V   T   I   V   C   V   A   N   K   Y   F   P   D   V
361   ACTGTCCTCA TCTTCCCACC AGCTGCTGAT CAGGTGGCAA CTGGAACAGT CACCATCGTG TGTGTGGCGA ATAAATACTT TCCGGATGTC
      TGACAGGAGT AGAAGGGTGG TCGACGACTA GTCCACCGTT GACCCTTGTCA GTGGTAGCAC ACACAGCCGCT TATTTATGAA AGGGCTACAG

+1    T   V   T   W   E   V   D   G   T   T   Q   T   T   G   I   E   N   S   K   T   P   Q   N   S   A   D   C   T   Y   N
451   ACCGTCACCT GGGAGGTGGA TGGCACCACC CAAACAACTG GCATCGAGAA CAGTAAAACA CCGCAGAATT CTGCAGATTG TACCTACAAC
      TGGCAGTGGA CCCTCCACCT ACCGTGGTGG GTTTGTTGAC CGTAGCTCTT GTCATTTTGT GGCGTCTTAA GACGTCTAAC ATGGATGTTG
      ──────────────────────────────────────────────────────── Rab K RP 100.0% ────────────────────────────────────────────────────────

+1    L   S   S   T   L   T
541   CTCAGCAGCA CTCTGACACT
      GAGTCGTCGT GAGACTGTGA
```

Figure 10A (nucleic acid: SEQ ID No: 41; protein SEQ ID No. 44)

Figure 10B (nucleic acid: SEQ ID No: 42; protein SEQ ID No: 45)

```
     +1  D   P   V   L   T   Q   T   P   S   S   A   C   E   P   V   G   G   T   V   T   I   K   C   Q   A   S   E   S   I   S
             Rab Vk5 FP  84.1%
      1  GACCCTGTGC TGACCCAGAC TCCATCTTCC GCGTGTGAAC CTGTGGAGG CACAGTCACC ATCAAGTGCC AGGCCAGTGA GAGCATTAGT
         CTGGGACACG ACTGGGTCTG AGGTAGAAGG CGCACACTTG GACACCCTCC GTGTCAGTGG TAGTTCACGG TCCGGTCACT CTCGTAATCA

+1  S   R   L   A   W   Y   Q   Q   K   P   G   Q   P   P   K   L   L   I   Y   G   A   S   T   L   A   S   G   V   P   S
     91  AGTAGATTAG CCTGGTATCA GCAGAAACCA GGGCAGTCTC CCAAGCTCCT GATCTATTCT GCATCCACTC TGGCATCTGG GGTCCCATCG
         TCATCTAATC GGACCATAGT CGTCTTTGGT CCCGTCAGAG GGTTCGAGGA CTAGATAAGA CGTAGGTGAG ACCGTAGACC CCAGGGTAGC

+1  R   F   K   G   S   G   S   G   T   E   Y   T   L   T   I   S   D   L   K   C   A   D   A   A   T   Y   Y   C   Q   N
                                                                                                   Rab VLkCDR3 BarI For 79.2%
    181  CGGTTCAAAG GCAGTGGATC TGGGACAGAG TACACTCTCA CCATCAGCGA CCTGGAGTGT GCCGATGCTG CCACTTACTA CTGTCAAAAC
         GCCAAGTTTC CGTCACCTAG ACCCTGTCTC ATGTGAGAGT GGTAGTCGCT GGACCTCACA CGGCTACGAC GGTGAATGAT GACAGTTTTG

+1  N   G   S   G   S   S   A   V   A   P   T   P   G   E   B   T   K   L   L   E   I   K   R   D   P   V   A   P
    271  AATAATGGTG GTAGTGGTAG TAGTGCTGTC GTCGCTTTCA CCTTTGGCGA GGAGACCAAG CTGGAGATCA AACGTGATCC AGTTGCACCT
         TTATTACCAC CATCACCATC ATCACGACAG CAGCGAAAGT GGAAACCGCT CCTCTGGTTC GACCTCTAGT TTGCACTAGG TCAACGTGGA
                                                                                          Rab VLkCDR3 BarI Rev1 73.5%

+1  T   V   L   I   F   P   P   A   A   D   Q   V   A   T   G   T   V   T   V   C   V   A   N   K   Y   F   P   D   V
    361  ACTGTCCTCA TCTTCCCACC AGCTGCTGAT CAGGTGGCAA CTGGAACAGT CACCGTCTGC GTGGCGA ATAAATACTT TCCCGATGTC
         TGACAGGAGT AGAAGGGTGG TCGACGACTA GTCCACCGTT GACCCTTGTCA GTGGTAGCAC ACACCGCT TATTTATGAA AGGGCTACAG

+1  T   V   T   K   B   V   D   G   T   T   Q   T   T   G   I   E   N   S   K   T   F   Q   N   S   A   D   C   T   Y   N
    451  ACCGTCACCT GGGAGGTGGA TGGCACCACC CAAACAACTG GCATCGAGAA CAGTAAAACA CCGCAGAATT CTGCAGATTG TACCTACAAC
         TGGCAGTGGA CCCTCCACCT ACCGTGGTGG GTTTGTTGAC CGTAGCTCTT GTCATTTTGT GGGCGTCTTAA GACGTCTAAC ATGGATGTTG
                                                                          Rab K RP  100.0%

+1  L   G   S   S   T   L   T
    541  CTCAGCAGCA CTCTGACACT
         GAGTCGTCGT GAGACTGTGA
```

Figure 11
A)
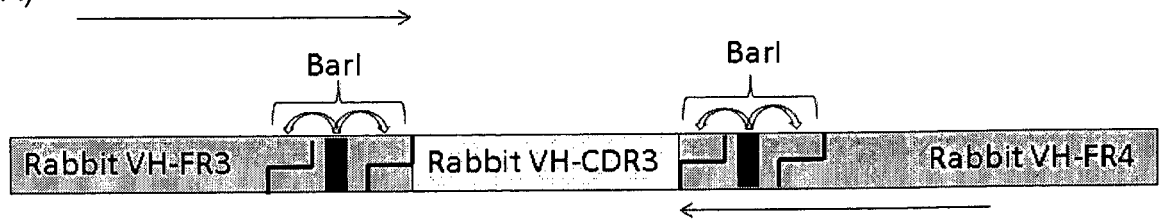
B)
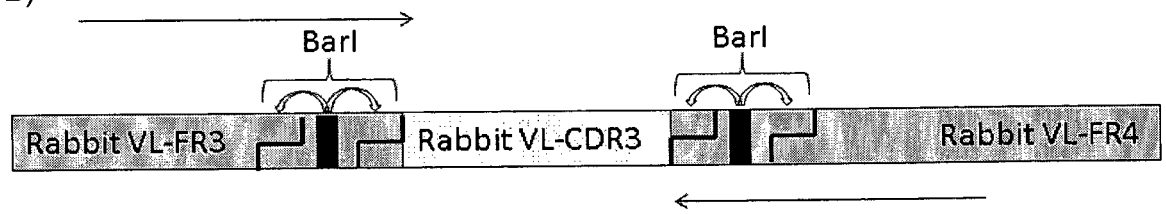
Figure 12
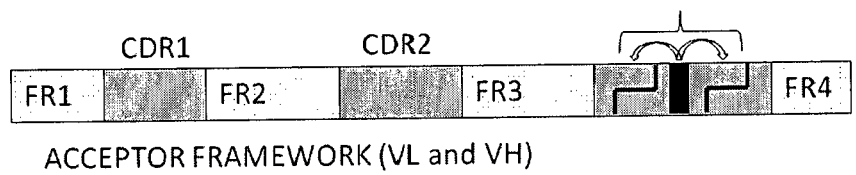
ACCEPTOR FRAMEWORK (VL and VH)
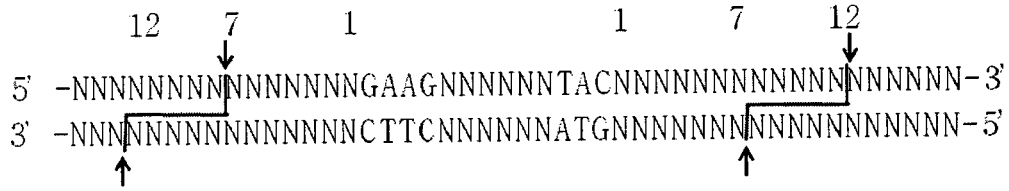
(SEQ ID No: 46)
Figure 13
A) (SEQ ID No: 51)
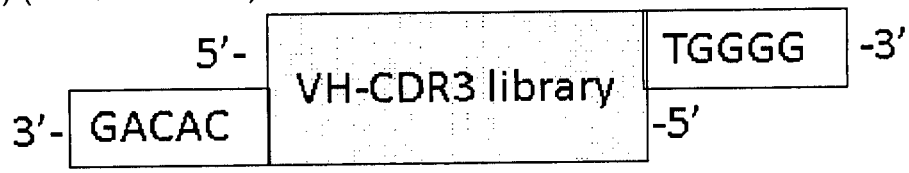

Figure 13 (continued)
B)
C) (SEQ ID No: 52)
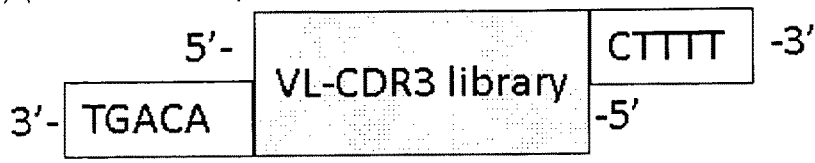
D)
Figure 14
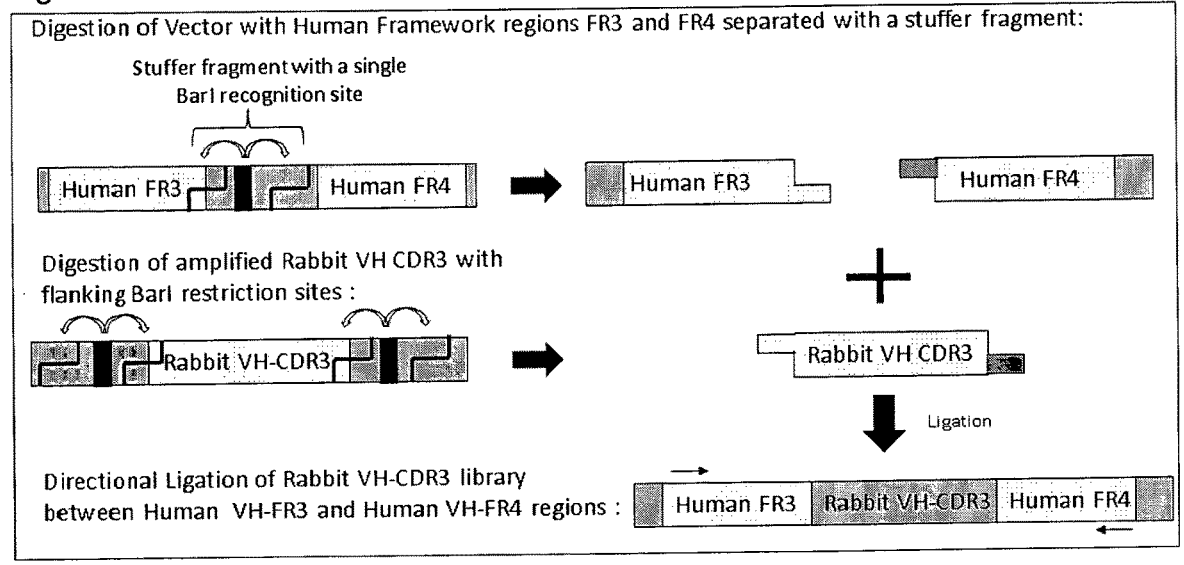

Figure 19
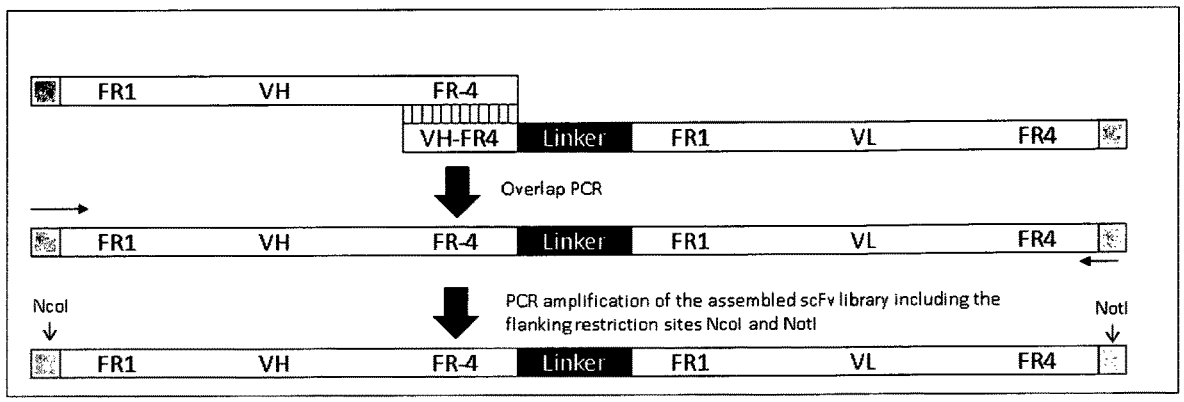
Figure 20
(SEQ ID No: 57, SEQ ID No: 58)
200 Oligos: VH: 3'-GGCTCCTGTG CCGGCACATA ATGACACNAC CCCGGTCCCC TGTGATCAGT GGCAGAGTTC-5'
VH-CDR3
200 Oligos: VL: 3'-TCGGACTTCT ACAACGTTGA ATAATGACAN GAAAACCGCC TCCCTGGTTC CACC-5'
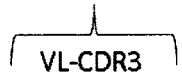
VL-CDR3

Figure 21 (SEQ ID Nos: 53 to SEQ ID No: 56)
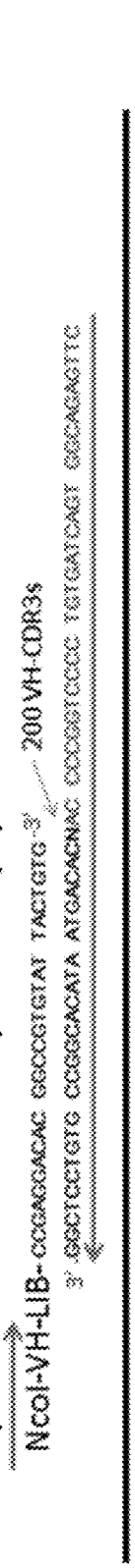
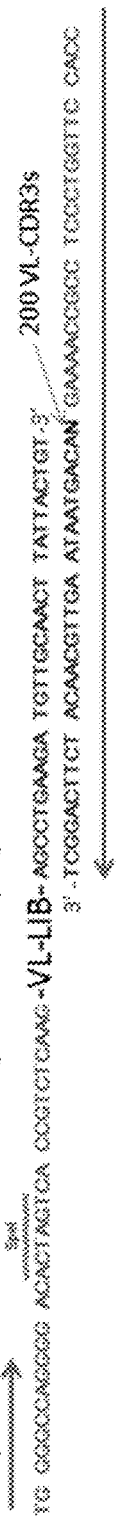
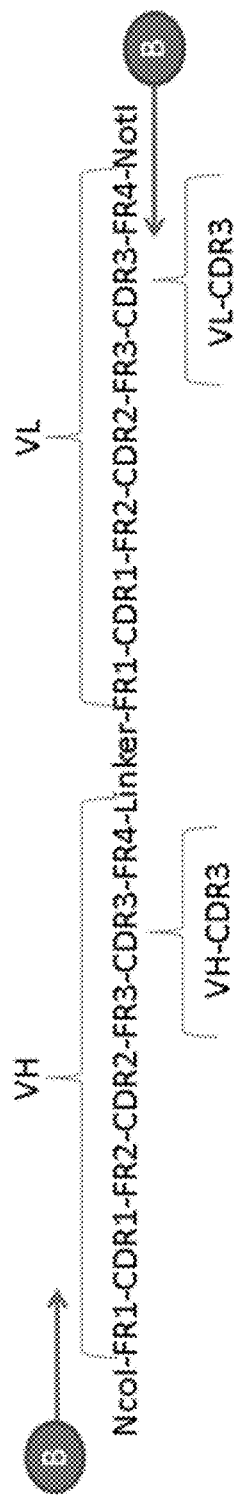

Figure 24
(SEQ ID No: 59 to SEQ ID No: 75)

A)
```
>3SO_42      C A R V Y D D Y G D D Y F D
>3PO_1       C A R V Y D D Y G D D Y F N
>2S1_29      C A R V Y D D Y G D D Y F D
>2P1_2       C V R V Y D D Y G D D Y F T L
>3BO_22      C A R V Y D D Y G D D Y F N L
>3PO_19      C A R V Y D D Y G D D Y F N L
>3P_23       C A R V Y D D Y G D D Y F N L
>Consensus   C A R V Y D D Y G D D Y F N L
```

B)
```
>3SO_31      C A R E S G Y Y P D Y A G Y G Y A Y G M D P
>3P_9        C A R E S G Y Y P D Y A G Y G Y A Y G M D P
>3PO_37      C A R E S G Y Y A D Y A G Y G Y A Y G M D P
>2P1_1       C A R E S D Y Y A D Y A G Y G Y A Y G M D P
>2B1_18      C A R E S D Y Y S D Y A G Y G Y A Y G M D P
>2B1_31      C A R E S G Y Y A D Y A G L G Y A Y G M D P
>3S_37       C A R E S G Y Y A D Y G G Y G Y A Y G M D P
>2S1_17      C A R E S G Y Y A D Y G G Y G Y A Y G M D P
>Consensus   C A R E S G Y Y A D Y A G Y G Y A Y G M D P
```

Figure 25
(SEQ ID No: 76 to SEQ ID No: 96)

|     |         |                                         | # of sequences within group |
|-----|---------|-----------------------------------------|-----------------------------|
| >A  | C A R   | V Y D D Y G D D Y F N I                 | 61                          |
| >B  | C A R   | E S G Y Y A D Y A G Y G Y A Y G M D P   | 52                          |
| >C  | C A R   | A E G Y D D W H L S L                   | 8                           |
| >G  | C A R   | D S Y D D Y G D W G G M D P             | 6                           |
| >E  | C A R   | D I Y D D Y G D P T R S D L             | 5                           |
| >I  | C A R   | E D E Y A E Y Y F D L                   | 4                           |
| >D  | C A R   | A K N D D Y G D P D S L D L             | 3                           |
| >H  | C A R   | E A D G A Y T G Y G Y S Y G M D P       | 3                           |
| >K  | C A R   | Y N A D D Y G D Y Y G L D P             | 3                           |
| >Q  | C A R   | E G D W S Y S L D L                     | 3                           |
| >F  | C A R   | D S S G W G R L D L                     | 2                           |
| >J  | C A R   | S N Y G A L D L                         | 2                           |
| >R  | C A R   | G T G Y A G Y G D A T G G F N I         | 2                           |
| >S  | C A R   | P L V S G W V F G G M D L               | 2                           |
| >L  | C A R   | A L Y G D H T F D P                     | 1                           |
| >M  | C A R   | A Y G S N G G Y N P G R L D L           | 1                           |
| >N  | C A R   | D D W F Y F D L                         | 1                           |
| >O  | C A R   | D S L G G F D L                         | 1                           |
| >P  | C A R   | E F N Y D A Y S D Y Y A L D P           | 1                           |
| >T  | C V R   | D P A Y S Y V M                         | 1                           |
| >U  | C V R   | G Y P G G S V G G D L                   | 1                           |

Figure 27
(SEQ ID No: 97 to SEQ ID No: 101)

| clone | Kd (M) |
|-------|--------|
| 3SO_31 | 9.3E-9 |
| 3P_9 | 1.4E-8 |
| 2S1_17 | 6.7E-8 |
| 2P1_1 | 9.9E-8 |
| 2B1_18 | 1.2E-7 |

| | | | | | | | | | | | | | | | | | | | | |
|--|--|--|--|--|--|--|--|--|--|--|--|--|--|--|--|--|--|--|--|--|
| C | A | R | E | S | G | Y | Y | P | D | Y | A | G | Y | G | Y | A | Y | G | M | D | P |
| C | A | R | E | S | G | Y | Y | P | D | Y | A | G | Y | G | Y | A | Y | G | M | D | P |
| C | A | R | E | S | G | Y | Y | A | D | Y | G | G | Y | G | Y | A | Y | G | M | D | P |
| C | A | R | E | S | D | Y | Y | A | D | Y | A | G | Y | G | Y | A | Y | G | M | D | P |
| C | A | R | E | S | D | Y | Y | S | D | Y | A | G | Y | G | Y | A | Y | G | M | D | P |

Figure 31
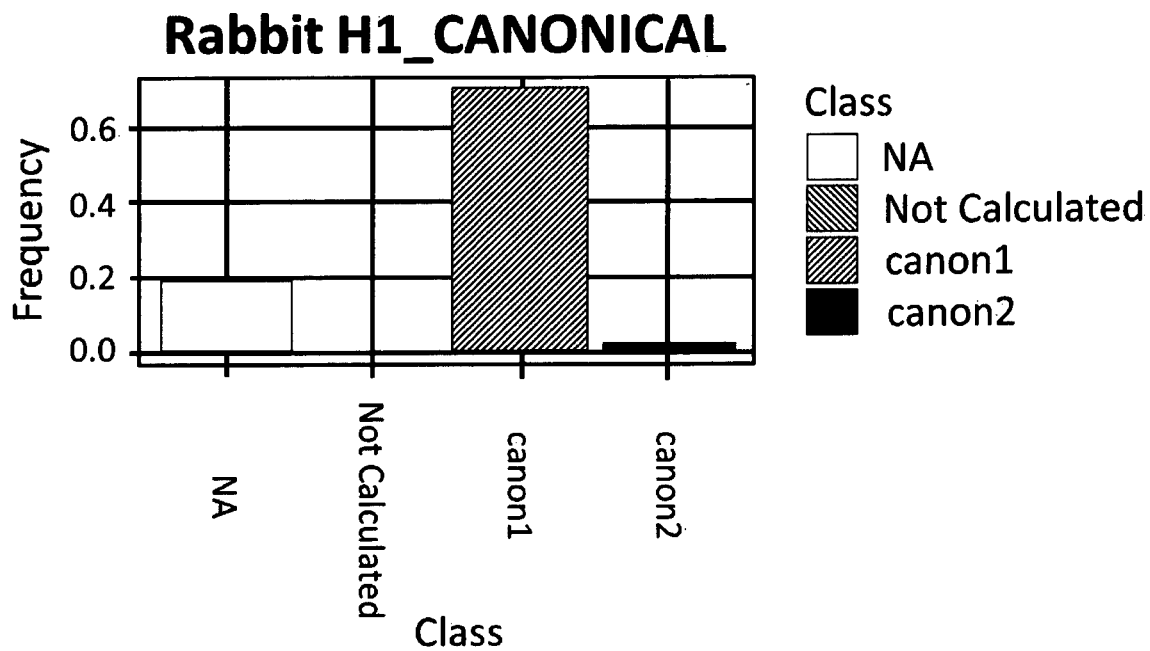
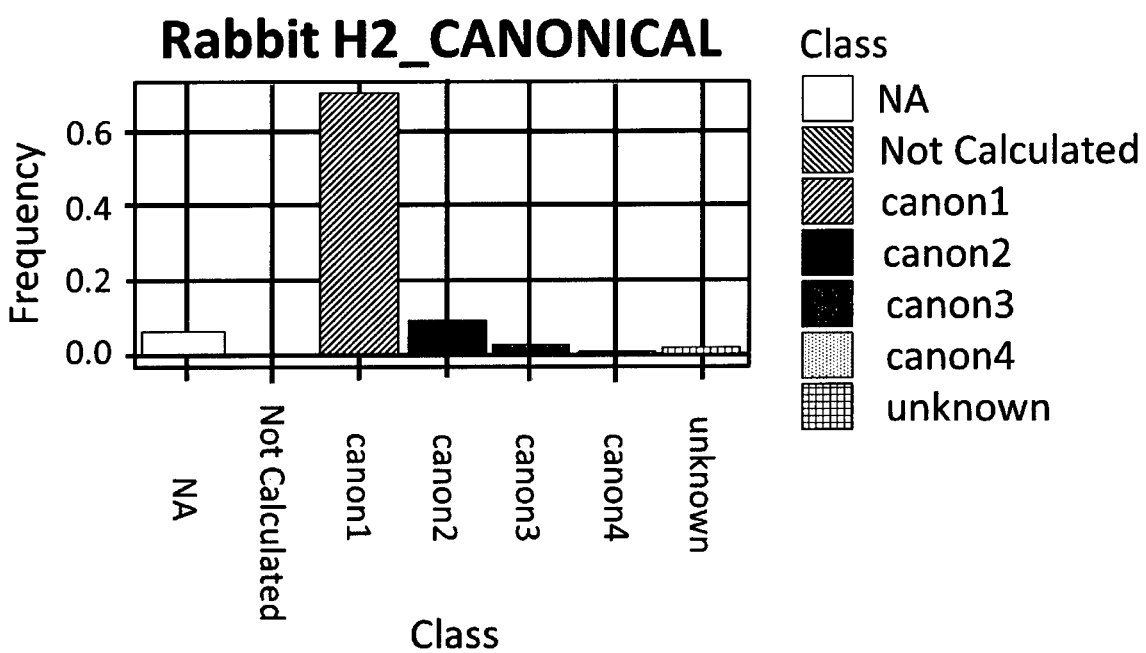

Figure 31 (continued)
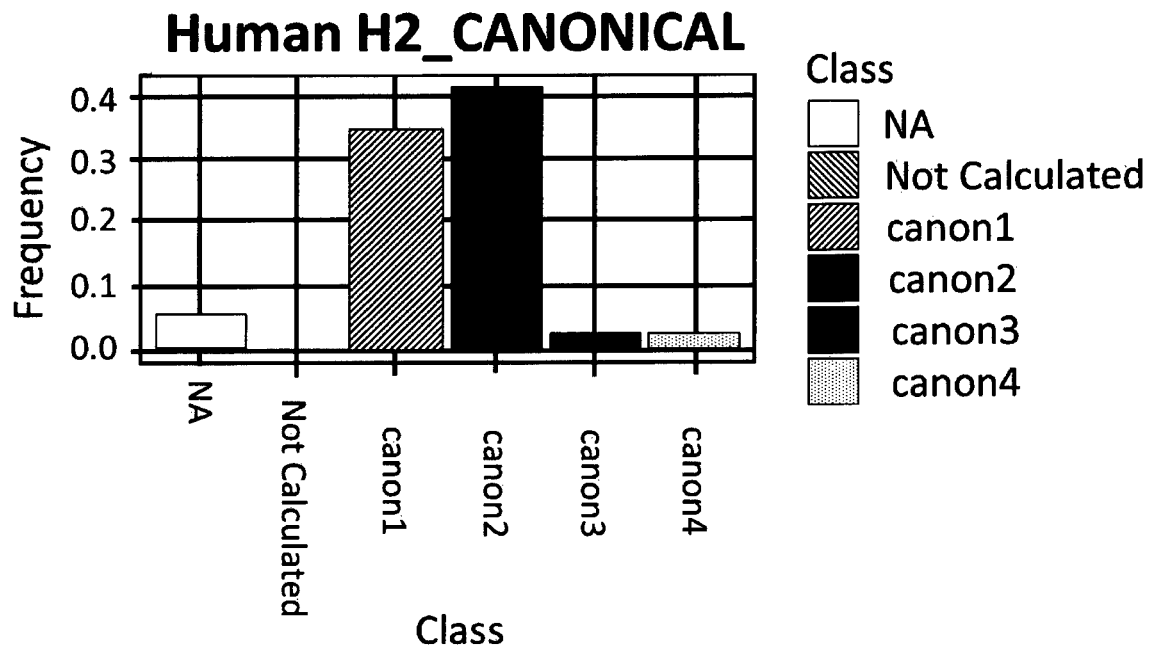
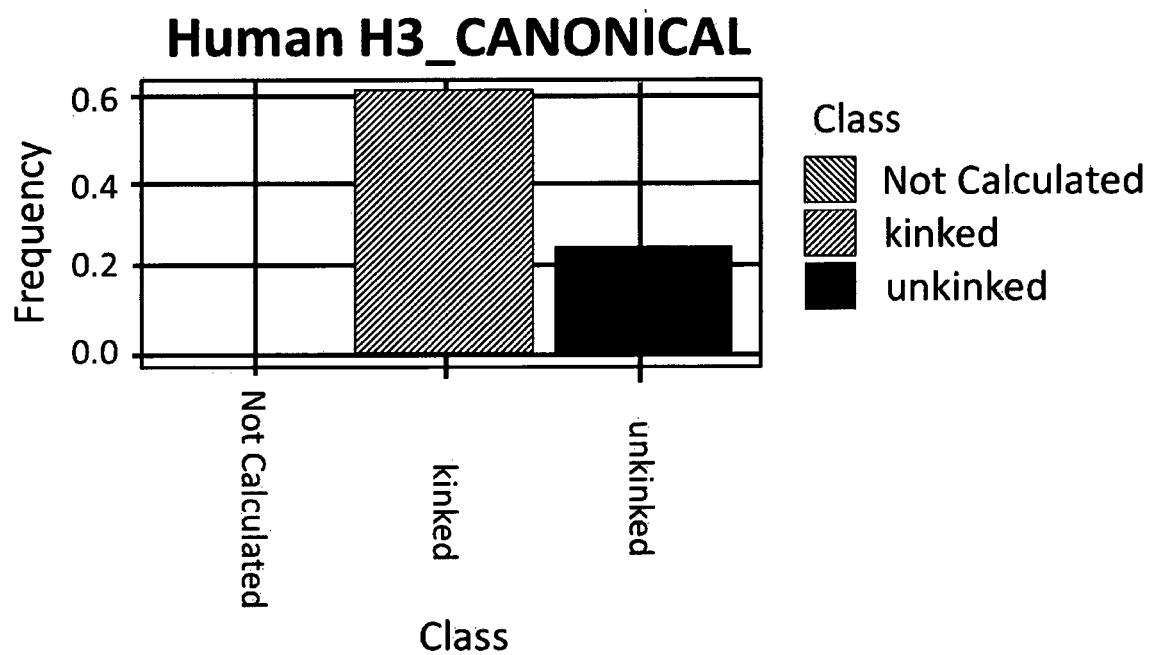

Figure 31 (continued)
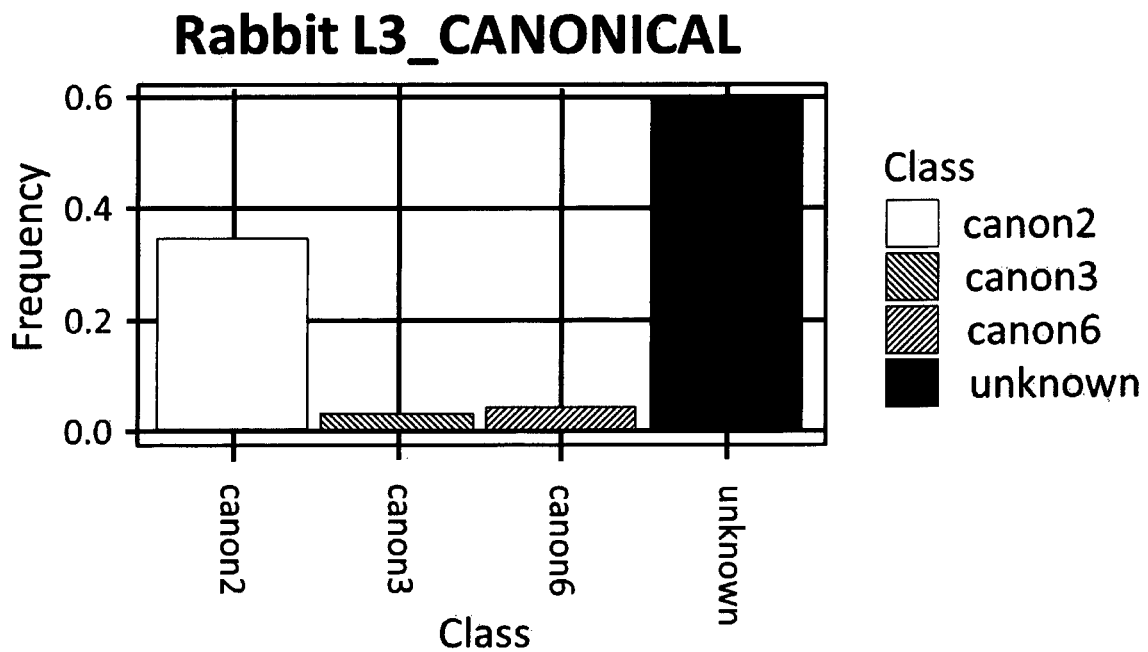
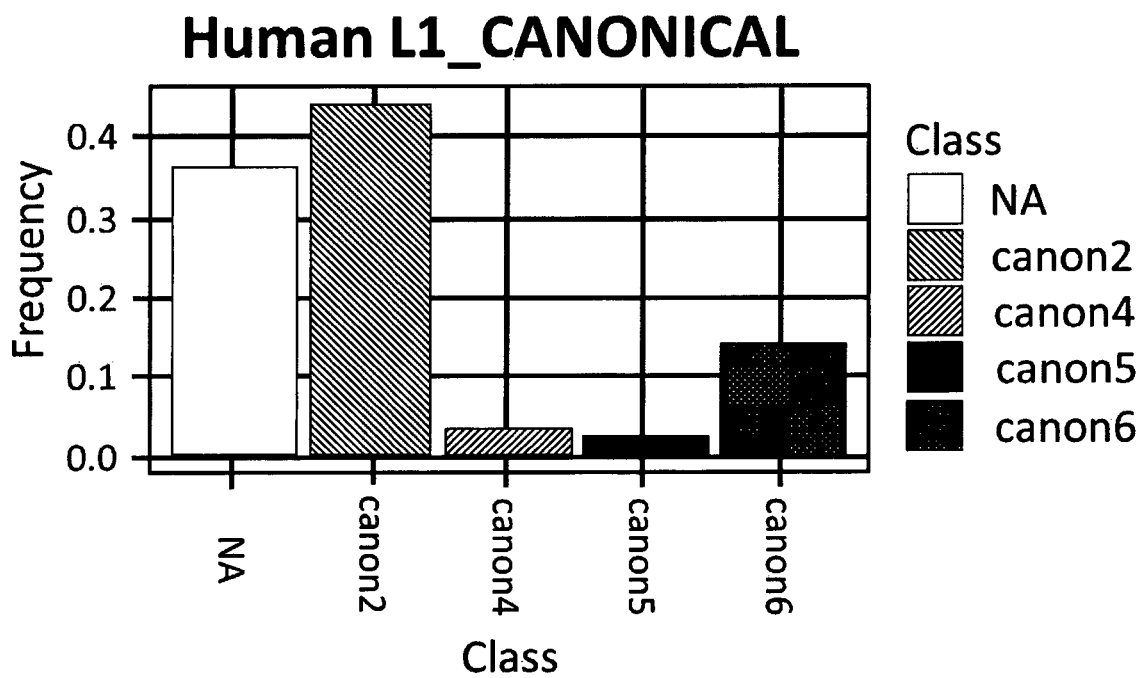

Figure 32 A)
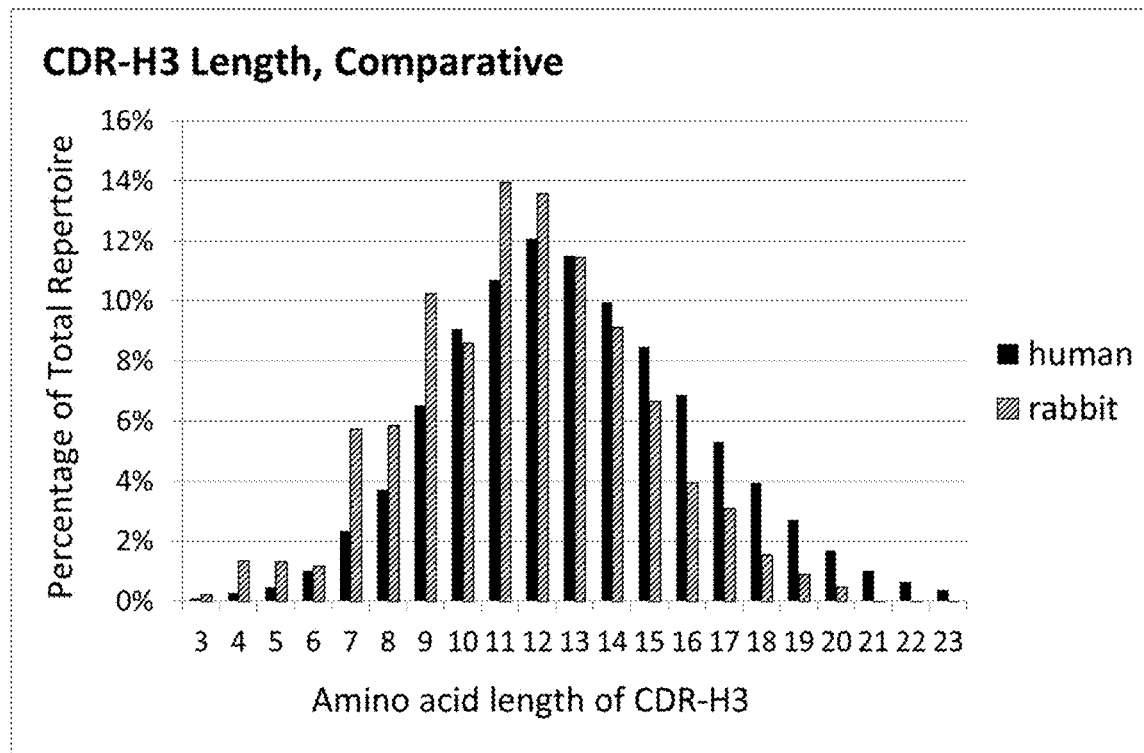
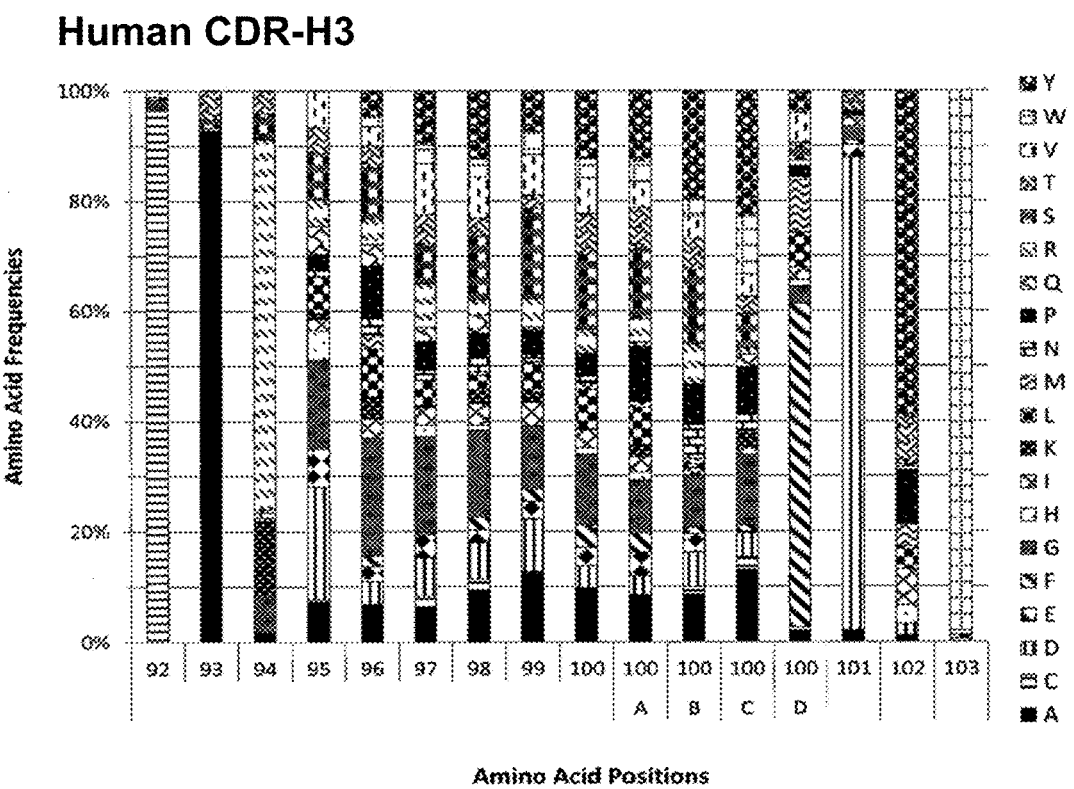

Figure 32 A) (continued)
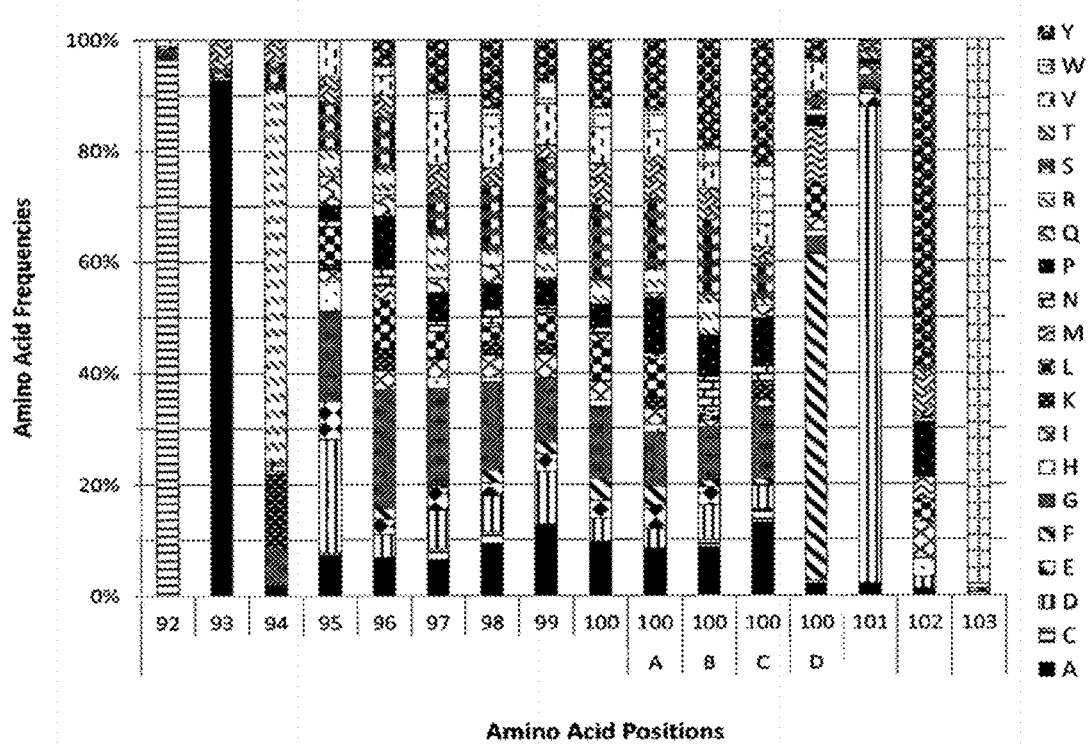

Figure 32 B)
CDR-H3 Length, Comparative
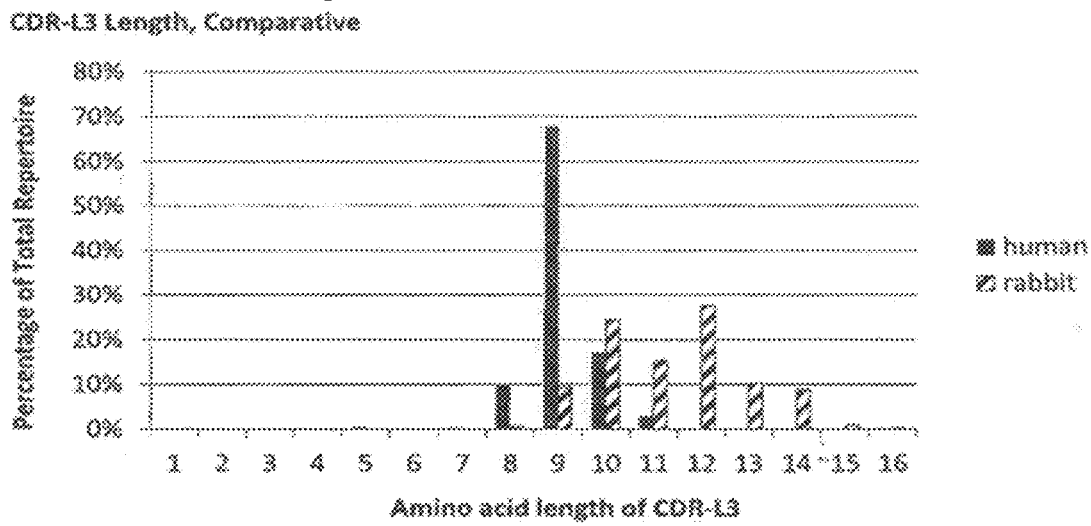
Human CDR-L3
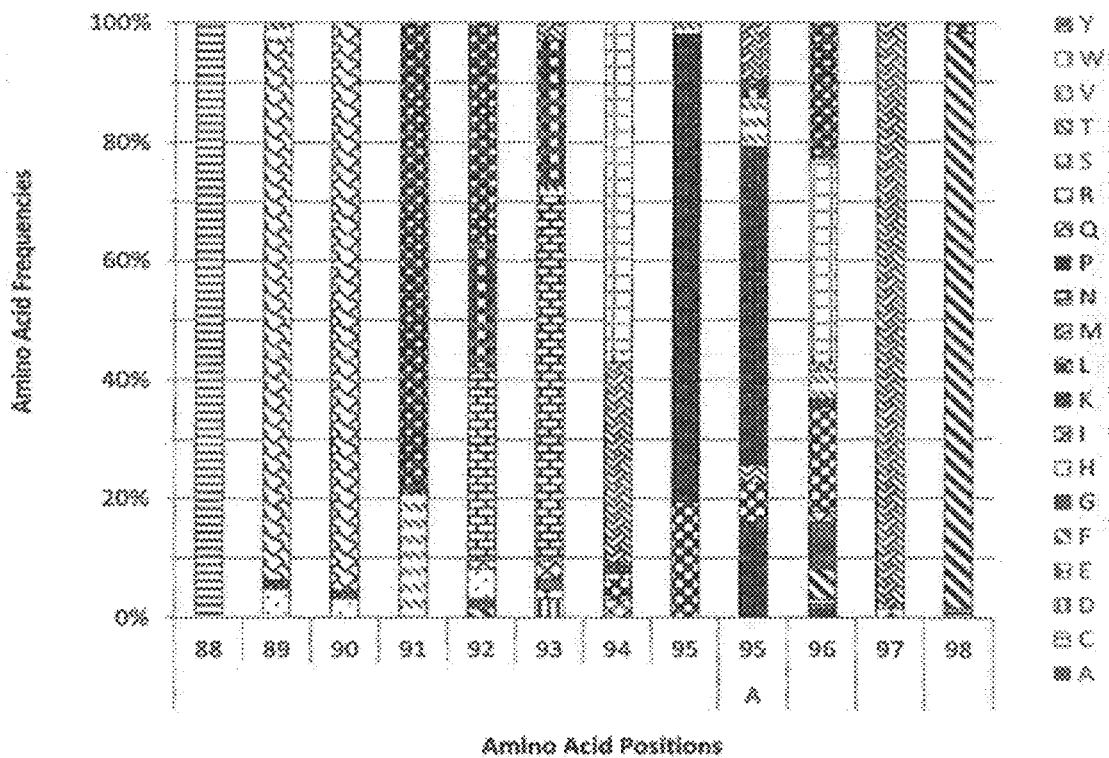

Figure 32 B) (continued)
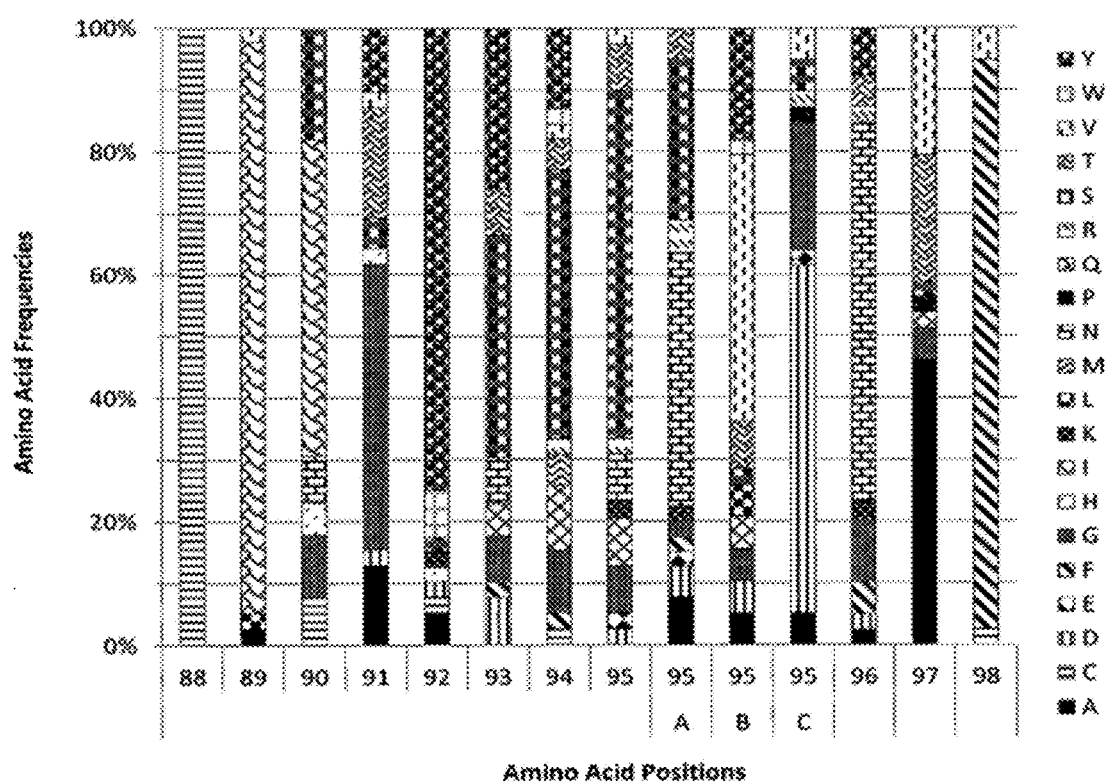

Figure 34
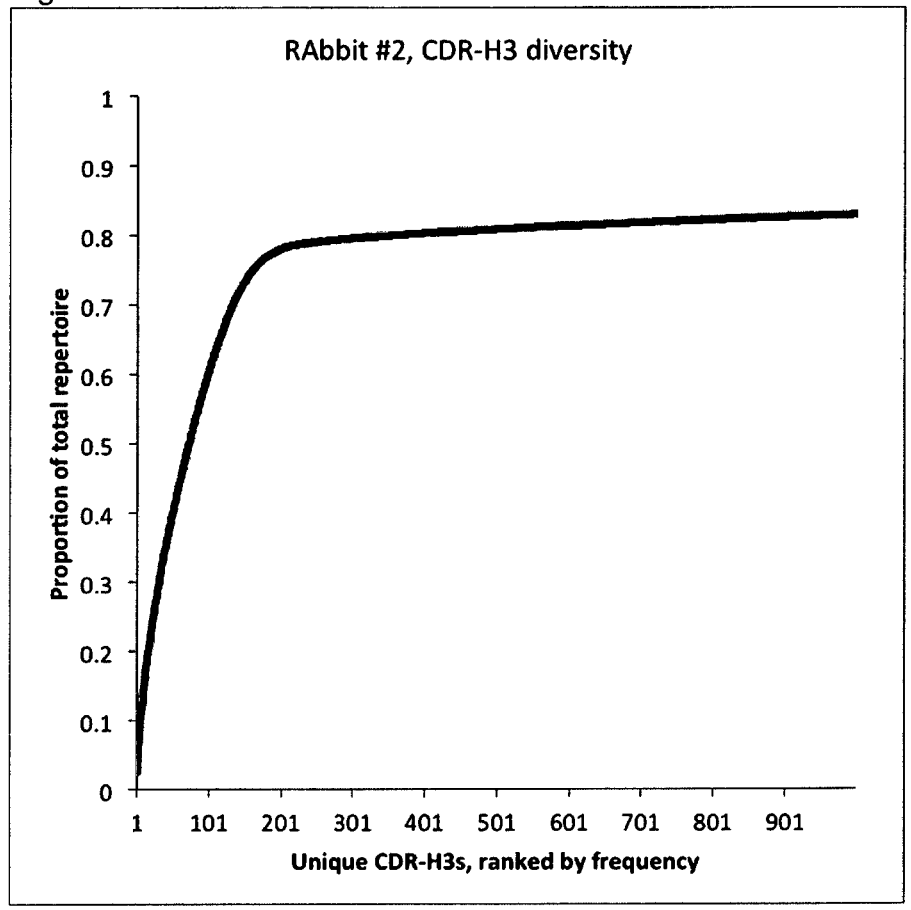
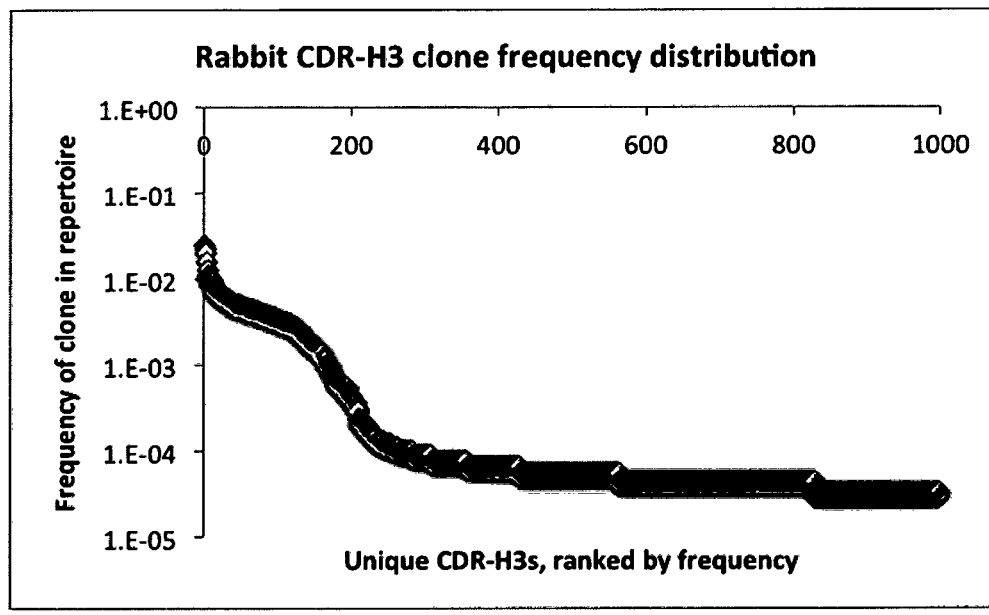

Figure 34 (continued)
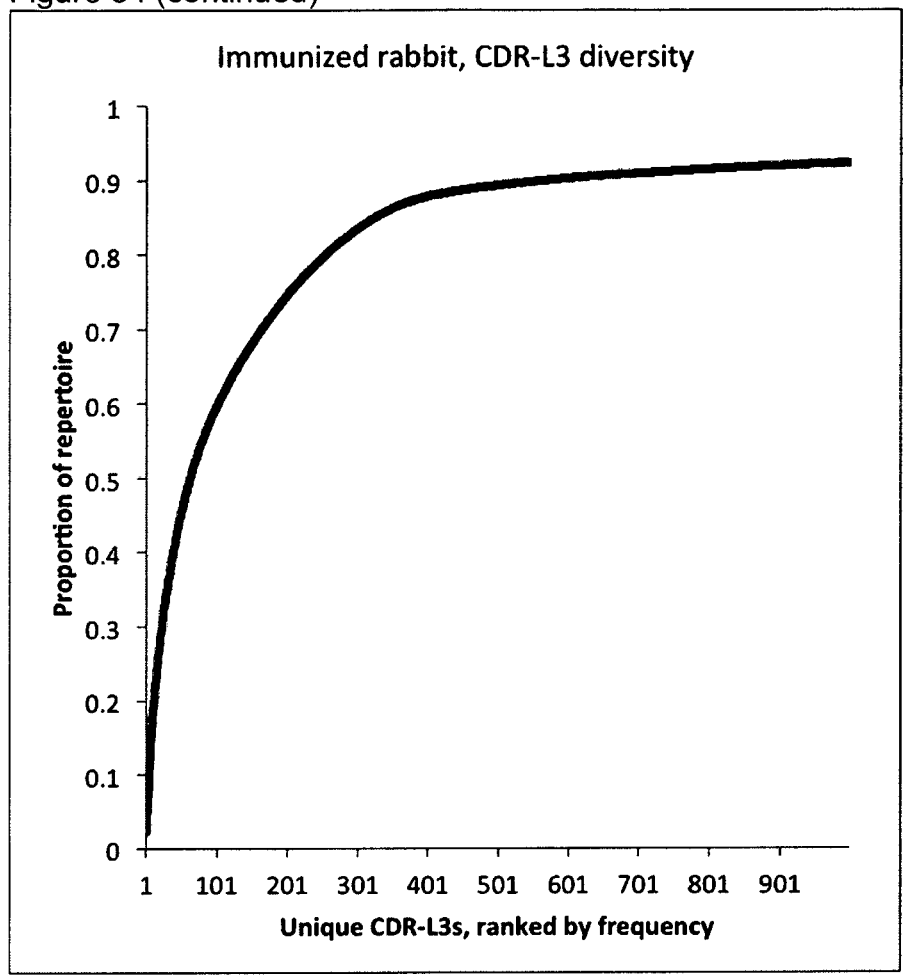
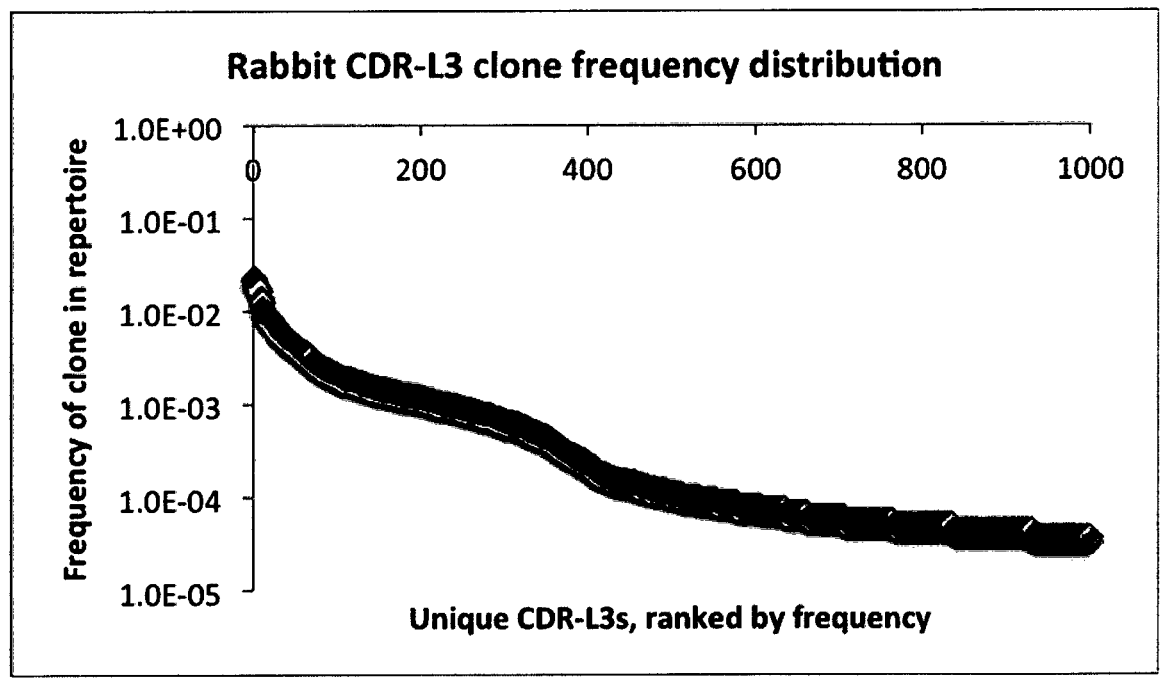

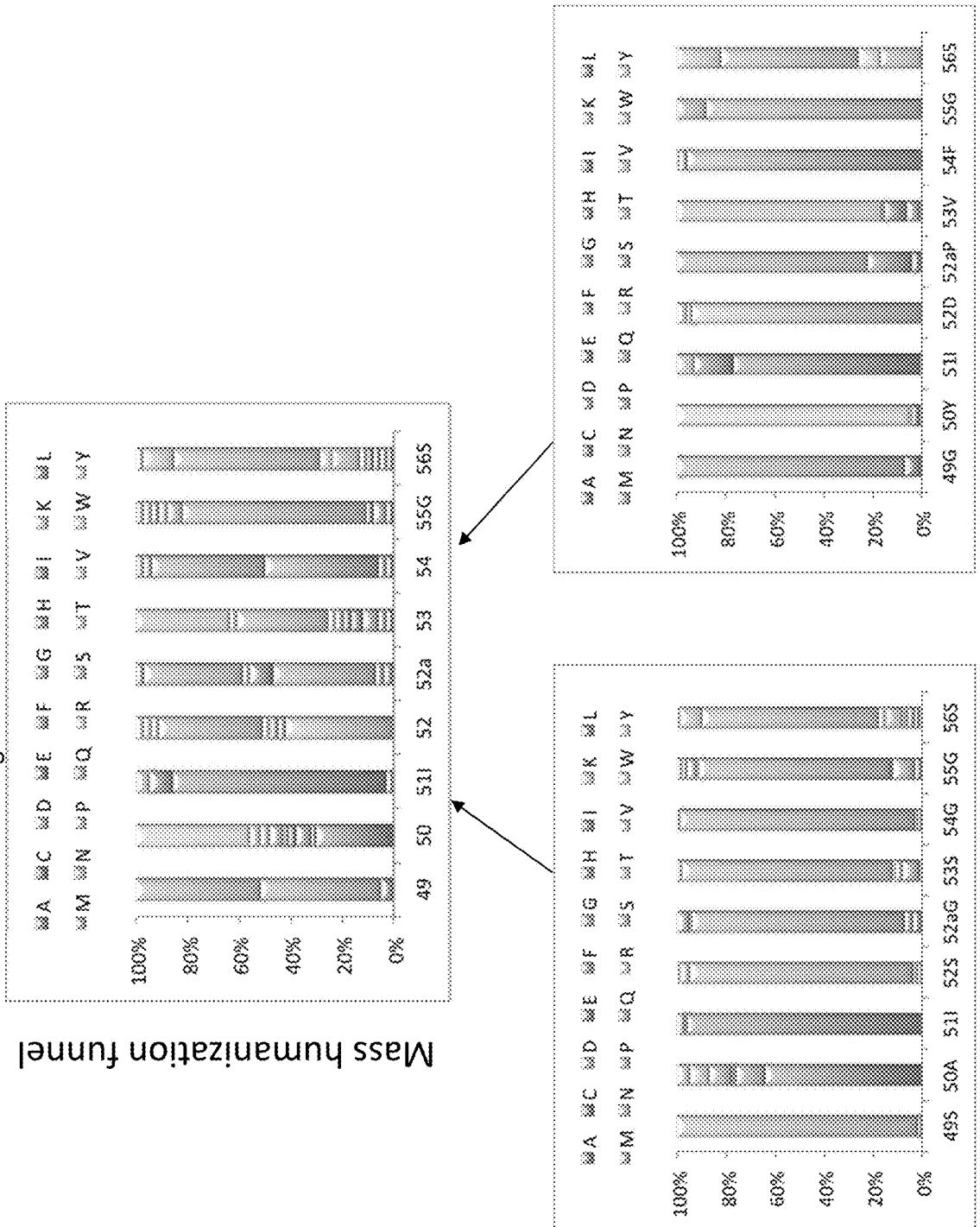

Figure 36 (SEQ ID Nos 102-123)
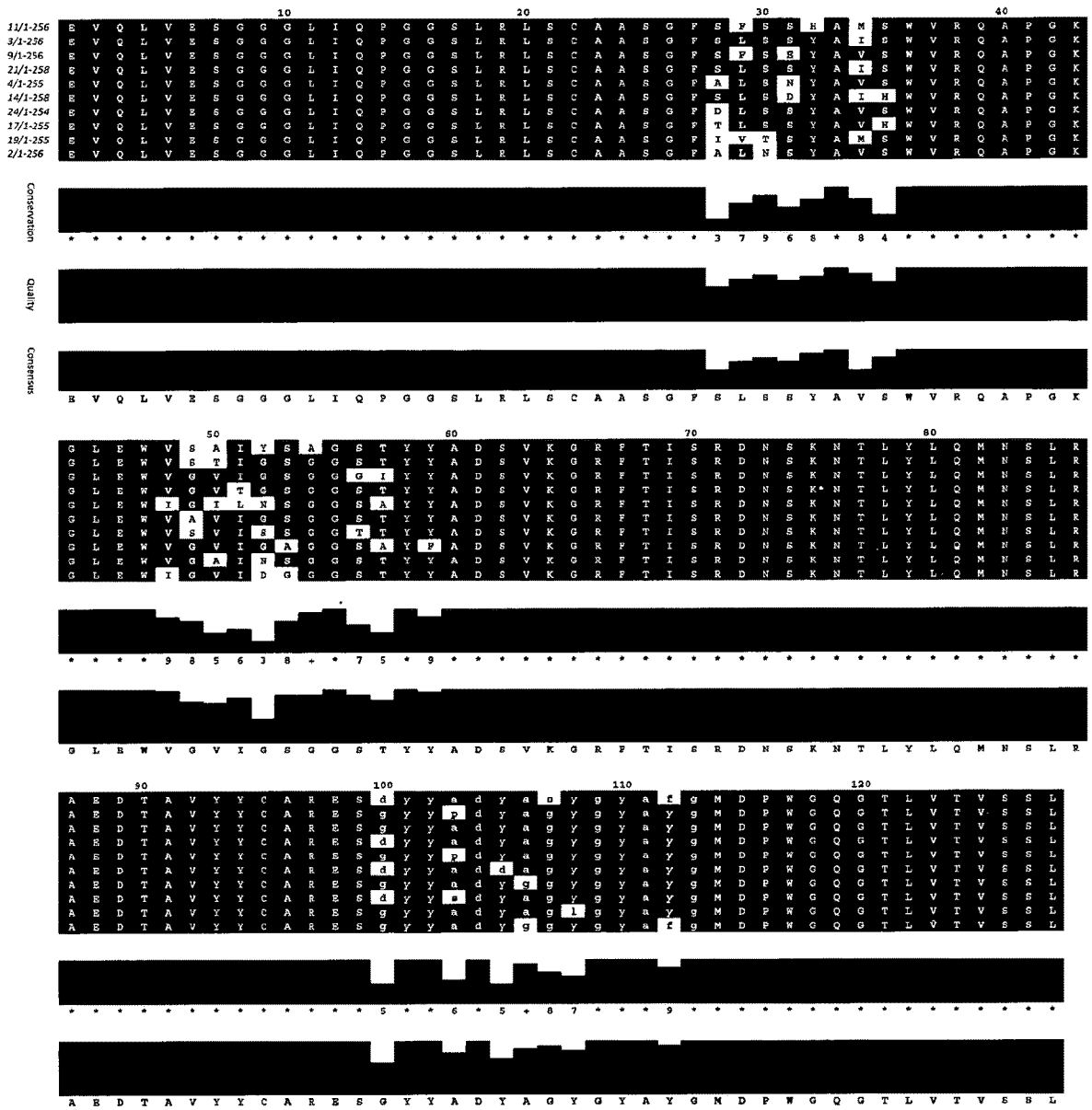

METHOD FOR MASS HUMANIZATION OF RABBIT ANTIBODIES

RELATED APPLICATIONS

This application is a 35 U.S.C. § 371 filing of International Patent Application No. PCT/EP2016/000701, filed Apr. 29, 2016, which claims priority to European Patent Application No. 15001304.3, filed Apr. 30, 2015. Each of the aforementioned applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 8, 2020, is named 597330_IBHW-002US_Updated_SL.txt and is 73,191 bytes in size.

The present invention relates to a method for producing a population of nucleic acids encoding at least one protein comprising at least one immunoglobulin variable domain having a rabbit-derived CDR3 amino acid sequence embedded in essentially human framework sequences, as well as to a population of nucleic acids and a population of proteins relates thereto and uses thereof.

Inseparably connected with the advent of antibodies for human therapy are strategies to generate sequences that are not recognized as foreign by the human immune system. Up to the present animals are used to induce the generation of target specific antibodies in vivo and even the largest and most advanced in vitro generated libraries of human antibodies have not fully replaced the B-cells of immunized animals as source of antibodies for therapeutic applications. The continuous use of animal-derived antibodies raised a vivid and persistent interest in humanization strategies to transform a non-human antibody into a safe drug for human therapy.

Jones et al. (Peter T. Jones, Paul H. Dear, Jefferson Foote, Michael S. Neuberger and Greg Winter, Nature 321: 522, 1986) published the humanization of a mouse antibody by CDR grafting nearly three decades ago. Riechmann et al. (Lutz Riechmann, Michael Clark, Herman Waldmann and Greg Winter, Nature 332: 323, 1988), used the method in 1988 to humanize Campath® (Alemtuzumab), the first humanized antibody applied for therapeutic use. Since that time, developing and refining methods to predict required mutations in framework regions and CDRs that are essential to retain affinity and binding specificity, are subject of numerous publications, pioneered by Carter et al. (Paul Carter, Len Presta, Cornelia M. Gorman, Joh B. B. Ridgway, Dennis Henner, Wai Lee T. Wong, Ann M. Rowland, Claire Kotts, Monique E. Carver and Michael Shepard, PNAS 89: 4285, 1992) who humanized Herceptin® (Trastuzumab).

Despite the tremendous gain of knowledge and improvement of antibody modeling software, CDR grafting is prone to turn into a lengthy procedure of trial and error, depending on sufficient structural information as well as on the experience and a lucky hand of the executing scientist.

Humanizations by guided selections (Jane Osbourn, Maria Groves and Tristan Vaughan, Methods 36: 61, 2005) follow a different route. Libraries with either the VH or the VL of a non-human antibody paired with a set of their respective human counterparts are generated and subjected to selections. The human variable domains of the identified chimeric intermediates are combined, or again paired with a set of human counterparts and subjected to selections. In contrast to the CDR grafting, all traces of the non-human origin of antibodies humanized by guided selections are eliminated and resulting antibodies are to be called human rather than humanized.

However, the method did not reach a similar level of awareness as the humanization via CDR grafting, lacking a comparable number of successful examples published in the literature.

A common drawback of CDR grafting and humanization by guided selections is their limitation to one or a few antibodies at a time. CDR grafting is a highly individual process considering the structure of the respective antibody-antigen complex. Although the general approach of humanizations by guided selections allows a higher capacity, the library size is not infinite and limits the number of input candidates.

This patent application describes a method that is applicable to all rabbit-derived antibodies and allows humanizations in high throughput and short time frames with reliable success rates.

In one embodiment, the present invention relates to a method for producing a population of nucleic acids encoding at least one protein comprising at least one immunoglobulin variable domain having a rabbit-derived CDR3 amino acid sequence embedded in essentially human framework sequences, wherein the method comprises the following steps:

(a) providing at least one nucleic acid encoding a rabbit-derived complementarity determining region 3 (CDR3) amino acid sequence or an amino acid sequence further encompassing 1, 2, or 3 amino acids N-terminal and/or C-terminal of the rabbit-derived CDR3 amino acid sequence, (b) generating a population of nucleic acids encoding at least one protein comprising at least one immunoglobulin variable domain having a rabbit CDR3 amino acid sequence of step (a) embedded in essentially human framework sequences, wherein the human framework sequences comprise a first human framework region (FR1), a second human framework region (FR2), a third human framework region (FR3), and a fourth human framework region (FR4), such that the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a rabbit-derived CDR3 amino acid sequence, wherein the nucleic acid sequences encoding the CDR1 and CDR2 amino acid sequences are diversified among the population of nucleic acids encoding at least one protein comprising at least one immunoglobulin variable domain, wherein each nucleic acid sequence encoding a CDR1 or CDR2 amino acid sequence is independently based i) on a nucleic acid sequence encoding a human CDR1 or CDR2, respectively, or ii) on a nucleic acid sequence encoding a rabbit CDR1 or CDR2, respectively, wherein at least some of the nucleic acid sequences encoding a CDR1 or CDR2 amino acid sequence have been modified to encode at least one amino acid present in rabbit CDR1 or CDR2 amino acid sequences, respectively, in case of human CDR1 or CDR2, respectively, or to encode at least one amino acid present in human CDR1 or CDR2 amino acid sequences, respectively, in case of rabbit CDR1 or CDR2, respectively, and wherein the human FR1, FR2, FR3 and FR4 regions are human framework regions selected to provide a scaffold conducive for rabbit CDR3 amino acid sequences, with the proviso:
that the two C-terminal amino acids of FR2 are optionally non-human, and
that the two C-terminal amino acids of FR3 are optionally non-human.

The present invention is in particular advantageous for mass humanization of rabbit antibodies, wherein a plurality of rabbit antibodies are to be humanized efficiently. Preferably, the plurality of rabbit antibodies are humanized in parallel and/or without determining the amino acid sequences of the rabbit antibodies to be humanized.

Accordingly, in a preferred embodiment, the present invention relates to a method for producing a population of 20 or more nucleic acids, each encoding at least one protein comprising at least one immunoglobulin variable domain having a rabbit-derived CDR3 amino acid sequence embedded in essentially human framework sequences, wherein the nucleic acid sequences encoding the rabbit-derived CDR3 amino acid sequences are diversified among the population of nucleic acids encoding at least one protein comprising at least one immunoglobulin variable domain, wherein the method comprises the following steps:

(a) providing at least 10 nucleic acids each encoding a rabbit-derived complementarity determining region 3 (CDR3) amino acid sequence or an amino acid sequence further encompassing 1, 2, or 3 amino acids N-terminal and/or C-terminal of the rabbit-derived CDR3 amino acid sequence, (b) generating a population of 20 or more nucleic acids, each encoding at least one protein comprising at least one immunoglobulin variable domain having a rabbit CDR3 amino acid sequence of step (a) embedded in essentially human framework sequences, wherein the human framework sequences comprise a first human framework region (FR1), a second human framework region (FR2), a third human framework region (FR3), and a fourth human framework region (FR4), such that the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a rabbit-derived CDR3 amino acid sequence, wherein the nucleic acid sequences encoding the CDR1 and CDR2 amino acid sequences are diversified among the population of nucleic acids encoding at least one protein comprising at least one immunoglobulin variable domain, wherein each nucleic acid sequence encoding a CDR1 or CDR2 amino acid sequence is independently based i) on a nucleic acid sequence encoding a human CDR1 or CDR2, respectively, or ii) on a nucleic acid sequence encoding a rabbit CDR1 or CDR2, respectively, wherein at least some of the nucleic acid sequences encoding a CDR1 or CDR2 amino acid sequence have been modified to encode at least one amino acid present in rabbit CDR1 or CDR2 amino acid sequences, respectively, in case of human CDR1 or CDR2, respectively, or to encode at least one amino acid present in human CDR1 or CDR2 amino acid sequences, respectively, in case of rabbit CDR1 or CDR2, respectively, and wherein the human FR1, FR2, FR3 and FR4 regions are human framework regions selected to provide a scaffold conducive for rabbit CDR3 amino acid sequences, and wherein the nucleic acid sequences encoding the rabbit-derived CDR3 amino acid sequences or the amino acid sequence further encompassing 1, 2, or 3 amino acids N-terminal and/or C-terminal of the rabbit-derived CDR3 amino acid sequence are diversified among the population of nucleic acids encoding at least one protein comprising at least one immunoglobulin variable domain, and wherein at least 10 of the nucleic acids of the population encode different CDR3 amino acid sequences, with the proviso:
that the two C-terminal amino acids of FR2 are optionally non-human, and
that the two C-terminal amino acids of FR3 are optionally non-human.

In one further preferred embodiment, at least 50% of the nucleic acids of the population encode different CDR3 amino acid sequences.

The methods and populations allow for efficient mass humanization of rabbit antibodies. The rabbit is a species which is in particular suitable for mass humanization of antibodies raised in a non-human mammal for several reasons:

Firstly, the majority of the rabbit repertoire can be mapped to two heavy chain frameworks and two light chain frameworks. By comparison, the human repertoire uses 50 heavy chain and 70 light chain frameworks, and the mouse repertoire uses over 100 heavy chain frameworks. Having only two frameworks greatly simplifies the "landscape of all possible humanizations", as it becomes possible to map all possible humanizations to two human V-gene heavy chain scaffolds and two V-gene light chain scaffolds. This reduces the cost and complexity of the library construction, and moreover, improves the chance of successful mass humanization.

As an example, a hypothetical non-human antibody that requires a specific heavy and light chain scaffold to successfully humanize is to be considered. If a skilled person had to try all human heavy chain and light chain scaffold combinations, only one out of every 3500 possible heavy and light combinations (50 VH*70 VL) would be capable of potentially accepting the graft. Consequently, 99.97% of the library would be useless. In contrast, with the rabbit where there are only 2 heavy chain scaffolds and 2 light chain scaffolds, one out of four combinations would be correct (2 VH*2 VL), allowing 25% of the library to be a potential successful graft space for every clone. When considering a mass humanization of ~1000 lineages after an immunization, only the latter can mathematically succeed.

Secondly, the rabbit produces high affinity antibodies using both a hyperdiverse CDR-H3 as well as a hyperdiverse CDR-L3. This is in contrast to mice and humans, where almost all of the diversity is driven by the CDR-H3. The rabbit thus has greater capacity to generate unique binders across a greater surface area of CDR3 loops. By effectively doubling the "specificity space" that is transferred by the method of the invention, this results in a higher probability of success during the mass humanization process.

Thirdly, the rabbit undergoes gene conversion as an affinity maturation strategy. This process introduces abrupt changes in the frameworks not unlike a humanization: affinity matured binders are those clones that both resemble the initial scaffold frameworks and can tolerate this process. Thus, gene conversion likely selects for clones that are CDR-H3/-L3 driven in their specificity and can accommodate affinity maturation replacement in the scaffold CDR-H1/-H2/-L1/-L2 regions, making them particularly well suited for humanization.

"A population of nucleic acids" is understood as 2 or more nucleic acids, preferably 2, 3, 4, 5, 6, 7, 8, 9, 10, 50, 100, 150, 200 or more nucleic acids, wherein at least 2 of the nucleic acids of the population exhibit different nucleic sequences, more preferably wherein at least 2, 3, 4, 5, 6, 7, 8, 9, 10, 50, 100, 150, 200 or more nucleic acids of the population exhibit different nucleic sequences, and/or wherein at least 50%, at least 80%, at least 90%, at least 95%, at least 96%, at least 97%, at least 98%, at least 99% or 100% of the nucleic acids of the population exhibit different nucleic sequences.

According to the method of the invention, an encoded protein comprises at least one immunoglobulin variable domain, preferably 1, 2, 3, 4 or more immunoglobulin variable domains, more preferably 1 or 2 immunoglobulin variable domains. For example, a variable heavy immunoglobulin domain may be paired with a variable light domain to provide an antigen binding site; such as in a scFv as described in the examples. Alternatively, independent regions, e.g., a variable heavy domain alone or a variable light domain alone may be used. An immunoglobulin variable domain comprises CDR1, CDR2 and CDR3 sequences. In particular, an immunoglobulin variable heavy domain comprises CDR-1H, CDR-2H and CDR-3H sequences, and an immunoglobulin variable light domain comprises CDR-1L, CDR-2L and CDR-3L sequences.

Accordingly, in one preferred embodiment, the proteins of the population each comprise one (1) immunoglobulin variable domain having a rabbit-derived CDR3 amino acid sequence embedded in essentially human framework sequences of the invention as described above. Preferably, the proteins comprising one immunoglobulin variable domain having a rabbit-derived CDR3 amino acid sequence embedded in essentially human framework sequences each comprise a VH domain, or a VL domain, or a heavy chain of an antibody or a fragment thereof comprising the VH domain, or a light chain of an antibody or a fragment thereof comprising the VL domain and/or is selected from a single domain antibody. In a more preferred embodiment, the population of proteins each comprising one immunoglobulin variable comprises at least one protein comprising a VH domain and comprises at least one protein comprising a VL domain. This allows for pairing within the population of proteins. Alternatively, the population may be paired with proteins of a separate population comprising a VH domain or VL domain respectively.

In another preferred embodiment, the proteins of the population each comprise 2, 3, 4 or more immunoglobulin variable domains having a rabbit-derived CDR3 amino acid sequence embedded in essentially human framework sequences of the invention as described above. In a more preferred embodiment, the proteins of the population each comprise 2 immunoglobulin variable domains having a rabbit-derived CDR3 amino acid sequence embedded in essentially human framework sequences of the invention as described above. It is preferred that the proteins of the population comprise a VH domain and a VL domain, or a heavy chain of an antibody or a fragment thereof comprising the VH domain, and a light chain of an antibody or a fragment thereof comprising the VL domain or an scFv, even more preferably an scFv. An scFv library of the invention is described in the Examples. In further more preferred embodiment, the encoded proteins or proteins of the inventions are selected from an immunoglobulin molecule, a disulfide linked Fv, a monoclonal antibody, an scFv, a diabody, a multispecific antibody, a Fab, a Fab', a bispecific antibody; a F(ab')2, an scFv or an Fv, more preferably an scFv. An scFv library of the invention is described in the Examples.

Further, in one preferred embodiment, the nucleic acids of the population encode proteins each comprising one immunoglobulin variable domain having a rabbit-derived CDR3 amino acid sequence embedded in essentially human framework sequences of the invention as described above. Preferably, the encoded proteins comprising one immunoglobulin variable domain having a rabbit-derived CDR3 amino acid sequence embedded in essentially human framework sequences each comprise a VH domain, or a VL domain, or a heavy chain of an antibody or a fragment thereof comprising the VH domain, or a light chain of an antibody or a fragment thereof comprising the VL domain and/or are selected from a single domain antibody. In a more preferred embodiment, the population of nucleic acids encoding proteins each comprising one immunoglobulin variable comprises at least one nucleic acid encoding a protein comprising a VH domain and comprises at least one nucleic acid encoding a protein comprising a VL domain. This allows for pairing within the population of proteins encoded by the nucleic acids of the population. Alternatively, the population encoding proteins comprising one VL domain or one VH domain only, may be paired with a separate population of nucleic acids encoding proteins comprising a VH domain or VL domain, respectively.

In another preferred embodiment, the nucleic acids of the population encode proteins each comprising 2, 3, 4 or more immunoglobulin variable domains having a rabbit-derived CDR3 amino acid sequence embedded in essentially human framework sequences of the invention as described above. In a more preferred embodiment, the nucleic acids of the population encode proteins, wherein each protein comprises 2 immunoglobulin variable domains having a rabbit-derived CDR3 amino acid sequence embedded in essentially human framework sequences of the invention as described above. It is preferred that the encoded to proteins of the population comprise a VH domain and a VL domain, or a heavy chain of an antibody or a fragment thereof comprising the VH domain, and a light chain of an antibody or a fragment thereof comprising the VL domain, or an scFv, even more preferably an scFv. An scFv library of the invention is described in the Examples.

In further more preferred embodiment, the encoded proteins or proteins of the subject-matter of the invention are selected from an immunoglobulin molecule, a disulfide linked Fv, a monoclonal antibody, an scFv, a diabody, a multispecific antibody, a Fab, a Fab', a bispecific antibody; a F(ab')2, an scFv or an Fv, more preferably an scFv. An scFv library of the invention is described in the Examples.

A "rabbit CDR3 amino acid sequence" is understood as an amino acid sequence which is identical to a CDR3 amino sequence naturally occurring in a rabbit antibody. CDR3 regions resulting after an immunization are also considered to be natural. The CDR3 amino sequence may be a CDR-3L or a CDR-3H amino acid sequence.

A "rabbit-derived CDR3 amino acid sequence" is understood as an amino acid sequence which is identical to a CDR3 amino sequence naturally occurring in a rabbit antibody, or which contains 1, 2, 3, 4, or 5 amino acid mutations compared to a CDR3 amino sequence naturally occurring in a rabbit antibody, preferably wherein the mutation is a conservative mutation.

Conservative amino acid substitutions, as one of ordinary skill in the art will appreciate, are substitutions that replace an amino acid residue with one imparting similar or better (for the intended purpose) functional and/or chemical characteristics. For example, conservative amino acid substitutions are often ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). The purpose for making a substitution is not significant and can include, but is by no means limited to, replacing a residue with one better able to maintain or enhance the structure of the molecule, the charge or hydrophobicity of the molecule, or the size of the molecule. For instance, one may desire simply to substitute a less desired residue with one of the same polarity or charge. Such modifications can be introduced by standard techniques known in the art, such as site-directed mutagenesis and PCR-mediated mutagenesis. In the context of the present invention, a "conservative amino acid substitution" is preferably defined by a substitution within a class of amino acids reflected in the following table:

| Amino acid residue classes for conservative substitutions | Amino acids |
|---|---|
| Acidic residues (i.e. residues with acidic side chain) | Asp, Glu |
| Basic residues (i.e. residues with basic side chain) | Lys, Arg, His |
| Polar uncharged residues (i.e. residues with uncharged polar side chain) | glycine, asparagine, glutamine, serine, threonine, tyrosine, cysteine, tryptophan |
| Nonpolar Uncharged residues (i.e. residues with uncharged nonpolar side chain) | alanine, valine, leucine, isoleucine, proline, phenylalanine, methionine |
| Beta-branched residues (i.e. side chains with beta-branched side chain) | threonine, valine, isoleucine |
| Aromatic residues (i.e. residues with aromatic side chains) | tyrosine, phenylalanine, tryptophan |

Nucleic acid molecules of the present invention may be in the form of RNA, such as mRNA or cRNA, or in the form of DNA, including, for instance, cDNA and genomic DNA e.g. obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand. Nucleic acid molecule as used herein also refers to, among other, single- and double-stranded DNA, DNA that is a mixture of single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, nucleic acid molecule as used herein refers to triple-stranded regions comprising RNA or DNA or both RNA and DNA.

The nucleic acids may be originally formed in vitro or in a cell in culture, in general, by the manipulation of nucleic acids by endonucleases and/or exonucleases and/or polymerases and/or ligases and/or recombinases or other methods known to the skilled practitioner to produce the nucleic acids.

The term "embedded in essentially human framework sequences" is understood as that the CDR3-derived sequence is located within the framework sequences to yield an immunoglobulin variable domain. For example, a skilled person is aware that a CDR-3L amino acid sequence is located between FR3 and FR4 framework regions of the light chain in case of an immunoglobulin light chain variable domain.

"Human framework sequences" are understood as framework sequences which are naturally occurring human framework sequences. The nucleic acids encoding the human framework sequences may contain silent mutations as compared to the naturally occurring nucleic acids encoding the human framework sequences and/or sequences that are a result of the degeneration of the genetic code. There are 20 natural amino acids, most of which are specified by more than one codon. Therefore, all nucleotide sequences are included which result in the human framework sequences as defined above.

An "essentially human framework sequence" is understood as a framework sequence which exhibits at least 90%, preferably at least 95%, 96%, 97%, 98%, or 99% sequence identity to a naturally occurring human framework sequence. In a preferred embodiment, the essentially human framework sequence consists of FR1, FR2, FR3 and FR4 regions, which are human FR1, FR2, FR3 and FR4 regions, with the proviso that the two C-terminal amino acids of FR2 are optionally non-human, and that the two C-terminal amino acids of FR3 are optionally non-human, more preferably, the two C-terminal amino acids of heavy FR2 are optionally non-human, and that the two C-terminal amino acids of heavy FR3 are optionally non-human. In an even more preferred embodiment, the non-human amino acids of FR2 and/or FR3 are rabbit FR2 and/or FR3 amino acids of the corresponding positions.

The percentage of sequence identity can be determined e.g. by sequence alignment. Methods of alignment of sequences for comparison are well known in the art. Various programs and alignment algorithms have been described e.g. in Smith and Waterman, Adv. Appl. Math. 2: 482, 1981 or Pearson and Lipman, Proc. Natl. Acad. Sci. U.S.A. 85: 2444, 1988.

The NCBI Basic Local Alignment Search Tool (BLAST) (Altschul et al., J. Mol. Biol. 215: 403-410, 1990) is available from several sources, including the National Center for Biotechnology Information (NCBI, Bethesda, Md.) and on the Internet, for use in connection with the sequence analysis programs blastp, blastn, blastx, tblastn and tblastx. Amino acid sequences are typically characterized using the NCBI Blast 2.0, gapped blastp set to default parameters. For comparisons of amino acid sequences of at least 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment is performed using the Blast 2 sequences function, employing the PAM30 matrix set t default parameters (open gap 9, extension gap 1 penalties). Methods for determining sequence identity over such short windows such as 15 amino acids or less are described at the website that is maintained by the National Center for Biotechnology Information in Bethesda, Md.

The percentage of sequence homology can be determined by counting the positions with identical amino acids plus the positions with conservative amino acid substitutions from an alignment produced with the method described above.

"An amino acid sequence further encompassing 1, 2, or 3 amino acids N-terminal and/or C-terminal of the rabbit-derived CDR3 amino acid sequence" is understood as that the rabbit-derived CDR3 amino acid sequence, preferably the rabbit-CDR3 amino acid sequence further comprises 1, 2, or 3 amino acids N-terminal of the rabbit-derived CDR3 amino acid sequence, and/or 1, 2, or 3 amino acids C-terminal of the rabbit-derived CDR3 amino acid sequence. In a preferred embodiment, the rabbit-derived CDR3 amino acid sequence further encompassing 1, 2, or 3 amino acids N-terminal and/or C-terminal of the rabbit-derived CDR3 amino acid sequence is a rabbit-derived amino acid sequence comprising a rabbit-derived CDR3 amino acid sequence or rabbit CDR3 amino acid sequence, more preferably a rabbit amino acid sequence comprising a rabbit CDR3 amino acid sequence.

A "rabbit-derived amino acid sequence" is understood as an amino acid sequence which is identical to a amino sequence naturally according in a rabbit antibody, or which contains 1, 2, 3, 4, or 5 amino acid mutations compared to an amino sequence naturally occurring in a rabbit antibody, preferably wherein the mutation is a conservative mutation.

In a preferred embodiment, the rabbit specificity determining region (SDR) of an antibody encompassing a CDR3 region, more preferably of a CDR-3H region is provided. According to the invention, an SDR of a rabbit CDR-3H encompasses 2 amino acids N-terminal to the rabbit CDR-3H region, and optionally 1 amino acid C-terminal to the rabbit CDR-3H region (underlined):

(SEQ ID NO: 124)

wherein
$Y_1$ is a naturally occurring amino acid, preferably $Y_1$ is A,
$Y_2$ is a naturally occurring amino acid, preferably $Y_2$ is R.
$X_n$ represents a CDR3-H sequence. Accordingly, n is an integer between 1 and 50, preferably between 3 and 25 amino acids, more preferably between 5 and 21, and each X independently represents a naturally occurring amino acid.

The sequence "AR" is most common at the positions $Y_1Y_2$ both in rabbit antibodies and human antibodies. Accordingly, it is preferred that $Y_1$ is A and/or $Y_2$ is R. However, also other amino acids may be independently present at the indicated positions.

The position directly C-terminal to CDR3-H is always "W" both in humans and rabbits. Accordingly, this position is preferably not varied.

The position directly N-terminal to $Y_1Y_2$ is always "C" both in humans and rabbits.

According to the method of the invention, at least one nucleic acid encoding a rabbit-derived complementarity determining region 3 (CDR3) amino acid sequence or an amino acid sequence further encompassing 1, 2, or 3 amino acids N-terminal and/or C-terminal of the rabbit-derived CDR3 amino acid sequence is provided.

According to a preferred embodiment of a method of the invention, at least one nucleic acid encoding a rabbit-derived complementarity determining region 3 (CDR3) amino acid sequence or an amino acid sequence further encompassing 1 or 2, in particular 2 amino acids N-terminal of the rabbit-derived CDR3 amino acid sequence and optionally 1 amino acid C-terminal to the rabbit CDR-3H region is provided, more preferably wherein the rabbit-derived CDR3 amino acid sequence is a the rabbit-derived CDR-3H amino acid sequence, even more preferably a rabbit CDR-3H amino acid sequence. Therefore, in one particularly preferred embodiment, at least one nucleic acid encoding an SDR of a rabbit CDR-3H is provided, in particular wherein the SDR encompasses 2 amino acids N-terminal to the rabbit CDR-3H region.

In a further preferred embodiment, 1, 2, 3, 4, 5, 6, 7, 8, 9, 10, 15, 20, 30, 40, 50, 60, 70, 80, 90, 100, $10^3$, $10^4$, $10^5$ or more nucleic acids as defined above are provided. In general, the methods and populations of the invention are suitable for mass hybridization of rabbit antibodies, and for providing a mass humanized library suitable for this purpose. Therefore, it is preferred that more than one, preferably 2, 3, 4, 5, 6, 7, 8, 9, 10, 15, 20, 30, 40, 50, 60, 70, 80, 90, 100, $10^3$, $10^4$, $10^5$ or more nucleic acids as defined above are provided. Preferably, 1, 2, 3, 4, 5, 6, 7, 8, 9, 10, 15, 20, 30, 40, 50, 60, 70, 80, 90, 100, $10^3$, $10^4$, $10^5$ or more different nucleic acids as defined above are provided.

For efficient mass hybridization, it is preferred that the same method is used for transferring the rabbit or rabbit-derived CDR3 regions into an Acceptor Framework of the invention, to obtain the population of nucleic acids of step (b) of the invention, which preferably represents nucleic acids encoding a humanized library for rabbit antibodies. Therefore, it is preferred to provide either always CDR3 regions of the rabbit antibodies, or always a CDR3 region which further encompasses 1, 2, or 3 amino acids N-terminal and/or C-terminal of the rabbit-derived CDR3 amino acid sequence.

Therefore, in a further preferred embodiment, more than one, preferably 2, 3, 4, 5, 6, 7, 8, 9, 10, 15, 20, 30, 40, 50, 60, 70, 80, 90, 100, $10^3$, $10^4$, $10^5$ or more nucleic acids as defined above are provided, wherein the each nucleic acid encodes a rabbit-derived complementarity determining region 3 (CDR3) amino acid sequence, preferably a rabbit complementarity determining region 3 (CDR3) amino acid sequence. Therefore, in a further preferred embodiment, preferably 2, 3, 4, 5, 6, 7, 8, 9, 10, 15, 20, 30, 40, 50, 60, 70, 80, 90, 100, $10^3$, $10^4$, $10^5$ or more different nucleic acids as defined above are provided, wherein the each nucleic acid encodes a rabbit-derived complementarity determining region 3 (CDR3) amino acid sequence, preferably a rabbit complementarity determining region 3 (CDR3) amino acid sequence.

In a yet further preferred embodiment, more than one, preferably 2, 3, 4, 5, 6, 7, 8, 9, 10, 15, 20, 30, 40, 50, 60, 70, 80, 90, 100, $10^3$, $10^4$, $10^5$ or more nucleic acids as defined above are provided, wherein the each nucleic acid encodes a rabbit-derived complementarity determining region 3 (CDR3) amino acid sequence, preferably a rabbit complementarity determining region 3 (CDR3) amino acid sequence, which further encompasses 1, 2, or 3 amino acids N-terminal and/or C-terminal of the rabbit-derived CDR3 amino acid sequence, more preferably wherein the rabbit complementarity determining region 3 (CDR3) amino acid sequence further encompasses 1 or 2, in particular 2 amino acids N-terminal of the rabbit-derived CDR3 amino acid sequence, even more preferably wherein the rabbit-derived CDR3 amino acid sequence is a the rabbit-derived CDR-3H amino acid sequence, even more preferably a rabbit CDR-3H amino acid sequence.

In a yet further preferred embodiment, 20, 30, 40, 50, 60, 70, 80, 90, 100, $10^3$, $10^4$, $10^5$ or more nucleic acids as defined above are provided, wherein the each nucleic acid encodes a rabbit-derived complementarity determining region 3 (CDR3) amino acid sequence, preferably a rabbit complementarity determining region 3 (CDR3) amino acid sequence, which further encompasses 1, 2, or 3 amino acids N-terminal and/or C-terminal of the rabbit-derived CDR3 amino acid sequence, more preferably wherein the rabbit complementarity determining region 3 (CDR3) amino acid sequence further encompasses 1 or 2, in particular 2 amino acids N-terminal of the rabbit-derived CDR3 amino acid sequence, even more preferably wherein the rabbit-derived CDR3 amino acid sequence is a the rabbit-derived CDR-3H amino acid sequence, even more preferably a rabbit CDR-3H amino acid sequence. In a yet further preferred embodiment, 20, 30, 40, 50, 60, 70, 80, 90, 100, $10^3$, $10^4$, $10^5$ or more different nucleic acids as defined above are provided, wherein the each nucleic acid encodes a rabbit-derived complementarity determining region 3 (CDR3) amino acid sequence, preferably a rabbit complementarity determining region 3 (CDR3) amino acid sequence, which further encompasses 1, 2, or 3 amino acids N-terminal and/or C-terminal of the rabbit-derived CDR3 amino acid sequence, more preferably wherein the rabbit complementarity determining region 3 (CDR3) amino acid sequence further encompasses 1 or 2, in particular 2 amino acids N-terminal of the rabbit-derived CDR3 amino acid sequence, even more preferably wherein the rabbit-derived CDR3 amino acid sequence is a the rabbit-derived CDR-3H amino acid sequence, even more preferably a rabbit CDR-3H amino acid sequence.

"interspaced by" in the context of the methods of the invention is understood that two amino acid sequences are connected via the interspacing amino acid sequence, preferably by peptide linkages. For example, a protein comprising the structure FR1-CDR1-FR2 is understood as that FR1 and FR2 regions are interspaced by a CDR1.

"CDR1 and CDR2 amino acid sequences are diversified among the population" is understood as that at least 2 of the nucleic acids of the population exhibit different CDR1 nucleic sequences, in particular different CDR-1H and/or CDR-1L sequences, and/or at least 2 of the nucleic acids of the population exhibit different CDR2 nucleic sequences, in particular different CDR-2H and/or CDR-2L sequences, more preferably wherein at least 2, 3, 4, 5, 6, 7, 8, 9, 10, 50, 100, 150, 200 or more nucleic acids of the population exhibit different CDR1 and/or CDR2 nucleic sequences, and/or wherein at least 50%, at least 80%, at least 90%, at least 95%, at least 96%, at least 97%, at least 98%, at least 99% or 100% of the nucleic acids of the population exhibit different CDR1 and/or CDR2 nucleic sequences.

In an even more preferred embodiment, at least 50%, at least 80%, at least 90% or at least 95% of the nucleic acids of the population do not comprise a sequence encoding a human CDR1 sequence and/or a human CDR2 sequence, in particular a human CDR1 sequence and a human CDR2 sequence.

In a further even more preferred embodiment, at least 50%, at least 80%, at least 90%, at least 95%, at least 96%, at least 97%, at least 98%, at least 99% or 100% of the nucleic acids of the population do not comprise a sequence encoding a rabbit CDR1 sequence and/or a rabbit CDR2 sequence, in particular a rabbit CDR1 sequence and a rabbit CDR2 sequence.

According to the method of the invention, each nucleic acid sequence encoding a CDR1 or CDR2 amino acid sequence is independently based i) on a nucleic acid sequence encoding a human CDR1 or CDR2, respectively, or ii) on a nucleic acid sequence encoding a rabbit CDR1 or CDR2, respectively. "Based on" is understood as that, in case of a CDR1 sequence, the CDR1 amino acid sequence contains at least 3, 4, 5, 6, 7, 8, 9 or more, for example all, amino acids of a human CDR1 (in case of i) or of a rabbit CDR1 (in case of ii) respectively, and/or exhibits at least 30%, at least 50%, at least 80%, at least 90%, at least 95%, or 100% sequences identity to a human CDR1 (in case of i) or to a rabbit CDR1 (in case of ii), respectively.

In one preferred embodiment of the present invention, at least 5 nucleic acids of a population of nucleic acids of the present invention exhibit different CDR1 and/or CDR2 nucleic sequences, more preferably at least 6, 7, 8, 9, 10, 50, 100, 150, 200 or more nucleic acids of the population exhibit different CDR1 and/or CDR2 nucleic sequences.

In a further preferred embodiment of the present invention, at least 80% of the nucleic acids of a population of the present invention exhibit different CDR1 and/or CDR2 nucleic sequences, more preferably at least 90%, at least 95%, at least 96%, at least 97%, at least 98%, at least 99% or 100% of the nucleic acids of the population exhibit different CDR1 and/or CDR2 nucleic sequences.

In a further preferred embodiment of the present invention, the nucleic acid sequences encoding the CDR1 and CDR2 amino acid sequences are diversified among each set of framework regions. Such diversification among each set of framework regions is for example described in the Examples. For example, the nucleic acid sequences encoding the CDR1 and CDR2 amino acid sequences are diversified among the set of the human VH3-23 framework regions, and/or the set of the human VH3-53 framework regions, and/or the set of the human Vk1-27 framework regions, and/or the set of the Vk3-20 framework regions. For example, in case the population comprises different nucleic acids each encoding human VH3-23 framework regions, the nucleic acid sequences encoding the CDR1 and CDR2 amino acid sequences are diversified among the different nucleic acids.

The resulting population or library thus is a novel entity with surprisingly beneficial properties, that is neither rabbit nor human, but a hybrid repertoire exploring the space between. In particular, the hybrid repertoire exploring the space between rabbit and human is established within the CDR1 and CDR2 regions, whereas the framework regions are human, optionally with the proviso that the two C-terminal amino acids of FR2 are optionally non-human, and that the two C-terminal amino acids of FR3 are optionally non-human.

In a preferred embodiment, 1, 2, 3, or 4, or more different sets of framework regions comprising a first human framework region (FR1), a second human framework region (FR2), a third human framework region (FR3), and a fourth human framework region (FR4) are present in the VH domains, and/or 1, 2, 3, or 4 or more different sets of framework regions comprising a first human framework region (FR1), a second human framework region (FR2), a third human framework region (FR3), and a fourth human framework region (FR4) are present in the VL domains.

Accordingly, in a preferred embodiment, at least some of the nucleic acid sequences encoding a CDR1 or CDR2 amino acid sequence have been modified to encode at least one, preferably 1, 2, 3, 4, 5 or more amino acid present in rabbit CDR1 or CDR2 amino acid sequences, respectively, in case of human CDR1 or CDR2, respectively, or to encode at least one, preferably 1, 2, 3, 4, 5 or more amino acid present in human CDR1 or CDR2 amino acid sequences, respectively, in case of rabbit CDR1 or CDR2, respectively.

In a preferred embodiment, at least 50%, more preferably at least 80%, at least 90%, at least 95%, at least 96%, at least 97%, at least 98%, at least 99% or 100% of the nucleic acid sequences encoding a CDR1 or CDR2 amino acid sequence have been modified to encode at least one amino acid present in rabbit CDR1 or CDR2 amino acid sequences, respectively, in case of human CDR1 or CDR2, respectively, or to encode at least one amino acid present in human CDR1 or CDR2 amino acid sequences, respectively, in case of rabbit CDR1 or CDR2, respectively.

It is preferred that the nucleic acid sequences encoding a CDR1 or CDR2 amino acid sequence are not modified to encode all amino acid present in rabbit CDR1 or CDR2 amino acid sequences, respectively, in case of a human CDR1 or CDR2 amino acid sequence, respectively.

It is understood that the sequence comparisons apply to the respective CDR1 regions; e.g. a CDR-1H region based on a human CDR-1H is compared to human CDR-1H regions.

A "scaffold conducive for rabbit CDR3 amino acid sequences" is understood as an immunoglobulin scaffold which is suitable for a successful graft of a rabbit CDR3 amino acid sequence to yield a correctly folded antibody for at least 30%, at least 50%, or at least 60%, 70% or 80% of grafted rabbit CDR3 amino acid sequences, and/or which exhibits at least 30%, at least 50%, at least 80%, or at least 90%, framework homology to a rabbit framework, and/or which exhibits at least 30%, at least 50%, at least 80%, or at least 90% CDR1 and/or CDR2 homology to rabbit CDR1 and CDR2, respectively, and/or wherein the CDR1 and/or CDR2 have identical amino acid sequence lengths as rabbit CDR1 and CDR2, respectively, and/or wherein the CDR sequences exhibit equivalent canonical structures as rabbit CDR sequences, and/or which exhibit equivalent spatial orientations of CDR loops as rabbit VH and VL chains, preferably which exhibit similar heavy/light (H/L) interface mount angles. The rationale is that the framework scaffold serves to enable the formation of an antigen binding surface comparable to the antigen binding surface in a rabbit antibody consisting of the grafted CDR3 sequences and amino acids from CDR1 and CDR2 regions of heavy and light variable domains. Ideally, the antigen binding surface of the rabbit antibody is rebuilt in the human surrounding, requiring a comparable spatial orientation of all six CDR loops. Thus, if the selected essentially human framework sequences are selected to be similar to the rabbit frameworks, and/or the respective germline encoded CDR1 and CDR2 are similar to the rabbit in sequence, structure and/or spatial orientation, it will maximize the likelihood that affinity will be retained in the mass humanized antibodies.

"Equivalent canonical structure" according to the present invention is understood as similar canonical classification of their CDR1 and CDR2 structure, respectively, e.g. as determined by crystal structure or as predicted by amino acid motif as determined by methods exemplarily set forth in Al-Lazikani, B. et al. Standard conformations for the canonical structures of immunoglobulins. Journal of Molecular Biology 273, 927-948 (1997)).

"Equivalent spatial orientation of CDR loops as VH and VL chains" according to the present invention is preferably understood as that they exhibit similar heavy/light (H/L) interface mount angles. The heavy/light (H/L) interface mount angle is measured as the degree shift of the central axis of the light chain Fv compared to a fixed superposition of heavy chain Fv in a predicted or observed crystal structures. Non-limiting exemplary methods of determining the H/L interface mount angle, alternately referred to as the packing angle, can be found in Dunbar et al. ABangle: characterizing the VH-VL orientation in antibodies. Protein Engineering, Design, and Selection 26, 611-620 (2013).

Determining CDR regions and framework regions can be performed by methods known in the art, as for example described in the chapter Protein Sequence and Structure Analysis of Antibody Variable Domains (in: Antibody Engineering Lab Manual, 2001 (Ed.: Duebel, S. and Kontermann, R., Springer-Verlag, Heidelberg).

For example, the CDR regions can be determined using the Kabat nomenclature, as described in Kabat et al. (Sequences of Proteins of Immunological Interest, 5th Ed. Public Health Service, National Institutes of Health, Bethesda, Md. (1991)), the Chothia nomenclature, as for example described in Al-Lazikani et al., ((1997) JMB 273, 927-948), the Martin nomenclature or the Contact nomenclature, as described in MacCallum, R. M., Martin, A. C. R. and Thornton, J. T. (1996; Antibody-antigen interactions: Contact analysis and binding site topography. J. Mol. Biol. 262, 732-745).

On overview on the location of a CDR region is found below:

| Loop | Kabat | Chothia | Contact |
| --- | --- | --- | --- |
| L1 | L24--L34 | L24--L34 | L30--L36 |
| L2 | L50--L56 | L50--L56 | L46--L55 |
| L3 | L89--L97 | L89--L97 | L89--L96 |
| H1 | H31--H35B (Kabat Numbering) | H26--H32..34 | H30--H35B |
| H1 | H31--H35 (Chothia Numbering) | H26--H32 | H30--H35 |
| H2 | H50--H65 | H52--H56 | H47--H58 |
| H3 | H95--H102 | H95--H102 | H93--H101 |

In a preferred embodiment, a merger of the Kabat and Chothia nomenclature is applied to define the CDR regions. According to the present invention, every position that is part of a CDR according to either the Kabat or the Chothia definition is preferably a CDR position. Positions that are neither within the Kabat CDR nor the Chothia CDR are preferably framework positions according to the present invention.

CDR-H3 has a length of 1 to 50 amino acids, preferably 3 to 25 amino acids, and preferably starts 33 residues after the end of CDR-H2 and always 2 after a Cys. Residues before CDR-H3 are preferably Cys-XXX-XXX, and are typically Cys-Ala-Arg. Residues after CDR-H3 are preferably Trp-Gly-XXX-Gly (SEQ ID NO: 125).

By the populations and methods of the invention, general solutions to a rabbit antibody repertoire is provided, instead of providing single solutions to a single antibody example, thereby allowing mass humanization of rabbit antibodies and providing humanized antibodies binding to a target of interest specifically and/or with high affinity.

The human FR1, FR2, FR3 and FR4 regions are human framework regions with the proviso that the two C-terminal amino acids of FR2 are optionally non-human, and that the two C-terminal amino acids of FR3 are optionally non-human.

Human FR1, FR2, FR3 and FR4 regions are FR1, FR2, FR3 and FR4 regions which are naturally occurring in humans. As described above, the two C-terminal amino acids of FR2 are optionally non-human, and that the two C-terminal amino acids of FR3 are optionally non-human.

Therefore, the FR1 and FR4 regions of the invention are human FR1 and FR4 regions. As also described above, it is possible that a nucleic acid encoding a rabbit-derived CDR3 amino acid sequence, preferably a rabbit-CDR3 amino acid sequence, further comprising 1, 2, or 3 amino acids N-terminal of the rabbit-derived CDR3 amino acid sequence, and/or 1, 2, or 3 amino acids C-terminal of the rabbit-derived CDR3 amino acid sequence is provided, in particular in case a nucleic acid encoding a rabbit SDR as described above is provided. For example, an SDR comprising the CDR-3H and further containing 2 amino acids N-terminal thereof may be grafted. In such embodiment, the following further N-terminal amino acids $Y_1$ and $Y_2$ are embedded, resulting in 2 C-terminal non-human, namely rabbit, FR3 amino acids:

(SEQ ID NO: 124)

wherein $Y_1, Y_2$ and $X_n$ are as defined above.

The N-terminal "C" is also present in human heavy FR3 sequences, and the C-terminal "W" is also present in human heavy FR4 sequences. Accordingly, in case the FR3 and FR4 regions are interspaced by a rabbit-derived CDR3 amino acid sequence of the structure $CY_1Y_2|X_n|W$ (SEQ ID NO: 124), the resulting FR3 heavy region will contain rabbit-derived, in particular rabbit amino acids in the two C-terminal positions $Y_1Y_2$, whereas the remaining parts of the FR3 heavy region will be human, and the FR4 heavy region will be human.

Therefore, in an other preferred embodiment, at least one nucleic acid encoding a rabbit CDR3 sequence is provided according to step (a) and grafted according to step (b), such that the human FR3 and FR4 regions are interspaced by a rabbit CDR3 amino acid sequence, also the resulting FR3 and FR4 regions will be human.

Further, FR2 is a human FR2 framework region, or the two C-terminal amino acids of FR2 are optionally non-human.

In one preferred embodiment, FR2 is a human FR2 framework region.

In another preferred embodiment, the two C-terminal amino acids of FR2 are non-human, whereas the remaining sequence of FR2 is human.

In particular, the two positions N-terminal to CDR-H2 (i.e. positions X10 and X11) are "VS" in the human:

CDR-H2: GLEW VS|X12X13X14X15X16X17X18X19X20X2 1X22X23DSVKG|RFT (SEQ ID NO: 126).

In one preferred embodiment, V and/or S at positions X10 and X11 are independently non-human, preferably rabbit, in the heavy FR2 region.

In the Examples, a library was generated using two sets of heavy chain frameworks (FR1, FR2, FR3, and FR4), wherein the positions X10 and X11 of heavy FR2 are diversified as follows:

X10: Ile, Val
X11: Ala, Gly, or Ser

Therefore, in a more preferred embodiment, the following amino acids are present at the two C-terminal amino acids $Z_1Z_2$ of FR2 in at least one nucleic acid of the population:
$Z_1$: Ile or Val
$Z_2$: Ala, Gly or Ser In a further preferred embodiment, at least 2, 3, 4, 5, 6, 7, 8, 9, 10, 50, 100, 150, 200 or more nucleic acids of the population exhibit different amino acids at the two C-terminal amino acids of human FR2, more preferably at positions X10 and X11 of heavy human FR2.

Various methods are available for providing a population of nucleic acids according to step (b) of the method of the invention, starting from nucleic acids of step (a).

A nucleic acid according to the present invention is preferably a DNA or a RNA.

For example, it is possible to generate a population of nucleic acids, such as a DNA library relating to VL or VH domains each comprising a rabbit CDR3, by chemical synthesis, wherein the FR regions and CDR1 and CDR2 regions are as defined above.

The nucleic acids encoding VH and VL domains can subsequently be assembled into suitable sequences encoding proteins capable of display, such a nucleic acid encoding a Fab, Fv or scFv comprised in a display vector, such as a phage display vector. The resulting constructs may then be used to select proteins, in particular antibodies or fragments thereof, with the desired affinity, specificity and stability.

For example, it is possible to generate a set of oligonucleotides comprising sequences encoding rabbit CDR3 regions (see FIG. 20) and add those via PCR to pre-amplified VH and VL libraries with the features of the invention.

As shown in FIG. 21, this can be followed by a PCR to assemble the VH and VL sequences into a suitable antibody format for display, such as an scFv. Subsequently, the construct can be ligated into a suitable display vector, such as a phagemid vector as in the Examples, via flanking restriction sites.

Therefore, in a yet further preferred embodiment, the nucleic acids of step (a) are provided by
(1) determining the nucleic acid sequence(s) of at least one CDR3 region, preferably CDR-3H and CDR-3L region, of at least one rabbit antibody, or of a region further comprising 1, 2, or 3 amino acids N-terminal of the rabbit CDR3 amino acid sequence,
(2) providing at least one oligonucleotide, which has the following structure: FR3'-CDR3-FR4',
wherein FR3' represents a sequence encoding a human FR3 region, or a fragment thereof comprising the C-terminal end of the FR3 region, and
wherein FR4' represents a sequence encoding a human FR4 region, or a fragment thereof comprising the N-terminal end of the FR4 region,
(3) generating the population of nucleic acids of (b) by PCR, in particular encompassing overlap PCR.

As described above, the C-terminal end of the FR3 region may be human, or may contain 1, 2 or 3 C-terminal non-human amino acids, preferably the C-terminal end of the FR3 region may contain the C-terminal amino acids $Y_1Y_2$, as described above.

Determining the nucleic acid sequence of a CDR3 region of gene encoding an antibody can be performed by sequencing methods known in the art.

An oligonucleotide can be produced by methods known in the art, such as solid phase synthesis.

In a preferred embodiment, the population of nucleic acids encodes proteins comprising at least a VH domain and at least one VL domain, more preferably the nucleic acids encode an scFv.

In a preferred embodiment, step (3) comprises:
generating a population of nucleic acids encoding at least one variable domain by PCR using a population of template nucleic acids, wherein the template nucleic acids comprise Acceptor Framework nucleic acids of the invention.

Thereby, a library comprising a VH domain, or a VL domain, respectively, is generated.

In a further preferred, a population of nucleic acids encoding a protein comprising a VH domain and a VL domain, in particular an scFv, according to the invention is generated.

Therefore, in a more preferred embodiment, step (3) further comprises generating nucleic acids encoding a protein comprising a VH domain and a VL domain, in particular an scFv, by overlap PCR.

In a further preferred embodiment, the nucleic acids of the population are subsequently cloned into a suitable vector, such as a vector for display in cells, such as phage display vector, yeast display vector, a vector allowing for ribosome display or a vector allowing for mRNA display. Methods suitable for cloning are known in the art. In particular, suitable recognition site(s) for a restriction endonuclease may be introduced at the ends of the nucleic acids by PCR, which are subsequently used for cloning into an expression vector.

It is understood that FR3 and FR4 are heavy chain FR3 and FR4 in case of CDR-3H, and that FR3 and FR4 are light chain FR3 and FR4 in case of CDR-3L.

In a preferred embodiment, the nucleic acid sequence moieties FR3' and FR4', respectively, both independently have a length which allows for stable base pairing with the corresponding complementary strand under suitable conditions. In particular, the length of FR3' and FR4' independently is at least about 15 nucleotides, preferably at least about 15, 16, 17, 18, 19, 20, 21, 22, 23, 24, 25, 26, 27, 28, 29, 30, 31, 32, 33, 43, 35 or more nucleotides. For example, the length is up to 50, 75 or 100 nucleotides. For example, FR3' may be a nucleic acid encoding human FR3. For example, FR4' may be a nucleic acid encoding human FR4.

Therefore, in a preferred embodiment, step (a) of the method of the invention comprises:
generating a population of nucleic acids comprising:
(i) a sequence encoding a human FR3 region, or a fragment thereof comprising the C-terminal end of the FR3 region,
(ii) a sequence encoding a rabbit-derived CDR3 amino acid sequence or an amino acid sequence further encompassing 1, 2, or 3 amino acids N-terminal and/or C-terminal of the rabbit-derived CDR3 amino acid sequence, and
(iii) a sequence encoding a human FR4 region, or a fragment thereof comprising the N-terminal end of the FR4 region,
with the proviso that the two C-terminal amino acids of FR3 are optionally non-human, more preferably wherein at least 10 of the nucleic acids of the population encode different CDR3 amino acid sequences.

In a yet further preferred embodiment, at least 50% of the nucleic acids of the population encode different CDR3 amino acid sequences Therefore, in a further preferred embodiment, step (a) of the method of the invention comprises:
generating a population of 20 or more nucleic acids, each comprising:
(i) a sequence encoding a human FR3 region, or a fragment thereof comprising the C-terminal end of the FR3 region,
(ii) a sequence encoding a rabbit-derived CDR3 amino acid sequence or an amino acid sequence further encompassing 1, 2, or 3 amino acids N-terminal and/or C-terminal of the rabbit-derived CDR3 amino acid sequence, and
(iii) a sequence encoding a human FR4 region, or a fragment thereof comprising the N-terminal end of the FR4 region,
with the proviso that the two C-terminal amino acids of FR3 are optionally non-human,
wherein the nucleic acid sequences encoding the rabbit-derived CDR3 amino acid sequences or the amino acid sequence further encompassing 1, 2, or 3 amino acids N-terminal and/or C-terminal of the rabbit-derived CDR3 amino acid sequence are diversified among the population of nucleic acids, and wherein at least 10 of the nucleic acids of the population encode different CDR3 amino acid sequences.

Alternatively, Acceptor Framework nucleic acid sequence may be provided, which comprise FR1, FR2, FR3 and FR4 regions, and CDR1 and CDR2 regions of the invention, respectively. Rabbit-derived CDR3 regions may be cloned into the Acceptor Framework nucleic acids by suitable methods, in particular using PCR and/or a restriction endonuclease. Such preferred embodiment of a method of the invention is shown in FIGS. 9, 11 to 19. Therefore, in a further preferred embodiment, step (b) of the method of the invention comprises:
(i) providing a population of Acceptor Framework nucleic acid sequences,
wherein each Acceptor Framework nucleic acid sequence comprises
nucleic acid sequences encoding a set of framework regions comprising a first human framework region (FR1), a second human framework region (FR2), a third human framework region (FR3), and a fourth human framework region (FR4),
wherein the FR1 and FR2 regions are interspaced by a complementarity determining region 1 (CDR1), the FR2 and FR3 regions are interspaced by a complementarity determining region 2 (CDR2), and the nucleic acid sequences encoding FR3 and FR4 regions are linked directly or are interspaced by a stuffer nucleic acid sequence, and
(ii) combining at least one nucleic acid sequence encoding a rabbit-derived CDR3 amino acid sequence with an Acceptor Framework nucleic acid sequence, so that the FR3 and FR4 regions are interspaced by a rabbit-derived CDR3 amino acid sequence or an amino acid sequence further encompassing 1, 2, or 3 amino acids N-terminal and/or C-terminal of the rabbit-derived CDR3 amino acid sequence,
with the proviso:
that the two C-terminal amino acids of FR2 are optionally non-human, and
that the two C-terminal amino acids of FR3 are optionally non-human.

In a preferred embodiment, step (ii) comprises combining at least 10 nucleic acid sequences each encoding a rabbit-derived CDR3 amino acid sequence with an Acceptor Framework nucleic acid sequence, so that each of the FR3 and FR4 regions are interspaced by a rabbit-derived CDR3 amino acid sequence or an amino acid sequence further encompassing 1, 2, or 3 amino acids N-terminal and/or C-terminal of the rabbit-derived CDR3 amino acid sequence.

An "Acceptor Framework nucleic acid" according to the present invention refers to a nucleic acid sequence that comprises the nucleic acid sequences encoding the FR1, FR2, FR3 and FR4 regions, and the nucleic acid sequences encoding a CDR1 and a CDR2 region or amino acid sequences that can fulfill the role of these CDRs, as defined herein, with the structure FR1-CDR1-FR2-CDR2-FR3-L-FR4, wherein L is either a direct linkage or a stuffer nucleic acid sequence, which direct linkage or stuffer nucleic acid sequence serves as the site of integration for a nucleic acid encoding a rabbit-derived CDR3 amino acid sequence, preferably a rabbit-CDR3 amino acid sequence, or a rabbit-derived CDR3 amino acid sequence, preferably a rabbit-CDR3 amino acid sequence further comprising 1, 2, or 3 amino acids N-terminal of the rabbit-derived CDR3 amino acid sequence, and/or 1, 2, or 3 amino acids C-terminal of the rabbit-derived CDR3 amino acid sequence.

Accordingly, an "Acceptor Framework" according to the present invention refers to a protein comprising the FR1, FR2, FR3 and FR4 regions, and the CDR1 and CDR2 regions, or amino acid sequences that can fulfill the role of these CDRs, as defined herein, with the structure FR1-CDR1-FR2-CDR2-FR3-L-FR4, wherein L is either a direct peptide linkage or a stuffer sequence, wherein the corresponding nucleic acid direct linkage or stuffer nucleic acid sequence serves as the site of integration for a nucleic acid encoding a rabbit-derived CDR3 amino acid sequence, preferably a rabbit-CDR3 amino acid sequence, or a rabbit-derived CDR3 amino acid sequence, preferably a rabbit-CDR3 amino acid sequence further comprising 1, 2, or 3 amino acids N-terminal of the rabbit-derived CDR3 amino acid sequence, and/or 1, 2, or 3 amino acids C-terminal of the rabbit-derived CDR3 amino acid sequence. The Acceptor Framework can be a variable heavy chain (VH) Acceptor Framework or a variable light chain (VL) Acceptor Framework, or can be a Framework comprising a variable heavy chain (VH) Acceptor Framework and a variable light chain (VL) Acceptor Framework, such as an scFv Acceptor Framework comprising insertion sites for CDR-3H and CDR-3L.

The terms "stuffer sequence" is used herein to refer to a nucleic acid sequence which allows integration, preferably by replacement, of a nucleic acid encoding a rabbit-derived CDR3 amino acid sequence, preferably a rabbit-CDR3 amino acid sequence, or a rabbit-derived CDR3 amino acid sequence, preferably a rabbit-CDR3 amino acid sequence further comprising 1, 2, or 3 amino acids N-terminal of the rabbit-derived CDR3 amino acid sequence, and/or 1, 2, or 3 amino acids C-terminal of the rabbit-derived CDR3 amino acid sequence. Typically, the stuffer sequence contains one or more suitable recognition sites for one or more restriction endonucleases. In the embodiment of the direct linkage, the sequence surrounding the linkage itself preferably contains one or more suitable recognition sites for one or more restriction endonucleases, allowing insertion at the site between FR3 and FR4. The use of the stuffer sequence allows for the in frame integration of a nucleic acid encoding a rabbit-derived CDR3 amino acid sequence or a sequence further comprising 1, 2, or 3 amino acids N-terminal of the rabbit-derived CDR3 amino acid sequence, and/or 1, 2, or 3 amino acids C-terminal of the rabbit-derived CDR3 amino acid sequence, such as an CDR3 SDR, which nucleic acid may be natural or synthetic, into the Acceptor Framework. Thus, upon integration, the stuffer sequence is preferably removed, and the coding region of a protein comprising at least one immunoglobulin variable domain is obtained. In particular, the immunoglobulin variable domain has the structure FR1-CDR1-FR2-CDR2-FR3-CDR3-FR4. Preferably, the stuffer sequence has a random sequence and/or has a length of about 1 to 2, 3, 4, 5, 6, 7, 8, 9, 10, 15, 20, 30, 40, 50 or 100 nucleotides.

According to the preferred embodiment, at least one nucleic acid sequence encoding a rabbit-derived CDR3 amino acid sequence is combined with an Acceptor Framework nucleic acid sequence. As described above, combining of the nucleic acid sequences may be achieved by methods known in the art. Preferably, an Acceptor Framework nucleic acid is digested with suitable restriction endonuclease(s). Further, a nucleic acid encoding a rabbit-derived CDR3 amino acid sequence or the amino acid sequence further encompassing 1, 2, or 3 amino acids N-terminal and/or C-terminal of the rabbit-derived CDR3 amino acid sequence is generated with ends which allow ligation. For example, blunt ends may be used. In this embodiment, no digestion is necessary. Alternatively, recognition site(s) may be incorporated in the nucleic acid encoding a rabbit-derived CDR3 amino acid sequence or the amino acid sequence further encompassing 1, 2, or 3 amino acids N-terminal and/or C-terminal of the rabbit-derived CDR3 amino acid sequence, followed by digestion with (a) corresponding restriction endonuclease(s). For example, a Type IIb restriction endonuclease, in particular BarI may be used, as for example shown in FIGS. 12 to 16.

In a further preferred embodiment of the method of the invention, the nucleic acid sequences encoding the rabbit-derived CDR3 amino acid sequences or the amino acid sequence further encompassing 1, 2, or 3 amino acids N-terminal and/or C-terminal of the rabbit-derived CDR3 amino acid sequence are diversified among the population of nucleic acids encoding at least one protein comprising at least one immunoglobulin variable domain.

"The nucleic acid sequences encoding the rabbit-derived CDR3 amino acid sequences or the amino acid sequence further encompassing 1, 2, or 3 amino acids N-terminal and/or C-terminal of the rabbit-derived CDR3 amino acid sequence are diversified among the population of nucleic acids" is understood as that at least 2 of the nucleic acids of the population encode different CDR3 amino acid sequences, in particular different CDR-3H and/or CDR-3L amino acid sequences, more preferably wherein at least 2, 3, 4, 5, 6, 7, 8, 9, 10, 20, 30, 40, 50, 60, 70, 80, 90, 100, 150, 200, $10^3$, $10^4$, $10^5$ or more encode different CDR3 amino acid sequences, in particular different CDR-3H and/or CDR-3L amino acid sequence, and/or wherein at least 50%, at least 80%, at least 90%, at least 95%, at least 96%, at least 97%, at least 98%, at least 99% or 100% of the nucleic acids of the population encode different CDR3 amino acid sequences, in particular different CDR-3H and/or CDR-3L amino acid sequences. In a more preferred embodiment the, sequences are diversified due to immunization of one or more rabbits with a target of interest. Preferably, the sequences are diversified within the CDR3 amino acid sequence, in case the sequence further encompasses 1, 2, or 3 amino acids N-terminal and/or C-terminal of the rabbit-derived CDR3 amino acid sequence.

It is preferred to use the sequences identical to the CDR3 regions of rabbit antibodies raised against the antigen of interest. As described above, the nucleic acids encoding a rabbit CDR3 region can be obtained e.g. by amplification, e.g. by PCR methods, or by chemical synthesis. Alternatively, an SDR region may be cloned, as in the examples. Such SDR region encompasses 2 further amino acids N-terminal of CDR3 in case of CDR-3H, as shown above. By using the rabbit CDR3 regions or a sequence further encompassing 1, 2, or 3 amino acids N-terminal of the rabbit CDR3 amino acid sequence, preferably further encompassing 1 or 2, in particular 2 amino acids, N-terminal of the rabbit CDR3 amino acid sequence, even more preferably wherein the rabbit CDR3 amino acid sequence is a rabbit CDR-3H amino acid sequence, efficient mass humanization of the rabbit antibodies can be achieved, with a high likelihood of obtaining a successful antibody graft for the CDR3. An SDR is known as a CDR plus an additional few additional boundary residues known in the art as "vernier zones", as defined above. As further described above, the rabbit CDR3 regions optionally further encompass 1 amino acid C-terminal of the rabbit CDR3 amino acid sequence. However, this position is invariate (namely W) between humans and rabbits.

Therefore, in a yet further preferred embodiment of the method of the invention, a nucleic acid sequence encoding a rabbit-derived CDR3 amino acid sequence is a nucleic acid sequence encoding a rabbit CDR3 amino acid sequence, or an amino acid sequence further encompassing 1, 2, or 3 amino acids N-terminal and optionally 1 amino acid C-terminal of the rabbit CDR3 amino acid sequence, preferably further encompassing 1 or 2, in particular 2 amino acids, N-terminal of the rabbit CDR3 amino acid sequence, even more preferably wherein the rabbit CDR3 amino acid sequence is a rabbit CDR-3H amino acid sequence, In a preferred embodiment, the CDR3 amino acid sequence is a rabbit CDR3 amino acid sequence. Such rabbit sequences are naturally occurring in the rabbit. Antibodies are preferably antibodies produced by B cells, in particular after immunization of the rabbit with an antigen of interest. Suitable immunization protocols and protocols for isolating sources of B cells are known in the art, such as bone marrow cells, PBMC cells or spleen cells, and are described in the Examples and FIG. 6. Therefore, in an even more preferred embodiment, the rabbit CDR3 amino acid sequence, or an amino acid sequence further encompassing 1, 2, or 3 amino acids N-terminal and optionally 1 amino acid C-terminal of the rabbit CDR3 amino acid sequence is obtained from a rabbit B cell, preferably a rabbit B cell from bone marrow, PBMC, lymph node or spleen, more preferably wherein the rabbit was immunized against an antigen of interest.

Therefore, in preferred embodiments of the invention, it is possible to use a plurality or all of the rabbit CDR3 sequences determined in one or more rabbits immunized with an antigen of interest.

In further preferred embodiments, a preselection of rabbit CDR3 sequences is performed in step (a). Such preselection can be performed as follows:
- RNA or DNA is extracted from a B cell source of at least one rabbit immunized against an antigen of interest, such as rabbit spleen, bone marrow, blood, or the lymph node,
- nucleic acids encoding the protein sequence comprising the CDR-3H and optionally CDR-3L regions of the antibody repertoire of the rabbits are amplified; in particular the VH and VL Fv fragment, or minimally the CDR-3H and optionally CDR-3L sequences are amplified,
- the amplified products are sequenced,
- the resulting sequences are analyzed to identify the translated or untranslated CDR-3H and optionally CDR-3L sequences,
- the frequency of the CDR-3H and optionally CDR-3L sequences, respectively, of the analyzed repertoire is analyzed, and trees of related CDR-3H and optionally CDR-3L sequences, respectively, are generated by single linkage,
- optionally, CDR-3H and optionally CDR-3L sequences which are also determined in a sample obtained from the at least one rabbit prior to immunization are excluded,
- candidate lineages are ranked by expansion, isotype, somatic hypermutation, tree complexity, and convergence,
- individual representatives of each lineage are selected and synthesized, wherein silent or non silent mutations or natural degeneracy can be incorporated during synthesis,
- generating a nucleic acid population of the invention comprising the rabbit CDR3 regions, e.g. by methods described above, e.g. using PCR and/or restriction endonucleases.

Therefore, in a particularly preferred embodiment, the rabbit CDR3 amino acid sequence, or an amino acid sequence further encompassing 1, 2, or 3 amino acids N-terminal and optionally 1 amino acid C-terminal of the rabbit CDR3 amino acid sequence is obtained by:
- determining the sequence of the rabbit CDR3 regions of the antibodies in a sample obtained from a rabbit immunized against an antigen of interest,
- determining the frequency of all rabbit CDR3 amino acid sequence in the sample and generating lineage trees or grouping CDR3 amino acid sequences based on sequence similarities,
- optionally excluding rabbit CDR3 amino acid sequence groups or sequences present in a sample from the rabbit prior to immunization,
- ranking candidate lineages or candidate groups by expansion, isotype, somatic hypermutation, tree complexity, group size and/or convergence,
- selecting an individual rabbit CDR3 amino acid sequence representative of at least one lineage or group, in particular of a plurality of lineages or group or all lineages or group, and
- generating a nucleic acid encoding a peptide comprising the individual rabbit CDR3 amino acid sequence, or a derivative thereof containing 1, 2 or 3 conservative amino acid mutations.

As described above, it is possible that the two C-terminal amino acids of the FR3, in particular of heavy FR3 are non-human, in particular in case an SDR encompassing a rabbit CDR-3H is amplified and grafted to obtain the nucleic acids of the population of the invention. As also described above, it is possible that two C-terminal amino acids of the FR2 region are non-human. In the Examples, a library was generated using two sets of heavy chain frameworks (FR1, FR2, FR3, and FR4), wherein the positions X10 and X11 of heavy FR2 are diversified as follows:
X10: Ile, Val
X11: Ala, Gly, or Ser.

Therefore, in a yet further preferred embodiment of the present invention, the sequence of the two C-terminal amino acids of the FR3 region is $Y_1Y_2$ as defined above, more preferably wherein $Y_1$ is A and/or $Y_2$ is R.

Further, in a yet other embodiment of the present invention, the sequence of the two C-terminal amino acids of the FR2 region is X1-X2,
wherein X1 is selected from I and V, and
wherein X2 is selected from A, G, S.

It is, however, also possible to incorporate sequences encoding peptide consisting of a rabbit-derived complementarity determining region 3 (CDR3) amino acid sequence. In this embodiment, it is preferred that the FR3 region, in particular the heavy FR3 region and the light FR3 region is human. Further, it is possible to use a human FR2 region. Therefore, in another preferred embodiment of the present invention, the FR2 region is human, and/or the FR3 region is human.

In one preferred embodiment of the invention, a cloning strategy as shown in FIGS. 11 and 12, or 14 to 19 may be employed. In particular, at least one recognition site for at least one restriction enzyme is incorporated into at least one nucleic acid encoding a rabbit-derived complementarity determining region 3 (CDR3) amino acid sequence or an amino acid sequence further encompassing 1, 2, or 3 amino acids N-terminal and/or C-terminal of the rabbit-derived CDR3 amino acid sequence. For example, two different or identical recognition sites may be added e.g. by PCR at the ends of the nucleic acids, for example for sites recognized by an orthodox Type II restriction endonuclease. In one preferred embodiment, a recognition site is present, which is recognized by a restriction endonuclease which cuts at both sides of the recognition site, in particular a Type IIb restriction endonuclease (see e.g. Pingoud A. and Jeltsch A., 2001, Nucleic Acids Research, 29(18): 3705-3727).

Therefore, in a further preferred embodiment of the present invention, (x) the at least one nucleic acid encoding a rabbit-derived complementarity determining region 3 (CDR3) amino acid sequence or an amino acid sequence further encompassing 1, 2, or 3 amino acids N-terminal and/or C-terminal of the rabbit-derived CDR3 amino acid sequence further comprises at least one recognition site for at least one restriction enzyme, and (xi) the nucleic acid sequences of the Acceptor Framework nucleic acid sequence encoding FR3 and FR4 regions are interspaced by a stuffer nucleic acid sequence comprising at least one restriction enzyme recognition site for at least one restriction enzyme.

As noted above, a recognition site for a restriction enzyme, which is capable of cutting at both sides of the recognition site may be used, as this allows for efficient cloning. Therefore, it is preferred that both the nucleic acids referring to the scaffold and the nucleic acids encoding CDR3 regions comprise a recognition site for such restriction enzyme. The terms "restriction enzyme" and "restriction endonuclease" are used interchangeably herein. The cloning can be achieved by digesting both nucleic acids with the restriction enzyme and ligating the fragments subsequently. Such steps can be performed by methods known to a skilled person.

Therefore, in a more preferred embodiment of the method of the invention, the nucleic acids of (x) and (xi) further comprise a recognition site for a restriction enzyme, which is capable of cutting at both sides of the recognition site.

Therefore, in an even more preferred embodiment of the method of the invention, step (ii) of the method comprises:

(ii1) digesting the at least one nucleic acid of (x) using a restriction enzyme that binds to the restriction enzyme recognition site of (x), and (ii2) digesting the stuffer nucleic acid sequence from the Acceptor Framework of (xi) using a restriction enzyme that binds to the restriction enzyme recognition site; and (ii3) ligating the digested nucleic acid sequences of steps (ii1) and (ii2), such that the nucleic acid sequence encoding the FR3 and FR4 region of a nucleic acid is interspaced by a nucleic acid sequence encoding the rabbit-derived CDR3 amino acid sequences or the amino acid sequence further encompassing 1, 2, or 3 amino acids N-terminal and/or C-terminal of the rabbit-derived CDR3 amino acid sequence, and that a sequence encoding a protein comprising at least one immunoglobulin variable domain is obtained, As shown in the Figures, BarI is a particularly useful restriction enzyme which is capable of cutting at both sides of the recognition site.

Therefore, in a further embodiment, the present invention relates to the use of BarI for cloning a nucleic acid encoding a least one CDR region into a nucleic acid encoding a protein comprising at least one variable domain.

Bar I is a restriction enzyme from *Bacillus sphaericus* which is commercially sold (SibEnzyme Ltd., Russia).

In a particularly preferred embodiment of the present invention, the restriction endonuclease which is capable of cutting at both sides of the recognition site is a Type IIb restriction endonuclease, most preferably BarI.

Therefore, in an even more preferred embodiment of the method of the invention, the at least 10 nucleic acids each encoding a rabbit-derived complementarity determining region 3 (CDR3) amino acid sequence or an amino acid sequence further encompassing 1, 2, or 3 amino acids N-terminal and/or C-terminal of the rabbit-derived CDR3 amino acid sequence further comprise at least one recognition site for at least one restriction enzyme.

In a more preferred embodiment of the method of the invention, step (ii) comprises:

(ii1) digesting the at least 10 nucleic acids of (x) using a restriction enzyme that binds to the restriction enzyme recognition site of (x), and (ii2) digesting the stuffer nucleic acid sequence from the Acceptor Framework of (xi) using a restriction enzyme that binds to the restriction enzyme recognition site; and (ii3) ligating the digested nucleic acid sequences of steps (ii1) and (ii2), such that the nucleic acid sequence encoding the FR3 and FR4 region of a nucleic acid is interspaced by a nucleic acid sequence encoding a rabbit-derived CDR3 amino acid sequence or an amino acid sequence further encompassing 1, 2, or 3 amino acids N-terminal and/or C-terminal of the rabbit-derived CDR3 amino acid sequence, and that sequences each encoding a protein comprising at least one immunoglobulin variable domain is obtained, more preferably wherein the restriction endonuclease which is capable of cutting at both sides of the recognition site is a Type IIb restriction endonuclease, more preferably BarI.

As also exemplified in the Examples, a method of the invention encompasses in one preferred embodiment the following steps:

Step 1: Cloning of Rabbit VH-CDR3 regions between Human VH-FR3 and Human VH-FR4 regions in an acceptor vector (see FIG. 14)

Step 2: Transformation of *E. coli* with the ligation from step 1 to generate a Rabbit VH-CDR3 library between Human VH-FR3 and Human VH-FR4 regions Step 3: PCR amplification using DNA template from transformed bacteria from step 2 of Rabbit VH-CDR3 library between Human VH-FR3 and Human VH-FR4 regions Step 4: Assembly of Rabbit VL-CDR3 regions into an acceptor vector containing synthesized human FR1, FR2 and FR3 domains and a library of CDR1 and CDR2 sequences Step 5: Transformation of *E. coli* with the ligation from step 4 to generate a Rabbit VL-CDR3 library between Human VL-FR3 and Human VL-FR4 regions Step 6: PCR amplification using a synthesized DNA template containing Human FR1, FR2 and FR3 domains and a library of VH-CDR1 and VH-CDR2

Step 7: Assembly of a VH variable region library containing Human Framework regions FR1, FR2 and FR3 separated by a library of CDR1 and CDR2 sequences and a library of Rabbit CDR3 sequences via overlap PCR Step 8: PCR of the VH variable region library from step 7 containing Human Framework regions FR1, FR2, FR3 and FR4 separated by a library of CDR1, CDR2 and a library of Rabbit CDR3 sequences Step 9: PCR amplification of a VL variable region library containing the C-terminal part of a Human VH-FR4 domain, a linker sequence, Human VL Framework domain regions FR1, FR2, FR3 and FR4 separated by a library of CDR1 and CDR2 sequences and a library of Rabbit VL-CDR3

Step 10: PCR assembly via overlap PCR of DNA fragments derived from steps 8 and 9 via their common human VH-FR4 sequence Therefore, a novel mass humanized library of scFv fragments comprising rabbit CDR3 regions is generated.

Optionally, the library may be cloned into a suitable display vector in a subsequent step.

Step 11: Cloning of the assembled scFv library in a phage display vector (in the Figures via NcoI and NotI), or into another suitable display vector, such as a vector for ribosome display, or yeast display.

As shown in the Examples of FIG. 3B, and in the Examples, the length of the CDR3 regions identified after selection varies. With the exemplary antigen lysozyme, the identified CDR3 regions have a length of between 5 and 21 amino acids for CDR-3H and of between 7 and 13 amino acids for CDR-3L.

Therefore, in a yet further preferred embodiment of the present invention, the diversified rabbit-derived CDR3 amino acid sequences or the amino acid sequence further encompassing 1, 2, or 3 amino acids N-terminal and/or C-terminal of the rabbit-derived CDR3 amino acid sequence are heavy chain CDR3 (CDR H3) sequences. In a particularly preferred embodiment, the heavy chain CDR3 (CDR H3) sequences have a length of between 1 to 50 amino acids or 3 to amino acids, even more preferably between 5 and 21 amino acids.

In a yet further preferred embodiment of the present invention, the diversified rabbit-derived CDR3 amino acid sequences or the amino acid sequence further encompassing 1, 2, or 3 amino acids N-terminal and/or C-terminal of the rabbit-derived CDR3 amino acid sequence are light chain CDR3 (CDR L3) sequences. In a particularly preferred embodiment, the light chain CDR3 (CDR L3) sequences have a length of between 3 to 20 amino acids or 5 to 20 amino acids, even more preferably between 7 and 13 amino acids.

It is preferred that the proteins of the population comprise a VH domain and a VL domain, or a heavy chain of an antibody or a fragment thereof comprising the VH domain, and a light chain of an antibody or a fragment thereof comprising the VL domain or an scFv, even more preferably an scFv. An scFv library of the invention is described in the Examples. In further more preferred embodiment, the encoded proteins or proteins of the inventions are selected from an immunoglobulin molecule, a disulfide linked Fv, a monoclonal antibody, an scFv, a diabody, a multispecific antibody, a Fab, a Fab', a bispecific antibody; a F(ab')2, an scFv or an Fv, more preferably an scFv. An scFv library of the invention is described in the Examples. In such preferred embodiment, the proteins of the population comprise a light chain CDR3 (CDR L3) sequence and a heavy chain CDR3 (CDR H3) sequence. The nucleic acids of the population comprise, in one preferred embodiment, both sequences encoding a light chain CDR3 (CDR L3) sequence and sequences encoding a heavy chain CDR3 (CDR H3) sequence, e.g. in case of nucleic acids encoding scFv. The nucleic acids of the population comprise, in a further preferred embodiment, (a) nucleic acids comprising sequences encoding a light chain CDR3 (CDR L3) sequence, and (b) nucleic acids comprising sequences encoding a heavy chain CDR3 (CDR H3) sequence, e.g. in case of nucleic acids encoding an immunoglobulin molecule, a disulfide linked Fv, a monoclonal antibody, a Fab, a Fab', a bispecific antibody; or a F(ab')2.

Further, in one preferred embodiment, the nucleic acids of the population encode proteins each comprising one immunoglobulin variable domain having a rabbit-derived CDR3 amino acid sequence embedded in essentially human framework sequences of the invention as described above. Preferably, the encoded proteins comprising one immunoglobulin variable domain having a rabbit-derived CDR3 amino acid sequence embedded in essentially human framework sequences each comprise a VH domain, or a VL domain, or a heavy chain of an antibody or a fragment thereof comprising the VH domain, or a light chain of an antibody or a fragment thereof comprising the VL domain and/or are selected from a single domain antibody. In a more preferred embodiment, the population of nucleic acids encoding proteins each comprising one immunoglobulin variable comprises at least one nucleic acid encoding a protein comprising a VH domain and comprises at least one nucleic acid encoding a protein comprising a VL domain. This allows for pairing within the population of proteins encoded by the nucleic acids of the population. Alternatively, the population encoding proteins comprising one VL domain or one VH domain only, may be paired with a separate population of nucleic acids encoding proteins comprising a VH domain or VL domain respectively.

Accordingly, the population of proteins comprises, in a further preferred embodiment, (a) proteins comprising a light chain CDR3 (CDR L3) sequence, and (b) proteins comprising a heavy chain CDR3 (CDR H3) sequence.

Alternatively, the population of proteins comprises (a) proteins comprising a light chain CDR3 (CDR L3) sequence, or (b) proteins comprising a heavy chain CDR3 (CDR H3) sequence.

Accordingly, the population of nucleic acids comprises, in a further preferred embodiment, (a) nucleic acids comprising sequences encoding a light chain CDR3 (CDR L3) sequence, and/or (b) nucleic acids comprising sequences encoding a heavy chain CDR3 (CDR H3) sequence.

In another preferred embodiment, the nucleic acids of the population encode proteins each comprising 2, 3, 4 or more immunoglobulin variable domains having a rabbit-derived CDR3 amino acid sequence embedded in essentially human framework sequences of the invention as described above. In a more preferred embodiment, the nucleic acids of the population encodes proteins, wherein each protein comprises 2 immunoglobulin variable domains having a rabbit-derived CDR3 amino acid sequence embedded in essentially human framework sequences of the invention as described above. It is preferred that the encoded proteins of the population comprise a VH domain and a VL domain, or a heavy chain of an antibody or a fragment thereof comprising the VH domain, and a light chain of an antibody or a fragment thereof comprising the VL domain or an scFv, even more preferably an scFv. An scFv library of the invention is described in the Examples.

In further more preferred embodiment, the encoded proteins or proteins of the subject-matter of the invention are selected from an immunoglobulin molecule, a disulfide linked Fv, a monoclonal antibody, an scFv, a diabody, a multispecific antibody, a Fab, a Fab', a bispecific antibody; a F(ab')2, an scFv or an Fv, more preferably an scFv. An scFv library of the invention is described in the Examples.

The nucleic acids encoding the CDR1 and CDR2 amino acid sequences are diversified among the population of nucleic acids encoding at least one protein comprising at least one immunoglobulin variable domain, wherein each nucleic acid sequence encoding a CDR1 or CDR2 amino acid sequence is independently based i) on a nucleic acid sequence encoding a human CDR1 or CDR2, respectively, or ii) on a nucleic acid sequence encoding a rabbit CDR1 or CDR2, respectively, wherein at least some of the nucleic acid sequences encoding a CDR1 or CDR2 amino acid sequence have been modified to encode at least one amino acid present in rabbit CDR1 or CDR2 amino acid sequences, respectively, in case of human CDR1 or CDR2, respectively, or to encode at least one amino acid present in human CDR1 or CDR2 amino acid sequences, respectively, in case of rabbit CDR1 or CDR2, respectively. In a preferred embodiment, at least 50%, more preferably at least 80%, at least 90%, at least 95%, at least 96%, at least 97%, at least 98%, at least 99% or 100% of the nucleic acid sequences encoding a CDR1 or CDR2 amino acid sequence have been modified to encode at least one amino acid present in rabbit CDR1 or CDR2 amino acid sequences, respectively, in case of human CDR1 or CDR2, respectively, or to encode at least one amino acid present in human CDR1 or CDR2 amino acid sequences, respectively, in case of rabbit CDR1 or CDR2, respectively.

A suitable method for obtaining diversified CDR1 and CDR2 sequences according to the invention encompass computationally integrating a plurality, such as $10^4$, $10^5$, or $10^6$-$10^7$ of simulated humanizations across the rabbit antibody repertoire and the human acceptor antibody repertoire, in order to generate a mathematically optimal Bayesian representation of the humanization space between rabbit and human, converting the probabilistic model to a frequentist interpretation, thereby obtaining a population or library. Each position ends up containing a probability of encountering the human germline residue, the rabbit germline residues, and the most common collection of affinity maturation residues from both species.

In a preferred embodiment, cysteine, and/or methionine residues are removed and/or the asparagine residue content is reduced, as these residues form biochemical liabilities.

By analyzing the CDR1 and CDR2 repertoires of rabbit and human, respectively, it was possible to identify and generate CDR1 and CDR2 diversified sequences that span rabbit germline, human germline, rabbit somatic hypermutation, human somatic hypermutation, and rabbit gene conversion at every position in CDR-H1, CDR-H2, CDR-L1, and CDR-L2. The resulting population or library thus is a novel entity with surprisingly beneficial properties, that is neither rabbit nor human, but a hybrid repertoire exploring the space between.

Therefore, in a yet further preferred embodiment of the present invention, the human or rabbit CDR1 regions and the human and rabbit CDR2 regions, on which the diversified CDR1 and CDR2 amino acid sequences are based, are selected from human germline CDR1 regions, human germline CDR2 regions, rabbit germline CDR1 regions, rabbit germline CDR2 regions, human somatic hypermutation CDR1 regions, human somatic hypermutation CDR2 regions, rabbit somatic hypermutation CDR1 regions, rabbit somatic hypermutation CDR2 regions, rabbit gene conversion CDR1 regions, and rabbit gene conversion CDR2 regions.

In a yet further preferred embodiment of the present invention, the diversified CDR1 and CDR2 amino acid sequences are CDR-H1, CDR-H2, CDR-L1 and/or CDR-L2 sequences.

In a preferred embodiment, the population includes at least one nucleic acid encoding a human CDR-H1, and/or a human CDR-H2, and/or a human CDR-L1 and/or a human CDR-L2 sequence.

In a further preferred embodiment, the population includes at least one nucleic acid encoding a rabbit CDR-H1, and/or a rabbit CDR-H2, and/or a rabbit CDR-L1 and/or a rabbit CDR-L2 sequence.

According to the invention, the human FR1, FR2, FR3 and FR4 regions are human framework regions selected to provide a scaffold conducive for rabbit CDR3 amino acid sequences, with the proviso that the two C-terminal amino acids of FR2 are optionally non-human, and that the two C-terminal amino acids of FR3 are optionally non-human.

Therefore, in one preferred embodiment, the population of the invention comprises at least one nucleic acid encoding a human FR1, a human FR2, a human FR3 and a human FR4 region, and a human CDR1, and a human CDR2 region.

In another preferred embodiment, the population of the invention comprises at least one nucleic acid encoding a human FR1, a human FR2, a human FR3 and a human FR4 region, and a rabbit CDR1, and a rabbit CDR2 region.

Therefore, in yet another preferred embodiment, the population of the invention does not contain a nucleic acid encoding a human FR1, a human FR2, a human FR3 and a human FR4 region, and a human CDR1, and a human CDR2 region.

Therefore, in yet another preferred embodiment, the population of the invention does not contain a nucleic acid encoding a human FR1, a human FR2, a human FR3 and a human FR4 region, and a rabbit CDR1, and a rabbit CDR2 region.

A suitable scaffold conducive for rabbit CDR3 amino acid sequences may be obtained by selecting a framework set by performing the following steps:

computational imputation of germline repertoire element centroids which are most utilized in functional rabbit antibodies generating an amino acid alignment of human frameworks compared to said computationally imputed rabbit frameworks and selecting the closest representatives, respectively, that have the same length of CDR-H1, CDR-H2, CDR-L1, and CDR-L2 and similar sequence composition, respectively, further reducing the number of candidates framework sequences by preferring templates that are known to be stable in the art and optionally have worked as previous drugs, further reducing the number of framework candidates by structurally modeling antibodies from rabbit and human using these frameworks and analyzing their structural superposition tolerance by root mean squared deviation (RMSD), and selecting a set of 1, 2, 3, 4, 5, 6, 7, 8, 9 or 10 heavy chain and 1, 2, 3, 4, 5, 6, 7, 8, 9 or 10 light chain frameworks comprising set of FR1, FR2, FR3 and FR4 regions, respectively.

In the Examples, a set of 2 heavy chain and 2 light chain frameworks comprising a set of FR1, FR2, FR3 and FR4 regions respectively, were selected. Moreover, the two C-terminal amino acids of heavy chain FR2 are optionally non-human, and the two C-terminal amino acids of heavy chain FR3 are optionally non-human, for example in case an SDR is grafted into a scaffold, or in case amino acids surrounding FR2 are substituted, as described above.

Therefore, in one preferred embodiment, the heavy FR1 to FR4 regions of VH3_23 and/or VH3_53 are used in the populations of the present invention.

Therefore, in one preferred embodiment, the light FR1 to FR4 regions of VK-1_27 and/or VK-3_20 are used in the populations of the present invention.

Therefore, in a yet further preferred embodiment of the present invention, the human FR1, FR2, FR3 and FR4 regions which are human framework regions selected to provide a scaffold conducive for rabbit CDR3 amino acid sequences are obtainable by:
(i) providing
   (a) a collection of sequences of naturally occurring human antibodies each comprising a set of human FR1, FR2, FR3 and FR4 regions; and
   (b) a collection of sequences of naturally occurring rabbit antibodies each comprising a set of rabbit FR1, FR2, FR3 and FR4 regions, and
(ii) identifying a plurality of sets of human FR1, FR2, FR3 and FR4 regions which provide a scaffold conducive for rabbit CDR3 amino acid sequences by
   determining the parameters framework homology, CDR homology, CDR lengths, CDR canonical structure, and spatial orientation of CDR loops, and
   selecting sets of human FR1, FR2, FR3 and FR4 regions which exhibit high scores for the parameters,
   and/or
   the two C-terminal amino acids of heavy chain FR2 are optionally non-human, and
   the two C-terminal amino acids of heavy chain FR3 are optionally non-human.

Therefore, in a preferred embodiment of the present invention, the human framework sequences independently comprise a set of human FR1, FR2, FR3 and FR4 regions selected from human VH3-23, human VH3-53, human Vk1-27, and/or Vk3-20 framework regions, with the proviso:
   that the two C-terminal amino acids of FR2 are optionally non-human, and
   that the two C-terminal amino acids of FR3 are optionally non-human.

In a further embodiment, the present invention relates to a population of nucleic acids encoding at least one protein comprising at least one immunoglobulin variable domain having a rabbit-derived CDR3 amino acid sequence embedded in essentially human framework sequences, obtainable by a method of the invention.

Such population preferably represents a library of rabbit CDR3 sequences, wherein mass humanization of the rabbit antibodies is achieved.

It is understood that the preferred embodiments described for the methods of the invention also apply for the populations of the present invention and uses thereof.

In a more preferred embodiment, the present invention relates to a population of nucleic acids encoding 20 or more proteins, each comprising at least one immunoglobulin variable domain having a rabbit-derived CDR3 amino acid sequence embedded in essentially human framework sequences, wherein the nucleic acid sequences encoding the rabbit-derived CDR3 amino acid sequences or the amino acid sequence further encompassing 1, 2, or 3 amino acids N-terminal and/or C-terminal of the rabbit-derived CDR3 amino acid sequence are diversified among the population of nucleic acids, obtainable by a method of the present invention.

In a preferred embodiment, a nucleic acid of the population is located in a vector. Such vector allows easy and efficient replication, cloning, selection and/or display, depending on the properties of such vector. Accordingly, a vector may additionally include nucleic acid sequences that permit it to replicate in the host cell, such as an origin of replication, one or more therapeutic genes and/or selectable marker genes and other genetic elements known in the art such as regulatory elements directing transcription, translation and/or secretion of the encoded protein. The vector may be used to transduce, transform or infect a cell, thereby causing the cell to express nucleic acids and/or proteins other than those native to the cell. The vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known (see, e.g. Sambrook et al, Molecular Cloning. A Laboratory Manual, 2d edition, Cold Spring Harbor Laboratory, New York (1989)). In one embodiment, the vector is a viral vector. Viral vectors include, but are not limited to, retroviral and adenoviral vectors.

Suitable host cells or cell lines for transfection include bacterial cells. For example, the various strains of *E. coli* are well-known as host cells in the field of biotechnology. Various strains of *B. subtilis, Pseudomonas, Streptomyces*, and other bacilli and the like may also be employed. Many strains of yeast cells known to those skilled in the art are also available as host cells for expression of the peptides of the present invention. Other fungal cells or insect cells such as *Spodoptera frugipedera* (Sf9) cells may also be employed as expression systems. Alternatively, mammalian cells, such as human endothelial kidney 293 cells, Chinese hamster ovary cells (CHO), the monkey COS-1 cell line or murine 3T3 cells derived from Swiss, BALB/c or NIH mice may be used. Still other suitable host cells, as well as methods for transfection, culture, amplification, screening, production, and purification are known in the art.

The host cells can be transfected, e.g. by conventional means such as electroporation with at least one expression vector containing a nucleic acid of the population of the invention under the control of a transcriptional regulatory sequence. The transfected or transformed host cell is then cultured under conditions that allow expression of the protein. The expressed protein(s) is(are) recovered, isolated, and optionally purified from the cell or from the culture medium, if expressed extracellularly by appropriate means known to one of skill in the art. For example, the proteins are isolated in soluble form following cell lysis, or extracted using known techniques, e.g. in guanidine chloride. If desired, the proteins of the invention are produced as a fusion protein, in particular in case display of the proteins is intended. The proteins may be further purified using any of a variety of conventional methods including, but not limited to: liquid chromatography such as normal or reversed phase, using HPLC, FPLC and the like; affinity chromatography such as with inorganic ligands or monoclonal antibodies; size exclusion chromatography; immobilized metal chelate chromatography; gel electrophoresis; and the like. One of skill in the art may select the most appropriate isolation and purification techniques.

In a more preferred embodiment, the nucleic acids are comprised in an expression vector suitable for display of the protein encoded by the nucleic acid on a virus, a cell or a surface. Typically, the nucleic acids encode fusion proteins comprising a protein comprising at least one immunoglobulin variable domain having a rabbit-derived CDR3 amino acid sequence embedded in essentially human framework sequences and a protein sequence which allows display on a virus, a cell or a surface.

In a further embodiment, the present invention relates to a population of proteins comprising at least one immunoglobulin variable domain having a rabbit-derived CDR3 amino acid sequence embedded in essentially human framework sequences, obtainable by
(i) expressing at least one protein encoded by the population of the invention above in a suitable expression system, and
(ii) optionally displaying at least one protein on a virus, a cell or a surface.

The cell is preferably a bacterial cell or a eukaryotic cell, such as a yeast cell.

The preferred embodiments for the method of the invention also apply to the population of proteins of the invention.

In a preferred embodiment, the present invention relates to a population of 20 or more proteins, each comprising at least one immunoglobulin variable domain having a rabbit-derived CDR3 amino acid sequence embedded in essentially human framework sequences, wherein the rabbit-derived CDR3 amino acid sequences or the amino acid sequence further encompassing 1, 2, or 3 amino acids N-terminal and/or C-terminal of the rabbit-derived CDR3 amino acid sequence are diversified among the population of proteins, obtainable by
(i) expressing 20 or more proteins encoded by the population of the invention above in a suitable expression system, and
(ii) optionally displaying 20 or more proteins on a virus, a cell or a surface.

In a further embodiment, the present invention relates to a population of proteins comprising at least one immunoglobulin variable domain having a rabbit-derived CDR3 amino acid sequence embedded in essentially human framework sequences, obtainable by
(i) expressing at least one protein encoded by a population of the invention above in a suitable expression system, and
(ii) displaying at least one protein on a virus, a cell or a surface.

In a preferred embodiment, the at least one protein is displayed on a mRNA, a ribosome, a bacterium, a virus or a yeast.

Preferably, at least 2, 3, 4, 5, 6, 7, 8, 9, 10, 50, 100, 150, 200 or more proteins encoded by a population of the invention are expressed in a suitable expression system.

In a more preferred embodiment, at least 2, 3, 4, 5, 6, 7, 8, 9, 10, 50, 100, 150, 200 or more proteins encoded by a population of the invention are displayed on a virus, a cell or a surface, preferably wherein the proteins are fusion proteins, such as a fusion protein to a minor coat protein of a bacterial phage or to Agap2p.

A number of display techniques are known in the art, which enable a connection between genotype and binding properties of the antibodies. For example, display may be achieved by phage display, yeast display, bacterial display, ribosome display mRNA. For example, phage display is well-established and is for example described in the present examples. In phage display, the protein comprising the antigen of interest is expressed as a polypeptide fusion to a bacteriophage coat protein and subsequently screened by binding to immobilized or soluble biotinylated ligand (e.g., Huse et al., '89; Clackson et al., '91; Marks et al., '92). Fusions are made most commonly to a minor coat protein, called the gene III protein (pIII), which is present in three to five copies at the tip of the phage. A phage constructed in this way can be considered a compact genetic "unit", possessing both the phenotype (binding activity of the displayed antibody) and genotype (the gene coding for that antibody) in one package. Phage display has been successfully applied to antibodies, DNA binding proteins, protease inhibitors, short peptides, and enzymes.

Antibodies possessing desirable binding properties are preferably selected by binding to immobilized antigen in a process called "panning". Phage-bearing nonspecific antibodies are removed by washing, and then the bound phage are eluted and amplified by infection of E. coli. This approach has been applied to generate antibodies against many antigens.

Yeast display methods are well-known to a skilled person and are for example described in WO 99/36569. Typically, fusion proteins comprising the yeast protein Aga2p are used for displaying the proteins of interest at the cell surface.

Ribosome display techniques are also known in the art and are for example described in Hanes, J.; Plückthun, A. (1997; Proc. Natl. Acad. Sci. U.S.A. 94 (10): 4937-42) and He M. and Taussig M. J. (2007; Nature Methods 4 (3): 281-288).

In a further embodiment, the present invention relates to a library comprising a plurality, preferably 2, 3, 4, 5, 6, 7, 8, 9, 10, 50, 100, 150, 200, $10^3$, $10^4$, $10^5$, $10^6$ or more of replicable genetic packages, that are capable of displaying at least 1, 2, 3, 4, 5, 6, 7, 8, 9, 10, 50, 100, 150, 200 or more proteins encoded by a population of the invention on a virus, a cell or a surface.

In a further embodiment, the present invention relates to a library comprising a plurality, preferably 2, 3, 4, 5, 6, 7, 8, 9, 10, 50, 100, 150, 200, $10^3$, $10^4$, $10^5$, $10^6$ or more of replicable genetic packages, that display at least 1, 2, 3, 4, 5, 6, 7, 8, 9, 10, 50, 100, 150, 200 or more proteins encoded by a population of the invention on a virus, a cell or a surface.

A replicable genetic package is understood as a biological complex comprising a nucleic acid, and at least one peptide encoded by the nucleic acid. Examples of replicable genetic packages include cells, spores, bacteria, viruses and bacteriophage. Thus, the particular replicable genetic package or library thereof can be selected from any one of the foregoing and/or include different combinations thereof. Replicable genetic packages are capable of replication either by self-replication, in combination with a host and/or a helper virus, or by in vitro replication, transcription and expression.

Bacteriophages including phagemids are preferred replicable genetic packages. Preferred phage are the filamentous phage (e.g., M13, fd and fl) and phagemid vectors derived therefrom. See, WO 91/19818; WO 91/18989; WO 92/01047; WO 92/06204; WO 92/18619. Other phage of E. coli, such as T7 phage, or phage of other bacterial species can also be used. Filamentous phages are 6 nm in diameter and up to one micron in length. It has been used extensively in peptide phage display. Its surface consists of five coat proteins, two of which, pIII and pVIII, have been used to display peptide libraries, pIII contains 406 amino acids and is present in three to five copies. The major coat protein, pVIII, which contains 50 amino acids, constitutes the bulk of the phage protein as it is present in approximately 2700 copies. The bacteriophage can also be a non-filamentous phage such as icosahedral phages T7 and lambda. The major coat protein of T7 phage is the gene 10 capsid protein, which contains 370 amino acids and is present in 415 copies.

In addition to phage, the replicable genetic package of the invention can include eukaryotic viruses (e.g. the Moloney murine leukemia virus; see, e.g., Han, et al., Proc. Natl. Acad. Sci. USA 92:9747-9751 (1995)) or spores (e.g. spores from *B. subtilis*; see, e.g., Donovan, et al., J. Mol. Biol. 196:1-10 (1987)). A variety of different cells can also be used as replicable genetic packages in the present invention. Examples of suitable bacterial cells include, but are not limited to, *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli*.

In a yet further embodiment, the present invention relates to a method for screening for at least one protein comprising at least one immunoglobulin variable domain, in particular antibodies or fragments thereof, in particular selected from Fab, scFv and Fv, which specifically binds to an antigen of interest, comprising the following steps:
a) providing a library comprising a plurality, preferably 2, 3, 4, 5, 6, 7, 8, 9, 10, 50, 100, 150, 200, $10^3$, $10^4$, $10^5$, $10^6$ or more of replicable genetic packages that display at least 1, 2, 3, 4, 5, 6, 7, 8, 9, 10, 50, 100, 150, 200 or more proteins encoded by a population of the invention on a virus, a cell or a surface,
b) contacting the library of a) with at least one antigen of interest or a fragment thereof comprising at least one potential epitope,
c) isolating at least one genetic package which exhibits the desired binding property, in particular affinity, and
d) optionally determining the sequence or part of the sequence of the nucleic acid encoding the protein comprising at least one immunoglobulin variable domain,
e) optionally repeating steps a) to d) one or more times with 2 or more genetic packages isolated in step c).

As explained above, affinity to the antigen may be determined. For example, this can be performed by surface plasmon resonance spectroscopy, e.g. using a Biacore apparatus. For example, proteins exhibiting an affinity (Kd) of $10^{-8}$, $10^{-7}$, $10^{-8}$, $10^{-9}$ or less may be selected and optionally used in further screening rounds.

In a yet further embodiment, the method of the invention may be repeated one or more times, for example 1, 2, 3, 4, 5 or more times. Thereby, additional selection rounds are performed.

In a preferred embodiment, at least 2 of the displayed proteins have different CDR3 amino acid sequences, in particular different CDR-3H and/or CDR-3L amino acid sequences,
more preferably wherein at least 2, 3, 4, 5, 6, 7, 8, 9, 10, 50, 100, 150, 200 or more of the displayed proteins have different CDR3 amino acid sequences, in particular different CDR-3H and/or CDR-3L amino acid sequences, and/or wherein at least 50%, at least 80%, at least 90%, at least 95%, at least 96%, at least 97%, at least 98%, at least 99% or 100% of the nucleic acids of the of the displayed proteins have different CDR3 amino acid sequences, in particular different CDR-3H and/or CDR-3L amino acid sequences.

In a further embodiment, the present invention relates to a population of nucleic acids encoding at least one protein comprising at least one immunoglobulin variable domain having a rabbit-derived CDR3 amino acid sequence embedded in essentially human framework sequences, wherein the human framework sequences comprise a first human framework region (FR1), a second human framework region (FR2), a third human framework region (FR3), and a fourth human framework region (FR4), such that the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a rabbit-derived CDR3 amino acid sequence, wherein the nucleic acid sequences encoding the CDR1 and CDR2 amino acid sequences are diversified among the population of nucleic acids encoding at least one protein comprising at least one immunoglobulin variable domain, wherein each nucleic acid sequence encoding a CDR1 or CDR2 amino acid sequence is independently based i) on a nucleic acid sequence encoding a human CDR1 or CDR2, respectively, or ii) on a nucleic acid sequence encoding a rabbit CDR1 or CDR2, respectively, wherein at least some of the nucleic acid sequences encoding a CDR1 or CDR2 amino acid sequence have been modified to encode at least one amino acid present in rabbit CDR1 or CDR2 amino acid sequences, respectively, in case of human CDR1 or CDR2, respectively, or to encode at least one amino acid present in human CDR1 or CDR2 amino acid sequences, respectively, in case of rabbit CDR1 or CDR2, respectively, and wherein the human FR1, FR2, FR3 and FR4 regions are human framework regions selected to provide a scaffold conducive for rabbit CDR3 amino acid sequences, with the proviso:

that the two C-terminal amino acids of FR2 are optionally non-human, and that the two C-terminal amino acids of FR3 are optionally non-human.

It is understood that the preferred embodiments for the methods of the invention also apply to the populations of nucleic acids of the invention.

In particular, the human FR1, FR2, FR3 and FR4 regions are human framework regions with the proviso that the two C-terminal amino acids of FR2 are optionally non-human, and that the two C-terminal amino acids of FR3 are optionally non-human.

Human FR1, FR2, FR3 and FR4 regions are FR1, FR2, FR3 and FR4 regions which are naturally occurring in humans. As described above, the two C-terminal amino acids of FR2 are optionally non-human, and that the two C-terminal amino acids of FR3 are optionally non-human. Therefore, the FR1 and FR4 regions of the invention are human FR1 and FR4 regions. As also described above, it is possible that a nucleic acid encoding a rabbit-derived CDR3 amino acid sequence, preferably a rabbit-CDR3 amino acid sequence, further comprising 1, 2, or 3 amino acids N-terminal of the rabbit-derived CDR3 amino acid sequence, and/or 1, 2, or 3 amino acids C-terminal of the rabbit-derived CDR3 amino acid sequence is embedded, in particular in case a nucleic acid encoding a rabbit SDR is embedded. For example an SDR comprising the CDR-3H may be embedded.

In such embodiment, the following sequence comprising further N-terminal amino acids $Y_1Y_2$ is embedded (underlined):

(SEQ ID NO: 124)

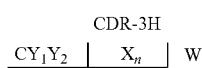

wherein $Y_1$ is a naturally occurring amino acid, preferably $Y_1$ is A,
$Y_2$ is a naturally occurring amino acid, preferably $Y_2$ is R.
$X_n$ represents a CDR3-H sequence. Accordingly, n is an integer between 1 and 50, preferably between 3 and 25 amino acids, more preferably between 5 and 21, and each X independently represents a naturally occurring amino acid.

The sequence "AR" is most common at the positions $Y_1Y_2$ both in rabbit antibodies and human antibodies. Accordingly, it is preferred that $Y_1$ is A and/or $Y_2$ is R. However, also other amino acids may be independently present at the indicated positions.

The position directly C-terminal to CDR3-H is always "W" both in humans and rabbits. Accordingly, this position is preferably not varied.

The position directly N-terminal to $Y_1Y_2$ is always "C" both in humans and rabbits. Therefore, the N-terminal "C" is also present in human heavy FR3 sequences, and the C-terminal "W" is also present in human heavy FR4 sequences. Accordingly, in case the FR3 and FR4 regions are interspaced by a rabbit-derived CDR3 amino acid sequence of the structure $CY_1Y_2|X_n|W$ (SEQ ID NO: 124), the resulting FR3 heavy region will contain rabbit-derived amino acids in the two C-terminal positions, whereas the remaining parts of the FR3 heavy region will be human, and the FR4 heavy region will be human.

Therefore, in another preferred embodiment, at least one nucleic acid encoding a rabbit CDR3 sequence is embedded, such that the human FR3 and FR4 regions are interspaced by a rabbit CDR3 amino acid sequence. Preferably, also the resulting FR3 and FR4 regions will be human.

Further, FR2 is a human FR2 framework region, or the two C-terminal amino acids of FR2 are optionally non-human. In one preferred embodiment, FR2 is a human FR2 framework region.

In another preferred embodiment, the two C-terminal amino acids of FR2 are non-human, whereas the remaining sequence of FR2 is human.

In particular, the two positions N-terminal to CDR-H2 (i.e. positions X10 and X11) are "VS" in the human:

In one preferred embodiment, V and/or S at positions X10 and X11 are independently non-human, preferably rabbit, in the heavy FR2 region.

In the Examples, a library was generated using two sets of heavy chain frameworks (FR1, FR2, FR3, and FR4), wherein the positions X10 and X11 of heavy FR2 are diversified as follows:

X10: Ile, Val
X11: Ala, Gly, or Ser

Therefore, in a more preferred embodiment, the following amino acids are present at the two C-terminal amino acids $Z_1Z_2$ of FR2 in at least one nucleic acid of the population:
$Z_1$: Ile or Val; $Z_2$: Ala, Gly or Ser.

In a further preferred embodiment, at least 2, 3, 4, 5, 6, 7, 8, 9, 10, 50, 100, 150, 200 or more nucleic acids of the population exhibit different amino acids at the two C-terminal amino acids of human FR2, more preferably at positions X10 and X11 of heavy human FR2.

In a further preferred embodiment, the population of nucleic acids encodes proteins comprising at least a VH domain and/or at least one VL domain, more preferably the nucleic acids encode an antibody, an scFv, a Fv or Fab.

The nucleic acids encoding the CDR1 and CDR2 amino acid sequences are diversified among the population of nucleic acids encoding at least one protein comprising at least one immunoglobulin variable domain, wherein each nucleic acid sequence encoding a CDR1 or CDR2 amino acid sequence is independently based i) on a nucleic acid sequence encoding a human CDR1 or CDR2, respectively, or ii) on a nucleic acid sequence encoding a rabbit CDR1 or CDR2, respectively, wherein at least some of the nucleic acid sequences encoding a CDR1 or CDR2 amino acid sequence have been modified to encode at least one amino acid present in rabbit CDR1 or CDR2 amino acid sequences, respectively, in case of human CDR1 or CDR2, respectively, or to encode at least one amino acid present in human CDR1 or CDR2 amino acid sequences, respectively, in case of rabbit CDR1 or CDR2, respectively.

A diversified CDR1 and CDR2 sequences according to the invention are obtainable by computationally integrating a plurality, such as $10^4$, $10^5$, $10^6$, $10^7$, $10^8$ or more of simulated humanizations across the rabbit antibody repertoire and the human acceptor antibody repertoire, in order to generate a mathematically optimal Bayesian representation of the humanization space between rabbit and human, converting the probabilistic model to a frequentist interpretation, thereby obtaining a population or library. Each position ends up containing a probability of encountering the human germline residue, the rabbit germline residues, and the most common collection of affinity maturation residues from both species.

In a preferred embodiment, cysteine, and/or methionine residues are removed and/or the asparagine residue content is reduced, as these residues form biochemical liabilities.

In a yet further preferred embodiment of the present invention, the human or rabbit CDR1 regions and the human and rabbit CDR2 regions, on which the diversified CDR1 and CDR2 amino acid sequences are based, are selected from human germline CDR1 regions, human germline CDR2 regions, rabbit germline CDR1 regions, rabbit germline CDR2 regions, human somatic hypermutation CDR1 regions, human somatic hypermutation CDR2 regions, rabbit somatic hypermutation CDR1 regions, rabbit somatic hypermutation CDR2 regions, rabbit gene conversion CDR1 regions, and rabbit gene conversion CDR2 regions.

In a yet further preferred embodiment of the present invention, the diversified CDR1 and CDR2 amino acid sequences are CDR-H1, CDR-H2, CDR-L1 and/or CDR-L2 sequences.

In a preferred embodiment, the population includes at least one nucleic acid encoding a human CDR-H1, and/or a human CDR-H2, and/or a human CDR-L1 and/or a human CDR-L2 sequence.

In a further preferred embodiment, the population includes at least one nucleic acid encoding a rabbit CDR-H1, and/or a rabbit CDR-H2, and/or a rabbit CDR-L1 and/or a rabbit CDR-L2 sequence.

According to the invention, the human FR1, FR2, FR3 and FR4 regions are human framework regions selected to provide a scaffold conducive for rabbit CDR3 amino acid sequences, with the proviso that the two C-terminal amino acids of FR2 are optionally non-human, and that the two C-terminal amino acids of FR3 are optionally non-human. Therefore, in one preferred embodiment, the population of the invention comprises at least one nucleic acid encoding a human FR1, a human FR2, a human FR3 and a human FR4 region, and a human CDR1, and a human CDR2 region.

In another preferred embodiment, the population of the invention comprises at least one nucleic acid encoding a human FR1, a human FR2, a human FR3 and a human FR4 region, and a rabbit CDR1, and a rabbit CDR2 region.

Therefore, in yet another preferred embodiment, the population of the invention does not contain a nucleic acid encoding a human FR1, a human FR2, a human FR3 and a human FR4 region, and a human CDR1, and a human CDR2 region. Therefore, in yet another preferred embodiment, the population of the invention does not contain a nucleic acid encoding a human FR1, a human FR2, a human FR3 and a human FR4 region, and a rabbit CDR1, and a rabbit CDR2 region.

A suitable scaffold conducive for rabbit CDR3 amino acid sequences is obtainable by selecting a framework set by performing the following steps:
  computational imputation of germline repertoire element centroids which are most utilized in functional rabbit antibodies
  generating an amino acid alignment of human frameworks compared to said computationally imputed rabbit frameworks and selecting the closest representatives, respectively, that have the same length of CDR-H1, CDR-H2, CDR-L1, and CDR-L2 and similar sequence composition, respectively,
  further reducing the number of candidates framework sequences by preferring templates that are known to be stable in the art and optionally have worked as previous drugs,
  further reducing the number of framework candidates by structurally modeling antibodies from rabbit and human using these frameworks and analyzing their structural superposition tolerance by root mean squared deviation (RMSD), and
  selecting a set of 1, 2, 3, 4, 5, 6, 7, 8, 9 or 10 heavy chain and 1, 2, 3, 4, 5, 6, 7, 8, 9 or 10 light chain frameworks comprising set of FR1, FR2, FR3 and FR4 regions, respectively.

In the Examples, a set of 2 heavy chain and 2 light chain frameworks comprising set of FR1, FR2, FR3 and FR4 regions respectively, were present. Moreover, the two C-terminal amino acids of heavy chain FR2 are optionally non-human, and the two C-terminal amino acids of heavy chain FR3 are optionally non-human, for example in case an SDR is grafted into a scaffold, or in case amino acids surrounding FR2 are substituted, as described above.

Therefore, in one preferred embodiment, the heavy FR1 to FR4 regions of VH3_23 and/or VH3_53 are used in the populations of the present invention.

Therefore, in one preferred embodiment, the light FR1 to FR4 regions of VK-1_27 and/or VK-3_20 are used in the populations of the present invention.

Therefore, in a yet further preferred embodiment of the present invention, the human FR1, FR2, FR3 and FR4 regions which are human framework regions selected to provide a scaffold conducive for rabbit CDR3 amino acid sequences are obtainable by:

(i) providing
  (a) a collection of sequences of naturally occurring human antibodies each comprising a set of human FR1, FR2, FR3 and FR4 regions; and
  (b) a collection of sequences of naturally occurring rabbit antibodies each comprising a set of rabbit FR1, FR2, FR3 and FR4 regions, and
(ii) identifying a plurality of sets of human FR1, FR2, FR3 and FR4 regions which provide a scaffold conducive for rabbit CDR3 amino acid sequences by
  determining the parameters framework homology, CDR homology, CDR lengths, CDR canonical structure, and spatial orientation of CDR loops, and
  selecting sets of human FR1, FR2, FR3 and FR4 regions which exhibit high scores for the parameters,
  and/or
  the two C-terminal amino acids of heavy chain FR2 are optionally non-human, and
  the two C-terminal amino acids of heavy chain FR3 are optionally non-human.

Therefore, in a preferred embodiment of the present invention, the human framework sequences independently comprise a set of human FR1, FR2, FR3 and FR4 regions selected from human VH3-23, human VH3-53, human Vk1-27, and/or Vk3-20 framework regions,
  with the proviso:
  that the two C-terminal amino acids of FR2 are optionally non-human, and
  that the two C-terminal amino acids of FR3 are optionally non-human.

In a further embodiment, the present invention relates to a population of proteins comprising at least one immunoglobulin variable domain having a rabbit-derived CDR3 amino acid sequence embedded in essentially human framework sequences, and wherein the proteins further comprise at least one moiety allowing display of the at least one protein on a virus, a cell, or a surface.

Suitable moieties, in particular protein moieties allowing display are known in the art and described herein, such as Aga2p and pIII.

The cell is preferably a bacterial cell or a eukaryotic cell, such as a yeast cell.

In a preferred embodiment, at least 2 of the nucleic acids of the population encode different CDR3 amino acid sequences, in particular different CDR-3H and/or CDR-3L amino acid sequences,
  more preferably wherein at least 2, 3, 4, 5, 6, 7, 8, 9, 10, 50, 100, 150, 200 or more encode different CDR3 amino acid sequences, in particular different CDR-3H and/or CDR-3L amino acid sequence, and/or
  wherein at least 50%, at least 80%, at least 90%, at least 95%, at least 96%, at least 97%, at least 98%, at least 99% or 100% of the nucleic acids of the population encode different CDR3 amino acid sequences, in particular different CDR-3H and/or CDR-3L amino acid sequences. In a more preferred embodiment the, sequences are diversified due to immunization of one or more rabbits with a target of interest. Preferably, the sequences are diversified within the CDR3 amino acid sequence, in case the sequence further encompasses 1, 2, or 3 amino acids N-terminal and/or C-terminal of the rabbit-derived CDR3 amino acid sequence.

The population of nucleic acids of the invention is particularly useful for mass humanization of rabbit antibodies and subsequent screening for antibodies for suitable binding properties for an antigen of interest.

By expressing the population of nucleic acids in a suitable expression system for display, a population of displayed, mass humanized proteins, in particular antibodies or antibody fragments such as scFv, Fv or Fab is obtained, which contain rabbit CDR3 or rabbit-derived CDR3 regions.

Therefore, in a further embodiment, the present invention relates to a population of proteins comprising at least one immunoglobulin variable domain having a rabbit-derived CDR3 amino acid sequence embedded in essentially human framework sequences, obtainable by
(i) expressing at least one protein encoded by a population of the invention above in a suitable expression system, and
(ii) displaying at least one protein on a virus, a cell or a surface.

Preferably, at least 2, 3, 4, 5, 6, 7, 8, 9, 10, 50, 100, 150, 200 or more proteins encoded by a population of the invention are expressed in a suitable expression system.

In a more preferred embodiment, at least 2, 3, 4, 5, 6, 7, 8, 9, 10, 50, 100, 150, 200 or more proteins encoded by a population of the invention are displayed on a virus, a cell or a surface, preferably wherein the proteins are fusion proteins, such as a fusion protein to a minor coat protein of a bacterial phage or to Agap2p.

By expressing the population of nucleic acids in a suitable expression system a population of mass humanized proteins, in particular antibodies or antibody fragments such as scFv, Fv or Fab is obtained, which contain rabbit CDR3 or rabbit-derived CDR3 regions.

Therefore, in a further embodiment, the present invention relates to a population of proteins comprising at least one immunoglobulin variable domain having a rabbit-derived CDR3 amino acid sequence embedded in essentially human framework sequences, wherein the human framework sequences comprise a first human framework region (FR1), a second human framework region (FR2), a third human framework region (FR3), and a fourth human framework region (FR4), such that the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a rabbit-derived CDR3 amino acid sequence, wherein the CDR1 and CDR2 amino acid sequences are diversified among the population of proteins comprising at least one immunoglobulin variable domain, wherein each CDR1 or CDR2 amino acid sequence is independently based
 i) on a human CDR1 or CDR2, respectively, or
 ii) on a rabbit CDR1 or CDR2, respectively, wherein at least some of the CDR1 or CDR2 amino acid sequences have been modified to comprise at least one amino acid present in rabbit CDR1 or CDR2 amino acid sequences, respectively, in case of human CDR1 or CDR2, respectively, or to comprise at least one amino acid present in human CDR1 or CDR2 amino acid sequences, respectively, in case of rabbit CDR1 or CDR2, respectively, and wherein the human FR1, FR2, FR3 and FR4 regions are human framework regions selected to provide a scaffold conducive for rabbit CDR3 amino acid sequences,
 with the proviso:
  that the two C-terminal amino acids of FR2 are optionally non-human, and
  that the two C-terminal amino acids of FR3 are optionally non-human.

In a more preferred embodiment, the present invention relates to a population of 20 or more nucleic acids, each encoding at least one protein comprising at least one immunoglobulin variable domain having a rabbit-derived CDR3 amino acid sequence embedded in essentially human framework sequences, wherein the human framework sequences comprise a first human framework region (FR1), a second human framework region (FR2), a third human framework region (FR3), and a fourth human framework region (FR4), such that the FR1 and FR2 regions are interspaced by a complementarity determining region 1 (CDR1), the FR2 and FR3 regions are interspaced by a complementarity determining region 2 (CDR2), and the FR3 and FR4 regions are interspaced by a rabbit-derived CDR3 amino acid sequence, wherein the nucleic acid sequences encoding the CDR1 and CDR2 amino acid sequences are diversified among the population of nucleic acids encoding at least one protein comprising at least one immunoglobulin variable domain, wherein each nucleic acid sequence encoding a CDR1 or CDR2 amino acid sequence is independently based
 i) on a nucleic acid sequence encoding a human CDR1 or CDR2, respectively, or
 ii) on a nucleic acid sequence encoding a rabbit CDR1 or CDR2, respectively, wherein at least some of the nucleic acid sequences encoding a CDR1 or CDR2 amino acid sequence have been modified to encode at least one amino acid present in rabbit CDR1 or CDR2 amino acid sequences, respectively, in case of human CDR1 or CDR2, respectively, or to encode at least one amino acid present in human CDR1 or CDR2 amino acid sequences, respectively, in case of rabbit CDR1 or CDR2, respectively, and wherein the human FR1, FR2, FR3 and FR4 regions are human framework regions selected to provide a scaffold conducive for rabbit CDR3 amino acid sequences, and wherein the nucleic acid sequences encoding the rabbit-derived CDR3 amino acid sequences or the amino acid sequences further encompassing 1, 2, or 3 amino acids N-terminal and/or C-terminal of the rabbit-derived CDR3 amino acid sequence are diversified among the population of nucleic acids, and wherein at least 10 of the nucleic acids of the population encode different CDR3 amino acid sequences,
 with the proviso:
  that the two C-terminal amino acids of FR2 are optionally non-human, and
  that the two C-terminal amino acids of FR3 are optionally non-human.

In a further preferred embodiment, at least 50% of the nucleic acids of the population encode different CDR3 amino acid sequences.

The populations or libraries of the invention are particularly suitable for mass humanization of rabbit antibodies and allow for generalizing the humanization process by providing scaffolds that represent the codified landscape of all intermediate humanization across rabbit and human with a population or library that explores the space between both species.

In a preferred embodiment, the present invention relates to a population of proteins comprising at least one immunoglobulin variable domain having a rabbit-derived CDR3 amino acid sequence embedded in essentially human framework sequences of the invention as described above, wherein the at least one protein comprising at least one immunoglobulin variable domain having a rabbit-derived CDR3 amino acid sequence embedded in essentially human framework sequences
 comprises a VH domain, or a VL domain, or a VH domain and a VL domain, or a heavy chain of an antibody or a fragment thereof comprising the VH domain, and/or a light chain of an antibody or a fragment thereof comprising the VL domain and/or an scFv, more preferably an scFv, and/or is selected from an immunoglobulin molecule, a disulfide linked Fv, a monoclonal antibody, an scFv, a single domain antibody, a diabody, a multispecific antibody, a Fab, a Fab', a bispecific antibody; a F(ab')2, or an Fv, more preferably an scFv, and wherein the at least one protein optionally further comprises at least one moiety allowing display of the at least one protein on a virus, a cell, or a surface.

In a more preferred embodiment, at least one protein optionally further comprises at least one moiety allowing display of the at least one protein on a virus, a cell, or a surface. Such moieties allowing display are described herein.

In a further preferred embodiment, the present invention relates to a population of proteins comprising at least one immunoglobulin variable domain having a rabbit-derived CDR3 amino acid sequence embedded in essentially human framework sequences of the invention as described above, wherein the at least one protein comprising at least one immunoglobulin variable domain having a rabbit-derived CDR3 amino acid sequence embedded in essentially human framework sequences, wherein one or more, preferably 1, 2, 3, or 4, different sets of framework regions comprising a first human framework region (FR1), a second human framework region (FR2), a third human framework region (FR3), and a fourth human framework region (FR4) are present in the VH domains, and/or one or more, preferably 1, 2, 3, or 4, different sets of framework regions comprising a first human framework region (FR1), a second human framework region (FR2), a third human framework region (FR3), and a fourth human framework region (FR4) are present in the VL domains, with the proviso:

that the two C-terminal amino acids of FR2 are optionally non-human, and that the two C-terminal amino acids of FR3 are optionally non-human.

Preferably, the different sets of framework regions are selected from human VH3-23, human VH3-53, human Vk1-27, and Vk3-20 framework regions.

Preferably, the different sets of heavy chain framework regions are selected from human VH3-23 and human VH3-53 framework regions.

Preferably, the different sets of light chain framework regions are selected from human Vk1-27 and human Vk3-20 framework regions.

Therefore, in a preferred embodiment of the present invention, the human framework sequences independently comprise a set of human FR1, FR2, FR3 and FR4 regions selected from human VH3-23, human VH3-53, human Vk1-27, and/or Vk3-20 framework regions, with the proviso:

that the two C-terminal amino acids of FR2 are optionally non-human, and that the two C-terminal amino acids of FR3 are optionally non-human.

In a preferred embodiment, the population the present invention comprising at least 20 proteins, each comprising at least one immunoglobulin variable domain having a rabbit-derived CDR3 amino acid sequence embedded in essentially human framework sequences as described above is characterized in that the at least 20 proteins comprising at least one immunoglobulin variable domain having a rabbit-derived CDR3 amino acid sequence embedded in essentially human framework sequences each comprise a VH domain, or a VL domain, or a VH domain and a VL domain, or a heavy chain of an antibody or a fragment thereof comprising the VH domain, and/or a light chain of an antibody or a fragment thereof comprising the VL domain and/or an scFv, more preferably an scFv, and/or each are selected from an immunoglobulin molecule, a disulfide linked Fv, a monoclonal antibody, an scFv, a single domain antibody, a diabody, a multispecific antibody, a Fab, a Fab', a bispecific antibody; a F(ab')2, or an Fv, more preferably an scFv, and wherein the at least 20 proteins each optionally further comprise at least one moiety allowing display of the at least 20 proteins on a virus, a cell, or a surface.

In a further more preferred embodiment,
(a) at least 5 proteins of the population exhibit different CDR1 and/or CDR2 amino acid sequence, more preferably at least 6, 7, 8, 9, 10, 50, 100, 150, 200 or more proteins of the population exhibit different CDR1 and/or CDR2 nucleic sequences, and/or
(b) at least 80% of the proteins of the population exhibit different CDR1 and/or CDR2 amino acid sequences, more preferably at least 90%, at least 95%, at least 96%, at least 97%, at least 98%, at least 99% or 100% of the nucleic acids of the population exhibit different CDR1 and/or CDR2 nucleic sequences.

In a yet further preferred embodiment, the CDR1 and CDR2 amino acid sequences are diversified among each set of framework regions.

It is understood that the preferred embodiments for the methods of the invention also apply to the populations of proteins of the invention.

In particular, the human FR1, FR2, FR3 and FR4 regions are human framework regions with the proviso that the two C-terminal amino acids of FR2 are optionally non-human, and that the two C-terminal amino acids of FR3 are optionally non-human.

Human FR1, FR2, FR3 and FR4 regions are FR1, FR2, FR3 and FR4 regions which are naturally occurring in humans. As described above, the two C-terminal amino acids of FR2 are optionally non-human, and that the two C-terminal amino acids of FR3 are optionally non-human. Therefore, the FR1 and FR4 regions of the invention are human FR1 and FR4 regions. As also described above, it is possible that a rabbit-derived CDR3 amino acid sequence, preferably a rabbit-CDR3 amino acid sequence, further comprising 1, 2, or 3 amino acids N-terminal of the rabbit-derived CDR3 amino acid sequence, and/or 1, 2, or 3 amino acids C-terminal of the rabbit-derived CDR3 amino acid sequence is embedded, in particular in case a rabbit SDR is embedded. For example an SDR comprising the CDR-3H may be embedded.

In such embodiment, the following sequence comprising further N-terminal amino acids $Y_1Y_2$ is embedded (underlined):

(SEQ ID NO: 124)

| <u>C$Y_1Y_2$</u> | CDR-3H<br><u>$X_n$</u> | W |
|---|---|---| wherein $Y_1$ is a naturally occurring amino acid, preferably $Y_1$ is A,
$Y_2$ is a naturally occurring amino acid, preferably $Y_2$ is R,
$X_n$ represents a CDR3-H sequence. Accordingly, n is an integer between 1 and 50, preferably between 3 and 25 amino acids, more preferably between 5 and 21, and each X independently represents a naturally occurring amino acid, The sequence "AR" is most common at the positions $Y_1Y_2$ both in rabbit antibodies and human antibodies. Accordingly, it is preferred that $Y_1$ is A and/or $Y_2$ is R. However, also other amino acids may be independently present at the indicated positions.

The position directly C-terminal to CDR3-H is always "W" both in humans and rabbits. Accordingly, this position is preferably not varied.

The position directly N-terminal to $Y_1Y_2$ is always "C" both in humans and rabbits. Therefore, the N-terminal "C" is also present in human heavy FR3 sequences, and the C-terminal "W" is also present in human heavy FR4 sequences. Accordingly, in case the FR3 and FR4 regions are interspaced by a rabbit-derived CDR3 amino acid sequence of the structure $CY_1Y_2|X_n|W$ (SEQ ID NO: 124), the resulting FR3 heavy region will contain rabbit-derived amino acids in the two C-terminal positions, whereas the remaining parts of the FR3 heavy region will be human, and the FR4 heavy region will be human.

Therefore, in another preferred embodiment, at least one rabbit CDR3 sequence is embedded, such that the human FR3 and FR4 regions are interspaced by a rabbit CDR3 amino acid sequence. Preferably, also the resulting FR3 and FR4 regions will be human.

Further, FR2 is a human FR2 framework region, or the two C-terminal amino acids of FR2 are optionally non-human. In one preferred embodiment, FR2 is a human FR2 framework region.

In another preferred embodiment, the two C-terminal amino acids of FR2 are non-human, whereas the remaining sequence of FR2 is human.

In particular, the two positions N-terminal to CDR-H2 (i.e. positions X10 and X11) are "VS" in the human:

CDR-H2: GLEW<u>VS</u>|X12X13X14X15X16X17X18X19X20X21X22X23DSVKG| RFT (SEQ ID NO: 126).

In one preferred embodiment, V and/or S at positions X10 and X11 are independently non-human, preferably rabbit, in the heavy FR2 region.

In the Examples, a library was generated using two sets of heavy chain frameworks (FR1, FR2, FR3, and FR4), wherein the positions X10 and X11 of heavy FR2 are diversified as follows:

X10: Ile, Val
X11: Ala, Gly, or Ser.

Therefore, in a more preferred embodiment, the following amino acids are present at the two C-terminal amino acids $Z_1Z_2$ of FR2 in at least one protein of the population: $Z_1$: Ile or Val; $Z_2$: Ala, Gly or Ser.

In a further preferred embodiment, at least 2, 3, 4, 5, 6, 7, 8, 9, 10, 50, 100, 150, 200 or more proteins of the population exhibit different amino acids at the two C-terminal amino acids of human FR2, more preferably at positions X10 and X11 of heavy human FR2.

In a further preferred embodiment, the proteins of the population comprise at least one VH domain and/or at least one VL domain, more preferably the proteins comprise or represent an antibody, an scFv, a Fv or Fab.

The CDR1 and CDR2 amino acid sequences are diversified among the population of proteins comprising at least one immunoglobulin variable domain, wherein each CDR1 or CDR2 amino acid sequence is independently based i) on a human CDR1 or CDR2, respectively, or ii) on a rabbit CDR1 or CDR2, respectively, wherein at least some of the CDR1 or CDR2 amino acid sequences have been modified to contain at least one amino acid present in rabbit CDR1 or CDR2 amino acid sequences, respectively, in case of human CDR1 or CDR2, respectively, or to contain at least one amino acid present in human CDR1 or CDR2 amino acid sequences, respectively, in case of rabbit CDR1 or CDR2, respectively.

Diversified CDR1 and CDR2 sequences according to the invention are obtainable by computationally integrating a plurality, such as $10^4, 10^5, 10^6, 10^7, 10^8$ or more of simulated humanizations across the rabbit antibody repertoire and the human acceptor antibody repertoire, in order to generate a mathematically optimal Bayesian representation of the humanization space between rabbit and human, converting the probabilistic model to a frequentist interpretation, thereby obtaining a population or library. Each position ends up containing a probability of encountering the human germline residue, the rabbit germline residues, and the most common collection of affinity maturation residues from both species.

In a preferred embodiment, cysteine, and/or methionine residues are removed and/or the asparagine residue content is reduced, as these residues form biochemical liabilities.

In a yet further preferred embodiment of the present invention, the human or rabbit CDR1 regions and the human and rabbit CDR2 regions, on which the diversified CDR1 and CDR2 amino acid sequences are based, are selected from human germline CDR1 regions, human germline CDR2 regions, rabbit germline CDR1 regions, rabbit germline CDR2 regions, human somatic hypermutation CDR1 regions, human somatic hypermutation CDR2 regions, rabbit somatic hypermutation CDR1 regions, rabbit somatic hypermutation CDR2 regions, rabbit gene conversion CDR1 regions, and rabbit gene conversion CDR2 regions.

In a yet further preferred embodiment of the present invention, the diversified CDR1 and CDR2 amino acid sequences are CDR-H1, CDR-H2, CDR-L1 and/or CDR-L2 sequences.

In a preferred embodiment, the population includes at least one human CDR-H1, and/or a human CDR-H2, and/or a human CDR-L1 and/or a human CDR-L2 sequence.

In a further preferred embodiment, the population includes at least one rabbit CDR-H1, and/or a rabbit CDR-H2, and/or a rabbit CDR-L1 and/or a rabbit CDR-L2 sequence.

According to the invention, the human FR1, FR2, FR3 and FR4 regions are human framework regions selected to provide a scaffold conducive for rabbit CDR3 amino acid sequences, with the proviso that the two C-terminal amino acids of FR2 are optionally non-human, and that the two C-terminal amino acids of FR3 are optionally non-human. Therefore, in one preferred embodiment, the population of the invention comprises at least one protein comprising a human FR1, a human FR2, a human FR3 and a human FR4 region, and a human CDR1, and a human CDR2 region.

In another preferred embodiment, the population of the invention comprises at least one protein comprising a human FR1, a human FR2, a human FR3 and a human FR4 region, and a rabbit CDR1, and a rabbit CDR2 region.

Therefore, in yet another preferred embodiment, the population of the invention does not contain a protein comprising a human FR1, a human FR2, a human FR3 and a human FR4 region, and a human CDR1, and a human CDR2 region.

Therefore, in yet another preferred embodiment, the population of the invention does not contain a protein comprising a human FR1, a human FR2, a human FR3 and a human FR4 region, and a rabbit CDR1, and a rabbit CDR2 region.

A suitable scaffold conducive for rabbit CDR3 amino acid sequences is obtainable by selecting a framework set by performing the following steps:
  computational imputation of germline repertoire element centroids which are most utilized in functional rabbit antibodies
  generating an amino acid alignment of human frameworks compared to said computationally imputed rabbit frameworks and selecting the closest representatives, respectively, that have the same length of CDR-H1, CDR-H2, CDR-L1, and CDR-L2 and similar sequence composition, respectively,
  further reducing the number of candidates framework sequences by preferring templates that are known to be stable in the art and optionally have worked as previous drugs,
  further reducing the number of framework candidates by structurally modeling antibodies from rabbit and human using these frameworks and analyzing their structural superposition tolerance by root mean squared deviation (RMSD), and
  selecting a set of 1, 2, 3, 4, 5, 6, 7, 8, 9 or 10 heavy chain and 1, 2, 3, 4, 5, 6, 7, 8, 9 or 10 light chain frameworks comprising set of FR1, FR2, FR3 and FR4 regions, respectively.

In the Examples, a set of 2 heavy chain and 2 light chain frameworks comprising set of FR1, FR2, FR3 and FR4 regions respectively, were present. Moreover, the two C-terminal amino acids of heavy chain FR2 are optionally non-human, and the two C-terminal amino acids of heavy chain FR3 are optionally non-human, for example in case an SDR is grafted into a scaffold, or in case amino acids surrounding FR2 are substituted, as described above.

In a preferred embodiment of the present invention, the human framework sequences independently comprise a set of human FR1, FR2, FR3 and FR4 regions selected from human VH3-23, human VH3-53, human Vk1-27, and/or Vk3-20 framework regions, with the proviso:
  that the two C-terminal amino acids of FR2 are optionally non-human, and
  that the two C-terminal amino acids of FR3 are optionally non-human.

Therefore, in one preferred embodiment, the heavy FR1 to FR4 regions of VH3_23 and/or VH3_53 are used in the populations of the present invention.

Therefore, in one preferred embodiment, the light FR1 to FR4 regions of VK-1_27 and/or VK-3_20 are used in the populations of the present invention.

Therefore, in a yet further preferred embodiment of the present invention, the human FR1, FR2, FR3 and FR4 regions which are human framework regions selected to provide a scaffold conducive for rabbit CDR3 amino acid sequences are obtainable by:
(i) providing
  (a) a collection of sequences of naturally occurring human antibodies each comprising a set of human FR1, FR2, FR3 and FR4 regions; and
  (b) a collection of sequences of naturally occurring rabbit antibodies each comprising a set of rabbit FR1, FR2, FR3 and FR4 regions, and
(ii) identifying a plurality of sets of human FR1, FR2, FR3 and FR4 regions which provide a scaffold conducive for rabbit CDR3 amino acid sequences by
  determining the parameters framework homology, CDR homology, CDR lengths, CDR canonical structure, and spatial orientation of CDR loops, and
  selecting sets of human FR1, FR2, FR3 and FR4 regions which exhibit high scores for the parameters,
and/or
  the two C-terminal amino acids of heavy chain FR2 are optionally non-human, and
  the two C-terminal amino acids of heavy chain FR3 are optionally non-human.

In a preferred embodiment, at least 2 of the proteins of the population comprise different CDR3 amino acid sequences, in particular different CDR-3H and/or CDR-3L amino acid sequences,
  more preferably wherein at least 2, 3, 4, 5, 6, 7, 8, 9, 10, 50, 100, 150, 200 or more proteins comprise different CDR3 amino acid sequences, in particular different CDR-3H and/or CDR-3L amino acid sequence, and/or
  wherein at least 50%, at least 80%, at least 90%, at least 95%, at least 96%, at least 97%, at least 98%, at least 99% or 100% of the proteins comprise different CDR3 amino acid sequences, in particular different CDR-3H and/or CDR-3L amino acid sequences. In a more preferred embodiment the sequences are diversified due to immunization of one or more rabbits with a target of interest. Preferably, the sequences are diversified within the CDR3 amino acid sequence, in case the sequence further encompasses 1, 2, or 3 amino acids N-terminal and/or C-terminal of the rabbit-derived CDR3 amino acid sequence.

The population of proteins of the invention is particularly useful for mass humanization of rabbit antibodies and subsequent screening for antibodies for suitable binding properties for an antigen of interest.

Further, the invention provides for Acceptor framework libraries, which are suitable for methods and uses of the present invention.

In a further embodiment, the present invention relates to a population of Acceptor Framework nucleic acid,
  wherein each Acceptor Framework nucleic acid comprises
  nucleic acids encoding a set of framework regions comprising a first human framework region (FR1), a second human framework region (FR2), a third human framework region (FR3), and a fourth human framework region (FR4),
  wherein the FR1 and FR2 regions are interspaced by a complementarity determining region 1 (CDR1), the FR2 and FR3 regions are interspaced by a complementarity determining region 2 (CDR2), and the nucleic acid sequences encoding FR3 and FR4 regions are linked directly or are interspaced by a stuffer nucleic acid sequence, and
  wherein the nucleic acid sequences encoding the CDR1 and CDR2 amino acid sequences are diversified among the population of nucleic acids encoding at least one protein comprising at least one immunoglobulin variable domain, wherein each nucleic acid sequence encoding a CDR1 or CDR2 amino acid sequence is independently based
  i) on a nucleic acid sequence encoding a human CDR1 or CDR2, respectively, or
  ii) on a nucleic acid sequence encoding a rabbit CDR1 or CDR2, respectively,
  wherein at least some of the nucleic acid sequences encoding a CDR1 or CDR2 amino acid sequence have been modified to encode at least one amino acid present in rabbit CDR1 or CDR2 amino acid sequences, respectively, in case of human CDR1 or CDR2, respectively, or to encode at least one amino acid present in human CDR1 or CDR2 amino acid sequences, respectively, in case of rabbit CDR1 or CDR2, respectively, and wherein the human FR1, FR2, FR3 and FR4 regions are human framework regions selected to provide a scaffold conducive for rabbit CDR3 amino acid sequences, with the proviso:

that the two C-terminal amino acids of FR2 are optionally non-human, and that the two C-terminal amino acids of FR3 are optionally non-human.

It is understood that the preferred embodiments for the methods of the invention and populations of the invention also apply to the populations of Acceptor Framework nucleic acids of the invention.

In particular, the human FR1, FR2, FR3 and FR4 regions are human framework regions with the proviso that the two C-terminal amino acids of FR2 are optionally non-human, and that the two C-terminal amino acids of FR3 are optionally non-human.

Human FR1, FR2, FR3 and FR4 regions are FR1, FR2, FR3 and FR4 regions which are naturally occurring in humans. As described above, the two C-terminal amino acids of FR2 are optionally non-human, and that the two C-terminal amino acids of FR3 are optionally non-human. Therefore, the FR1 and FR4 regions of the invention are human FR1 and FR4 regions. Preferably, the FR3 is human.

Further, FR2 is a human FR2 framework region, or the two C-terminal amino acids of FR2 are optionally non-human. In one preferred embodiment, FR2 is a human FR2 framework region.

In another preferred embodiment, the two C-terminal amino acids of FR2 are non-human, whereas the remaining sequence of FR2 is human.

In particular, the two positions N-terminal to CDR-H2 (i.e. positions X10 and X11) are "VS" in the human:

CDR-H2: GLEW<u>VS</u>|X12X13X14X15X16X17X18X19X20X21X22 X23DSVKG| RFT (SEQ ID NO: 126).

In one preferred embodiment, V and/or S at positions X10 and X11 are independently non-human, preferably rabbit, in the heavy FR2 region.

In the Examples, a library was generated using two sets of heavy chain frameworks (FR1, FR2, FR3, and FR4), wherein the positions X10 and X11 of heavy FR2 are diversified as follows:

X10: Ile, Val

X11: Ala, Gly, or Ser

Therefore, in a more preferred embodiment, the following amino acids are present at the two C-terminal amino acids $Z_1Z_2$ of FR2 in at least one nucleic acid of the population: $Z_1$: Ile or Val; $Z_2$: Ala, Gly or Ser.

In a further preferred embodiment, at least 2, 3, 4, 5, 6, 7, 8, 9, 10, 50, 100, 150, 200 or more nucleic acids of the population exhibit different amino acids at the two C-terminal amino acids of human FR2, more preferably at positions X10 and X11 of heavy human FR2.

The nucleic acids encoding the CDR1 and CDR2 amino acid sequences are diversified among the population of Acceptor Framework nucleic acids, wherein each nucleic acid sequence encoding a CDR1 or CDR2 amino acid sequence is independently based i) on a nucleic acid sequence encoding a human CDR1 or CDR2, respectively, or ii) on a nucleic acid sequence encoding a rabbit CDR1 or CDR2, respectively, wherein at least some of the nucleic acid sequences encoding a CDR1 or CDR2 amino acid sequence have been modified to encode at least one amino acid present in rabbit CDR1 or CDR2 amino acid sequences, respectively, in case of human CDR1 or CDR2, respectively, or to encode at least one amino acid present in human CDR1 or CDR2 amino acid sequences, respectively, in case of rabbit CDR1 or CDR2, respectively.

Accordingly, in a preferred embodiment, at least some of the nucleic acid sequences encoding a CDR1 or CDR2 amino acid sequence have been modified to encode at least one, preferably 1, 2, 3, 4, 5 or more amino acid present in rabbit CDR1 or CDR2 amino acid sequences, respectively, in case of human CDR1 or CDR2, respectively, or to encode at least one, preferably 1, 2, 3, 4, 5 or more amino acid present in human CDR1 or CDR2 amino acid sequences, respectively, in case of rabbit CDR1 or CDR2, respectively.

In a preferred embodiment, at least 50%, more preferably at least 80%, at least 90%, at least 95%, at least 96%, at least 97%, at least 98%, at least 99% or 100% of the nucleic acid sequences encoding a CDR1 or CDR2 amino acid sequence have been modified to encode at least one amino acid present in rabbit CDR1 or CDR2 amino acid sequences, respectively, in case of human CDR1 or CDR2, respectively, or to encode at least one amino acid present in human CDR1 or CDR2 amino acid sequences, respectively, in case of rabbit CDR1 or CDR2, respectively.

It is preferred that the nucleic acid sequences encoding a CDR1 or CDR2 amino acid sequence are not modified to encode all amino acid present in rabbit CDR1 or CDR2 amino acid sequences, respectively, in case of human CDR1 or CDR2, respectively.

In an even more preferred embodiment, at least 50%, at least 80%, at least 90%, or at least 95% of the nucleic acids of the population do not comprise a sequence encoding a human CDR1 sequence and/or a human CDR2 sequence, in particular a human CDR1 sequence and a human CDR2 sequence.

In a further even more preferred embodiment, at least 50%, at least 80%, at least 90%, at least 95%, at least 96%, at least 97%, at least 98%, at least 99% or 100% of the nucleic acids of the population do not comprise a sequence encoding a rabbit CDR1 sequence and/or a rabbit CDR2 sequence, in particular a rabbit CDR1 sequence and a rabbit CDR2 sequence.

Diversified CDR1 and CDR2 sequences according to the invention are obtainable by computationally integrating a plurality, such as $10^4$, $10^5$, $10^6$, $10^7$, $10^8$ or more of simulated humanizations across the rabbit antibody repertoire and the human acceptor antibody repertoire, in order to generate a mathematically optimal Bayesian representation of the humanization space between rabbit and human, converting the probabilistic model to a frequentist interpretation, thereby obtaining a population or library. Each position ends up containing a probability of encountering the human germline residue, the rabbit germline residues, and the most common collection of affinity maturation residues from both species.

In a preferred embodiment, cysteine, and/or methionine residues are removed and/or the asparagine residue content is reduced, as these residues form biochemical liabilities.

In a yet further preferred embodiment of the present invention, the human or rabbit CDR1 regions and the human and rabbit CDR2 regions, on which the diversified CDR1 and CDR2 amino acid sequences are based, are selected from human germline CDR1 regions, human germline CDR2 regions, rabbit germline CDR1 regions, rabbit germline CDR2 regions, human somatic hypermutation CDR1 regions, human somatic hypermutation CDR2 regions, rabbit somatic hypermutation CDR1 regions, rabbit somatic hypermutation CDR2 regions, rabbit gene conversion CDR1 regions, and rabbit gene conversion CDR2 regions.

In a yet further preferred embodiment of the present invention, the diversified CDR1 and CDR2 amino acid sequences are CDR-H1, CDR-H2, CDR-L1 and/or CDR-L2 sequences.

In a preferred embodiment, the population includes at least one nucleic acid encoding a human CDR-H1, and/or a human CDR-H2, and/or a human CDR-L1 and/or a human CDR-L2 sequence.

In a further preferred embodiment, the population includes at least one nucleic acid encoding a rabbit CDR-H1, and/or a rabbit CDR-H2, and/or a rabbit CDR-L1 and/or a rabbit CDR-L2 sequence.

In a yet further preferred embodiment, at least 5 nucleic acids of the population exhibit different CDR1 and/or CDR2 nucleic sequences, more preferably at least 6, 7, 8, 9, 10, 50, 100, 150, 200 or more nucleic acids of the population exhibit different CDR1 and/or CDR2 nucleic sequences.

In a yet further preferred embodiment, at least 80% of the nucleic acids of the population exhibit different CDR1 and/or CDR2 nucleic sequences, more preferably at least 90%, at least 95%, at least 96%, at least 97%, at least 98%, at least 99% or 100% of the nucleic acids of the population exhibit different CDR1 and/or CDR2 nucleic sequences.

In a yet further preferred embodiment, the nucleic acid sequences encoding the CDR1 and CDR2 amino acid sequences are diversified among each set of framework regions.

According to the invention, the human FR1, FR2, FR3 and FR4 regions are human framework regions selected to provide a scaffold conducive for rabbit CDR3 amino acid sequences, with the proviso that the two C-terminal amino acids of FR2 are optionally non-human, and that the two C-terminal amino acids of FR3 are optionally non-human. Therefore, in one preferred embodiment, the population of the invention comprises at least one nucleic acid encoding a human FR1, a human FR2, a human FR3 and a human FR4 region, and a human CDR1, and a human CDR2 region.

In another preferred embodiment, the population of the invention comprises at least one nucleic acid encoding a human FR1, a human FR2, a human FR3 and a human FR4 region, and a rabbit CDR1, and a rabbit CDR2 region.

Therefore, in yet another preferred embodiment, the population of the invention does not contain a nucleic acid encoding a human FR1, a human FR2, a human FR3 and a human FR4 region, and a human CDR1, and a human CDR2 region.

Therefore, in yet another preferred embodiment, the population of the invention does not contain a nucleic acid encoding a human FR1, a human FR2, a human FR3 and a human FR4 region, and a rabbit CDR1, and a rabbit CDR2 region.

A suitable scaffold conducive for rabbit CDR3 amino acid sequences is obtainable by selecting a framework set by performing the following steps:
computational imputation of germline repertoire element centroids which are most utilized in functional rabbit antibodies
generating an amino acid alignment of human frameworks compared to said computationally imputed rabbit frameworks and selecting the closest representatives, respectively, that have the same length of CDR-H1, CDR-H2, CDR-L1, and CDR-L2 and similar sequence composition, respectively,
further reducing the number of candidates framework sequences by preferring templates that are known to be stable in the art and optionally have worked as previous drugs,
further reducing the number of framework candidates by structurally modeling antibodies from rabbit and human using these frameworks and analyzing their structural superposition tolerance by root mean squared deviation (RMSD), and
selecting a set of 1, 2, 3, 4, 5, 6, 7, 8, 9 or 10 heavy chain and 1, 2, 3, 4, 5, 6, 7, 8, 9 or 10 light chain frameworks comprising set of FR1, FR2, FR3 and FR4 regions, respectively.

In the Examples, a set of 2 heavy chain and 2 light chain frameworks comprising set of FR1, FR2, FR3 and FR4 regions respectively, were present. Moreover, the two C-terminal amino acids of heavy chain FR2 are optionally non-human, and the two C-terminal amino acids of heavy chain FR3 are optionally non-human, for example in case an SDR is grafted into a scaffold, or in case amino acids surrounding FR2 are substituted, as described above.

Therefore, in one preferred embodiment, the heavy FR1 to FR4 regions of VH3_23 and/or VH3_53 are used in the populations of the present invention.

Therefore, in one preferred embodiment, the light FR1 to FR4 regions of VK-1_27 and/or VK-3_20 are used in the populations of the present invention.

Therefore, in a yet further preferred embodiment of the present invention, the human FR1, FR2, FR3 and FR4 regions which are human framework regions selected to provide a scaffold conducive for rabbit CDR3 amino acid sequences are obtainable by:
(i) providing
   (a) a collection of sequences of naturally occurring human antibodies each comprising a set of human FR1, FR2, FR3 and FR4 regions; and
   (b) a collection of sequences of naturally occurring rabbit antibodies each comprising a set of rabbit FR1, FR2, FR3 and FR4 regions, and
(ii) identifying a plurality of sets of human FR1, FR2, FR3 and FR4 regions which provide a scaffold conducive for rabbit CDR3 amino acid sequences by
   determining the parameters framework homology, CDR homology, CDR lengths, CDR canonical structure, and spatial orientation of CDR loops, and
   selecting sets of human FR1, FR2, FR3 and FR4 regions which exhibit high scores for the parameters,
   and/or
   the two C-terminal amino acids of heavy chain FR2 are optionally non-human, and
   the two C-terminal amino acids of heavy chain FR3 are optionally non-human.

In a further embodiment, the present invention relates to a population of Acceptor Framework proteins,
wherein each Acceptor Framework protein comprises
a set of framework regions comprising a first human framework region (FR1), a second human framework region (FR2), a third human framework region (FR3), and a fourth human framework region (FR4),
wherein the FR1 and FR2 regions are interspaced by a complementarity determining region 1 (CDR1), the FR2 and FR3 regions are interspaced by a complementarity determining region 2 (CDR2), and the FR3 and FR4 regions are linked directly or are interspaced by a stuffer sequence, and
wherein the CDR1 and CDR2 amino acid sequences are diversified among the population of Acceptor Framework proteins, wherein each CDR1 or CDR2 amino acid sequence is independently based
i) on a human CDR1 or CDR2, respectively, or
ii) on a rabbit CDR1 or CDR2, respectively,
wherein at least some of the CDR1 or CDR2 amino acid sequence have been modified to comprise at least one amino acid present in rabbit CDR1 or CDR2 amino acid sequences, respectively, in case of human CDR1 or CDR2, respectively, or to comprise at least one amino acid present in human CDR1 or CDR2 amino acid sequences, respectively, in case of rabbit CDR1 or CDR2, respectively,
and wherein the human FR1, FR2, FR3 and FR4 regions are human framework regions selected to provide a scaffold conducive for rabbit CDR3 amino acid sequences,
with the proviso:
that the two C-terminal amino acids of FR2 are optionally non-human, and
that the two C-terminal amino acids of FR3 are optionally non-human.

It is understood that the preferred embodiments for the methods of the invention and populations of the invention also apply to the populations of Acceptor Framework proteins of the invention.

In particular, the human FR1, FR2, FR3 and FR4 regions are human framework regions with the proviso that the two C-terminal amino acids of FR2 are optionally non-human, and that the two C-terminal amino acids of FR3 are optionally non-human.

Human FR1, FR2, FR3 and FR4 regions are FR1, FR2, FR3 and FR4 regions which are naturally occurring in humans. As described above, the two C-terminal amino acids of FR2 are optionally non-human, and that the two C-terminal amino acids of FR3 are optionally non-human. Therefore, the FR1 and FR4 regions of the invention are human FR1 and FR4 regions. Preferably, also the FR3 and FR4 region is human.

Further, FR2 is a human FR2 framework region, or the two C-terminal amino acids of FR2 are optionally non-human. In one preferred embodiment, FR2 is a human FR2 framework region.

In another preferred embodiment, the two C-terminal amino acids of FR2 are non-human, whereas the remaining sequence of FR2 is human.

In particular, the two positions N-terminal to CDR-H2 (i.e. positions X10 and X11) are "VS" in the human:
CDR-H2: GLEW<u>VS</u> IX12X13X14X15X16X17X18X19X20X21X2 2X23DSVKGI RFT (SEQ ID NO: 126).

In one preferred embodiment, V and/or S at positions X10 and X11 are independently non-human, preferably rabbit, in the heavy FR2 region.

In the Examples, a library was generated using two sets of heavy chain frameworks (FR1, FR2, FR3, and FR4), wherein the positions X10 and X11 of heavy FR2 are diversified as follows:
X10: Ile, Val
X11: Ala, Gly, or Ser Therefore, in a more preferred embodiment, the following amino acids are present at the two C-terminal amino acids $Z_1Z_2$ of FR2 in at least one protein of the population: $Z_1$: Ile or Val; $Z_2$: Ala, Gly or Ser.

In a further preferred embodiment, at least 2, 3, 4, 5, 6, 7, 8, 9, 10, 50, 100, 150, 200 or more proteins of the Acceptor Framework protein population exhibit different amino acids at the two C-terminal amino acids of human FR2, more preferably at positions X10 and X11 of heavy human FR2.

The CDR1 and CDR2 amino acid sequences are diversified among the population of Acceptor Framework proteins, wherein each CDR1 or CDR2 amino acid sequence is independently based i) on a human CDR1 or CDR2, respectively, or ii) on a rabbit CDR1 or CDR2, respectively, wherein at least some of the CDR1 or CDR2 amino acid sequences have been modified to contain at least one amino acid present in rabbit CDR1 or CDR2 amino acid sequences, respectively, in case of human CDR1 or CDR2, respectively, or to contain at least one amino acid present in human CDR1 or CDR2 amino acid sequences, respectively, in case of rabbit CDR1 or CDR2, respectively.

Diversified CDR1 and CDR2 sequences according to the invention are obtainable by computationally integrating a plurality, such as $10^4$, $10^5$, $10^6$, $10^7$, $10^8$ or more of simulated humanizations across the rabbit antibody repertoire and the human acceptor antibody repertoire, in order to generate a mathematically optimal Bayesian representation of the humanization space between rabbit and human, converting the probabilistic model to a frequentist interpretation, thereby obtaining a population or library. Each position ends up containing a probability of encountering the human germline residue, the rabbit germline residues, and the most common collection of affinity maturation residues from both species.

In a preferred embodiment, cysteine, and/or methionine residues are removed and/or the asparagine residue content is reduced, as these residues form biochemical liabilities.

In a yet further preferred embodiment of the present invention, the human or rabbit CDR1 regions and the human and rabbit CDR2 regions, on which the diversified CDR1 and CDR2 amino acid sequences are based, are selected from human germline CDR1 regions, human germline CDR2 regions, rabbit germline CDR1 regions, rabbit germline CDR2 regions, human somatic hypermutation CDR1 regions, human somatic hypermutation CDR2 regions, rabbit somatic hypermutation CDR1 regions, rabbit somatic hypermutation CDR2 regions, rabbit gene conversion CDR1 regions, and rabbit gene conversion CDR2 regions.

In a yet further preferred embodiment of the present invention, the diversified CDR1 and CDR2 amino acid sequences are CDR-H1, CDR-H2, CDR-L1 and/or CDR-L2 sequences.

In a preferred embodiment, the population of Acceptor Framework proteins includes at least one human CDR-H1, and/or a human CDR-H2, and/or a human CDR-L1 and/or a human CDR-L2 sequence.

In a further preferred embodiment, the population of Acceptor Framework proteins includes at least one rabbit CDR-H1, and/or a rabbit CDR-H2, and/or a rabbit CDR-L1 and/or a rabbit CDR-L2 sequence.

According to the invention, the human FR1, FR2, FR3 and FR4 regions are human framework regions selected to provide a scaffold conducive for rabbit CDR3 amino acid sequences, with the proviso that the two C-terminal amino acids of FR2 are optionally non-human, and that the two C-terminal amino acids of FR3 are optionally non-human. Therefore, in one preferred embodiment, the population of the invention comprises at least one protein comprising a human FR1, a human FR2, a human FR3 and a human FR4 region, and a human CDR1, and a human CDR2 region.

In another preferred embodiment, the population of the invention comprises at least one protein comprising a human FR1, a human FR2, a human FR3 and a human FR4 region, and a rabbit CDR1, and a rabbit CDR2 region.

Therefore, in yet another preferred embodiment, the population of the invention does not contain a protein comprising a human FR1, a human FR2, a human FR3 and a human FR4 region, and a human CDR1, and a human CDR2 region.

In a further more preferred embodiment,
(a) at least 5 proteins of the population exhibit different CDR1 and/or CDR2 amino acid sequence, more preferably at least 6, 7, 8, 9, 10, 50, 100, 150, 200 or more proteins of the population exhibit different CDR1 and/or CDR2 nucleic sequences, and/or
(b) at least 80% of the proteins of the population exhibit different CDR1 and/or CDR2 amino acid sequences, more preferably at least 90%, at least 95%, at least 96%, at least 97%, at least 98%, at least 99% or 100% of the nucleic acids of the population exhibit different CDR1 and/or CDR2 nucleic sequences.

In a further preferred embodiment, the CDR1 and CDR2 amino acid sequences are diversified among each set of framework regions.

Therefore, in yet another preferred embodiment, the population of the invention does not contain a protein comprising a human FR1, a human FR2, a human FR3 and a human FR4 region, and a rabbit CDR1, and a rabbit CDR2 region.

A suitable scaffold conducive for rabbit CDR3 amino acid sequences is obtainable by selecting a framework set by performing the following steps:
  computational imputation of germline repertoire element centroids which are most utilized in functional rabbit antibodies
  generating an amino acid alignment of human frameworks compared to said computationally imputed rabbit frameworks and selecting the closest representatives, respectively, that have the same length of CDR-H1, CDR-H2, CDR-L1, and CDR-L2 and similar sequence composition, respectively,
  further reducing the number of candidates framework sequences by preferring templates that are known to be stable in the art and optionally have worked as previous drugs,
  further reducing the number of framework candidates by structurally modeling antibodies from rabbit and human using these frameworks and analyzing their structural superposition tolerance by root mean squared deviation (RMSD), and
  selecting a set of 1, 2, 3, 4, 5, 6, 7, 8, 9 or 10 heavy chain and 1, 2, 3, 4, 5, 6, 7, 8, 9 or 10 light chain frameworks comprising set of FR1, FR2, FR3 and FR4 regions, respectively.

In the Examples, a set of 2 heavy chain and 2 light chain frameworks comprising set of FR1, FR2, FR3 and FR4 regions respectively, were present. Moreover, the two C-terminal amino acids of heavy chain FR2 are optionally non-human, and the two C-terminal amino acids of heavy chain FR3 are optionally non-human, for example in case an SDR is grafted into a scaffold, or in case amino acids surrounding FR2 are substituted, as described above.

Therefore, in one preferred embodiment, the heavy FR1 to FR4 regions of VH3_23 and/or VH3_53 are used in the populations of the present invention.

Therefore, in one preferred embodiment, the light FR1 to FR4 regions of VK-1_27 and/or VK-3_20 are used in the populations of the present invention.

Therefore, in a yet further preferred embodiment of the present invention, the human FR1, FR2, FR3 and FR4 regions which are human framework regions selected to provide a scaffold conducive for rabbit CDR3 amino acid sequences are obtainable by:

(i) providing
  (a) a collection of sequences of naturally occurring human antibodies each comprising a set of human FR1, FR2, FR3 and FR4 regions; and
  (b) a collection of sequences of naturally occurring rabbit antibodies each comprising a set of rabbit FR1, FR2, FR3 and FR4 regions, and
(ii) identifying a plurality of sets of human FR1, FR2, FR3 and FR4 regions which provide a scaffold conducive for rabbit CDR3 amino acid sequences by
  determining the parameters framework homology, CDR homology, CDR lengths, CDR canonical structure, and spatial orientation of CDR loops, and
  selecting sets of human FR1, FR2, FR3 and FR4 regions which exhibit high scores for the parameters,
  and/or
  the two C-terminal amino acids of heavy chain FR2 are optionally non-human, and
  the two C-terminal amino acids of heavy chain FR3 are optionally non-human.

In a further embodiment, the present invention relates to the use of a population of nucleic acids of the invention, or a population of proteins of the invention, for screening for proteins comprising at least one immunoglobulin variable domain, in particular antibodies or fragments thereof, which specifically bind to an antigen of interest. Preferably, the fragment of an antibody comprises at least one immunoglobulin variable domain, in a more preferred embodiment, the fragment of an antibody is a Fv, scFv or Fab.

Methods for screening via display methods are described in detail above.

A protein comprising at least one immunoglobulin variable domain, in particular an antibody or fragment thereof, is understood to specifically bind to an antigen when the protein binds to the antigen, preferably binds with an affinity of Kd of $10^{-6}$, $10^{-7}$, $10^{-8}$, $10^{-9}$ or less, and not bind to other polypeptides or binds to other polypeptides with at least 10-fold or at least 100-fold weaker affinity, preferably with a Kd of $10^{-6}$, $10^{-5}$, or more.

The strength, or affinity of immunological binding interactions can be expressed in terms of the dissociation constant (Kd) of the interaction, wherein a smaller Kd represents a greater affinity. The Kd value can be determined by methods known in the art at 25° C. by surface plasmon resonance spectroscopy.

In a preferred embodiment of the methods and uses of the invention, screening is performed by display of at least one protein on a virus, a cell, or a surface or screening is performed by display of proteins on a virus, a cell, or a surface.

"Native antibodies and immunoglobulins" are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of the beta-sheet structure. The CDRs in each chain are held together in close proximity by the FR regions and, with the CDRs from the other chain, contribute to the formation of the antigen-binding site of antibodies (see e.g. Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. The Fab fragment also contains the constant domain of the light chain and the first constant domain (CHI) of the heavy chain. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known. The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. In humans, there are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Polymerase chain reaction" or "FOR" refers to a procedure or technique in which minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol. 51:263 (1987); Erlich, ed., PCR Technology (Stockton Press, New York, 1989).

Polypeptide and peptide are understood as linear series of amino acid residues connected one to the other by peptide bonds between the alpha-amino and carboxy groups of adjacent residues.

A promoter is understood as recognition site on a DNA sequence or group of DNA sequences that provide an expression control element for a gene and to which RNA polymerase specifically binds and initiates RNA synthesis (transcription) of that sequence.

CDR-1H, CDR-2H, and CDR-3H denote immunoglobulin heavy chain complementarity determining region 1, 2 and 3 respectively.

VHFR1, VHFR2, and VHFR3 VHFR4 denote immunoglobulin heavy chain framework region 1, 2, 3 and 4 respectively.

CDR-1L, CDR-2L, and CDR-3L denote immunoglobulin light chain complementarity determining region 1, 2 and 3 respectively.

VLFR1, VLFR2, and VLFR3 VLFR4 denote immunoglobulin light chain framework region 1, 2, 3 and 4 respectively.

The term "at least" is used to indicate that optionally one or more than one further objects may be present.

"About" is understood to mean the indicated value+/− 10% standard deviation.

FIGURES

FIG. 1 shows the PCR results of Example 5 for capturing the Rabbit CDR3 repertoire via Nested PCR. A) Primary PCR. B) Secondary PCR.

FIG. 2 shows in A) to C) the gel purification of the 6 bands P3_23, B3_23, S3_23, P3_53, B3_53 and S3_53 according to the consecutive steps of Example 6.

FIG. 3 shows results of Example 7. A) NcoI/NotI digest performed with a DNA sample from each of the 12 retrieved sub libraries. The control digest was performed using 500 ng DNA, NcoI-HF (NEB) and NotI-HF(NEB) in 20 µl OUT-SMART restriction enzyme buffer (NEB) for 1.5 hours at 37° C. B) distribution of lengths of the VL-CDR3 (right column) and of the VH-CDR3 (left column).

FIG. 4 shows results of Example 8. A) Phage recovery after subsequent selection rounds 1 (left column), 2 (middle column) and 3 (right column). B) Phage recovery results after selection round 2. Output of a selection with antigen (right column) is compared to a mock selection round without antigen (left column).

FIG. 5 shows ELISA Results of clones obtained in selection round 2 from PBMC, bone marrow and spleen cells as source of B cells. For each clone, absorbance measured for binding in the presence of the antigen HEL is shown in the left column, and binding in the absence of the antigen HEL is shown in the right column, respectively. Following was observed after sequencing of ELISA hits obtained after selection round 2 and 3: 285 sequences; all in VH3-23 or VH3-53 and Vk1-27 or Vk3-20 framework; mutations in CDR1/2 of VH and VL; 176 unique VH CDR3/VL CDR3 combinations; 140 unique VH CDR3; 161 unique VL CDR3. It was further observed that all acceptor frameworks of the invention were active, and are preferably required for majority immune coverage after immunization.

FIG. 6A) shows Immunization Protocol of Rabbit R24752 with Hen Egg Lysozyme (HEL). B) shows ELISA with serum obtained at day 0, 7, 14 and 21 on lysozyme (HEL) and Bovine serum albumin (BSA).

FIG. 7 shows the organization of Human and Rabbit variable antibody domains. A) Human Variable Antibody Domains. B) Rabbit Variable Antibody Domains.

FIG. 8A) shows an example of a PCR amplification of a Rabbit VH variable region. The nucleotide sequences for both the coding and noncoding DNA strands are disclosed (SEQ ID NOs: 41 and 127, respectively). B) shows an example of a PCR amplification of a Rabbit VL variable region. The nucleotide sequences for both the coding and noncoding DNA strands are disclosed (SEQ ID NOs: 42 and 128, respectively).

FIG. 9 shows an example of human and rabbit Framework 3 and Framework 4 sequences surrounding the CDR3 region of VH and VL domains.

FIG. 10A) shows an example of PCR amplification of a Rabbit VH-CDR3 domain. The nucleotide sequences for both the coding and noncoding DNA strands are disclosed (SEQ ID NOs: 41 and 127, respectively). B) shows an example of PCR amplification of a Rabbit VL-CDR3 domain. The nucleotide sequences for both the coding and noncoding DNA strands are disclosed (SEQ ID NOs: 42 and 128, respectively).

FIG. 11A) shows PCR of a library of Rabbit VH-CDR3 via Rabbit VH-FR3 and VH-FR-4 specific primers. B) shows PCR of a library of Rabbit VL-CDR3 via Rabbit VL-FR3 and VL-FR-4 specific primers.

FIG. 12 shows BanI recognition site in Acceptor Framework. The nucleotide sequences for both the coding and noncoding DNA strands are disclosed (SEQ ID NOs: 46 and 129, respectively).

FIG. 13A) shows sticky ends after BarI digestion of the PCR product containing a library of Rabbit VH-CDR3. B) shows sticky ends after BarI digestion of the VH acceptor library. C) shows sticky ends after BarI digestion of the PCR product containing a library of Rabbit VL-CDR3. D) shows sticky ends after BarI digestion of the VL acceptor library.

FIG. 14 shows step 1 of a preferred method of the invention for generating an scFv library cloned in a phage display vector. Step 1: Cloning of Rabbit VH-CDR3 regions between Human VH-FR3 and Human VH-FR4 regions in an acceptor vector.

Figure 17:
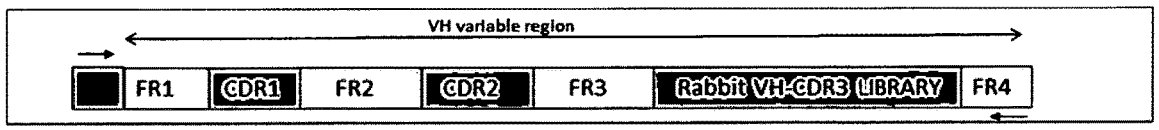
Figure 18:
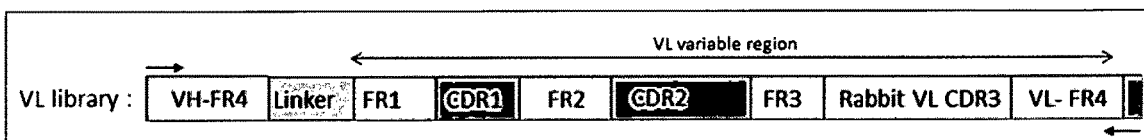

FIG. 17 shows step 8 of a preferred method of the invention for generating an scFv library cloned in a phage display vector. PCR of the VH variable region library from step 7 containing Human Framework regions FR1, FR2, FR3 and FR4 separated by a library of CDR1, CDR2 and a library of Rabbit CDR3 sequences FIG. 18 shows step 9 of a preferred method of the invention for generating an scFv library cloned in a phage display vector. Step 9: PCR amplification of a VL variable region library containing the C-terminal part of a Human VH-FR4 domain, a linker sequence, Human VL Framework domain regions FR1, FR2, FR3 and FR4 separated by a library of CDR1 and CDR2 sequences and a library of Rabbit VL-CDR3.

FIG. 19 shows step 10 of a preferred method of the invention for generating an scFv library cloned in a phage display vector. Step 10: PCR assembly via overlap PCR of DNA fragments derived from steps 8 and 9 via their common human VH-FR4 sequence.

Figure 22:
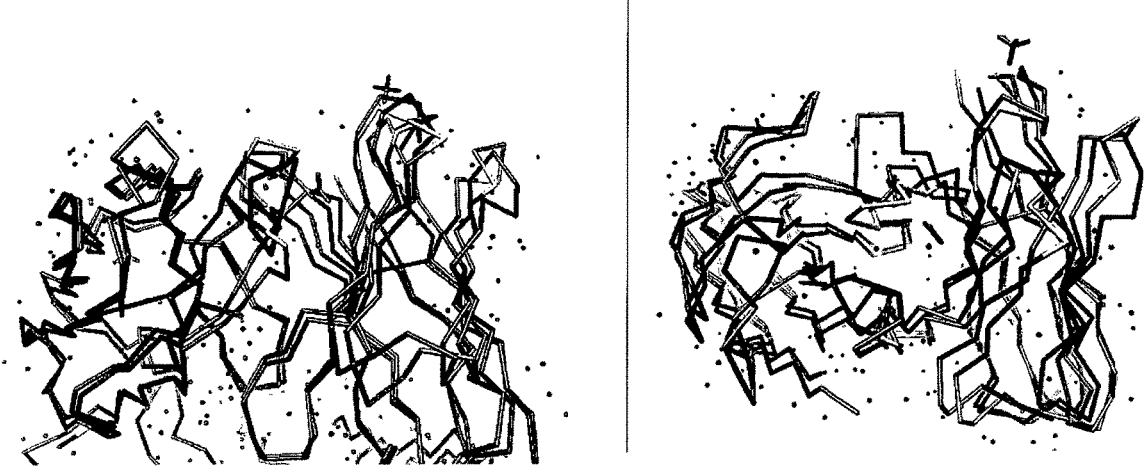
Figure 23:
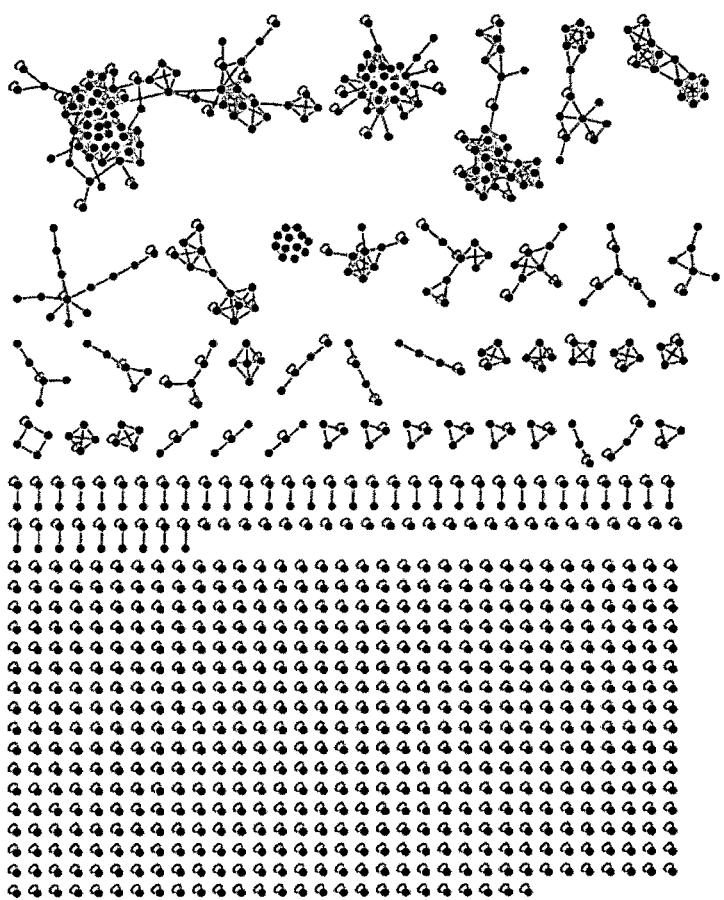

FIG. 20 shows oligonucleotides suitable for cloning rabbit-derived CDR3 sequences into an Acceptor Framework by without the use of a restriction enzyme recognition site within the oligonucleotide and/or by overlap PCR FIG. 21 shows the cloning strategy suitable for cloning rabbit-derived CDR3 sequences into an Acceptor Framework by without the use of a restriction enzyme recognition site within the oligonucleotide and/or by overlap PCR FIG. 22 shows the superposition of a rabbit antibody and an Acceptor Framework FIG. 23 shows responding lineages in the antibody sequence repertoire of an immunized rabbit FIG. 24 shows alignments of CDR-H3 sequences of group A (A) and group B (B). Point mutations within sequences of one VH CDR3 group are most likely the result of in vivo affinity maturation. VH CDR3 sequences of group B occurred exclusively in VH3-53 and would have been lost in libraries which use VH3-23 as acceptor framework.

FIG. 25 shows one representative of identified CDR3 groups and the number of sequences belonging to the respective group. 21 separated groups were present; 2 groups are highly prominent. DDYGD (SEQ ID NO: 43) motive selected throughout different groups. Some of the VL CDR3 occurred in combination with different VH CDR3, indicating VL CDR3 driven selections.

Figure 26:
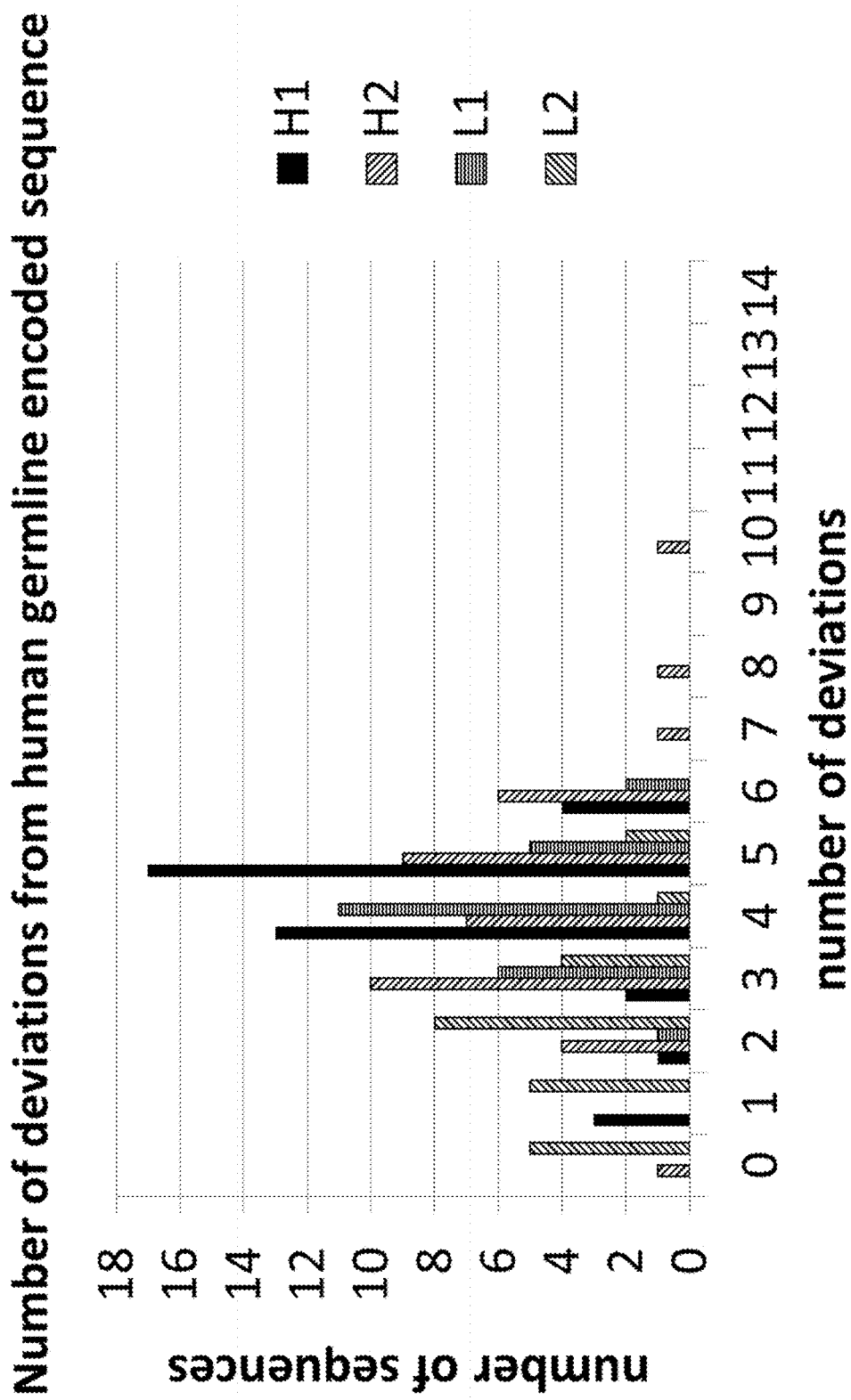
Figure 26:
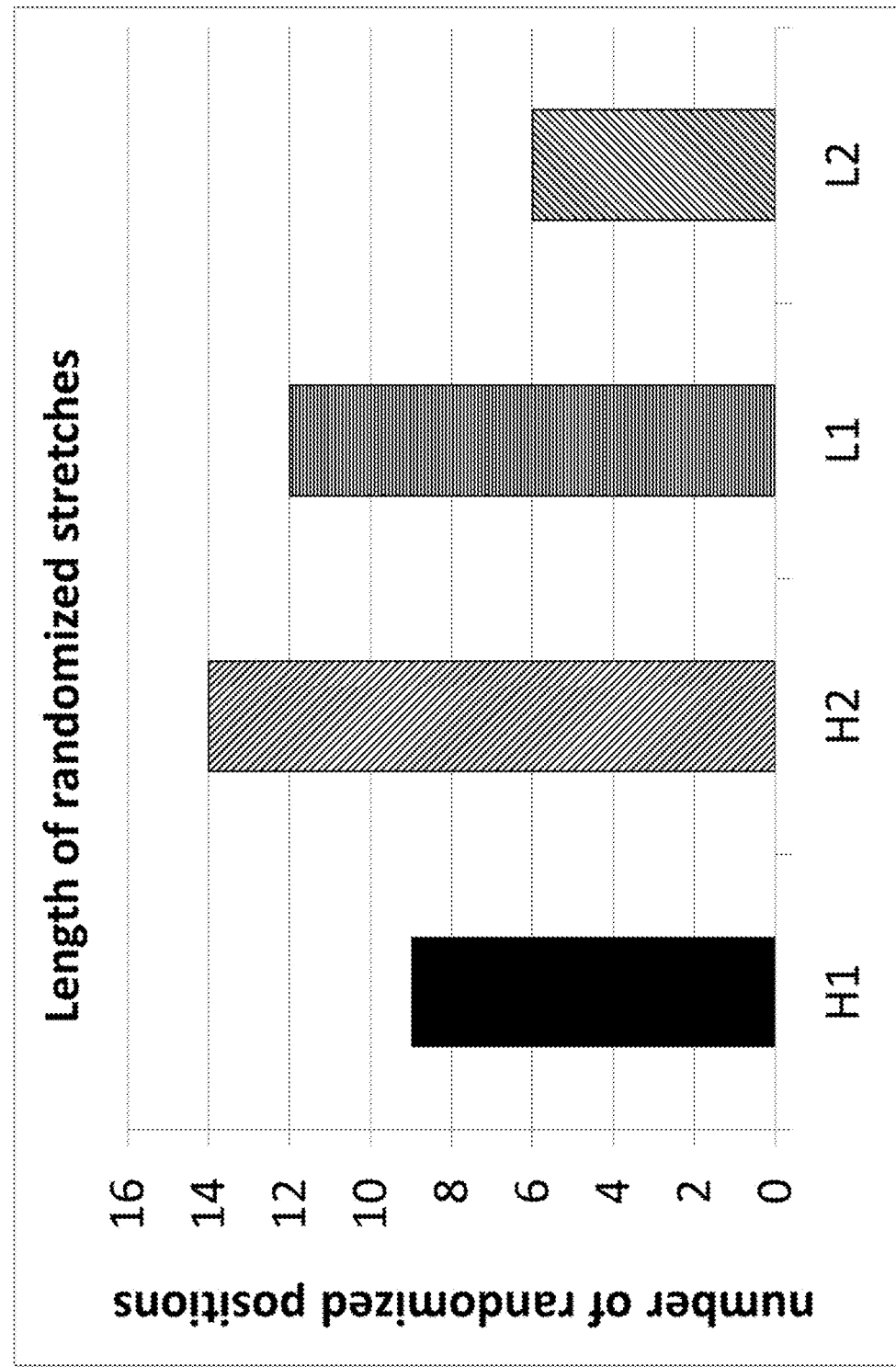

FIG. 26 shows the number of amino acid deviations from the human germline encoded sequence in CDR1 and CDR2 of VH and VL. H1 shows the highest mutation rate. Other regions are more conserved. It was further observed that the mutation pattern in CDR-H2 depends on the Acceptor framework, and that different VH CDR3 groups show different mutation patterns.

FIG. 27 shows the CDR-H3 sequences and affinities of selected group B sequences. It can be seen that multiple affinity maturation variants of the same antibody are humanized.

Figure 28:
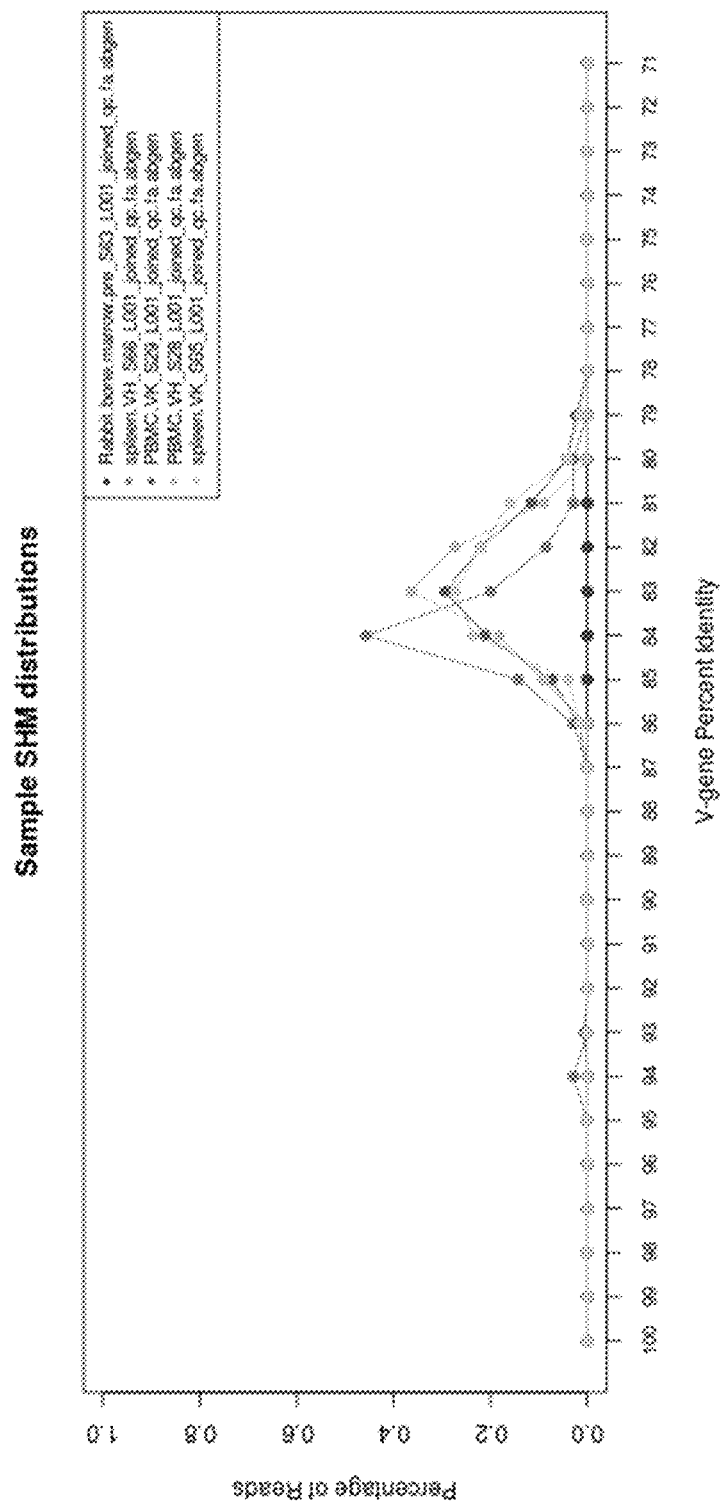

FIG. 28 shows the SHM distributions. It can be seen that rabbit antibody repertoires appear roughly 83% identical to closest human reference.

Figure 29:
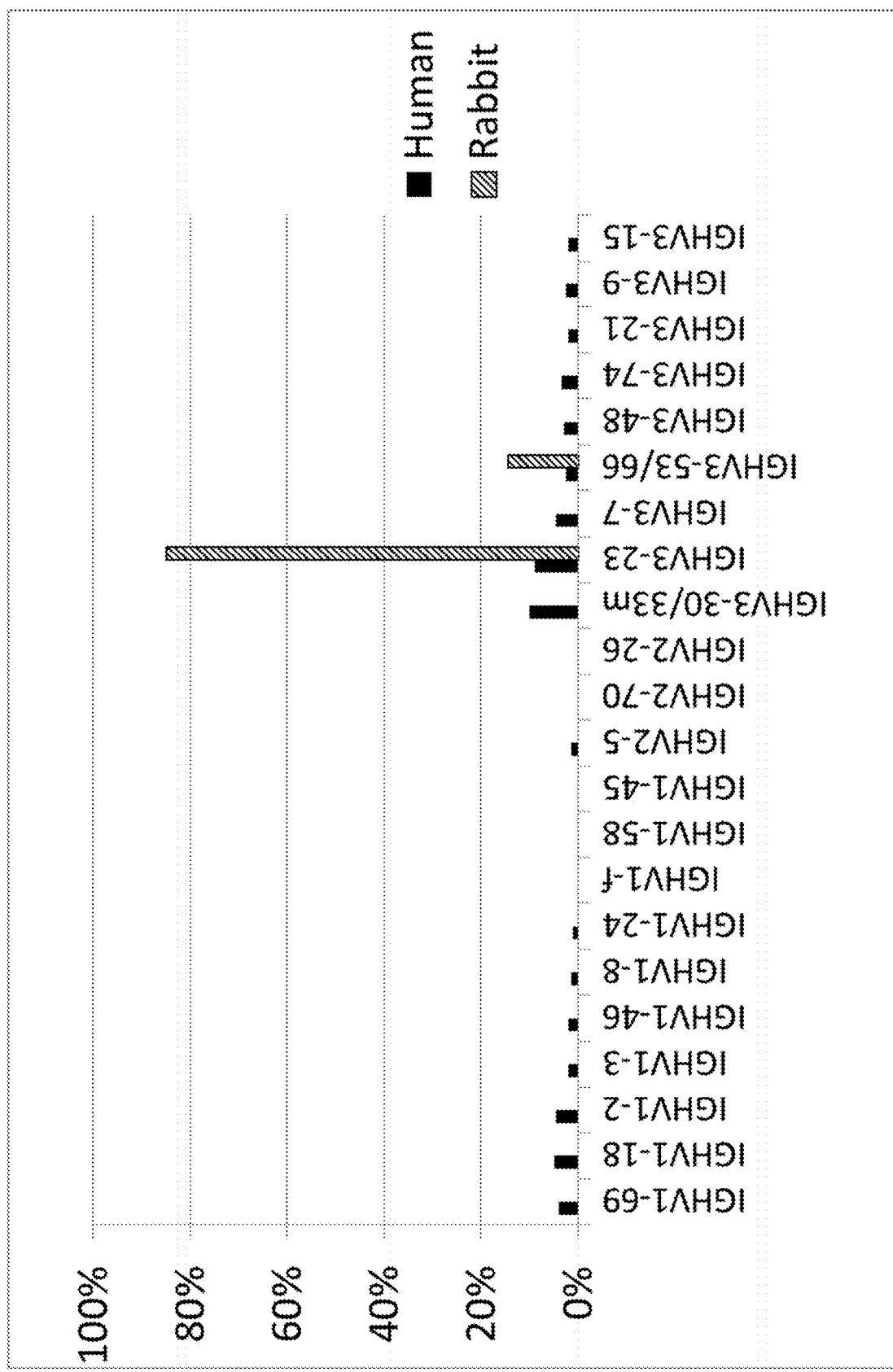
Figure 29:
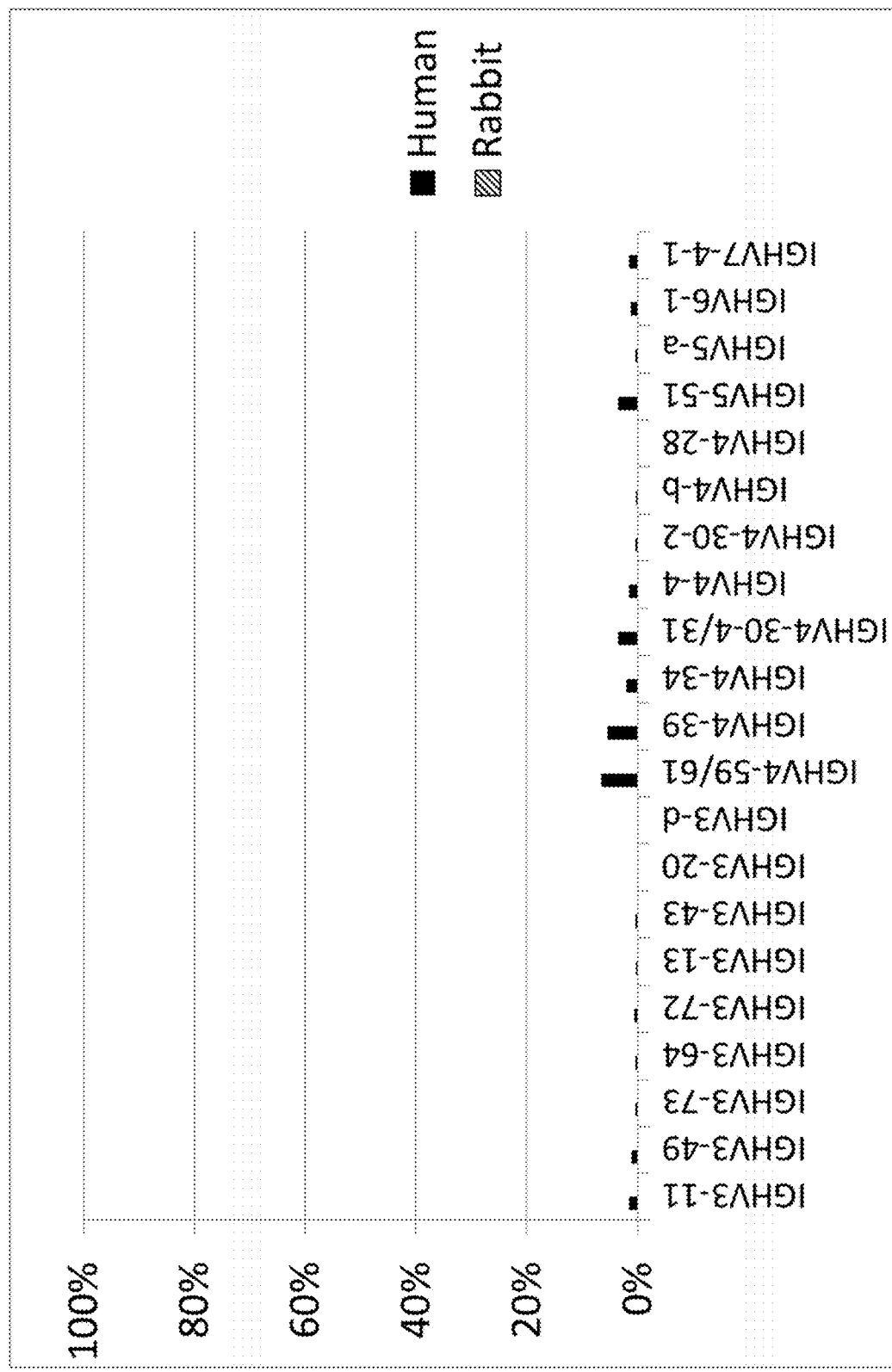

FIG. 29 shows the distribution of heavy chain scaffolds in the rabbit antibody repertoire. It can be seen that rabbit antibody repertoires use one dominant heavy chain scaffold.

Figure 30:
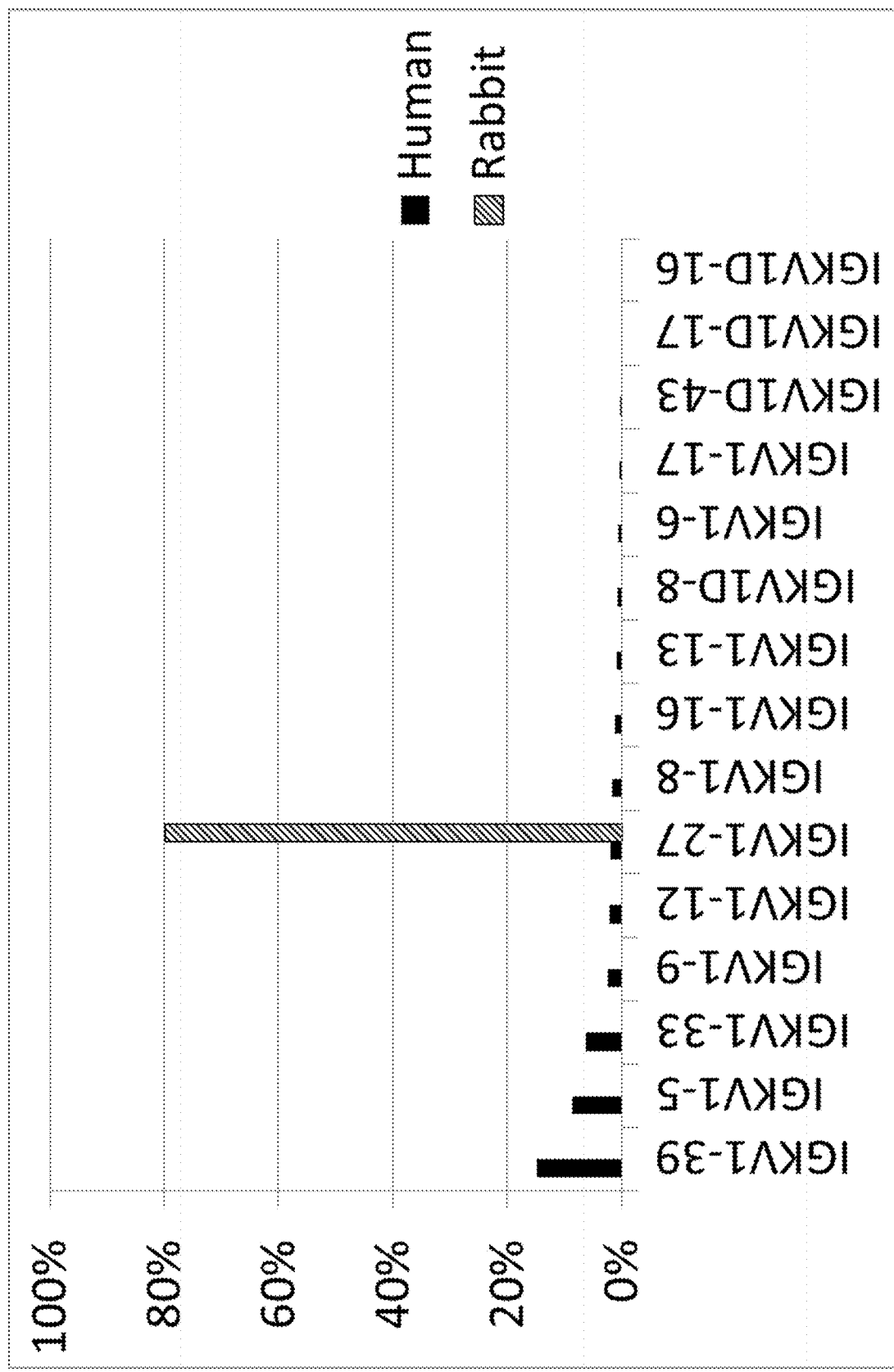
Figure 30:
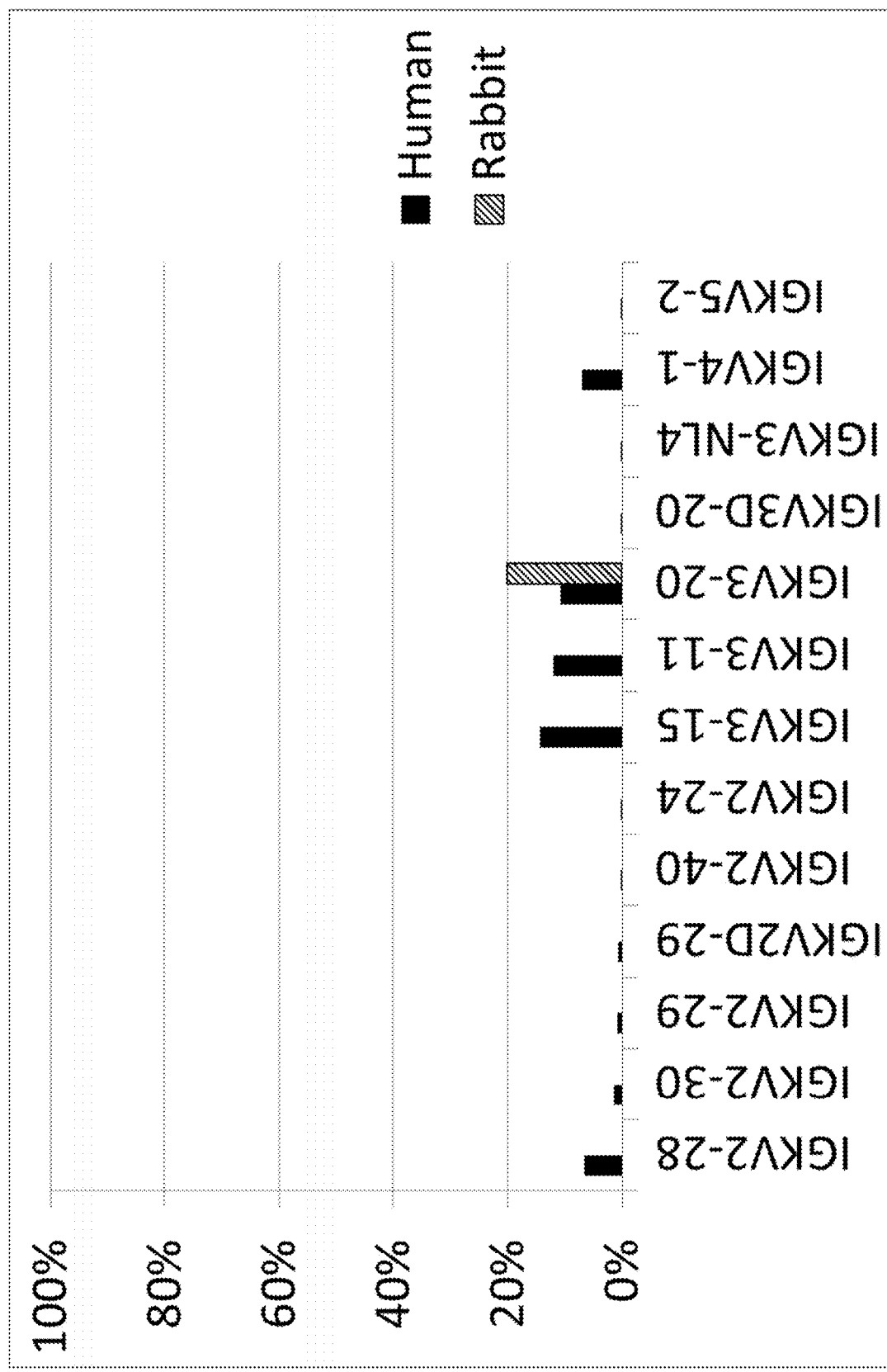

FIG. 30 shows the distribution of light chain scaffolds in the rabbit antibody repertoire. It can be seen that rabbit antibody repertoires use two dominant light chain scaffolds.

Figure 31:
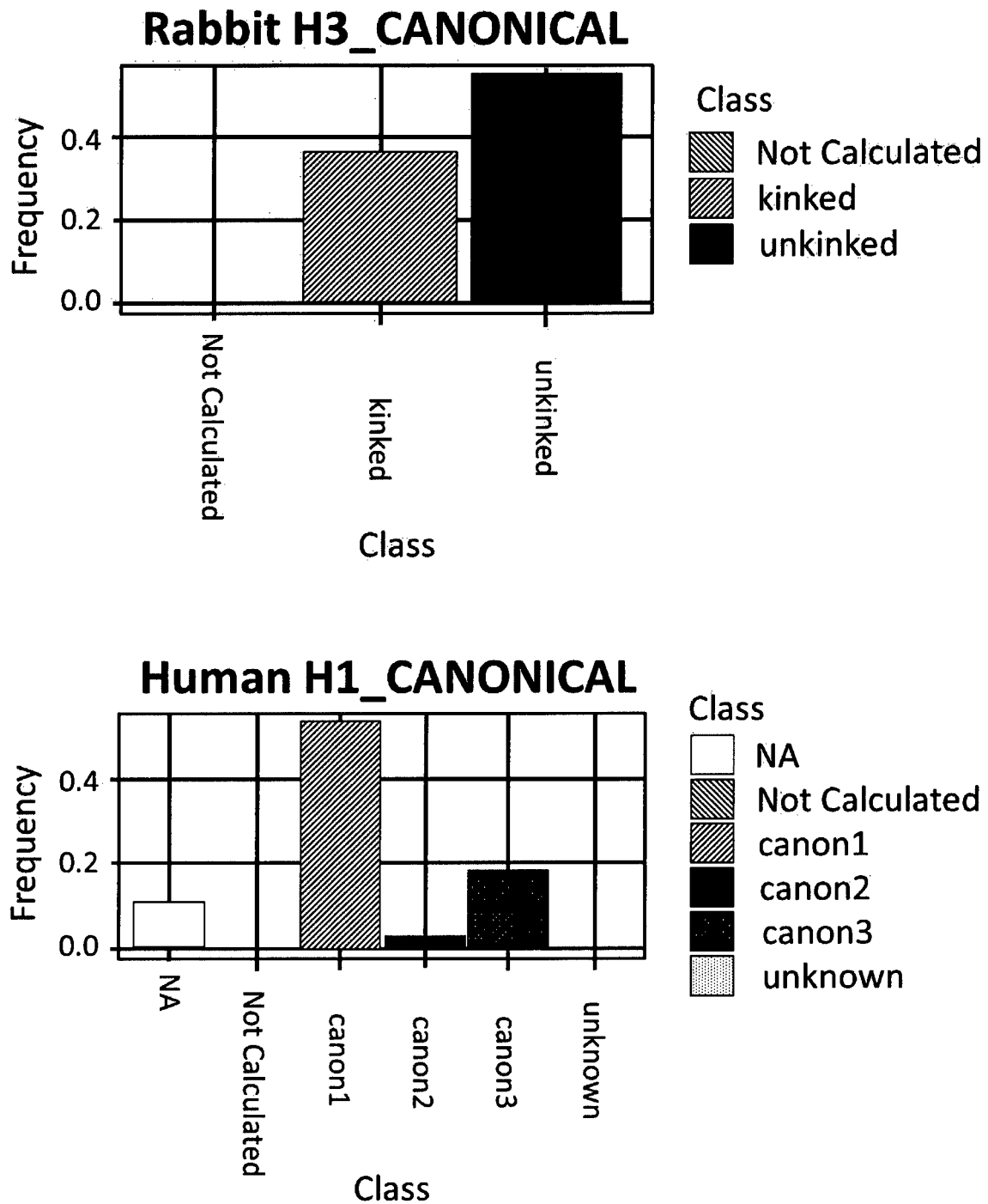
Figure 31:
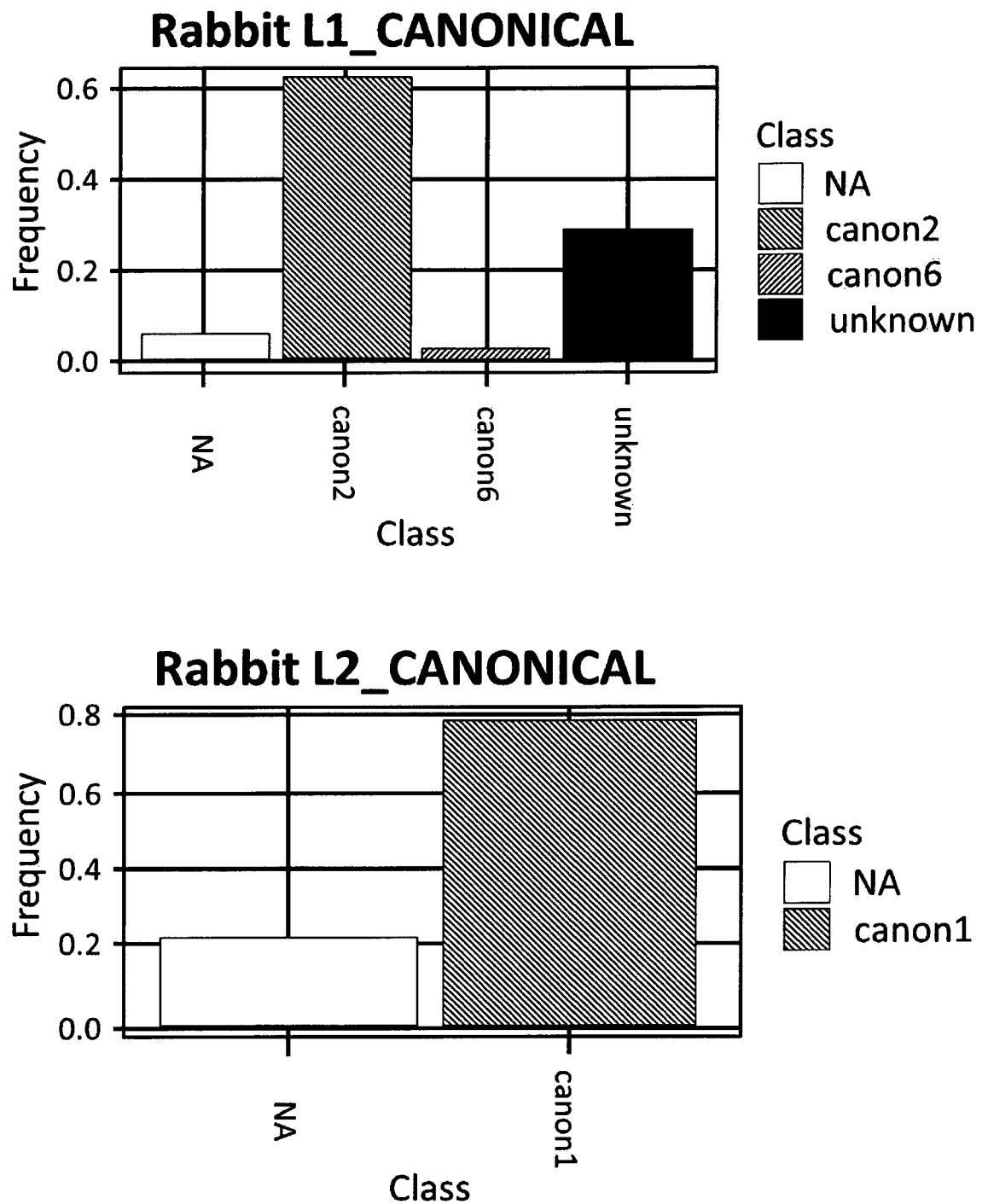
Figure 31:
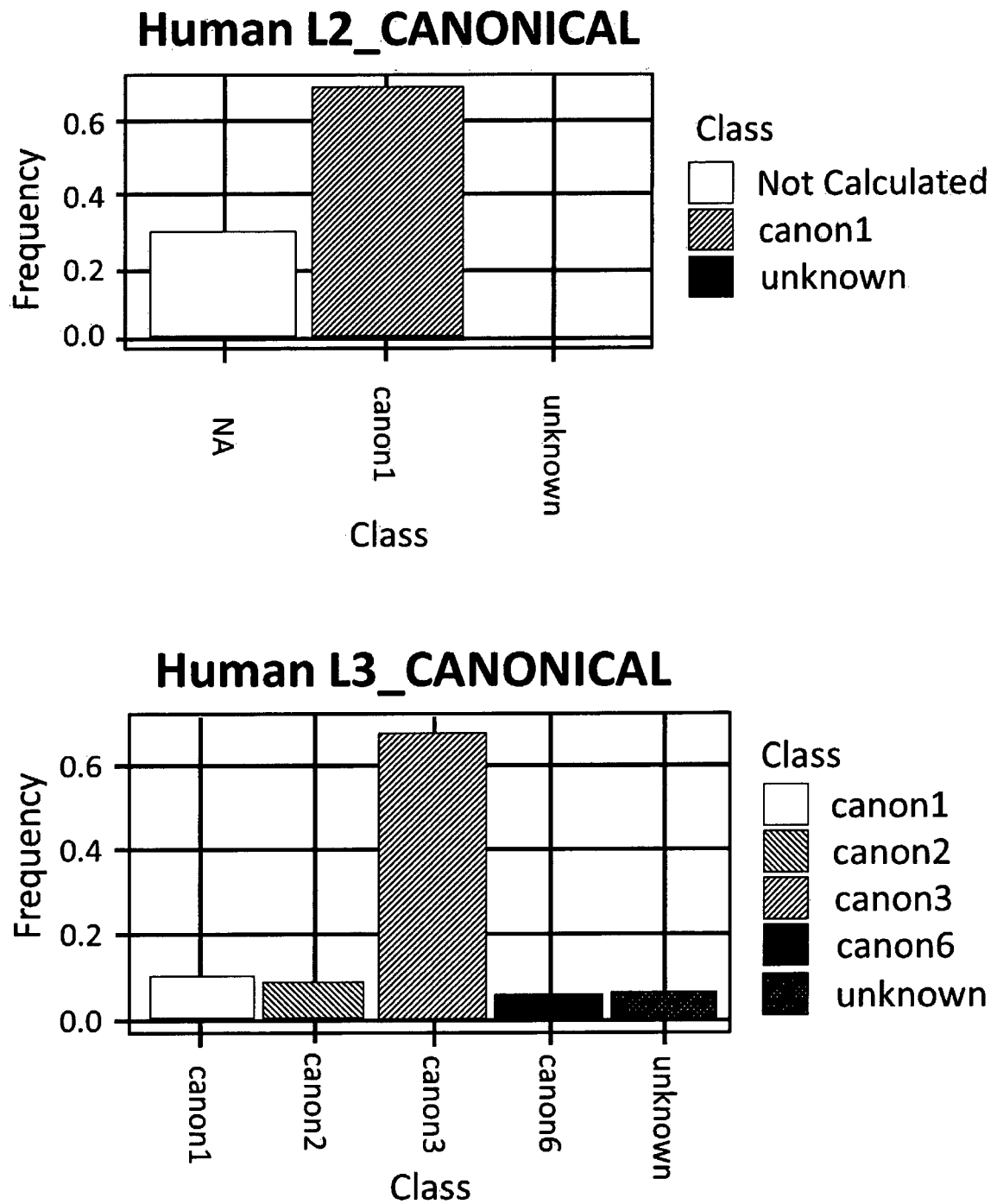

FIG. 31 shows that rabbit CDRs explore a subset of canonical classes in human. First row: rabbit VH; second row: human VH; third row: rabbit VK; fourth row: human VK.

FIG. 32 shows that rabbit has unusually diverse CDR-3L sequences that makes rabbit uniquely suited for mass humanization. A) distribution of length and composition of CDR-3H sequences in rabbit and human; B) distribution of length and composition of CDR-3L sequences in rabbit and human.

Figure 33:
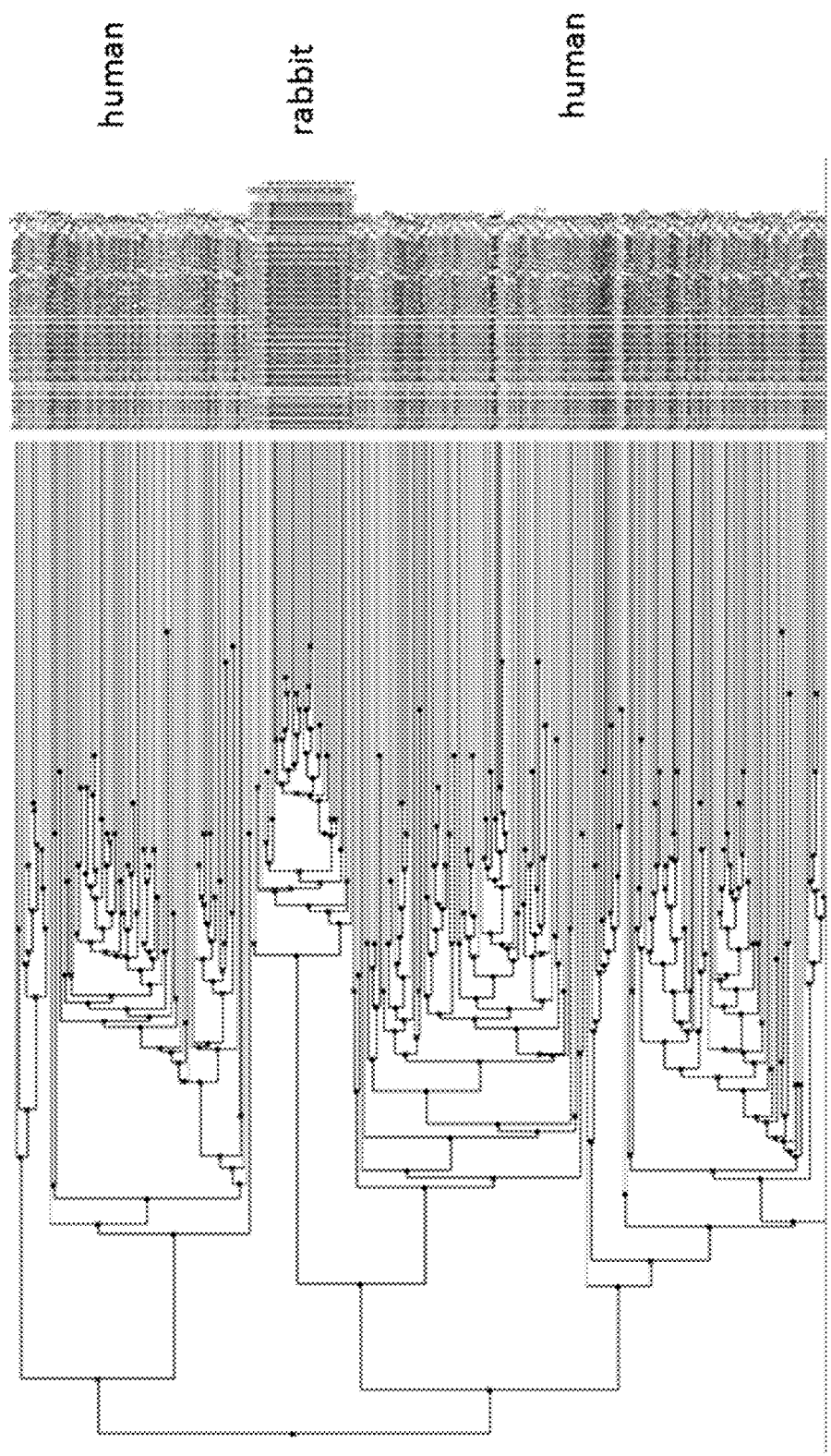

FIG. 33 shows V gene diversity in rabbit and human. Rabbit represents a subset of the V-gene diversity space of the human repertoire.

FIG. 34 shows the CDR3L and CDR3H clones frequency and distribution in a post-immunized rabbit. A post-immunized rabbit enriches approximately 200 unique CDR3Hs but >400 CDR3Ls.

Figure 36:
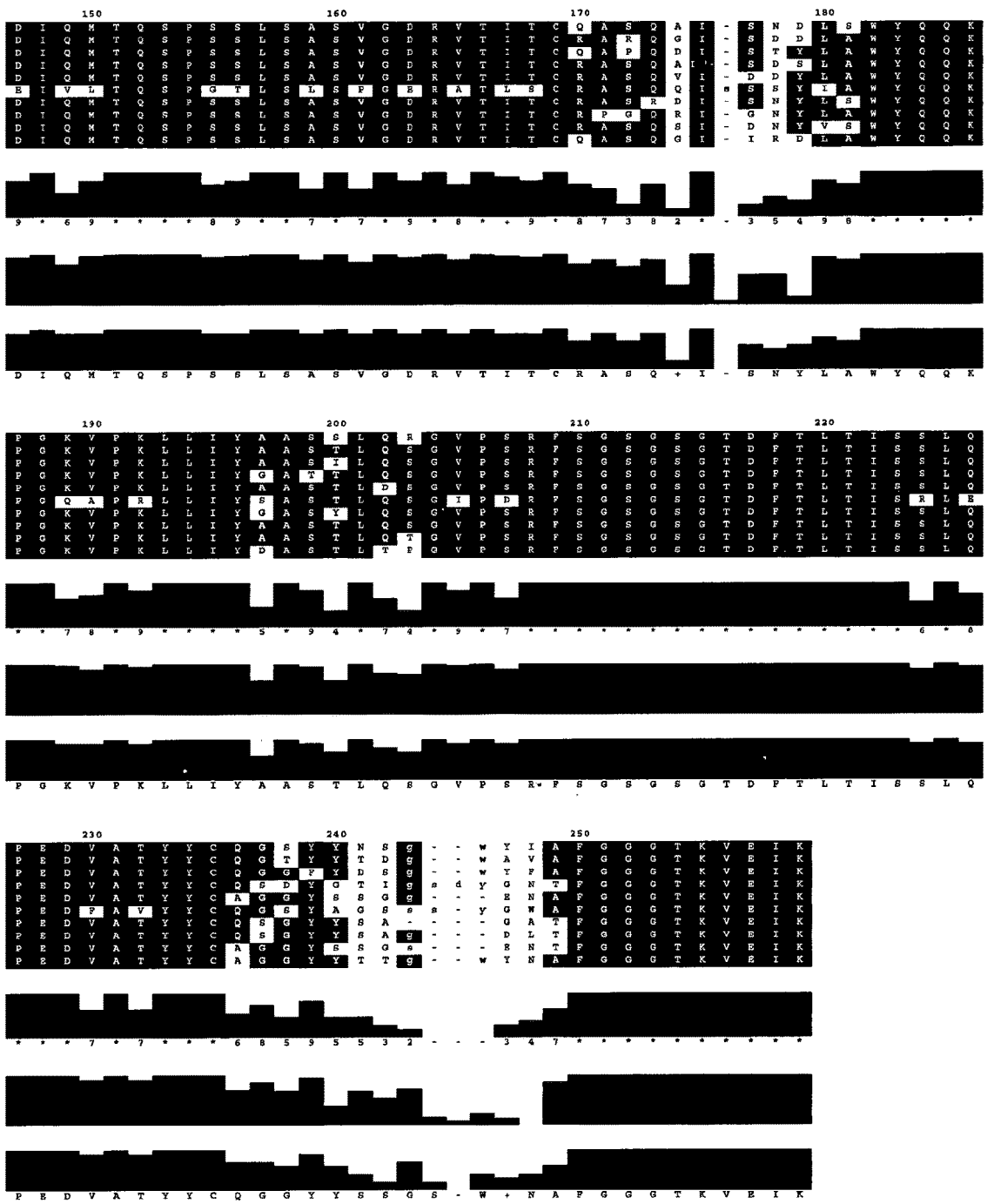

FIG. 35 shows that the mass humanization landscapes represent the intermediate average of all possible humanizations FIG. 36 shows that each CDR-3H-defined rabbit clone can undergo tens of thousands of successful humanizations.

EXAMPLES

The generation of humanized antibodies according to Examples 1 to 11 below was performed by the following steps representing a preferred embodiment of the present invention:
a) Immunization of Rabbits
b) Lymphocyte Preparation from different organs (Blood, Bone Marrow and spleen)
c) RNA Isolation
d) Separate PCR of Rabbit VH and VL variable regions
e) Separate Nested PCR of Rabbit VH and VL CDR3
f) Cloning and Assembly of Rabbit VH and VL CDR3 to yield Human variable VH and VL fragments
g) Cloning of obtained scFv into a phage display vector
h) Selection for specificity on antigen
i) Characterization of individual antibodies
List of oligonucleotides used in the Examples:

| Primer | Sequence in 5'-3' direction |
|---|---|
| 3-23 sense | TCGAGGAACAGCCTGCGCGCCGAGGACACGGCCG TATATTACTGTGCCGCGGCGAAGGACGTCTACGGG CGCCTGGGGCCAGGGGACACTAGTCACCGTCTCAA GCG (SEQ ID No: 1) |
| 3-53 sense | TCGAGCAAATGAACAGCCTGCGCGCCGAGGACACG GCCGTGTATTACTGTGCCGCGGCGAAGGACGTCTA CGGGCGCCTGGGGCCAGGGGACACTAGTCACCGT CTCAAGCG (SEQ ID No: 2) |
| Xho VH3-23 stuf For | AAAAAACTCGAGGAACAGCCTGCG (SEQ ID No: 3) |
| Xho VH3-53 stuf For | AAAAAACTCGAGCAAATGAACAGCCTG (SEQ ID No: 4) |
| Nhe VH stuf Rev | TTTTTTGCTAGCGCTTGAGACGGTGACT (SEQ ID No: 5) |
| K-RP | TGTTTTACTGTTCTCGATGCC (SEQ ID No: 6) |
| IgG-RP | GACTGACGGAGCCTTAGGTTGCC (SEQ ID No: 7) |
| Rab VH1 FP | CAGWCRGTGAAGGAGTCCGAGGG (SEQ ID No: 8) |
| Rab VH2 FP | CAGTCGBTGGRGGARTYCRGGGG (SEQ ID No: 9) |
| Rab VH3 FP | CAGVAGCAGCTGRWGGARTCCRS (SEQ ID No: 10) |
| Rab VH4 FP | CAGGAGCAGCWGRAGGAGTCCGG (SEQ ID No: 11) |
| Rab Vk1 FP | GCYCAAGKGCYRACCCAGACTSM (SEQ ID No: 12) |
| Rab Vk2 FP | GACVYTRTGCTGACCCAGACTSC (SEQ ID No: 13) |
| Rab Vk3 FP | GCAGCCGTGMTGACCCAGACWCC (SEQ ID No: 14) |
| Rab Vk4 FP | KATGKYRTGATGACCCAGACTSC (SEQ ID No: 15) |
| Rab Vk5 FP | GCSCWDGTGMTGACCCAGACTCC (SEQ ID No: 16) |
| Rab Vk6 FP | GCCATCRAWATGACCCAGACTCC (SEQ ID No: 17) |
| Rab VH CDR3 BarI For | TGACCAGTCTGACAGCCGAAGACACGGTACCCTAT TTCTGTG (SEQ ID No: 18) |
| Rab VH CDR3 BarI Rev 1 | CTTAGGTTGCCCTGARGAGAGTATGACSACTTCSCC TGGGCCCCA (SEQ ID No: 19) |
| Rab VH CDR3 BarI Rev 2 | CTTAGGTTGCCCTGARGAGAGTATGACSACTTCSCC CTGGCCCCA (SEQ ID No: 20) |
| Rab VH CDR3 BarI Rev 3 | CTTAGGTTGCCCTGARGAGAGTATGACSACTTCSCC TGTGCCCCA (SEQ ID No: 21) |
| Rab VLk CDR3 BarI For | CTCACCATCAGCGGTGTGCAGTGGAAGGATGCTTA CACTTACTACTGT (SEQ ID No: 22) |
| Rab CDR3 VLK BarI Rev 1 | AACTGGATCACGTTTGATTGTAACCTTGCTTCCAGC TCCAAAAGTCAAA (SEQ ID No: 23) |
| Rab CDR3 VLK BarI Rev 2 | AACTGGATCACATTTGATTGTAACATTGCTTCCAGC TCCAAAAGCCCAA (SEQ ID No: 24) |
| Rab CDR3 VLK BarI Rev 3 | AACTGGATCACCTTCGACGGTAACCTTGCTTCCTCC GCCAAAAGTATTAT (SEQ ID No: 25) |
| Rab CDR3 VLK BarI Rev 4 | AACTGGATCACGTTTGATTGTAAGTTTGCTTCCTGG GCCAAAAGTGGAT (SEQ ID No: 26) |
| Rab CDR3 VLK BarI Rev 5 | AACTGGATCACGTTTGATCGTAAGCTTGCTTCCCTC GCCAAAAGTGATT (SEQ ID No: 27) |
| Rab CDR3 VLK BarI Rev 6 | AACTGGATCACATAGGATCGTAAGCTCGCTTCCTCC GCCAAAAGCAGTT (SEQ ID No: 28) |
| Rab CDR3 VLK BarI Rev 7 | AACTGGATCACGTTTGATCGTAAGCTTGCTTCCTTC KCCAAAAGTGATC (SEQ ID No: 29) |
| Rab CDR3 VLK BarI Rev 8 | AACTGGATCACCTTTGACSGTAACCTCGCTTCCTCC GCCAAAAGCATTA (SEQ ID No: 30) |
| Rab CDR3 VLK BarI Rev 9 | AACTGGATCACRTTTGATCGTAACCATGCTTCCTGA GCCAAAAGYAAGT (SEQ ID No: 31) |
| Rab CDR3 VLK BarI Rev 10 | AACTGGATCACGTTTGATCGTAACCTTGCTTCCCGC ACCAAAAGTATTA (SEQ ID No: 32) |
| Rab CDR3 VLK BarI Rev 11 | AACTGGATCACGTTTGATTGTAAGTTTGCTTCCTGG GCCAAAAGTGGAT (SEQ ID No: 33) |
| Rab CDR3 VLK BarI Rev 12 | AACTGGATCACGTTTGATCGTAAGCTTGCTTCCCTC GCCAAAAGTGGTT (SEQ ID No: 34) |
| Rab CDR3 VLK BarI Rev 13 | AACTGGATCACRTTTGATCGTAACCATGCTTCCTGA GCCAAAAGCAAGT (SEQ ID No: 35) |
| B-Nco app8 For | AAGAAGAAGGTGTTCAATTGGACAAGAGAGAGGCC A (SEQ ID No: 36) |
| FR3 VH3_23 as | TAATATACGGCCGTGTCCTCGGCGCGCAGGCTGTT C (SEQ ID No: 37) |

-continued

| Primer | Sequence in 5'-3' direction |
|---|---|
| VH FR3-23 For | GAACAGCCTGCGCGCCGAGGACAC (SEQ ID No: 38) |
| pEX14 Rev | GAAAGGCCCAGTCTTTCGACTGAGCC (SEQ ID No: 39) |
| B-NotRev | CAGCTTTTGTTCCTAGTGATGGTGATGGTG (SEQ ID No: 40) |

Example 1: Generation of VH and VL FR1-CDR1-FR2-CDR2-FR3-(BarI Stuffer)-FR4 Acceptor Libraries 2 VH and 2 VL libraries, each containing a variability of $>10^9$ unique sequences, comprised within the CDR1 and CDR2 regions and a BarI recognition site containing stuffer fragment located between FR-3 and FR-4 were synthesized by GeneArt and cloned into bacterial shuttle vectors (Table 1 and Table 2).

TABLE 1

| | 14AF4B4C-VH3_23 | 14AF4B5C-VH3_53 |
|---|---|---|
| Vector Backbone | PUC | PUC |
| Resistance gene | Bla | Bla |
| Germline sequence variable fragment | VH-3_23 | VH-3_53 |
| Human VH-FR1 | + | + |
| Designed VH-CDR1 | + | + |
| Human VH-FR2 | + | + |
| Designed VH-CDR2 | + | + |
| Human VH-FR3 | + | + |
| BarI recognition site containing stuffer fragment | + | + |
| Human VH-FR4 | + | + |
| Theoretical diversity | $2 \times 10^{18}$ | $4.1 \times 10^{16}$ |
| Diversity in synthesized library | $>1 \times 10^{11}$ | $>1 \times 10^{11}$ |
| Diversity in cloned library | $>1 \times 10^{9}$ | $>1 \times 10^{9}$ |

TABLE 2

| | 14AF4B6C VK-1_27 | 14AF4B7C-VK-3_20 |
|---|---|---|
| Vector Backbone | pBR322 | pBR322 |
| Resistance gene | Bla | Bla |
| Synthesized DNA Fragment containing | | |
| Human VH-FR4 fragment | + | + |
| Linker | (Gly$_2$Ser)$_6$ (SEQ ID NO: 130) | (Gly$_2$Ser)$_6$ (SEQ ID NO: 130) |
| Germline sequence variable fragment | VK-1_27 | VK-3_20 |
| Human VL-FR1 | + | + |
| Designed VL-CDR1 | + | + |
| Human VL-FR2 | + | + |
| Designed VL-CDR2 | + | + |
| Human VL-FR3 | + | + |
| BarI recognition site containing stuffer fragment | + | + |
| Human VL-FR4 | + | + |
| Theoretical diversity | $4.3 \times 10^{14}$ | $1.5 \times 10^{16}$ |
| Diversity in synthesized library | $>1 \times 10^{11}$ | $>1 \times 10^{11}$ |
| Diversity in cloned library | $>1 \times 10^{9}$ | $>1 \times 10^{9}$ |

Example 2: Generation of VH Shuttle Vectors

TABLE 3

| Vector name | pVH-3_23 stuffer | pVH-3_53 stuffer |
|---|---|---|
| Vector Backbone | pBR322 | pBR322 |
| Resistance gene | Bla | Bla |
| Germline VH sequence | VH-3_23 | VH-3_53 |
| Human FR3 | + | + |
| BarI recognition site containing stuffer fragment | + | + |
| Human FR4 | + | + |

To construct the VH shuttle vectors (Table 3), single stranded DNA fragments (3-23 sense and 3-53 sense) containing human FR3 and FR4 regions interspaced with a BarI recognition site were PCR amplified (Table 4) with Pwo Taq MasterMix (NEB) and the indicated primers. The obtained PCR products were purified (PCR purification kit; Qiagen) and digested for 2 hours at 37° C. with the restriction enzymes XhoI (NEB) and NheI-HF (NEB) in a 50 µl reaction in OUTSMART restriction enzyme buffer (NEB). In addition, a pBR322 derived vector was digested for 2 hours at 37° C. with the restriction enzymes XhoI (NEB) and NheI-HF (NEB) in a 50 µl reaction in OUTSMART restriction enzyme buffer (NEB) and dephosphorylated for 40 minutes after the addition of 6.6 µl 10× rAPid buffer and 10 U of rAPid alkaline phosphatase (Roche). The XhoI/NheI digested PCR fragments were ligated into the XhoI/NheI digested and dephosphorylated vector with T4 DNA ligase (NEB), transformed into XL1-Blue bacteria (Agilent) via electroporation and plated on selective LB-agar/Ampicillin (100 µg/ml) plates. The sequence of the plasmids in the obtained colonies was verified via sequencing.

TABLE 4

| Template DNA | Forward Primer | Reverse Primer |
|---|---|---|
| 3-23 sense | Xho VH3-23 stuf For | Nhe VH stuf Rev |
| 3-53 sense | Xho VH3-53 stuf For | Nhe VH stuf Rev |

Example 3: Immunization of Rabbits and ELISA

New Zealand white rabbits, 12 weeks of age, were immunized with lysozyme (as an exemplary antigen). Antigen (0.3 mg per rabbit) was emulsified with non-toxic highly effective adjuvant containing 92.8% mineral oil, 3.48% TWEEN 80 surfactant, 3.48% Span 80, 0.23% lipo-polysaccharide (BioGenes) and administrated by intramuscular injection. The animals received up to four booster injections each at 1-week intervals. An exemplary immunization protocol is to showed in Table 5:

TABLE 5

| Immunization | Day | Antigen (µg/Rabbit) | Adjuvant |
|---|---|---|---|
| Initial | 0 | 300 | Adjuvant |
| First boost | 14 | 100 | Adjuvant |
| Second boost | 21 | 100 | Adjuvant |

TABLE 5-continued

| Immunization | Day | Antigen (μg/Rabbit) | Adjuvant |
| --- | --- | --- | --- |
| Third boost | 28 | 100 | Adjuvant |
| Final boost | 37 | 100 | PBS |

Blood samples were taken via marginal ear vein and tested by ELISA for antigen specific immune response. The animals which showed a high immune titer were finally boosted and after 5 days, spleen, femurs and blood were extracted.

An enzyme-linked immunosorbent assay (ELISA) was used to measure antigen specific antibody levels in animal sera. Microtiter plates (442404, Thermo-scientific) were coated with 10 μg/ml lysozyme in coating buffer (0.5 M carbonate-bicarbonate buffer, pH 9.6) and incubated at 4° C. overnight. Then, the plates were washed with washing solution (PBS, 0.05% TWEEN 20 surfactant) and blocked with 1% BSA in PBS for 1 hour at room temperature. After washing, 100 μl of diluted sera was added and incubated for 2 hour at room temperature. A negative control was performed with PBS. The plates were washed with washing solution and detected by goat anti-rabbit HRP-conjugated antibody (Ab6721, Abcam) diluted 1:20000 in blocking buffer. After washing, each well was incubated with 100 μl of TMB (50-76-00, KPL) substrate in the dark at room temperature for 15 minutes. Then, the reaction was stopped by adding 50 μl of 0.5 M H2SO4. The optical density (OD) of the each well was measured at 450/540 nm on a plate reader (TECAN, infinite M1000).

Single-cell suspension from spleen and bone marrow were obtained by sieving the corresponding tissues through a cell strainer. The cells were washed 2 times with DPBS and suspended in 10 ml PBS. Mononuclear cells (MNC) from different organs (spleen, bone marrow and Blood) were purified on Histopaque-1007 (10771, Sigma-Aldrich). Briefly, 2 times in PBS diluted 10 ml blood or the 10 ml single-cell suspension obtained from spleen and bone marrow were layered over 20 ml of Histopaque-1077 and centrifuged at 400 g, 60 min at 25° C. MNC containing interphase above the barrier between Histopaque-1077 and serum were collected and centrifuged at 960×g, 5 min at 4° C.

Example 4: RNA Isolation and cDNA Synthesis

Total RNA was isolated from $10^6$-$10^7$ MNC derived from blood, bone marrow or spleen with a SV Total RNA Isolation System kit (Promega) according to the manufacturer's protocol. Elution of the RNA was performed with 100 μL Nuclease-free water.

Primers IgG-RP and K-RP (Table 6) were diluted to 2 μM in DEPC treated water (SIGMA). Approximately 10-1000 ng RNA was melted for 5 minutes at 65° C. and cooled on ice. Subsequently, cDNA was prepared by addition of SuperScript III First-Strand Synthesis SuperMix/RNaseOut (Life Technologies) reaction mix and incubation for 1 hour at 50° C. Finally, the reverse transcriptase was inactivated by heating the reaction mixture to 85° C. for 5 minutes.

TABLE 6

| RNA source | PBMC | Bone Marrow | Spleen |
| --- | --- | --- | --- |
| Kappa cDNA primer | K-RP | K-RP | K-RP |
| IgG cDNA primer | IgG-RP | IgG-RP | IgG-RP |

Example 5: Capturing of the Rabbit CDR3 Repertoire Via Nested PCR and Subsequent Cloning

TABLE 7

| | Primer combination for Primary PCR | |
| --- | --- | --- |
| PCR fragment | VL Forward primer | VL Reverse Primer |
| Rabbit VH1 | RabVH1 FP | IgG-RP |
| Rabbit VH2 | RabVH2 FP | IgG-RP |
| Rabbit VH3 | RabVH3 FP | IgG-RP |
| Rabbit VH4 | RabVH4 FP | IgG-RP |
| | VH-Forward primer | VH Reverse Primer |
| Rabbit VK1 | Rab Vk1 FP | K-RP |
| Rabbit VK2 | Rab Vk2 FP | K-RP |
| Rabbit VK3 | Rab Vk3 FP | K-RP |
| Rabbit VK4 | Rab Vk4 FP | K-RP |
| Rabbit VK5 | Rab Vk5 FP | K-RP |
| Rabbit VK6 | Rab Vk6 FP | K-RP |

TABLE 8

| | Primer combination for Secondary PCR | |
| --- | --- | --- |
| PCR fragment | VH-CDR3 Forward primer | VH-CDR3 Reverse primer |
| Rabbit VH-CDR3_1 | Rab VH CDR3 BarI For | Rab VH CDR3 BarI Rev 1 |
| Rabbit VH-CDR3_2 | Rab VH CDR3 BarI For | Rab VH CDR3 BarI Rev 2 |
| Rabbit VH-CDR3_3 | Rab VH CDR3 BarI For | Rab VH CDR3 BarI Rev 3 |
| | VL-CDR3 Forward primer | VL-CDR3 Reverse primer |
| Rabbit VL-CDR3_1 | Rab VLk CDR3 BarI For | Rab CDR3 VLK BarI Rev 1 |
| Rabbit VL-CDR3_2 | Rab VLk CDR3 BarI For | Rab CDR3 VLK BarI Rev 2 |
| Rabbit VL-CDR3_3 | Rab VLk CDR3 BarI For | Rab CDR3 VLK BarI Rev 3 |
| Rabbit VL-CDR3_4 | Rab VLk CDR3 BarI For | Rab CDR3 VLK BarI Rev 4 |
| Rabbit VL-CDR3_5 | Rab VLk CDR3 BarI For | Rab CDR3 VLK BarI Rev 5 |
| Rabbit VL-CDR3_6 | Rab VLk CDR3 BarI For | Rab CDR3 VLK BarI Rev 6 |
| Rabbit VL-CDR3_7 | Rab VLk CDR3 BarI For | Rab CDR3 VLK BarI Rev 7 |

TABLE 8-continued

| | | |
|---|---|---|
| Rabbit VL-CDR3_8 | Rab VLk CDR3 BarI For | Rab CDR3 VLK BarI Rev 8 |
| Rabbit VL-CDR3_9 | Rab VLk CDR3 BarI For | Rab CDR3 VLK BarI Rev 9 |
| Rabbit VL-CDR3_10 | Rab VLk CDR3 BarI For | Rab CDR3 VLK BarI Rev 10 |
| Rabbit VL-CDR3_11 | Rab VLk CDR3 BarI For | Rab CDR3 VLK BarI Rev 11 |
| Rabbit VL-CDR3_12 | Rab VLk CDR3 BarI For | Rab CDR3 VLK BarI Rev 12 |
| Rabbit VL-CDR3_13 | Rab VLk CDR3 BarI For | Rab CDR3 VLK BarI Rev 13 |

For the primary PCR, the Rabbit VH and VL regions were PCR amplified from 2.5-250 ng of cDNA with 10 μM primers (Table 7) using Phusion DNA polymerase (NEB), Phusion buffer (NEB) and 10 mM dNTPs (Sigma) in a 50 μl reaction. The obtained VH and VL variable region PCR fragments (±300-400 base pairs) were purified with a NucleoSpin® Gel and PCR Clean-up kit (Macherey-Nagel). For amplification of the VH and VL CDR3 regions with flanking BarI restriction sites, a secondary PCR was performed on pooled purified VH and VL fragments with 10 μM biotinylated primers (Table 8), Phusion DNA polymerase (NEB), Phusion buffer (NEB) and 10 mM dNTPs (Sigma) in 50 μl reactions. The obtained VH-CDR3 (90-150 base pairs) and VL-CDR3 fragments (90-140 base pairs) were purified with a NucleoSpin® Gel and PCR Clean-up kit (Macherey-Nagel) but eluted with Qiagen elution buffer.

0.5-1 μg of the obtained VH- and VL-CDR3 PCR products were digested in a 50 μl reaction with 5-10 U BarI (SibEnzyme) in SEBuffer 2K for 3 hours at 37° C. To remove the flanking regions from the Rabbit VH and VL CDR3 DNA fragments, the BarI digested samples were incubated in the presence of 1M NaCl with 40 μl of Streptavidin beads (Dynabeads M-280 Invitrogen), 2× pre-washed with 200 μl of Tris buffered saline (TBS); pH 7.5) at room temperature. After agitating at 800 rpm for 20-30 minutes the beads were pelleted by a magnet and the supernatant retrieved.

The VH shuttle vectors for VH-CDR3 and the acceptor vectors for VL-CDR3 (10 μg) were digested with BarI in a 50 μl reaction with 10-20 U BarI (SibEnzyme) in SEBuffer 2K for 3 hours at 37° C. 10 μl of 10×rAPid buffer (Roche) was added and the vector fragments were dephosphorylated with 10 U rAPID for 40 minutes (Roche). After inactivation for 5 minutes at 75° C. and purification with a PCR cleanup kit (Qiagen) the purified DNA was used for ligation with the BarI digested VH-CDR3 and VL-CDR3 fragments with T4 DNA ligase (Roche) in ligation buffer (Roche) for 18 hours at 4° C. The DNA in the ligation mix was purified with Oligo Clean & Concentrator kit (ZymoResearch), eluted in 16 μl H$_2$O and used for electroporation of XL1-Blue bacteria. After 1 hour of incubation in SOC medium, the bacteria were plated on selective LB-Ampicillin (100 μg/ml) agarose plates and incubated overnight at 37° C. The obtained colony numbers are described in Table 9.

TABLE 9

| | Library complexity in Acceptor vectors | | |
|---|---|---|---|
| | PBMC (P) | Bone Marrow (B) | Spleen (S) |
| VH-CDR3 | $1.3 \times 10^6$ | $2.7 \times 10^5$ | $6.9 \times 10^5$ |
| VL-CDR3 | $7.8 \times 10^5$ | $4.8 \times 10^5$ | $5.7 \times 10^5$ |

The VH libraries containing the synthetic variation in CDR1 and CDR2 and the libraries containing rescued Rabbit VH-CDR3 repertoire were first PCR amplified separately (Table 10). The human VHFR1-VHFR3 library (±325 base pairs), including the variegated VH-CDR1 and VH-CDR2 regions, was amplified from the GeneArt VH libraries with a primer preceding the VH-FR1 region and a reverse primer which is complementary to the human FR3 region. The Rabbit VH-CDR3 repertoire was PCR-amplified (±160-180 base pairs) from DNA, obtained from the PBMC, bone marrow and spleen derived libraries, with a primer annealing in the human FR3 region and a primer annealing in the plasmid sequence 3' from the FR4 region.

TABLE 10

| | Synthetic Variation in CDR1 and CDR2 | | Natural diversity in Rabbit VH-CDR3, which is located between Human FR3 and Human FR4 in the VH shuttle libraries | | |
|---|---|---|---|---|---|
| | Libraries | | | Bone | |
| | pVH-3_23 | pVH3_53 | PBMC (P) | Marrow (B) | Spleen (S) |
| Forward Primer | B-Nco app8 For | B-Nco app8 For | VH FR3-23 For | VH FR3-23 For | VH FR3-23 For |
| Reverse Primer | FR3 VH3_23 as | FR3 VH3_23 as | pEX14 Rev | pEX14 Rev | pEX14 Rev |

The DNA from the two libraries was assembled via PCR based on the overlap within the human FR3 regions which is present in both fragments. First 10 PCR cycles were performed without primers using an annealing temperature/extension temperature of 68° C. for 45 seconds, followed by 20 cycles with the outer primers B-Ncoapp8For and pEX14Rev and an extension time of 50 seconds at 68° C. The obtained 6 bands (P3_23, B3_23, S3_23, P3_53, B3_53 and S3_53) were gel purified with a gel purification kit (Macherey-Nagel) followed by a second purification with a PCR purification kit (Macherey-Nagel).

Amplification of VL variable fragments from the six libraries with oligonucleotides SpeHuVHFR4For and B-NotRev was performed in a 50 µl reaction using ca. 100 ng of the GeneArt VL derived library, in which the Rabbit derived VL-CDR3 was inserted, as DNA template. The PCR conditions with Phusion DNA polymerase (NEB) were as follows: 30 seconds denaturation at 95° C., followed by 20 cycles of 20 seconds denaturation at 95° C., 20 seconds annealing at 60° C. and a 20 seconds extension at 72° C. The 20 cycles were followed by an additional 3 minutes extension at 72° C. The six obtained fragments (P1-27, P3-20, B1-27, B3-20, S1-27 and S3-20) were gel purified with a gel purification kit (Macherey-Nagel).

Example 6: Generation of scFv Library

Because the VH and VL libraries share a VH-FR4 framework region, this common DNA element was used to assemble the fragment into complete scFv encoding libraries (Table 11) via overlap PCR.

TABLE 11

| PBMC (P) | | | | Bone Marrow (B) | | | | Spleen (S) | | | |
|---|---|---|---|---|---|---|---|---|---|---|---|
| VH | | | | | | | | | | | |
| P3_23 | | P3_53 | | B3_23 | | B3_53 | | S3_23 | | S3_53 | |
| VK | | | | | | | | | | | |
| P1-27 | P3-20 | P1-27 | P3-20 | B1-27 | B3-20 | B1-27 | B3-20 | S1-27 | S3-20 | S1-27 | S3-20 |
| scFv Library | | | | | | | | | | | |
| 1 | 2 | 3 | 4 | 5 | 6 | 7 | 8 | 9 | 10 | 11 | 12 |

VH (120 ng) and VK (140 ng) DNA fragments were added to a PCR mix containing 10 mM dNTPs (Invitrogen), Phusion DNA polymerase (NEB) in Phusion HF buffer (NEB) in a final volume of 50 µl. After an initial denaturation for 30 seconds at 95° C., 25 PCR cycles were performed without primers using a melting temperature of 95° C. for 20 seconds, an annealing temperature of 65° C. for 60 seconds and an extension at 68° C. for 60 seconds, followed by 15 PCR cycles with the biotinylated outer primers B-Ncoapp8For and B-NotRev applying a melting temperature of 95° C. for 20 seconds and an extension time of 50 seconds at 68° C. The 15 cycles were followed by an additional 3 minutes extension at 68° C.

The obtained scFv library encoding DNA fragments were purified with a PCR purification kit (Macherey-Nagel) and digested for 1 hour at 37° C. with NcoI-HF(NEB) and NotI-HF(NEB) in OUTSMART restriction enzyme buffer (NEB). After inactivation of the enzymes at 80° C. for 20 min, 16 µl of 5M NaCl was added and, to remove the biotinylated digested ends, the mixture was applied to streptavidin beads and incubated for 45 minutes at 25° C. Subsequently, the beads were pelleted with a magnet and the DNA was extracted from the supernatant with a PCR purification kit (Macherey-Nagel).

Phagemid vector was digested NcoI-HF(NEB) and NotI-HF(NEB) in OUTSMART restriction enzyme buffer(NEB) for 2 hours at 37° C. Then, 10 µl of 10×rAPid buffer (Roche) was added and the vector fragments were dephosphorylated with 10 U rAPID for 40 minutes (Roche). After inactivation for 5 minutes at 75° C. and purification with a PCR cleanup kit (QIAGEN) the purified scFv library encoding DNA was used for the ligation.

Example 7: Generation of the Assembled scFv Antibody Phagemid Libraries in E. coli For the ligation 500 ng NcoI/NotI digested and dephosphorylated phagemid vector was mixed with ±300 ng of NcoI/NotI digested scFv encoding DNA (ratio vector:insert=1:3) and ligated with T4 DNA ligase (Roche) in ligase buffer (Roche) for 18 hours at 4° C. Prior to the transformation, the ligated DNA was purified with a ZymoResearch kit and eluted in 15 µl H$_2$O. The transformation was performed by adding 2 µl of the purified DNA to 40 µl of electrocompetent XL1-Blue cells (Agilent) and electroporation. After 1 hour of incubation in SOC medium at 37° C., the bacteria were plated on selective LB-Ampicillin (100 µg/ml) agarose plates and incubated overnight at 37° C. The total of obtained colony numbers is described for each organ in Table 12.

TABLE 12

| | Library size |
|---|---|
| Bone Marrow | $2.7 \times 10^8$ |
| PBMC | $2.4 \times 10^8$ |
| Spleen | $2.4 \times 10^8$ |

To show that the majority of the obtained scFv library contained an insert of the expected size (±850 base pairs), an NcoI/NotI digest was performed with a DNA sample from each of the 12 retrieved sub libraries. The control digest was performed using 500 ng DNA, NcoI-HF (NEB) and NotI-HF(NEB) in 20 µl OUTSMART restriction enzyme buffer (NEB) for 1.5 hours at 37° C.

Further quality control was performed by analyzing the scFv encoding DNA in the libraries via sequencing of 96 individual clones. Both the two VH and VL libraries were found to be evenly distributed and to have an intact open reading frame (Table 13). In addition, the length of the VL-CDR3 was distributed between 7 and 13 amino acids and for the VH-CDR3 between 5 and 21 amino acids.

TABLE 13

| | Frequency of VH/VL families |
|---|---|
| VH-3_23 | 33 |
| VH-3_53 | 48 |
| VK1-27 | 34 |
| VK3-20 | 38 |

To assess the variation within the CDR3 regions, the VH- and VL-CDR3 sequences of ±100 clones were analyzed and most of the CDR3 were found to be unique (Table 14).

TABLE 14

| | Number of clones | |
|---|---|---|
| Occurrence | VH-CDR3 | VL-CDR3 |
| 1 x | 76 | 111 |
| 2 x | 4 | 5 |
| 3 x | 2 | 0 |
| 4 x | 0 | 1 |
| 5 x | 1 | 0 |

Example 8: Phage Rescue and Selection of Specific Libraries

For phage production, the cultures were inoculated from glycerol stocks of the 3 libraries (P, B, and S) in 250 ml LB-GAT to an $OD_{600}$ of 0.05 in a 2 L flask 200 rpm at 37° C. At $OD_{600}$ of 0.5-0.7, the bacteria were infected with M13K07-helperphage (moi of 10) and incubated for 30 minutes at 37° C. without agitation, followed by incubation for 30 minutes at 37° C. with 200 rpm. The medium was changed via centrifugation at 3000 rpm in a HERAEUS Megafuge 1.0 for 15 minutes, the supernatant discarded, and the pellet resuspended in 200 ml $LB_{AK}$ (ampicillin 100 µg/ml, Kanamycin 50 µg/ml) medium and incubate over night at 30° C. with 200 rpm.

The bacterial debris was removed via centrifugation (Sorvall SLA3000) for 20 minutes at 6000 rpm. After addition of 0.15 vol of PEG/NaCl to the supernatant, followed by incubation on ice for 1.5 hour, the phages were pelleted for 1 hour at 10.000 rpm at 4° C. (Sorvall SLA3000). The supernatant was removed and the phage pellets were resuspended in 40 ml phage dilution buffer and transferred into a 50 ml falcon tube. After gently agitation for 30 min at 4° C., the PEG precipitation was repeated with the addition of 0.15 vol of PEG/NaCl and incubation on ice for 30 min. The phages were precipitated by centrifugation for 30 min 4000 rpm at 4° C. (Sorvall F13S-14x50cy) and the supernatant discarded. The pelleted phages were gently resuspended in phage dilution buffer, centrifuged at 15.000 g for 30 min at 4° C. (Sorvall F13S-14x50cy), the supernatant was transferred into a new tube, and, after addition of 50% glycerol to the supernatant to obtain a final 20% concentration, the phage were stored at −80° C.

Phage titers were determined via infection of XL1-Blue with serial dilutions of the obtained phage and subsequent plating on LB-GAT plates. Selection of specific phage from each of the three scFv phagemid libraries (P, B and S) was performed after 3 subsequent depletion steps: 2×a 1 hour depletion of $5×10^{11}$ rescued phage on 250 µl of blocked StreptavidinDynabeads (M-280 Life Technologies) in 2 ml PBS containing 4% Biotin Free-milk (LabScientific) at RT, followed by an overnight depletion at 4° C.

For the first round of selection, the StreptavidinDynabeads were removed with a magnet and the supernatant was incubated with biotinylated lysozyme (100 nM) in 2 ml PBS containing 4% Biotin Free-milk at room temperature. After a 3 hour incubation, the phage-lysozyme mix was added to unused blocked StreptavidinDynabeads and rotated at room temperature for 45 min. The beads were then washed: 10 times with 1 mL PBS, containing 0.1% biotin free-milk and 0.1% TWEEN 20 surfactant, via a repeated short spin, capture of the beads with a magnet followed by removal of the supernatant. For elution, 1 mL of Phage Elution Buffer (0.1 M Gly, pH 2.2+Neutral Red) was added to the washed beads and rotated at room temperature. After 10 min the beads were removed with a magnet and the supernatant containing the eluted phage added to fresh tubes containing 150 µL 2 M TRIS (pH 8) and 150 µL LB.

The neutralized eluted phages were added to 10 mL of actively growing XL1 ($OD_{600}$=0.5-0.7), incubated for 30 min at 37° C. without shaking and for 15 min at 37° C. at 150 rpm. The bacteria were pelleted at 4000×g at 4° C. for 10 minutes, the supernatant removed and the pellet was resuspended in 1 mL of LB-GAT medium. Dilutions: $10^{-2}$, $10^{-3}$, and $10^{-4}$ were prepared in LB-GAT and plated on small LB-GAT plates to analyze the phage recovery while the remainder was plated on large LB-GAT plates. After overnight growth, the bacteria were harvested with 6 mL LB-GAT media and after the addition of 50% glycerol to a final 20% concentration, stored as glycerol stock at −80° C. The plates with the serial dilutions indicated that $1×10^5$-$1×10^6$ colonies were obtained from each library Phage derived from round-I were rescued as described before and applied in the second round of selection, starting with a single depletion step by incubating $2×10^{11}$ rescued phage on 250 µl of blocked StreptavidinDynabeads (M-280 Life Technologies) in 2 ml PBS containing 4% Biotin Free-milk (LabScientific) for 1 hour at RT. The StreptavidinDynabeads were removed with a magnet and the supernatants were incubated with or without Biotinylated lysozyme (100 nM) in 2 ml PBS containing 4% Biotin Free-milk at room temperature. After 3 hour incubation, the phage mixes were added to unused blocked StreptavidinDynabeads and rotated at room temperature for 45 min. The beads were washed, phage eluted, rescued, plated and the bacteria were harvested as described above. The plates with the serial dilutions indicated that $1×10^6$-$1×10^7$ colonies were obtained from the libraries incubated with the biotinylated antigen whereas only $1×10^4$-$1×10^5$ colonies were obtained if the antigen was omitted.

Phage derived from the second round were rescued as described before. Selections on lysozyme were performed initially as described for selection round-II with incubation of $2×10^{11}$ phage and a concentration of 25 nM biotinylated lysozyme and washing as described before. However, after the last washing step the beads were split into two fractions:

A) Eluted and processed as described above

B) Resuspended and incubated with 1 mL of non-biotinylated lysozyme (1 µM) and rotated at RT for 1 hour and then eluted and processed as described above For both methods, A) panning in solution and B) Off-rate selection, the phage recovery was between $1×10^7$ and $5×10^7$.

TABLE 15

| Library | Abbreviation | R1 5E+11 phage | R2 2E+11 phage | R3 1E+11 phage |
|---|---|---|---|---|
| PBMC | P | 100 nM biot-HEL | 100 nM biot-HEL | 25 nM biot-HEL |
| BM | B | 100 nM biot-HEL | 100 nM biot-HEL | 25 nM biot-HEL |
| Spleen | S | 100 nM biot-HEL | 100 nM biot-HEL | 25 nM biot-HEL |

Example 9: ELISA of Individual scFv

Individual colonies, grown on LB-GAT plates, were used for picking into 2 ml masterblocks (Greiner #780271) with 1.25 ml $LB_{GAT}$ media and incubated at 37° C./210 rpm. The next day, 70 µl of the overnight culture was inoculated into a new masterblock with 1.25 ml $LB_{GAT}$ media and cultivated at 37° C. with 200 rpm. After 6 hours, the masterblock was centrifugated at 3800 rpm for 20 minutes at 4° C. (Megafuge 1.0R). The medium was discarded and the pellet resuspended in 1.25 ml LB containing ampicillin (100 ug/ml), Tetracycline (30 µg/ml) and IPTG (1 mM) and incubated overnight at 21° C. with 200 rpm. The following day, the plates were centrifugated at 3800 rpm for 20 minutes at 4° C. (Megafuge 1.0R) and the media discarded. To extract the scFv, the pellets were resuspended in 400 µl DPBS and 5 cycles of freeze/thawing were applied. After the fifth cycle, 12.8 µl of DNaseI mix (150 µg/mL DNaseI, 20 mM $MgCl_2$, 2 mM $MnCl_2$ in DPBS) was added to each well and incubated at room temperature with 200 rpm. After a 30 minutes incubation the plates were centrifuged (Megafuge 1.0R) to remove the bacterial debris at 3800 rpm for 20 min at 4° C. and the supernatants transferred to a 0.5 ml plate (Nunc #267334) for storage at −80° C.

For the ELISA, MaxiSorb plates (Nunc) were coated overnight at 4° C. with 50 µl per well of neutravidin (Pierce) at 5 µg/mL in DPBS (Life Technologies), washed 3 times with 300 µl PBS/0.05% TWEEN 20 surfactant and blocked with PBS/0.05% TWEEN 20 surfactant/1% BSA at 200 µl per well. After blocking for 1 hour at room temperature, the plates were washed 3 times with 300 µl PBST. Every first column was incubated at 50 µl per well with biotinylated lysozyme (GeneTex), diluted to 5 µg/ml in PBS/0.05% TWEEN 20 surfactant/1% BSA, and every second column with PBS/0.05% TWEEN 20 surfactant/1% BSA. After 1 hour incubation at room temperature, the plates were washed 3 times with 300 µl PBST per well and subsequently incubated with bacterial scFv extracts at 50 µl/well, such that each scFv was applied in a well with and into a neighbouring well without antigen. After the incubation with scFv, each well was washed 3 times with 300 µl PBST and incubated with 50 µl TMB substrate. After 7.5 minutes the colorimetric reaction was stopped by the addition of 50 µl 0.5M $H_2SO_4$ per well and the absorbance was measured at 450 nm.

Figure 1:
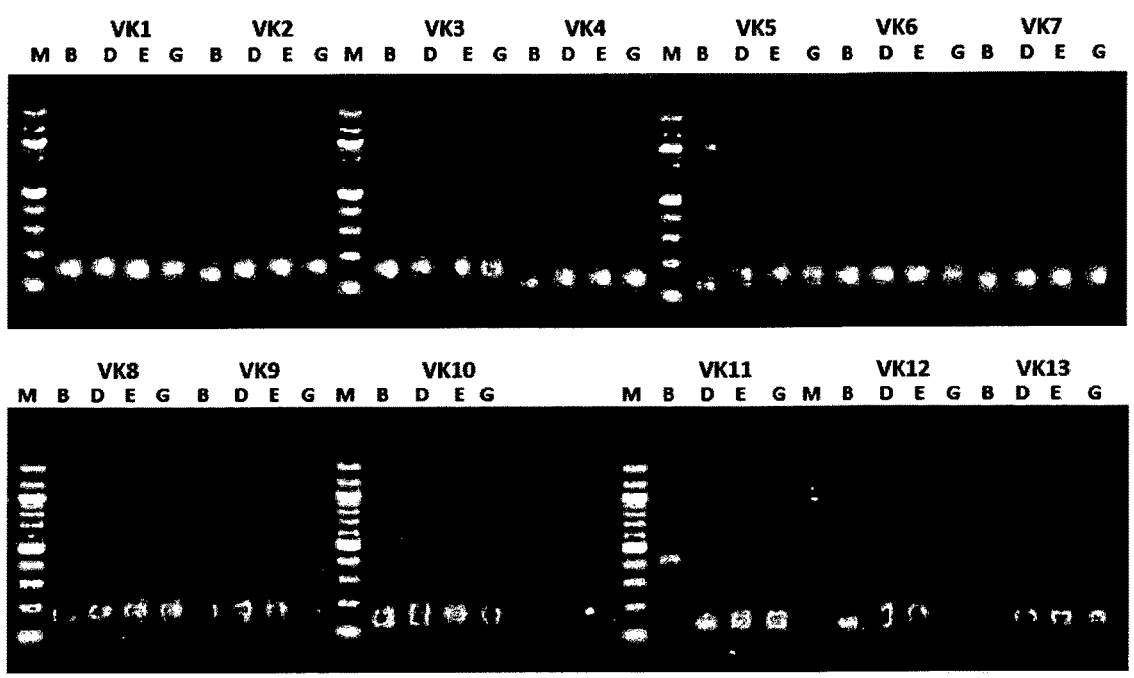
Figure 5:
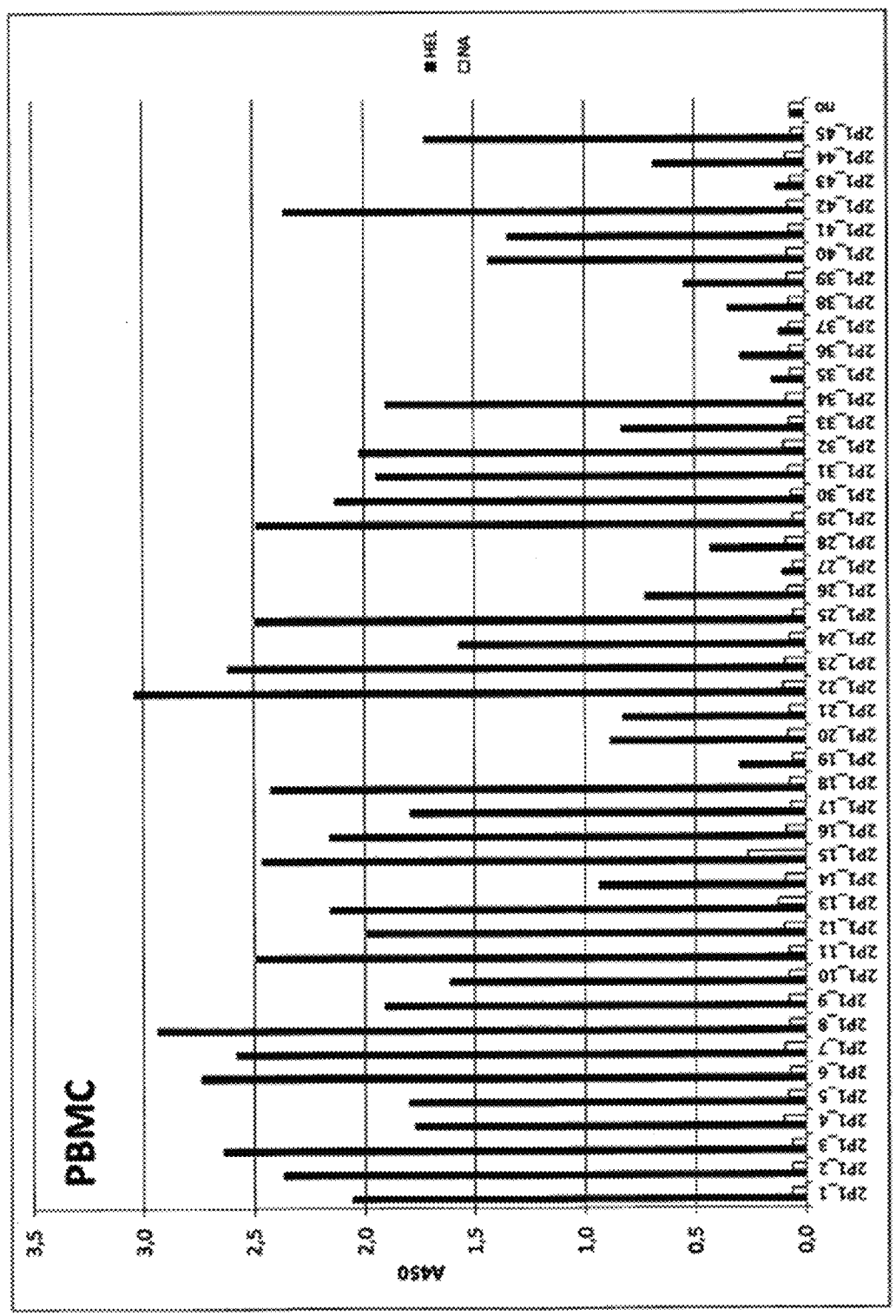
Figure 5:
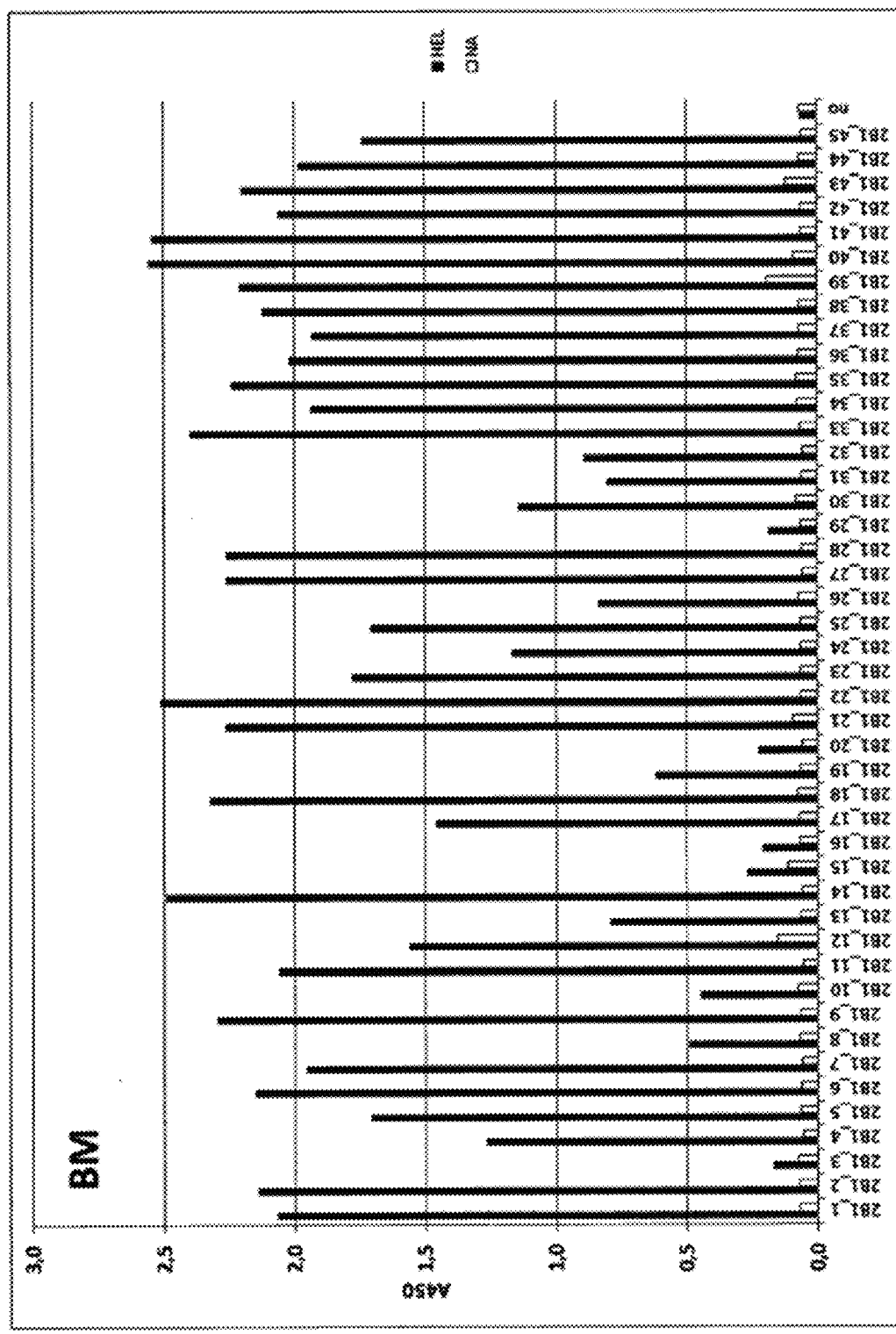
Figure 5:
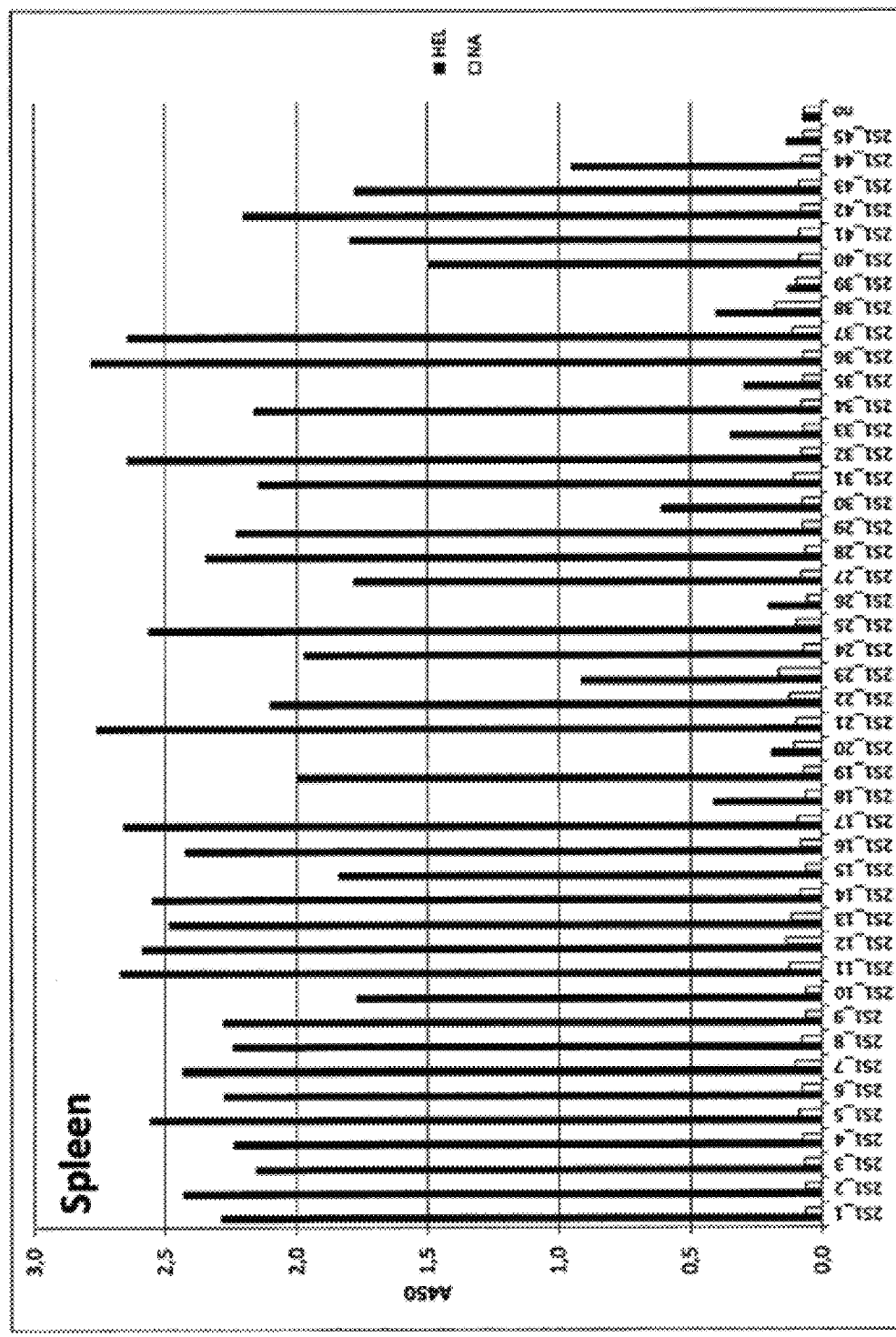

ELISA Results from clones obtained in selection round 2 are shown in FIG. 5.

Example 10: Sequencing of ELISA Hits

Clones with detectable binding in ELISA were inoculated on $LB_A$ agar plates and sent for Sanger sequencing to an external service provider (GATC Biotech AG, Konstanz).

All sequenced clones showed framework regions that correspond to the selected human acceptor frameworks and contained mutations in the CDR1 and CDR2 of the heavy and light chain.

From 285 sequenced clones 176 unique VH CDR3/VL CDR3 combinations with 140 unique VH CDR3 and 161 unique VL CDR3 sequences were identified. Some of the VH CDR3 sequences were clearly related and appear to be the result of the in vivo affinity maturation in the immunized rabbit. As an example some individual sequences of VH CDR3 group A and B are shown in FIG. 24. 21 separated VH CDR3 groups were identified and one representative of each group is included in FIG. 25. A DDYGD (SEQ ID No: 43) motive appears to be favored during selections throughout different VH CDR3 lineages. This motive is present in the biggest VH CDR3 group and occurs in the majority of analyzed sequences.

The VH CDR3 sequences of group A were found in VH3-23 as well as in VH3-53 framework, whereas the group B VH CDR3 sequences appeared exclusively in VH3-53 framework. This large group of affinity matured VH CDR3 sequences would most likely have been lost in libraries using VH3-23 as acceptor framework.

CDR1/2 sequences were compared to the germline encoded sequence of the corresponding acceptor framework and mutations were counted. H1 shows the highest mutation rate, other regions are more conserved (FIG. 26).

Figure 9:
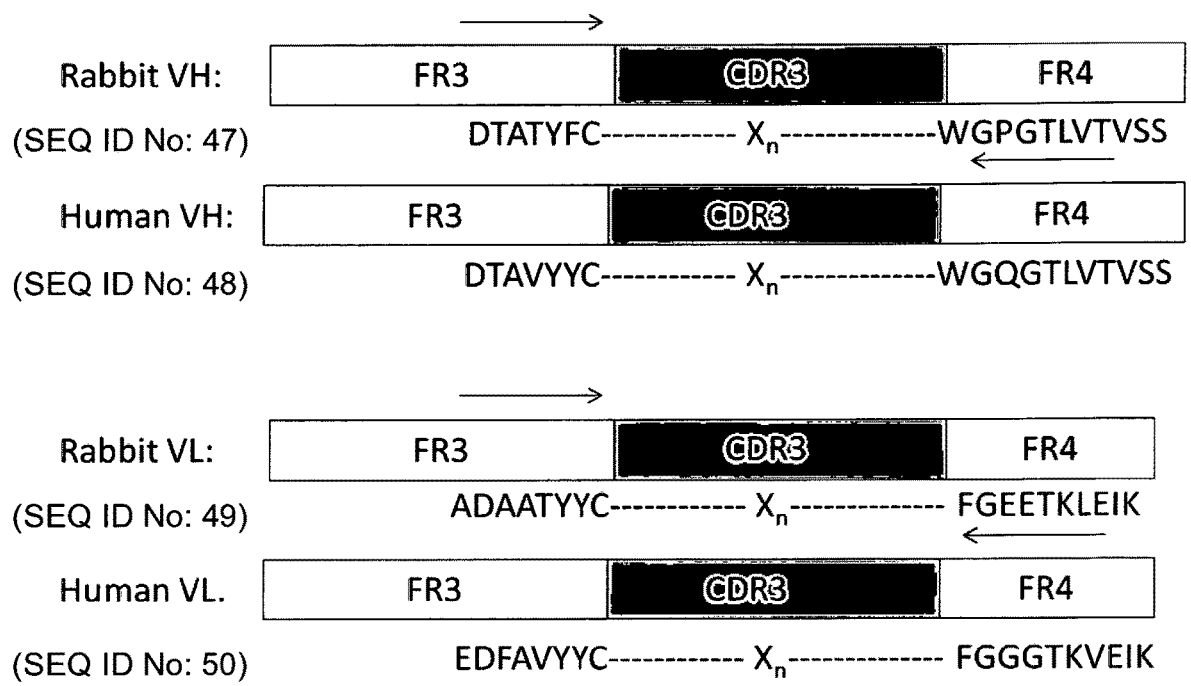
Figure 10:
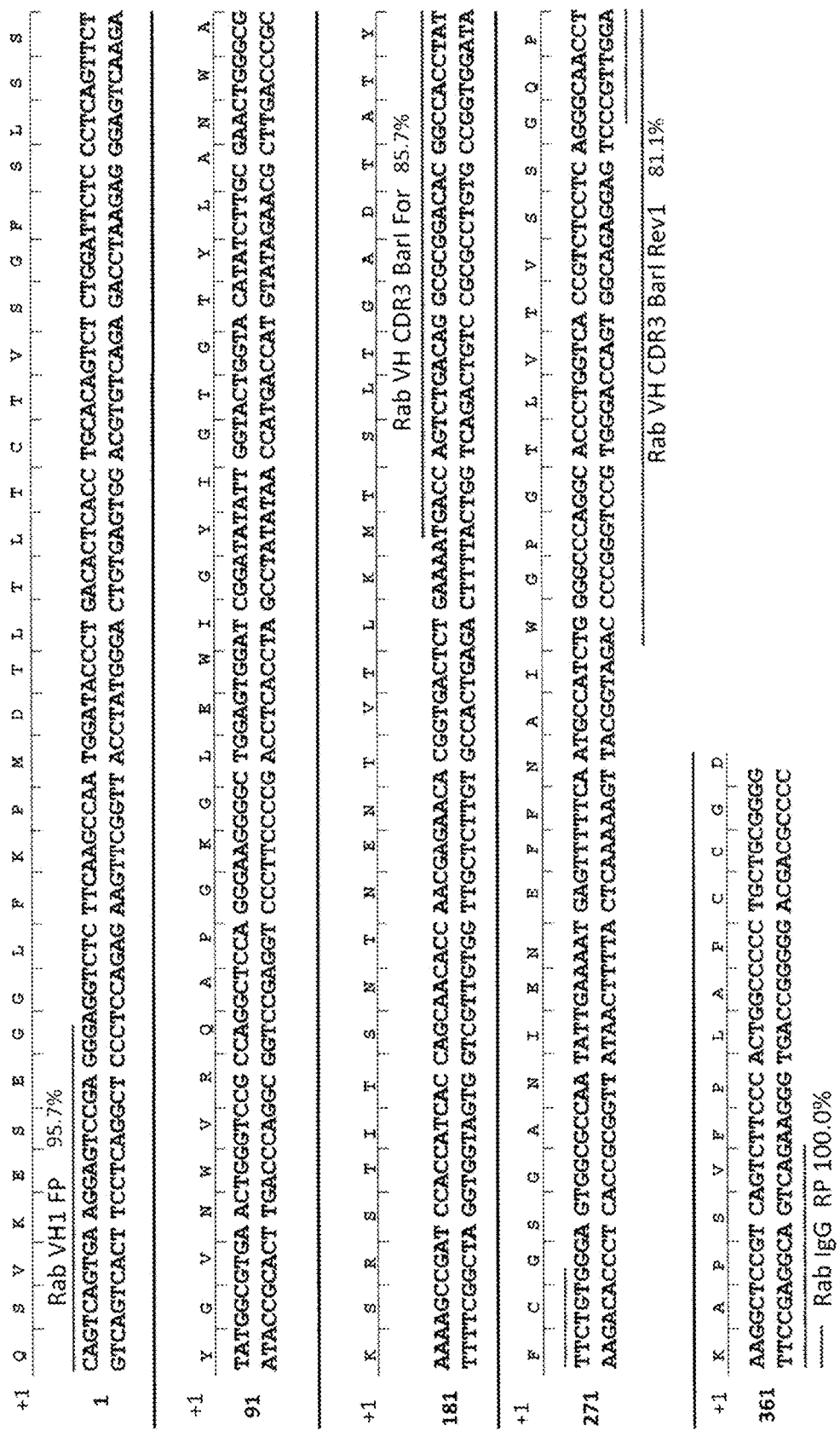
Figure 15:
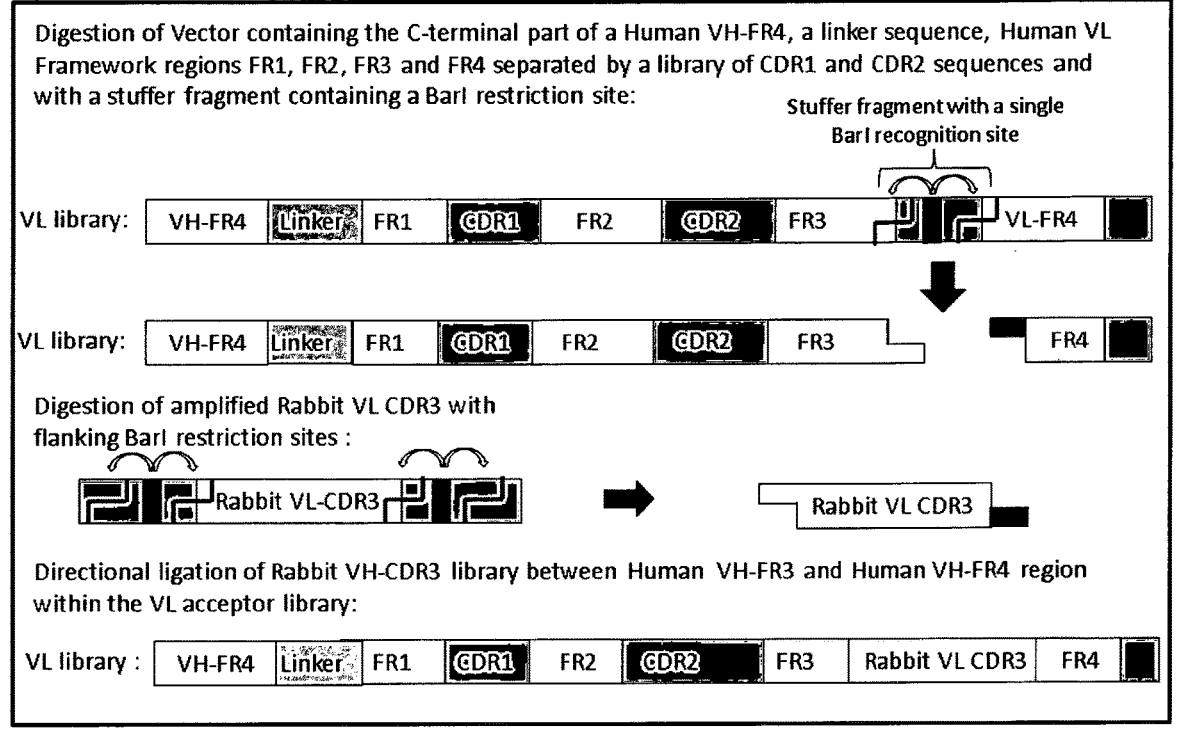
FIG. 15 shows step 4 of a preferred method of the invention for generating an scFv library cloned in a phage display vector. Step 4: Assembly of Rabbit VL-CDR3 regions into an acceptor vector containing synthesized Human FR1, FR2 and FR3 domains and a library of CDR1 and CDR2 sequences.
Figure 16:
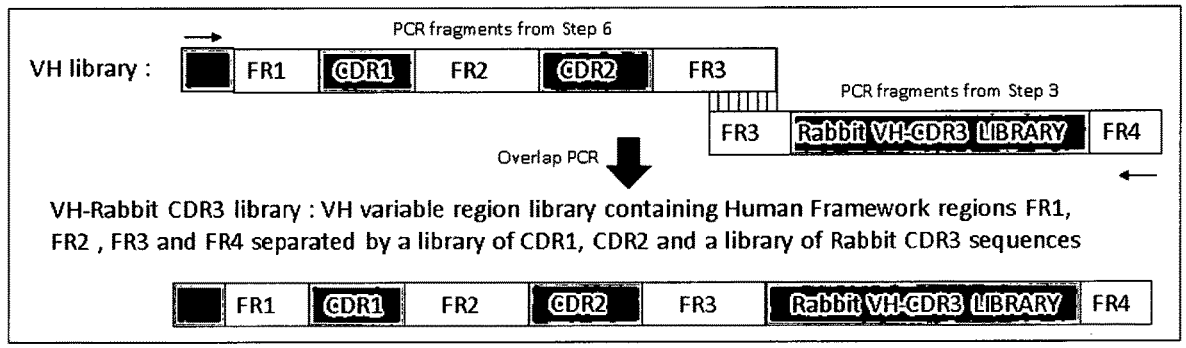
FIG. 16 shows step 7 of a preferred method of the invention for generating an scFv library cloned in a phage display vector. Step 7: Assembly of a VH variable region library containing Human Framework regions FR1, FR2 and FR3 separated by a library of CDR1 and CDR2 sequences and a library of Rabbit CDR3 sequences via overlap PCR.

The alignment shown in FIG. 9 reveals different mutations that were observed for different VH CDR3 groups and also for different acceptor frameworks within one VH CDR3 group, demonstrating the complexity of the interplay between VH CDR3, acceptor frameworks and beneficial mutations in CDR1/2 that is best addressed with the described libraries.

Example 11: SPR Measurement

The anti-His antibody provided in the anti his capture kit from GE Healthcare (order number 28-9950-56) was coupled to the flow cells of a CM5 chip via amine coupling chemistry. 11668.2 and 11288.1 RU were coupled to Fc1 and Fc2, respectively.

The assay was run in a Biacore X100, according to the following protocol: ScFv were captured in a concentration of 5 µg/ml in Fc2 with a flow rate of 5 µl/min and a contact time of 60 sec. Capture levels ranged from 450 to 1.400 RU. In single cycle experiments with a contact time of 90 sec, a flow rate of 30 µl/min and dissociation time of 300 sec the binding of lysozyme (GeneTex, GTX82960) was measured in series of five two-fold dilutions, spanning a concentration range from 100 to 6.75 nM. Results were corrected by referencing with Fc1, without captured scFv and with a blank without lysozyme for every scFv. The curves were fitted with a 1:1 binding model to determine the Kd, koff and kon values.

The best Kd values were measured for scFv from VH CDR3 group B. Differences in affinities within this group most likely reflect the influence of somatic mutations that happened during affinity maturation in the immunized rabbit (FIG. 27).

Mass humanization of rabbit antibodies according to the present invention delivers multiple humanized antigen-specific hits. It represents a highly potent method to isolate humanized antibodies from rabbit immune repertoires.

The invention claimed is:

1. A method for producing a population of 20 or more different nucleic acids, each encoding at least one protein comprising at least one immunoglobulin variable domain comprising a rabbit CDR3 amino acid sequence embedded in human framework sequences, wherein the nucleic acid sequences encoding the rabbit CDR3 amino acid sequences are diversified among the population, wherein the method comprises the following steps:

(a) providing, simultaneously, at least 10 nucleic acids each encoding a rabbit complementarity determining region 3 (CDR3) amino acid sequence, and (b) generating the population of 20 or more different nucleic acids, each encoding at least one protein comprising at least one immunoglobulin variable domain comprising a rabbit CDR3 amino acid sequence embedded in human framework sequences, wherein the human framework sequences consist of a first human framework region (human FR1), a second human framework region (human FR2), a third human framework region (human FR3), and a fourth human framework region (human FR4), such that the human FR1 and human FR2 regions are interspaced by a complementarity determining region 1 (CDR1), the human FR2 and human FR3 regions are interspaced by a complementarity determining region 2 (CDR2), and the human FR3 and human FR4 regions are interspaced by a rabbit CDR3 amino acid sequence, wherein each nucleic acid sequence encoding the CDR1 or the CDR2 amino acid sequence of the variable domain is independently based i) on a nucleic acid sequence encoding a human CDR1 or a human CDR2, respectively, wherein at least one of the nucleic acid sequences encoding the CDR1 or the CDR2 amino acid sequence has been modified to encode at least one amino acid present in a rabbit CDR1 or a rabbit CDR2 amino acid sequence, respectively, or ii) on a nucleic acid sequence encoding a rabbit CDR1 or a rabbit CDR2, respectively, wherein at least one of the nucleic acid sequences encoding the CDR1 or the CDR2 amino acid sequence has been modified to encode at least one amino acid present in a human CDR1 or a human CDR2 amino acid sequence, respectively, wherein at least 80% of the nucleic acids of the population encode different CDR1 and different CDR2 amino acid sequences, and wherein the human FR1, human FR2, human FR3 and human FR4 regions are human framework regions selected to provide a scaffold conducive for rabbit CDR3 amino acid sequences, wherein (1) the scaffold yields a correctly folded antibody for at least 30% of grafted rabbit CDR3 amino acid sequences; and/or (2) the scaffold exhibits at least 30% framework homology to a rabbit framework wherein at least 10 of the nucleic acids of the population encode different CDR3 amino acid sequences, and wherein the two C-terminal amino acids of human FR2 are optionally non-human, and the two C-terminal amino acids of human FR3 are optionally non-human.

2. The method of claim 1, wherein step (b) comprises:
(i) providing a population of Acceptor Framework nucleic acid sequences,
wherein each Acceptor Framework nucleic acid sequence comprises
nucleic acid sequences encoding a set of framework regions comprising the human FR1, the human FR2, the human FR3, and the human FR4,
wherein the human FR1 and human FR2 regions are interspaced by CDR1, the human FR2 and human FR3 regions are interspaced by CDR2, and the nucleic acid sequences encoding human FR3 and human FR4 regions are linked directly or are interspaced by a stuffer nucleic acid sequence, and
(ii) combining at least 10 nucleic acid sequences each encoding the rabbit CDR3 amino acid sequence with an Acceptor Framework nucleic acid sequence, so that each of the human FR3 and human FR4 regions are interspaced by the rabbit CDR3 amino acid sequence, and wherein
the two C-terminal amino acids of human FR2 are optionally non-human, and
the two C-terminal amino acids of human FR3 are optionally non-human.

3. The method of claim 1, wherein the rabbit CDR3 amino acid sequences are obtained from a rabbit B cell and wherein the rabbit from which the rabbit B cell is obtained was immunized against an antigen of interest.

4. The method of claim 1, wherein at least one of the rabbit CDR3 amino acid sequences is obtained by:
(a) determining the sequence of the rabbit CDR3 regions of the antibodies in a sample obtained from a rabbit immunized against an antigen of interest,
(b) determining the frequency of all rabbit CDR3 amino acid sequences in the sample and generating lineage trees or grouping CDR3 amino acid sequences based on sequence similarities,
(c) optionally excluding rabbit CDR3 amino acid sequence groups or sequences present in a sample from the rabbit prior to immunization, (d) ranking candidate lineages or candidate groups by expansion, isotype, somatic hypermutation, tree complexity, group size and/or convergence,
(e) selecting an individual rabbit CDR3 amino acid sequence representative of at least one lineage or group, and
(f) generating a nucleic acid encoding a peptide comprising the individual rabbit CDR3 amino acid sequence.

5. The method of claim 4, wherein the selecting an individual rabbit CDR3 amino acid sequence representative of at least one lineage or group is selecting an individual rabbit CDR3 amino acid sequence representative of a plurality of lineages or groups or all lineages or groups.

6. The method of claim 1, wherein
(a) the sequence
(i) of the two C-terminal amino acids of the human FR3 region are non-human, and/or
(ii) of the two C-terminal amino acids of the human FR2 region is X1-X2,
wherein X1 is selected from I and V, and
wherein X2 is selected from A, G, and S,
or
(b) the human FR2 region is fully human, and/or the human FR3 region is fully human,
and/or
(c) at least 50% of the nucleic acids of the population encode different CDR3 amino acid sequences.

7. The method of claim 6, wherein the sequence of the two C-terminal amino acids of the human FR3 region is a rabbit sequence.

8. The method of claim 2, wherein
(x) the at least 10 nucleic acids each encoding the rabbit CDR3 amino acid sequence further comprise at least one recognition site for at least one restriction enzyme, and
(xi) the nucleic acid sequences of the Acceptor Framework nucleic acid sequence encoding human FR3 and human FR4 regions are interspaced by the stuffer nucleic acid sequence, wherein the stuffer nucleic acid sequence comprises at least one restriction enzyme recognition site for at least one restriction enzyme.

9. The method of claim 8, wherein the nucleic acids of (x) and (xi) further comprise a recognition site for a restriction enzyme, which is capable of cutting at both sides of the recognition site.

10. The method of claim 8, wherein step (ii) comprises:
(ii1) digesting the at least 10 nucleic acids of (x) using a restriction enzyme that binds to the restriction enzyme recognition site of (x);
(ii2) digesting the stuffer nucleic acid sequence from the Acceptor Framework of (xi) using a restriction enzyme that binds to the restriction enzyme recognition site; and
(ii3) ligating the digested nucleic acid sequences of steps (ii1) and (ii2), such that the nucleic acid sequence encoding the human FR3 and human FR4 region of a nucleic acid is interspaced by a nucleic acid sequence encoding the rabbit CDR3 amino acid sequence, and that sequences each encoding a protein comprising at least one immunoglobulin variable domain are obtained.

11. The method of claim 8, wherein the restriction enzyme is a Type IIb restriction endonuclease.

12. The method of claim 11, wherein the Type IIb restriction endonuclease is BarI.

13. The method of claim 1, wherein
(a) the rabbit CDR3 amino acid sequences encode heavy chain CDR3 (CDR H3) sequences, and/or
(b) the rabbit CDR3 amino acid sequences encode light chain CDR3 (CDR L3) sequences, and/or
(c) the human or rabbit CDR1 regions and the human or rabbit CDR2 regions, on which the CDR1 and CDR2 amino acid sequences are based, are selected from human germline CDR1 regions, human germline CDR2 regions, rabbit germline CDR1 regions, rabbit germline CDR2 regions, human somatic hypermutation CDR1 regions, human somatic hypermutation CDR2 regions, rabbit somatic hypermutation CDR1 regions, rabbit somatic hypermutation CDR2 regions, rabbit gene conversion CDR1 regions, and rabbit gene conversion CDR2 regions, and/or
(d) the human FR1, human FR2, human FR3 and human FR4 regions which are human framework regions selected to provide a scaffold conducive for rabbit CDR3 amino acid sequences are obtainable by:
  (i) providing
    (1) a collection of sequences of naturally occurring human antibodies each comprising a set of human FR1, human FR2, human FR3 and human FR4 regions; and
    (2) a collection of sequences of naturally occurring rabbit antibodies each comprising a set of rabbit FR1, rabbit FR2, rabbit FR3 and rabbit FR4 regions, and
  (ii) identifying a plurality of sets of human FR1, human FR2, human FR3 and human FR4 regions which provide a scaffold conducive for rabbit CDR3 amino acid sequences by
    (1) determining the parameters framework homology, CDR homology, CDR lengths, CDR canonical structure, and spatial orientation of CDR loops, and
    (2) selecting sets of human FR1, human FR2, human FR3 and human FR4 regions based on the parameters, and/or
(e) the two C-terminal amino acids of a heavy chain human FR2 are optionally non-human, and/or
(f) the two C-terminal amino acids of a heavy chain human FR3 are optionally non-human, and/or
(g) the human framework sequences independently comprise a set of human FR1, human FR2, human FR3 and human FR4 regions selected from human VH3-23, human VH3-53, human Vkl-27, and/or Vk3-20 framework regions, wherein
the two C-terminal amino acids of human FR2 are optionally-non-human, and
the two C-terminal amino acids of human FR3 are optionally-non-human.

14. The method of claim 13, wherein
(a) the heavy chain CDR3 (CDR H3) sequences comprise a length of between 1 to 50 amino acids; and/or
(b) the light chain CDR3 (CDR L3) sequences comprise a length of between 3 to 20 amino acids.

15. The method of claim 1, wherein each of the at least one proteins encoded by the population of 20 or more different nucleic acids further comprises 1, 2, or 3 amino acids C-terminal to the human FR3 and N-terminal to the rabbit CDR3.

16. The method of claim 1, wherein each of the at least one proteins encoded by the population of 20 or more different nucleic acids further comprises 1, 2, or 3 amino acids C-terminal to the rabbit CDR3 and N-terminal to the human FR4.

17. The method of claim 1, wherein each of the at least one proteins encoded by the population of 20 or more different nucleic acids further comprises 1, 2, or 3 amino acids C-terminal to the human FR3 and N-terminal to the rabbit CDR3, and
wherein each of the at least one proteins encoded by the population of 20 or more different nucleic acids further comprises 1, 2, or 3 amino acids C-terminal to the rabbit CDR3 and N-terminal to the human FR4.

* * * * *

SEQUENCE LISTING

<160> NUMBER OF SEQ ID NOS: 130

<210> SEQ ID NO 1
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 3-23 sense oligonucleotide

<400> SEQUENCE: 1
tcgaggaaca gcctgcgcgc cgaggacacg gccgtatatt actgtgccgc ggcgaaggac      60
gtctacgggc gcctggggcc aggggacact agtcaccgtc tcaagcg                  107

<210> SEQ ID NO 2
<211> LENGTH: 112
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: 3-53 sense oligonucleotide

<400> SEQUENCE: 2
tcgagcaaat gaacagcctg cgcgccgagg acacggccgt gtattactgt gccgcggcga    60
aggacgtcta cgggcgcctg gggccagggg acactagtca ccgtctcaag cg           112

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Xho VH3-23 stuf For oligonucleotide

<400> SEQUENCE: 3
aaaaaactcg aggaacagcc tgcg                                           24

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Xho VH3-53 stuf For oligonucleotide

<400> SEQUENCE: 4
aaaaaactcg agcaaatgaa cagcctg                                        27

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Nhe VH stuf Rev oligonucleotide

<400> SEQUENCE: 5 tttttttgcta gcgcttgaga cggtgact                                      28

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: K-RP oligonucleotide

<400> SEQUENCE: 6
tgttttactg ttctcgatgc c                                              21

```
<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: IgG-RP oligonucleotide

<400> SEQUENCE: 7
gactgacgga gccttaggtt gcc                                           23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RabVH1 FP oligonucleotide

<400> SEQUENCE: 8
cagwcrgtga aggagtccga ggg                                           23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RabVH2 FP oligonucleotide

<400> SEQUENCE: 9
cagtcgbtgg rggartycrg ggg                                           23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RabVH3 FP oligonucleotide

<400> SEQUENCE: 10
cagvagcagc tgrwggartc crs                                           23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RabVH4 FP oligonucleotide

<400> SEQUENCE: 11
caggagcagc wgraggagtc cgg                                           23

<210> SEQ ID NO 12
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Rab Vk1 FP oligonucleotide

<400> SEQUENCE: 12
gcycaagkgc yracccagac tsm                                              23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab Vk2 FP oligonucleotide

<400> SEQUENCE: 13
gacvytrtgc tgacccagac tsc                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab Vk3 FP oligonucleotide

<400> SEQUENCE: 14
gcagccgtgm tgacccagac wcc                                              23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab Vk4 FP oligonucleotide

<400> SEQUENCE: 15
katgkyrtga tgacccagac tsc                                              23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab Vk5 FP oligonucleotide

<400> SEQUENCE: 16
gcscwdgtgm tgacccagac tcc                                              23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Rab Vk6 FP oligonucleotide

<400> SEQUENCE: 17
gccatcrawa tgacccagac tcc                                         23

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab VH CDR3 BarI For oligonucleotide

<400> SEQUENCE: 18
tgaccagtct gacagccgaa gacacggtac cctatttctg tg                    42

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab VH CDR3 BarI Rev 1 oligonucleotide

<400> SEQUENCE: 19
cttaggttgc cctgargaga gtatgacsac ttcscctggg cccca                 45

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab VH CDR3 BarI Rev 2 oligonucleotide

<400> SEQUENCE: 20
cttaggttgc cctgargaga gtatgacsac ttcsccctgg cccca                 45

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab VH CDR3 BarI Rev 3 oligonucleotide

<400> SEQUENCE: 21
cttaggttgc cctgargaga gtatgacsac ttcscctgtg cccca                 45

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab VLk CDR3 BarI For oligonucleotide

<400> SEQUENCE: 22
ctcaccatca gcggtgtgca gtggaaggat gcttacactt actactgt                48

<210> SEQ ID NO 23
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab CDR3 VLK BarI Rev 1 oligonucleotide

<400> SEQUENCE: 23
aactggatca cgtttgattg taaccttgct tccagctcca aaagtcaaa                49

<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab CDR3 VLK BarI Rev 2 oligonucleotide

<400> SEQUENCE: 24
aactggatca catttgattg taacattgct tccagctcca aaagcccaa                49

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab CDR3 VLK BarI Rev 3 oligonucleotide

<400> SEQUENCE: 25
aactggatca ccttcgacgg taaccttgct tcctccgcca aaagtattat               50

<210> SEQ ID NO 26
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab CDR3 VLK BarI Rev 4 oligonucleotide

<400> SEQUENCE: 26
aactggatca cgtttgattg taagtttgct tcctgggcca aaagtggat                49

<210> SEQ ID NO 27
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab CDR3 VLK BarI Rev 5 oligonucleotide

<400> SEQUENCE: 27
aactggatca cgtttgatcg taagcttgct tccctcgcca aaagtgatt                49

<210> SEQ ID NO 28

```
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab CDR3 VLK BarI Rev 6 oligonucleotide

<400> SEQUENCE: 28
aactggatca cataggatcg taagctcgct tcctccgcca aaagcagtt            49

<210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab CDR3 VLK BarI Rev 7 oligonucleotide

<400> SEQUENCE: 29
aactggatca cgtttgatcg taagcttgct tccttckcca aaagtgatc            49

<210> SEQ ID NO 30
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab CDR3 VLK BarI Rev 8 oligonucleotide

<400> SEQUENCE: 30
aactggatca cctttgacsg taacctcgct tcctccgcca aaagcatta            49

<210> SEQ ID NO 31
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab CDR3 VLK BarI Rev 9 oligonucleotide

<400> SEQUENCE: 31
aactggatca crtttgatcg taaccatgct tcctgagcca aaagyaagt            49

<210> SEQ ID NO 32
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rab CDR3 VLK BarI Rev 10 oligonucleotide

<400> SEQUENCE: 32
aactggatca cgtttgatcg taaccttgct tcccgcacca aaagtatta            49

<210> SEQ ID NO 33
<211> LENGTH: 49
<212> TYPE: DNA
<213> ORGANISM: Artificial Sequence
<220> FEATURE:
```

<223> OTHER INFORMATION: Description of Artificial Sequence: Synthetic
oligonucleotide
<220> FEATURE:
<223> OTHER INFORMATION: Rab CDR3 VLK BarI Rev 11 oligonucleotide

<400> SEQUENCE: 33
aactggatca cgtttgattg taagtttgct tcctgggcca aaagtggat                49

<210> SEQ ID NO 34
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Rab CDR3 VLK BarI Rev 12 oligonucleotide

<400> SEQUENCE: 34
aactggatca cgtttgatcg taagcttgct tccctcgcca aaagtggtt                49

<210> SEQ ID NO 35
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Rab CDR3 VLK BarI Rev 13 oligonucleotide

<400> SEQUENCE: 35
aactggatca crtttgatcg taaccatgct tcctgagcca aaagcaagt                49

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: B-Nco app8 For oligonucleotide

<400> SEQUENCE: 36
aagaagaagg tgttcaattg gacaagagag aggcca                              36

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: FR3 VH3_23 as oligonucleotide

<400> SEQUENCE: 37
taatatacgg ccgtgtcctc ggcgcgcagg ctgttc                              36

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: VH FR3-23 For oligonucleotide

<400> SEQUENCE: 38
gaacagcctg cgcgccgagg acac                                          24

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pEX14 Rev oligonucleotide

<400> SEQUENCE: 39
gaaaggccca gtctttcgac tgagcc                                        26

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: B-NotRev oligonucleotide

<400> SEQUENCE: 40
cagcttttgt tcctagtgat ggtgatggtg                                    30

<210> SEQ ID NO 41
<211> LENGTH: 400
<212> TYPE: DNA
<213> ORGANISM: Oryctolagus cuniculus

<400> SEQUENCE: 41
cagtcagtga aggagtccga gggaggtctc ttcaagccaa tggataccct gacactcacc    60
tgcacagtct ctggattctc cctcagttct tatggcgtga actgggtccg ccaggctcca   120 gggaagggc tggagtggat cggatatatt ggtactggta catatcttgc gaactgggcg   180
aaaagccgat ccaccatcac cagcaacacc aacgagaaca cggtgactct gaaaatgacc   240
agtctgacag cgcgggacac ggccacctat ttctgtggga gtggcgccaa tattgaaaat   300 gagttttca atgccatctg ggcccaggc accctggtca ccgtctcctc agggcaacct   360
aaggctccgt cagtcttccc actggccccc tgctgcgggg                        400

<210> SEQ ID NO 42
<211> LENGTH: 560
<212> TYPE: DNA
<213> ORGANISM: Oryctolagus cuniculus

<400> SEQUENCE: 42
gaccctgtgc tgacccagac tccatcttcc gcgtgtgaac ctgtgggagg cacagtcacc    60
atcaagtgcc aggccagtga gagcattagt agtagattag cctggtatca gcagaaacca   120
gggcagtctc ccaagctcct gatctattct gcatccactc tggcatctgg ggtcccatcg   180
cggttcaaag gcagtggatc tgggacagag tacactctca ccatcagcga cctggagtgt   240
gccgatgctg ccacttacta ctgtcaaaac aataatggtg gtagtggtag tagtagtgct   300
gtcgctttca ccttggcga ggagaccaag ctggagatca acgtgatcc agttgcacct   360 actgtcctca tcttcccacc agctgctgat caggtggcaa ctggaacagt caccatcgtg   420

```
tgtgtggcga taaatactt tcccgatgtc accgtcacct gggaggtgga tggcaccacc    480
caaacaactg gcatcgagaa cagtaaaaca ccgcagaatt ctgcagattg tacctacaac    540
ctcagcagca ctctgacact                                                560
```

<210> SEQ ID NO 43
<211> LENGTH: 5
<212> TYPE: PRT
<213> ORGANISM: Oryctolagus cuniculus

<400> SEQUENCE: 43

Asp Asp Tyr Gly Asp
1               5

<210> SEQ ID NO 44
<211> LENGTH: 134
<212> TYPE: PRT
<213> ORGANISM: Oryctolagus cuniculus

<400> SEQUENCE: 44

Gln Ser Val Lys Glu Ser Glu Gly Gly Leu Phe Lys Pro Met Asp Thr
1               5                   10                  15

Leu Thr Leu Thr Cys Thr Val Ser Gly Phe Ser Leu Ser Ser Tyr Gly
            20                  25                  30

Val Asn Trp Val Arg Gln Ala Pro Gly Lys Gly Leu Glu Trp Ile Gly
        35                  40                  45

Tyr Ile Gly Thr Gly Thr Tyr Leu Ala Asn Trp Ala Lys Ser Arg Ser
    50                  55                  60

Thr Ile Thr Ser Asn Thr Asn Glu Asn Thr Val Thr Leu Lys Met Thr
65                  70                  75                  80

Ser Leu Thr Gly Ala Asp Thr Ala Thr Tyr Phe Cys Gly Ser Gly Ala
                85                  90                  95

Asn Ile Glu Asn Glu Phe Phe Asn Ala Ile Trp Gly Pro Gly Thr Leu
            100                 105                 110

Val Thr Val Ser Ser Gly Gln Pro Lys Ala Pro Ser Val Phe Pro Leu
        115                 120                 125

Ala Pro Cys Cys Gly Asp
    130

<210> SEQ ID NO 45
<211> LENGTH: 186
<212> TYPE: PRT
<213> ORGANISM: Oryctolagus cuniculus

<400> SEQUENCE: 45

Asp Pro Val Leu Thr Gln Thr Pro Ser Ser Ala Cys Glu Pro Val Gly
1               5                   10                  15

Gly Thr Val Thr Ile Lys Cys Gln Ala Ser Glu Ser Ile Ser Ser Arg
            20                  25                  30

Leu Ala Trp Tyr Gln Gln Lys Pro Gly Gln Ser Pro Lys Leu Leu Ile
        35                  40                  45

Tyr Ser Ala Ser Thr Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Asn Asn Asn Gly Gly Ser Gly
                85                  90                  95

Ser Ser Ser Ala Val Ala Phe Thr Phe Gly Glu Glu Thr Lys Leu Glu

```
                    100                 105                 110
Ile Lys Arg Asp Pro Val Ala Pro Thr Val Leu Ile Phe Pro Pro Ala
            115                 120                 125

Ala Asp Gln Val Ala Thr Gly Thr Val Thr Ile Val Cys Val Ala Asn
    130                 135                 140

Lys Tyr Phe Pro Asp Val Thr Val Thr Trp Glu Val Asp Gly Thr Thr
145                 150                 155                 160

Gln Thr Thr Gly Ile Glu Asn Ser Lys Thr Pro Gln Asn Ser Ala Asp
            165                 170                 175

Cys Thr Tyr Asn Leu Ser Ser Thr Leu Thr
            180                 185

<210> SEQ ID NO 46
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Bar I recognition and digestion site
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (20)..(25)
<223> OTHER INFORMATION: a, c, t, g, unknown or other
<220> FEATURE:
<221> NAME/KEY: modified_base
<222> LOCATION: (29)..(46)
<223> OTHER INFORMATION: a, c, t, g, unknown or other

<400> SEQUENCE: 46
nnnnnnnnnn nnnnngaagn nnnnntacnn nnnnnnnnnn nnnnnn            46

<210> SEQ ID NO 47
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CDR3 sequence
<220> FEATURE:
<221> NAME/KEY: MOD_RES
<222> LOCATION: (8)..(57)
<223> OTHER INFORMATION: Any amino acid
<220> FEATURE:
<221> NAME/KEY: MISC_FEATURE
<222> LOCATION: (8)..(57)
<223> OTHER INFORMATION: May or may not be present

<400> SEQUENCE: 47

Asp Thr Ala Thr Tyr Phe Cys Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Trp Gly Pro Gly Thr Leu Val
    50                  55                  60

Thr Val Ser Ser
65
```

```
<210> SEQ ID NO 48
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CDR3 sequence
<220> FEATURE:
<221> NAME/KEY: MOD_RES
<222> LOCATION: (8)..(57)
<223> OTHER INFORMATION: Any amino acid
<220> FEATURE:
<221> NAME/KEY: MISC_FEATURE
<222> LOCATION: (8)..(57)
<223> OTHER INFORMATION: May or may not be present

<400> SEQUENCE: 48

Asp Thr Ala Val Tyr Tyr Cys Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Trp Gly Gln Gly Thr Leu Val
    50                  55                  60

Thr Val Ser Ser
65

<210> SEQ ID NO 49
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CDR3 sequence
<220> FEATURE:
<221> NAME/KEY: MOD_RES
<222> LOCATION: (9)..(58)
<223> OTHER INFORMATION: Any amino acid
<220> FEATURE:
<221> NAME/KEY: MISC_FEATURE
<222> LOCATION: (9)..(58)
<223> OTHER INFORMATION: May or may not be present

<400> SEQUENCE: 49

Ala Asp Ala Ala Thr Tyr Tyr Cys Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Phe Gly Glu Glu Thr Lys
    50                  55                  60

Leu Glu Ile Lys
65

<210> SEQ ID NO 50
<211> LENGTH: 68
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<223> OTHER INFORMATION: CDR3 sequence
<220> FEATURE:
<221> NAME/KEY: MOD_RES
<222> LOCATION: (9)..(58)
<223> OTHER INFORMATION: Any amino acid
<220> FEATURE:
<221> NAME/KEY: MISC_FEATURE
<222> LOCATION: (9)..(58)
<223> OTHER INFORMATION: May or may not be present

<400> SEQUENCE: 50

Glu Asp Phe Ala Val Tyr Tyr Cys Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Phe Gly Gly Gly Thr Lys
    50                  55                  60

Val Glu Ile Lys
65

<210> SEQ ID NO 51
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH-CDR3 library
<220> FEATURE:
<221> NAME/KEY: modified_base
<222> LOCATION: (6)..(155)
<223> OTHER INFORMATION: a, c, t, g, unknown or other
<220> FEATURE:
<221> NAME/KEY: misc_feature
<222> LOCATION: (6)..(155)
<223> OTHER INFORMATION: May or may not be present

<400> SEQUENCE: 51
gacacnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnntgggg                           160

<210> SEQ ID NO 52
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL-CDR3 library
<220> FEATURE:
<221> NAME/KEY: modified_base
<222> LOCATION: (6)..(155)
<223> OTHER INFORMATION: a, c, t, g, unknown or other
<220> FEATURE:
<221> NAME/KEY: misc_feature
<222> LOCATION: (6)..(155)
<223> OTHER INFORMATION: May or may not be present

<400> SEQUENCE: 52
tgacannnnn nnnnnnnnnn nnnnnnnnnn nnnnnnnnnn nnnnnnnnnn nnnnnnnnnn      60
```

```
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnctttt                          160
```

<210> SEQ ID NO 53
<211> LENGTH: 883
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: NcoI-VH-Library
<220> FEATURE:
<221> NAME/KEY: modified_base
<222> LOCATION: (1)..(856)
<223> OTHER INFORMATION: a, c, t, g, unknown or other
<220> FEATURE:
<221> NAME/KEY: misc_feature
<222> LOCATION: (1)..(856)
<223> OTHER INFORMATION: May or may not be present

<400> SEQUENCE: 53

```
nnnnnnnnnn nnnnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnccga ggacacggcc gtgtattact gtg                      883
```

<210> SEQ ID NO 54
<211> LENGTH: 209
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH-CDR3 sequences
<220> FEATURE:
<221> NAME/KEY: modified_base
<222> LOCATION: (33)..(182)
<223> OTHER INFORMATION: a, c, t, g, unknown or other
<220> FEATURE:
<221> NAME/KEY: misc_feature
<222> LOCATION: (33)..(182)
<223> OTHER INFORMATION: May or may not be present

<400> SEQUENCE: 54

```
cttgagacgg tgactagtgt cccctggccc cannnnnnnn nnnnnnnnnn nnnnnnnnnn     60
```

```
nnnnnnnnnn nnnnnnnnnn nnnnnnnnnn nnnnnnnnnn nnnnnnnnnn nnnnnnnnnn      120
nnnnnnnnnn nnnnnnnnnn nnnnnnnnnn nnnnnnnnnn nnnnnnnnnn nnnnnnnnnn      180
nncacagtaa tacacggccg tgtcctcgg                                        209
```

<210> SEQ ID NO 55
<211> LENGTH: 911
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL library
<220> FEATURE:
<221> NAME/KEY: modified_base
<222> LOCATION: (33)..(882)
<223> OTHER INFORMATION: a, c, t, g, unknown or other
<220> FEATURE:
<221> NAME/KEY: misc_feature
<222> LOCATION: (33)..(882)
<223> OTHER INFORMATION: May or may not be present

<400> SEQUENCE: 55

```
tggggccagg ggacactagt caccgtctca agnnnnnnnn nnnnnnnnnn nnnnnnnnnn       60
nnnnnnnnnn nnnnnnnnnn nnnnnnnnnn nnnnnnnnnn nnnnnnnnnn nnnnnnnnnn      120
nnnnnnnnnn nnnnnnnnnn nnnnnnnnnn nnnnnnnnnn nnnnnnnnnn nnnnnnnnnn      180
nnnnnnnnnn nnnnnnnnnn nnnnnnnnnn nnnnnnnnnn nnnnnnnnnn nnnnnnnnnn      240
nnnnnnnnnn nnnnnnnnnn nnnnnnnnnn nnnnnnnnnn nnnnnnnnnn nnnnnnnnnn      300
nnnnnnnnnn nnnnnnnnnn nnnnnnnnnn nnnnnnnnnn nnnnnnnnnn nnnnnnnnnn      360
nnnnnnnnnn nnnnnnnnnn nnnnnnnnnn nnnnnnnnnn nnnnnnnnnn nnnnnnnnnn      420
nnnnnnnnnn nnnnnnnnnn nnnnnnnnnn nnnnnnnnnn nnnnnnnnnn nnnnnnnnnn      480
nnnnnnnnnn nnnnnnnnnn nnnnnnnnnn nnnnnnnnnn nnnnnnnnnn nnnnnnnnnn      540
nnnnnnnnnn nnnnnnnnnn nnnnnnnnnn nnnnnnnnnn nnnnnnnnnn nnnnnnnnnn      600
nnnnnnnnnn nnnnnnnnnn nnnnnnnnnn nnnnnnnnnn nnnnnnnnnn nnnnnnnnnn      660
nnnnnnnnnn nnnnnnnnnn nnnnnnnnnn nnnnnnnnnn nnnnnnnnnn nnnnnnnnnn      720
nnnnnnnnnn nnnnnnnnnn nnnnnnnnnn nnnnnnnnnn nnnnnnnnnn nnnnnnnnnn      780
nnnnnnnnnn nnnnnnnnnn nnnnnnnnnn nnnnnnnnnn nnnnnnnnnn nnnnnnnnnn      840
nnnnnnnnnn nnnnnnnnnn nnnnnnnnnn nnnnnnnnnn nnagcctgaa gatgttgcaa      900
cttattactg t                                                           911
```

<210> SEQ ID NO 56
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL-CDR3 sequences
<220> FEATURE:
<221> NAME/KEY: modified_base
<222> LOCATION: (25)..(174)
<223> OTHER INFORMATION: a, c, t, g, unknown or other
<220> FEATURE:
<221> NAME/KEY: misc_feature
<222> LOCATION: (25)..(174)
<223> OTHER INFORMATION: May or may not be present

<400> SEQUENCE: 56

-continued

```
ccaccttggt ccctccgcca aaagnnnnnn nnnnnnnnnn nnnnnnnnnn      60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnacagta  180
ataagttgca acatcttcag gct                                         203

<210> SEQ ID NO 57
<211> LENGTH: 209
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH-CDR3 sequence
<220> FEATURE:
<221> NAME/KEY: modified_base
<222> LOCATION: (28)..(177)
<223> OTHER INFORMATION: a, c, t, g, unknown or other
<220> FEATURE:
<221> NAME/KEY: misc_feature
<222> LOCATION: (28)..(177)
<223> OTHER INFORMATION: May or may not be present

<400> SEQUENCE: 57
ggctcctgtg ccggcacata atgacacnnn nnnnnnnnnn nnnnnnnnnn nnnnnnnnnn   60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnacc  180 ccggtccct gtgatcagtg gcagagttc                                    209

<210> SEQ ID NO 58
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL-CDR3 sequence
<220> FEATURE:
<221> NAME/KEY: modified_base
<222> LOCATION: (30)..(179)
<223> OTHER INFORMATION: a, c, t, g, unknown or other
<220> FEATURE:
<221> NAME/KEY: misc_feature
<222> LOCATION: (30)..(179)
<223> OTHER INFORMATION: May or may not be present

<400> SEQUENCE: 58
tcggacttct acaacgttga ataatgacan nnnnnnnnnn nnnnnnnnnn nnnnnnnnnn   60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnng  180
aaaaccgcct ccctggttcc acc                                         203

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 1

<400> SEQUENCE: 59
```

Cys Ala Arg Val Tyr Asp Asp Tyr Gly Asp Asp Tyr Phe Asp Ile
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 2

<400> SEQUENCE: 60

Cys Ala Arg Val Tyr Asp Asp Tyr Gly Asp Asp Tyr Phe Asn Ile
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 3

<400> SEQUENCE: 61

Cys Ala Arg Val Tyr Asp Asp Tyr Gly Asp Asp Tyr Phe Asp Leu
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 4

<400> SEQUENCE: 62

Cys Val Arg Val Tyr Asp Asp Tyr Gly Asp Asp Tyr Phe Thr Leu
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 5

<400> SEQUENCE: 63

Cys Ala Arg Val Tyr Asp Asp Tyr Gly Asp Asp Tyr Phe Asn Leu
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 6

```
<400> SEQUENCE: 64

Cys Ala Arg Val Tyr Asp Asp Tyr Gly Asp Asp Tyr Phe Asn Leu
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 7

<400> SEQUENCE: 65

Cys Ala Arg Val Tyr Asp Asp Tyr Gly Asp Asp Tyr Phe Asn Leu
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 8

<400> SEQUENCE: 66

Cys Ala Arg Val Tyr Asp Asp Tyr Gly Asp Asp Tyr Phe Asn Leu
1               5                   10                  15

<210> SEQ ID NO 67
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 9

<400> SEQUENCE: 67

Cys Ala Arg Glu Ser Gly Tyr Tyr Pro Asp Tyr Ala Gly Tyr Gly Tyr
1               5                   10                  15

Ala Tyr Gly Met Asp Pro
            20

<210> SEQ ID NO 68
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 10

<400> SEQUENCE: 68

Cys Ala Arg Glu Ser Gly Tyr Tyr Pro Asp Tyr Ala Gly Tyr Gly Tyr
1               5                   10                  15

Ala Tyr Gly Met Asp Pro
            20

<210> SEQ ID NO 69
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 11

<400> SEQUENCE: 69

Cys Ala Arg Glu Ser Gly Tyr Tyr Ala Asp Tyr Ala Gly Tyr Gly Tyr
1               5                   10                  15

Ala Tyr Gly Met Asp Pro
            20

<210> SEQ ID NO 70
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 12

<400> SEQUENCE: 70

Cys Ala Arg Glu Ser Asp Tyr Tyr Ala Asp Tyr Ala Gly Tyr Gly Tyr
1               5                   10                  15

Ala Tyr Gly Met Asp Pro
            20

<210> SEQ ID NO 71
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 13

<400> SEQUENCE: 71

Cys Ala Arg Glu Ser Asp Tyr Tyr Ser Asp Tyr Ala Gly Tyr Gly Tyr
1               5                   10                  15

Ala Tyr Gly Met Asp Pro
            20

<210> SEQ ID NO 72
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 14

<400> SEQUENCE: 72

Cys Ala Arg Glu Ser Gly Tyr Tyr Ala Asp Tyr Ala Gly Leu Gly Tyr
1               5                   10                  15

Ala Tyr Gly Met Asp Pro
            20

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence: Synthetic
```

```
          peptide
<220> FEATURE:
<223> OTHER INFORMATION: VH CDR3 Example 15

<400> SEQUENCE: 73

Cys Ala Arg Glu Ser Gly Tyr Tyr Ala Asp Tyr Gly Gly Tyr Gly Tyr
1               5                   10                  15

Ala Phe Gly Met Asp Pro
            20

<210> SEQ ID NO 74
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 16

<400> SEQUENCE: 74

Cys Ala Arg Glu Ser Gly Tyr Tyr Ala Asp Tyr Gly Gly Tyr Gly Tyr
1               5                   10                  15

Ala Tyr Gly Met Asp Pro
            20

<210> SEQ ID NO 75
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3 Example 17

<400> SEQUENCE: 75

Cys Ala Arg Glu Ser Gly Tyr Tyr Ala Asp Tyr Ala Gly Tyr Gly Tyr
1               5                   10                  15

Ala Tyr Gly Met Asp Pro
            20

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -A

<400> SEQUENCE: 76

Cys Ala Arg Val Tyr Asp Asp Tyr Gly Asp Asp Tyr Phe Asn Ile
1               5                   10                  15

<210> SEQ ID NO 77
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -B

<400> SEQUENCE: 77
```

Cys Ala Arg Glu Ser Gly Tyr Tyr Ala Asp Tyr Ala Gly Tyr Gly Tyr
1               5                   10                  15

Ala Tyr Gly Met Asp Pro
            20

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -C

<400> SEQUENCE: 78

Cys Ala Arg Ala Glu Gly Tyr Asp Asp Trp His Leu Ser Leu
1               5                   10

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -G

<400> SEQUENCE: 79

Cys Ala Arg Asp Ser Tyr Asp Asp Tyr Gly Asp Trp Gly Gly Met Asp
1               5                   10                  15

Pro

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -E

<400> SEQUENCE: 80

Cys Ala Arg Asp Ile Tyr Asp Asp Tyr Gly Asp Pro Thr Arg Ser Asp
1               5                   10                  15

Leu

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -I

<400> SEQUENCE: 81

Cys Ala Arg Glu Asp Glu Tyr Ala Glu Tyr Tyr Phe Asp Leu
1               5                   10

<210> SEQ ID NO 82
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: VH CDR3, sequence -D

<400> SEQUENCE: 82

Cys Ala Arg Ala Lys Asn Asp Asp Tyr Gly Asp Pro Asp Ser Leu Asp
1               5                   10                  15

Leu

<210> SEQ ID NO 83
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -H

<400> SEQUENCE: 83

Cys Ala Arg Glu Ala Asp Gly Ala Tyr Thr Gly Tyr Gly Tyr Ser Tyr
1               5                   10                  15

Gly Met Asp Pro
            20

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -K

<400> SEQUENCE: 84

Cys Ala Arg Tyr Asn Ala Asp Asp Tyr Gly Asp Tyr Tyr Gly Leu Asp
1               5                   10                  15

Pro

<210> SEQ ID NO 85
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -Q

<400> SEQUENCE: 85

Cys Ala Arg Glu Gly Asp Trp Ser Tyr Ser Leu Asp Leu
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -F

<400> SEQUENCE: 86
```

Cys Ala Arg Asp Ser Ser Gly Trp Gly Arg Leu Asp Leu
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -J

<400> SEQUENCE: 87

Cys Ala Arg Ser Asn Tyr Gly Ala Leu Asp Leu
1               5                   10

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -R

<400> SEQUENCE: 88

Cys Ala Arg Gly Thr Gly Tyr Ala Gly Tyr Gly Asp Ala Thr Gly Gly
1               5                   10                  15

Phe Asn Ile

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -S

<400> SEQUENCE: 89

Cys Ala Arg Pro Leu Val Ser Gly Trp Val Phe Gly Gly Met Asp Leu
1               5                   10                  15

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -L

<400> SEQUENCE: 90

Cys Ala Arg Ala Leu Tyr Gly Asp His Thr Phe Asp Pro
1               5                   10

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -M

```
<400> SEQUENCE: 91

Cys Ala Arg Ala Tyr Gly Ser Asn Gly Gly Tyr Asn Pro Gly Arg Leu
1               5                   10                  15
Asp Leu

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -N

<400> SEQUENCE: 92

Cys Ala Arg Asp Asp Trp Phe Tyr Phe Asp Leu
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -O

<400> SEQUENCE: 93

Cys Ala Arg Asp Ser Leu Gly Gly Phe Asp Leu
1               5                   10

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -P

<400> SEQUENCE: 94

Cys Ala Arg Glu Phe Asn Tyr Asp Ala Tyr Ser Asp Tyr Tyr Ala Leu
1               5                   10                  15
Asp Pro

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -T

<400> SEQUENCE: 95

Cys Val Arg Asp Pro Ala Tyr Ser Tyr Val Met
1               5                   10

<210> SEQ ID NO 96
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: VH CDR3, sequence -U

<400> SEQUENCE: 96

Cys Val Arg Gly Tyr Pro Gly Gly Ser Val Gly Gly Asp Leu
1               5                   10

<210> SEQ ID NO 97
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -3SO_31

<400> SEQUENCE: 97

Cys Ala Arg Glu Ser Gly Tyr Tyr Pro Asp Tyr Ala Gly Tyr Gly Tyr
1               5                   10                  15

Ala Tyr Gly Met Asp Pro
            20

<210> SEQ ID NO 98
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -3P_9

<400> SEQUENCE: 98

Cys Ala Arg Glu Ser Gly Tyr Tyr Pro Asp Tyr Ala Gly Tyr Gly Tyr
1               5                   10                  15

Ala Tyr Gly Met Asp Pro
            20

<210> SEQ ID NO 99
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -2S1_17

<400> SEQUENCE: 99

Cys Ala Arg Glu Ser Gly Tyr Tyr Ala Asp Tyr Gly Tyr Gly Tyr
1               5                   10                  15

Ala Tyr Gly Met Asp Pro
            20

<210> SEQ ID NO 100
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -2P1_1
```

<400> SEQUENCE: 100

Cys Ala Arg Glu Ser Asp Tyr Tyr Ala Asp Tyr Ala Gly Tyr Gly Tyr
1               5                   10                  15

Ala Tyr Gly Met Asp Pro
            20

<210> SEQ ID NO 101
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3, sequence -2B1_18

<400> SEQUENCE: 101

Cys Ala Arg Glu Ser Asp Tyr Tyr Ser Asp Tyr Ala Gly Tyr Gly Tyr
1               5                   10                  15

Ala Tyr Gly Met Asp Pro
            20

<210> SEQ ID NO 102
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VH chain clone, -11/1-256
      sequence fragment

<400> SEQUENCE: 102

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Phe Ser Ser His
            20                  25                  30

Ala Met Ser Trp Val Arg Gln Ala Pro Gly Lys Gly Leu Glu Trp Val
        35                  40                  45

Ser Ala Ile Tyr Ser Ala Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Ser Asp Tyr Tyr Ala Asp Tyr Ala Ser Tyr Gly Tyr Ala Phe
            100                 105                 110

Gly Met Asp Pro Trp Gly Gln Gly Thr Leu Val Thr Val Ser Ser Leu
        115                 120                 125

<210> SEQ ID NO 103
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VL chain clone, -11/1-256
      fragment

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ala Ile Ser Asn Asp
            20                  25                  30

Leu Ser Trp Tyr Gln Gln Lys Pro Gly Lys Val Pro Lys Leu Leu Ile
        35                  40                  45

Tyr Ala Ala Ser Ser Leu Gln Arg Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gly Ser Tyr Tyr Asn Ser Gly
                85                  90                  95

Trp Tyr Ile Ala Phe Gly Gly Gly Thr Lys Val Glu Ile Lys
            100                 105                 110

<210> SEQ ID NO 104
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VH chain clone, -3/1-256
      fragment

<400> SEQUENCE: 104

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Leu Ser Ser Tyr
            20                  25                  30

Ala Ile Ser Trp Val Arg Gln Ala Pro Gly Lys Gly Leu Glu Trp Val
        35                  40                  45

Ser Thr Ile Gly Ser Gly Gly Ser Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Ser Gly Tyr Tyr Pro Asp Tyr Ala Gly Tyr Gly Tyr Ala Tyr
            100                 105                 110

Gly Met Asp Pro Trp Gly Gln Gly Thr Leu Val Thr Val Ser Ser Leu
        115                 120                 125

<210> SEQ ID NO 105
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VL chain clone, -3/1-256
      fragment

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Arg Gln Gly Ile Ser Asp Asp
            20                  25                  30

```
Leu Ala Trp Tyr Gln Gln Lys Pro Gly Lys Val Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gly Thr Tyr Tyr Thr Asp Gly
                 85                  90                  95

Trp Ala Val Ala Phe Gly Gly Gly Thr Lys Val Glu Ile Lys
                100                 105                 110
```

<210> SEQ ID NO 106
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VH chain clone, -9/1-256
      fragment

<400> SEQUENCE: 106

```
Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Ser Phe Ser Glu Tyr
             20                  25                  30

Ala Val Ser Trp Val Arg Gln Ala Pro Gly Lys Gly Leu Glu Trp Val
         35                  40                  45

Gly Val Ile Gly Ser Gly Gly Ile Tyr Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Glu Ser Gly Tyr Tyr Ala Asp Tyr Ala Gly Tyr Gly Tyr Ala Tyr
            100                 105                 110

Gly Met Asp Pro Trp Gly Gln Gly Thr Leu Val Thr Val Ser Ser Leu
            115                 120                 125
```

<210> SEQ ID NO 107
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VL chain clone, -9/1-256
      fragment

<400> SEQUENCE: 107

```
Asp Ile Gln Met Thr Gln Ser Pro Ser Ser Leu Ser Ala Ser Val Gly
 1               5                  10                  15

Asp Arg Val Thr Ile Thr Cys Gln Ala Pro Gln Asp Ile Ser Thr Tyr
             20                  25                  30

Leu Ala Trp Tyr Gln Gln Lys Pro Gly Lys Val Pro Lys Leu Leu Ile
         35                  40                  45

Tyr Ala Ala Ser Ile Leu Gln Ser Gly Val Pro Ser Arg Phe Ser Gly
 50                  55                  60
```

```
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gly Gly Phe Tyr Asp Ser Gly
                 85                  90                  95

Trp Tyr Phe Ala Phe Gly Gly Gly Thr Lys Val Glu Ile Lys
            100                 105                 110

<210> SEQ ID NO 108
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VH chain clone, -21/1-258
      fragment

<400> SEQUENCE: 108

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Ser Leu Ser Ser Tyr
             20                  25                  30

Ala Ile Ser Trp Val Arg Gln Ala Pro Gly Lys Gly Leu Glu Trp Val
             35                  40                  45

Gly Val Thr Gly Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Arg Glu Ser Asp Tyr Tyr Ala Asp Tyr Ala Gly Tyr Gly Tyr Ala Tyr
            100                 105                 110

Gly Met Asp Pro Trp Gly Gln Gly Thr Leu Val Thr Val Ser Ser Leu
            115                 120                 125

<210> SEQ ID NO 109
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VL chain clone, -21/1-258
      fragment

<400> SEQUENCE: 109

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Ser Asp Ser
             20                  25                  30

Leu Ala Trp Tyr Gln Gln Lys Pro Gly Lys Val Pro Lys Leu Leu Ile
             35                  40                  45

Tyr Gly Ala Thr Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Ser Asp Tyr Gly Thr Ile Gly
             85                  90                  95
```

Ser Asp Tyr Gly Asn Thr Phe Gly Gly Gly Thr Lys Val Glu Ile Lys
            100                 105                 110

<210> SEQ ID NO 110
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VH chain clone, -4/1-255
      fragment

<400> SEQUENCE: 110

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ala Leu Ser Asn Tyr
            20                  25                  30

Ala Val Ser Trp Val Arg Gln Ala Pro Gly Lys Gly Leu Glu Trp Ile
        35                  40                  45

Gly Ile Leu Asn Ser Gly Gly Ser Ala Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Ser Gly Tyr Tyr Pro Asp Tyr Ala Gly Tyr Gly Tyr Ala Tyr
            100                 105                 110

Gly Met Asp Pro Trp Gly Gln Gly Thr Leu Val Thr Val Ser Ser Leu
        115                 120                 125

<210> SEQ ID NO 111
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VL chain clone, -4/1-255
      fragment

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Asp Asp Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Ala Gly Gly Tyr Ser Ser Gly Gly
                85                  90                  95

Glu Asn Ala Phe Gly Gly Gly Thr Lys Val Glu Ile Lys
            100                 105

<210> SEQ ID NO 112
<211> LENGTH: 128

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VH chain clone, -14/1-258
      fragment

<400> SEQUENCE: 112

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Leu Ser Asp Tyr
            20                  25                  30

Ala Ile His Trp Val Arg Gln Ala Pro Gly Lys Gly Leu Glu Trp Val
        35                  40                  45

Ala Val Ile Gly Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Ser Asp Tyr Tyr Ala Asp Asp Ala Gly Tyr Gly Tyr Ala Tyr
            100                 105                 110

Gly Met Asp Pro Trp Gly Gln Gly Thr Leu Val Thr Val Ser Ser Leu
        115                 120                 125

<210> SEQ ID NO 113
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VL chain clone, -14/1-258
      fragment

<400> SEQUENCE: 113

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gln Ile Ser Ser Ser
            20                  25                  30

Tyr Ile Ala Trp Tyr Gln Gln Lys Pro Gly Gln Ala Pro Arg Leu Leu
        35                  40                  45

Ile Tyr Ser Ala Ser Thr Leu Gln Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gly Ser Tyr Ala Gly Ser
                85                  90                  95

Ser Ser Tyr Gly Trp Ala Phe Gly Gly Gly Thr Lys Val Glu Ile Lys
            100                 105                 110

<210> SEQ ID NO 114
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: Rabbit humanization VH chain clone, -24/1-254
    fragment

<400> SEQUENCE: 114

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Asp Leu Ser Ser Tyr
            20                  25                  30

Ala Val Ser Trp Val Arg Gln Ala Pro Gly Lys Gly Leu Glu Trp Val
        35                  40                  45

Ser Val Ile Ser Ser Gly Gly Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Ser Gly Tyr Tyr Ala Asp Tyr Gly Gly Tyr Gly Tyr Ala Tyr
            100                 105                 110

Gly Met Asp Pro Trp Gly Gln Gly Thr Leu Val Thr Val Ser Ser Leu
        115                 120                 125

<210> SEQ ID NO 115
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Rabbit humanization VL chain clone, -24/1-254
    2.

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Ser Asn Tyr
            20                  25                  30

Leu Ser Trp Tyr Gln Gln Lys Pro Gly Lys Val Pro Lys Leu Leu Ile
        35                  40                  45

Tyr Gly Ala Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Gly Tyr Tyr Ser Ala Gly
                85                  90                  95

Ala Thr Phe Gly Gly Gly Thr Lys Val Glu Ile Lys
            100                 105

<210> SEQ ID NO 116
<211> LENGTH: 128
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Rabbit humanization VH chain clone, -17/1-255
    fragment

<400> SEQUENCE: 116

Glu Val Gln Leu Val Glu Ser Gly Gly Gly Leu Ile Gln Pro Gly Gly

```
                    1               5                  10                 15
Ser Leu Arg Leu Ser Cys Ala Ala Ser Gly Phe Thr Leu Ser Ser Tyr
                   20                  25                 30

Ala Val His Trp Val Arg Gln Ala Pro Gly Lys Gly Leu Glu Trp Val
                   35                  40                 45

Gly Val Ile Gly Ala Gly Gly Ser Ala Tyr Phe Ala Asp Ser Val Lys
                   50                  55                 60

Gly Arg Phe Thr Ile Ser Arg Asp Asn Ser Lys Asn Thr Leu Tyr Leu
65                 70                  75                     80

Gln Met Asn Ser Leu Arg Ala Glu Asp Thr Ala Val Tyr Tyr Cys Ala
                   85                  90                 95

Arg Glu Ser Asp Tyr Tyr Ser Asp Tyr Ala Gly Tyr Gly Tyr Ala Tyr
                  100                 105                110

Gly Met Asp Pro Trp Gly Gln Gly Thr Leu Val Thr Val Ser Ser Leu
                  115                 120                125
```

<210> SEQ ID NO 117
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VL chain clone, -17/1-255
      fragment

<400> SEQUENCE: 117

```
Asp Ile Gln Met Thr Gln Ser Pro Ser Ser Leu Ser Ala Ser Val Gly
1               5                  10                 15

Asp Arg Val Thr Ile Thr Cys Arg Pro Gly Gln Arg Ile Gly Asn Tyr
                   20                  25                 30

Leu Ala Trp Tyr Gln Gln Lys Pro Gly Lys Val Pro Lys Leu Leu Ile
                   35                  40                 45

Tyr Ala Ala Ser Thr Leu Gln Ser Gly Val Pro Ser Arg Phe Ser Gly
                   50                  55                 60

Ser Gly Ser Gly Thr Asp Phe Thr Leu Thr Ile Ser Ser Leu Gln Pro
65                 70                  75                     80

Glu Asp Val Ala Thr Tyr Tyr Cys Gln Ser Gly Tyr Tyr Ser Ala Gly
                   85                  90                 95

Asp Leu Thr Phe Gly Gly Gly Thr Lys Val Glu Ile Lys
                  100                 105
```

<210> SEQ ID NO 118
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VH chain clone, -19/1-255
      fragment

<400> SEQUENCE: 118

```
Glu Val Gln Leu Val Glu Ser Gly Gly Gly Leu Ile Gln Pro Gly Gly
1               5                  10                 15

Ser Leu Arg Leu Ser Cys Ala Ala Ser Gly Phe Ile Val Thr Ser Tyr
                   20                  25                 30

Ala Met Ser Trp Val Arg Gln Ala Pro Gly Lys Gly Leu Glu Trp Val
```

```
                35                  40                  45

Gly Ala Ile Asn Ser Gly Gly Ser Thr Tyr Tyr Ala Asp Ser Val Lys
            50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Glu Ser Gly Tyr Tyr Ala Asp Tyr Ala Gly Leu Gly Tyr Ala Tyr
            100                 105                 110

Gly Met Asp Pro Trp Gly Gln Gly Thr Leu Val Thr Val Ser Ser Leu
        115                 120                 125

<210> SEQ ID NO 119
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VL chain clone, -19/1-255
      fragment

<400> SEQUENCE: 119

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asp Asn Tyr
            20                  25                  30

Val Ser Trp Tyr Gln Gln Lys Pro Gly Lys Val Pro Lys Leu Leu Ile
        35                  40                  45

Tyr Ala Ala Ser Thr Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Ala Gly Gly Tyr Ser Ser Gly Ser
                85                  90                  95

Glu Asn Thr Phe Gly Gly Gly Thr Lys Val Glu Ile Lys
            100                 105

<210> SEQ ID NO 120
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VH chain clone, -2/1-256
      fragment

<400> SEQUENCE: 120

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Ala Leu Asn Ser Tyr
            20                  25                  30

Ala Val Ser Trp Val Arg Gln Ala Pro Gly Lys Gly Leu Glu Trp Ile
        35                  40                  45

Gly Val Ile Asp Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
```

```
                65                  70                  75                  80
Gln Met Asn Ser Leu Arg Ala Glu Asp Thr Ala Val Tyr Tyr Cys Ala
                    85                  90                  95

Arg Glu Ser Gly Tyr Tyr Ala Asp Tyr Gly Gly Tyr Gly Tyr Ala Phe
                100                 105                 110

Gly Met Asp Pro Trp Gly Gln Gly Thr Leu Val Thr Val Ser Ser Leu
                115                 120                 125
```

<210> SEQ ID NO 121
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit humanization VL chain clone, -2/1-256
      fragment

<400> SEQUENCE: 121

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Ile Arg Asp
                20                  25                  30

Leu Ala Trp Tyr Gln Gln Lys Pro Gly Lys Val Pro Lys Leu Leu Ile
            35                  40                  45

Tyr Asp Ala Ser Thr Leu Thr Pro Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Ala Gly Gly Tyr Tyr Thr Thr Gly
                85                  90                  95

Trp Tyr Asn Ala Phe Gly Gly Gly Thr Lys Val Glu Ile Lys
                100                 105                 110
```

<210> SEQ ID NO 122
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Consensus_VH

<400> SEQUENCE: 122

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Leu Ser Ser Tyr
                20                  25                  30

Ala Val Ser Trp Val Arg Gln Ala Pro Gly Lys Gly Leu Glu Trp Val
            35                  40                  45

Gly Val Ile Gly Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Ser Gly Tyr Tyr Ala Asp Tyr Ala Gly Tyr Gly Tyr Ala Tyr
                100                 105                 110
```

```
Gly Met Asp Pro Trp Gly Gln Gly Thr Leu Val Thr Val Ser Ser Leu
            115                 120                 125
```

```
<210> SEQ ID NO 123
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Consensus_VL
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (99)..(99)
<223> OTHER INFORMATION: Any amino acid

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Xaa Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gly Gly Tyr Tyr Ser Ser Gly
                85                  90                  95

Ser Trp Xaa Asn Ala Phe Gly Gly Gly Thr Lys Val Glu Ile Lys
            100                 105                 110
```

```
<210> SEQ ID NO 124
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(53)
<223> OTHER INFORMATION: Any naturally occurring amino acid
<220> FEATURE:
<221> NAME/KEY: MISC_FEATURE
<222> LOCATION: (4)..(53)
<223> OTHER INFORMATION: This region may encompass 1-50 residues
<220> FEATURE:
<223> OTHER INFORMATION: See specification as filed for detailed
      description of substitutions and preferred embodiments

<400> SEQUENCE: 124

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Trp
    50
```

```
<210> SEQ ID NO 125
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 125

Trp Gly Xaa Gly
1

<210> SEQ ID NO 126
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(18)
<223> OTHER INFORMATION: Any amino acid
<220> FEATURE:
<223> OTHER INFORMATION: See specification as filed for detailed
      description of substitutions and preferred embodiments

<400> SEQUENCE: 126

Gly Leu Glu Trp Val Ser Xaa Xaa Xaa Xaa Xaa Xaa Xaa Xaa Xaa Xaa
1               5                   10                  15

Xaa Xaa Asp Ser Val Lys Gly Arg Phe Thr
            20                  25

<210> SEQ ID NO 127
<211> LENGTH: 400
<212> TYPE: DNA
<213> ORGANISM: Oryctolagus cuniculus

<400> SEQUENCE: 127
ccccgcagca gggggccagt gggaagactg acggagcctt aggttgccct gaggagacgg      60
tgaccagggt gcctgggccc cagatggcat tgaaaaactc attttcaata ttggcgccac     120
tcccacagaa ataggtggcc gtgtccgcgc ctgtcagact ggtcattttc agagtcaccg     180
tgttctcgtt ggtgttgctg gtgatggtgg atcggctttt cgcccagttc gcaagatatg     240
taccagtacc aatatatccg atccactcca gccccttccc tggagcctgg cggacccagt     300
tcacgccata agaactgagg gagaatccag agactgtgca ggtgagtgtc agggtatcca     360
ttggcttgaa gagacctccc tcggactcct tcactgactg                           400

<210> SEQ ID NO 128
<211> LENGTH: 560
<212> TYPE: DNA
<213> ORGANISM: Oryctolagus cuniculus

<400> SEQUENCE: 128
agtgtcagag tgctgctgag gttgtaggta caatctgcag aattctgcgg tgttttactg      60
ttctcgatgc cagttgtttg ggtggtgcca tccacctccc aggtgacggt gacatcggga     120
aagtatttat tcgccacaca cacgatggtg actgttccag ttgccacctg atcagcagct     180
```

```
ggtgggaaga tgaggacagt aggtgcaact ggatcacgtt tgatctccag cttggtctcc    240
tcgccaaagg tgaaagcgac agcactacta ctaccactac caccattatt gttttgacag    300
tagtaagtgg cagcatcggc acactccagg tcgctgatgg tgagagtgta ctctgtccca    360
gatccactgc ctttgaaccg cgatgggacc ccagatgcca gagtggatgc agaatagatc    420
aggagcttgg gagactgccc tggtttctgc tgataccagg ctaatctact actaatgctc    480
tcactggcct ggcacttgat ggtgactgtg cctcccacag gttcacacgc ggaagatgga    540
gtctgggtca gcacagggtc                                                560

<210> SEQ ID NO 129
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(18)
<223> OTHER INFORMATION: a, c, t, g, unknown or other
<220> FEATURE:
<221> NAME/KEY: modified_base
<222> LOCATION: (22)..(27)
<223> OTHER INFORMATION: a, c, t, g, unknown or other
<220> FEATURE:
<221> NAME/KEY: modified_base
<222> LOCATION: (32)..(46)
<223> OTHER INFORMATION: a, c, t, g, unknown or other

<400> SEQUENCE: 129
nnnnnnnnnn nnnnnnnngt annnnnnctt cnnnnnnnnn nnnnnn                    46

<210> SEQ ID NO 130
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Gly Ser Gly Gly Ser Gly Gly Ser Gly Gly Ser Gly Gly Ser Gly
1               5                   10                  15

Gly Ser
```